United States Patent [19]
Kimball et al.

[11] Patent Number: 5,583,146
[45] Date of Patent: Dec. 10, 1996

[54] HETEROCYCLIC THROMBIN INHIBITORS

[75] Inventors: Spencer D. Kimball, East Windsor; Jagabandhu Das, Mercerville; Wan F. Lau, Lawrenceville, all of N.J.; Steven E. Hall, Chapel Hill, N.C.; Wen-Ching Han, Newtown, Pa.

[73] Assignee: Bristol-Myers Squibb Company, Princeton, N.J.

[21] Appl. No.: 373,334

[22] Filed: Jan. 17, 1995

Related U.S. Application Data

[63] Continuation-in-part of Ser. No. 146,714, Nov. 10, 1993, abandoned, and a continuation-in-part of Ser. No. 207,725, Mar. 14, 1994, abandoned, and a continuation-in-part of Ser. No. 207,726, Mar. 14, 1994, abandoned, and a continuation-in-part of Ser. No. 112,155, Aug. 26, 1993, abandoned, and a continuation-in-part of Ser. No. 213,964, Mar. 16, 1994, said Ser. No. 146,714, Nov. 10, 1993, abandoned, is a continuation-in-part of Ser. No. 112,153, Aug. 26, 1993, abandoned, which is a continuation-in-part of Ser. No. 984,640, Dec. 2, 1992, abandoned, said Ser. No. 207,725, is a continuation-in-part of Ser. No. 56,279, May 3, 1993, abandoned, said Ser. No. 207,726, is a continuation-in-part of Ser. No. 56,017, May 3, 1993, abandoned.

[51] Int. Cl.$^6$ .................. A61K 31/445; A61K 31/40; C07D 401/12; C07D 207/09; C07D 211; C07D 28

[52] U.S. Cl. .................. 514/326; 514/183; 514/200; 514/212; 514/231.5; 514/233.8; 514/234.5; 514/235.2; 514/235.5; 514/235.8; 514/236.8; 514/237.2; 514/252; 514/256; 514/258; 514/266; 514/303; 514/314; 514/316; 514/318; 514/319; 514/321; 540/200; 540/354; 540/480; 540/483; 540/544; 540/553; 540/597; 540/600; 540/603; 544/124; 544/127; 544/128; 544/129; 544/130; 544/133; 544/135; 544/137; 544/139; 544/141; 544/238; 544/242; 544/277; 544/283; 544/336; 546/118; 546/152; 546/190; 546/193; 546/198; 546/208; 546/209; 546/210; 546/211; 546/212; 546/214

[58] Field of Search .................. 540/200, 354, 540/480, 483, 544, 553, 597, 600, 603; 544/124, 127, 128, 129, 130, 133, 135, 137, 139, 141, 238, 242, 277, 283, 336; 546/118, 152, 190, 193, 198, 208, 209, 210, 211, 212, 214; 514/183, 200, 212, 231.5, 233.8, 234.5, 235.2, 235.5, 235.8, 236.8, 237.2, 252, 256, 258, 266, 303, 314, 316, 318, 319, 321, 326

[56] References Cited

U.S. PATENT DOCUMENTS

| 4,244,865 | 1/1981 | Ali et al. | 514/326 |
| 4,258,192 | 3/1981 | Okamoto et al. | 546/166 |

(List continued on next page.)

FOREIGN PATENT DOCUMENTS

| 479489 | 4/1992 | European Pat. Off. . |
| 526877 | 2/1993 | European Pat. Off. . |

(List continued on next page.)

OTHER PUBLICATIONS

Hackh's Chemical Dictionary, McGraw–Hill, p. 16 (1982).

(List continued on next page.)

*Primary Examiner*—Ceila Chang
*Attorney, Agent, or Firm*—Burton Rodney

[57] ABSTRACT

Heterocyclic thrombin inhibitors are provided which have the structure $$R^3-\underset{\underset{O}{\|}}{\overset{\overset{O}{\|}}{S}}-\underset{H}{N}-\underset{R}{\overset{H}{C}}-\overset{\overset{O}{\|}}{C}-N\begin{pmatrix}CH(R^2)R^1\\(CH_2)_n\end{pmatrix}G,$$

$$R^{6'}-\underset{H}{N}-\underset{R}{\overset{H}{C}}-\overset{\overset{O}{\|}}{C}-N\begin{pmatrix}CH(R^2)R^1\\(CH_2)_n-CH_2-Xa-Ra\end{pmatrix},$$

$$R^6-\underset{H}{N}-\underset{R}{\overset{H}{C}}-\overset{\overset{O}{\|}}{C}-N\begin{pmatrix}CH(R^2)R^1\\(CH_2)_n-CH_2-NH-Rb\end{pmatrix},$$

$$R_3-\underset{H}{N}-\underset{R}{\overset{H}{C}}-\overset{\overset{O}{\|}}{C}-N\begin{pmatrix}CH(R^2)R^1\\(CH_2)_n-C(=O)-NH-(CH_2)_p-Q-A-R^4\end{pmatrix},$$

or $$Alkyl_{1-2}-\underset{\underset{O}{\|}}{\overset{\overset{O}{\|}}{S}}-\underset{H}{N}-\underset{R}{\overset{H}{C}}-\overset{\overset{O}{\|}}{C}-N\begin{pmatrix}CH(R^2)R^1\\(CH_2)_n\end{pmatrix}G_x,$$

wherein n, R, $R^1$, $R^2$, $R^3$, G, $G_x$, $R^{6'}$, Ra, Xa, $R^6$, Rb, $R_3$, p, Q, A and $R^4$ are as defined herein.

13 Claims, No Drawings

U.S. PATENT DOCUMENTS

| | | | |
|---|---|---|---|
| 4,316,889 | 2/1982 | Sandor et al. | 514/326 |
| 4,346,078 | 8/1982 | Bajusz et al. | 514/326 |
| 4,904,661 | 2/1990 | Pilgrim et al. | 514/237.5 |
| 5,002,964 | 3/1991 | Lascalzo | 514/423 |
| 5,153,176 | 10/1992 | Abe et al. | 514/18 |
| 5,380,713 | 1/1995 | Balasubramanian et al. | 514/18 |

FOREIGN PATENT DOCUMENTS

| | | |
|---|---|---|
| 0669317A1 | 3/1995 | European Pat. Off. . |
| WO9311152 | 6/1993 | WIPO . |
| WO9429336 | 12/1994 | WIPO . |

OTHER PUBLICATIONS

Zablocki et al. "Potent in vitro and in vivo inhibitor of platelet aggregation based on the Arg–Gly–Asp–Phe sequence of fibrinogen . . . " J. Med. Chem. v36 pp. 1811–1819 (1993).

Robert M. Knabb et al, "In Vivo Characterization of a New Synthetic Thrombin Inhibitor," Thrombosis and Hemostasis (1992) 67, 56–59.

Charles V. Jackson et al, "Pharmacological Assessment of the Antithrombotic Activity of the Peptide Thrombin Inhibitor, D–Methyl–Phenylalanyl–Prolyl–Arginal (GYKI–14766), in a Canine Model of Coronary Artery Thrombosis," J. Pharm. Exp. Ther. (1992) 261, 546–552.

Greissbach, U. et al "Peptide aldehydes as inhibitors of proteolytic enzymes–synthetic aspects" CA102:181323a (1983).

Shuman, R. T. et al "Highly Selective Tripeptide Thrombin Inhibitors" J. Med. Chem. 36, 314–19 (1993).

Bajusz, S. et al "Highly Active and Selective Anticoagulants" J. Med. Chem. 33, 1729–35 (1990).

Rubini, E. et al "Synthesis of Isosteric Methylene–oxy Pseudodipeptide Analogues as Novel Amide Bond Surrogate Units" Tetrahedron 42, 6039–45 (1986).

Spatola, A. F. et al "Amide Bond Surrogates: Pseudopeptides and Macrocycles" Tetrahedron 44, 821–833 (1988).

McOmie, J. F. W. "Protective Groups in Organic Chemistry" Plenum Press, pp. 46, 55–57, 73 (1973).

Banner, D. et al "Serine Proteases: 3D Structures, Mechanisms of Action and Inhibitors" Prospect. Med. Chem. Bernard (Ed), Verlag Publishing, pp. 27–43 (1993).

Burger, A. "A Guide to the Chemical Basis of Drug Design" Wiley, Science, p. 15 (1984).

HETEROCYCLIC THROMBIN INHIBITORS

REFERENCE TO OTHER APPLICATIONS

This is a (1) continuation-in-part of application Ser. No. 146,714 filed Nov. 10, 1993, now abandoned, which is a continuation-in-part of application Ser. No. 112,153 filed Aug. 26, 1993, now abandoned, which is a continuation-in-part of application Ser. No. 984,640 filed Dec. 2, 1992, now abandoned. This is also, a (2) continuation-in-part of application Ser. No. 207,725 filed Mar. 14, 1994, now abandoned, which is a continuation-in-part of application Ser. No. 56,279 filed May 3, 1993, now abandoned; and a (3) continuation-in-part of application Ser. No. 207,726 filed Mar. 14, 1994, now abandoned, which is a continuation-in-part of application Ser. No. 56,017 filed May 3, 1993, now abandoned, and a (4) continuation-in-part of application Ser. No. 112,155 filed Aug. 26, 1993, now abandoned, and a (5) continuation-in-part of application Ser. No. 213,964 filed Mar. 16, 1994.

FIELD OF THE INVENTION

The present invention relates to heterocyclic compounds which are thrombin inhibitors and thus useful in inhibiting formation of thrombi.

DESCRIPTION OF THE FIRST EMBODIMENT OF THE INVENTION

In a first aspect or embodiment, the present invention relates to sulfonamido heterocyclic thrombin inhibitors which have the structure I

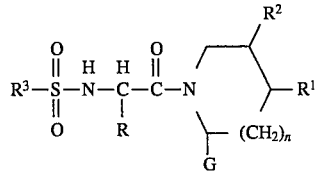

wherein G is an amido moiety which is

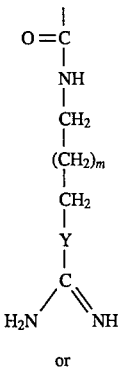

(G1)

or

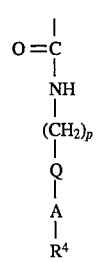

(G2)

including all stereoisomers thereof; and including all pharmaceutically acceptable salts thereof; wherein R is hydrogen, hydroxyalkyl, aminoalkyl, amidoalkyl, alkyl, cycloalkyl, aryl, arylalkyl, alkenyl, alkynyl, arylalkoxyalkyl, or an amino acid side chain, either protected or unprotected;

$R^1$ and $R^2$ are independently hydrogen, lower alkyl, cycloalkyl, aryl, hydroxy, alkoxy, oxo (also referred to as keto), thioxo (also referred to as thioketal), thioalkyl, thioaryl, amino or alkylamino; or $R^1$ and $R^2$ together with the carbons to which they are attached form a cycloalkyl, aryl, or heteroaryl ring; and $R^3$ is lower alkyl, aryl, arylalkyl, heteroaryl, quinolinyl or tetrahydroquinolinyl;

n is 0, 1 or 2;

m is 0, 1, 2 or 3;

Y is NH or S;

p is 0, 1 or 2;

Q is a single bond or

A is aryl or cycloalkyl, or an azacycloalkyl ring A of 3 to 7 carbons in the ring (4 to 8 total ring members) or an azaheteroalkyl ring A of 4 to 6 carbons in the ring (4 to 8 total ring members),

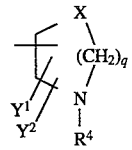

where X is $CH_2$, O, S or NH;

q is 0, 1, 2, 3 or 4 if X is $CH_2$;

q is 2, 3 or 4 if X is O, S or NH;

$Y^1$ and $Y^2$ are independently H, lower alkyl or halo; and $R^4$ is guanidine, amidine or aminomethyl;

where A is aryl or cycloalkyl, $R^4$ is guanidine, amidine or aminomethyl;

where A is azacycloalkyl or azaheteroalkyl, $R^4$ is amidine;

provided that where X is a hetero atom (that is, A is azaheteroalkyl), then there must be at least a 2-carbon chain between X and any N atom in the ring A or outside ring A;

and provided that where G is G1, then if $R^3$ is alkyl, the alkyl must contain at least 3 carbons.

In another embodiment of the invention, in the formula I compounds, $R^3$ is 10-camphor

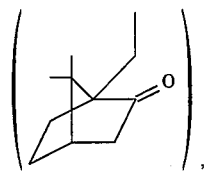

or pentamethylchroman

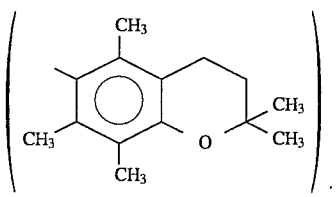

In still another embodiment of the formula I compounds, $R^3$ is pentaalkylphenyl, or trialkylphenyl such as pentafluorophenyl, pentamethylphenyl or 2,4,6-tri-isopropylphenyl.

In yet another embodiment of the formula I compounds, $R^3$ is 3-carboxyphenyl, 3-trifluoromethylphenyl or 4-carboxyphenyl.

Examples of the A ring (azacycloalkyl or azaheteroalkyl) which may be employed herein include

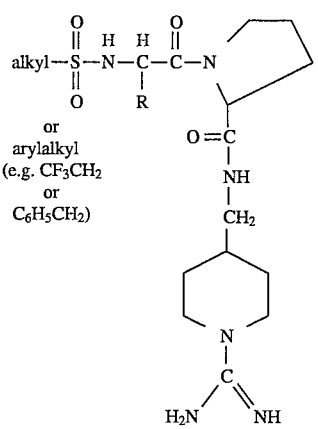

and the like.

Preferred are compounds of formula I wherein G is

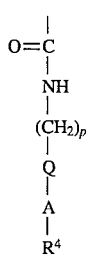

wherein Q is a single bond and A is an azacycloalkyl ring

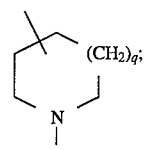

where q is 0 or 1; and
$R^4$ is amidino;
$R^3$ is lower alkyl or aryl;
R is aralkyl or hydroxyalkyl;
$R^1$ and $R^2$ are each H;
n is 0 or 1.

A more preferred embodiment of the heterocyclic thrombin inhibitors of the invention has the structure IA

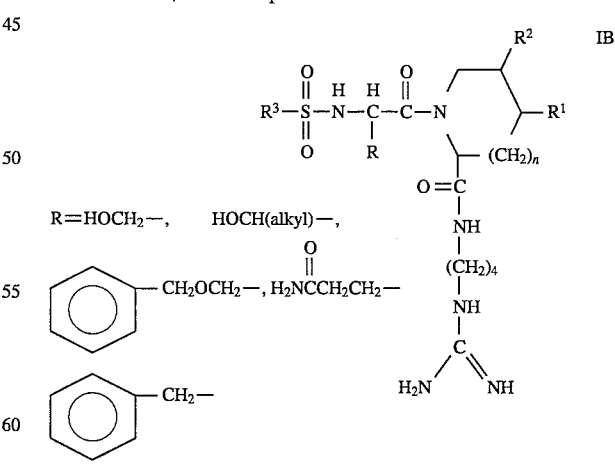

where R is aralkyl (preferably benzyl), aryl (preferably phenyl), or arylalkoxyalkyl (preferably benzyloxymethyl) and alkyl is preferably methyl, ethyl or propyl, including all stereoisomers thereof.

Other preferred compounds of formula I are those wherein G is G1, n is 0 or 1; m is 2; $R^3$ is aryl or alkyl; R is arylalkyl or hydroxyalkyl such as hydroxymethyl; $R^1$ is hydrogen or lower alkyl such as methyl or ethyl; $R^2$ is H; and Y is —NH—; and compounds of formula IB:

The compounds of formula I of the invention (first embodiment) wherein G is
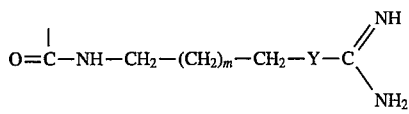
and Y is NH may be prepared according to the following Reaction Sequence I.
Reaction Sequence I
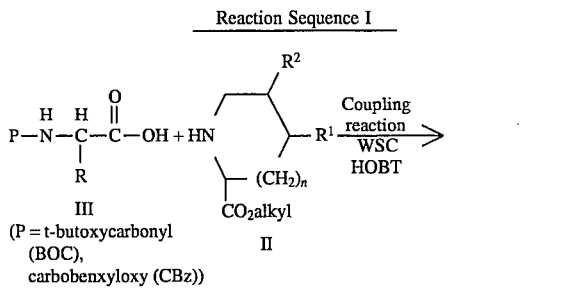
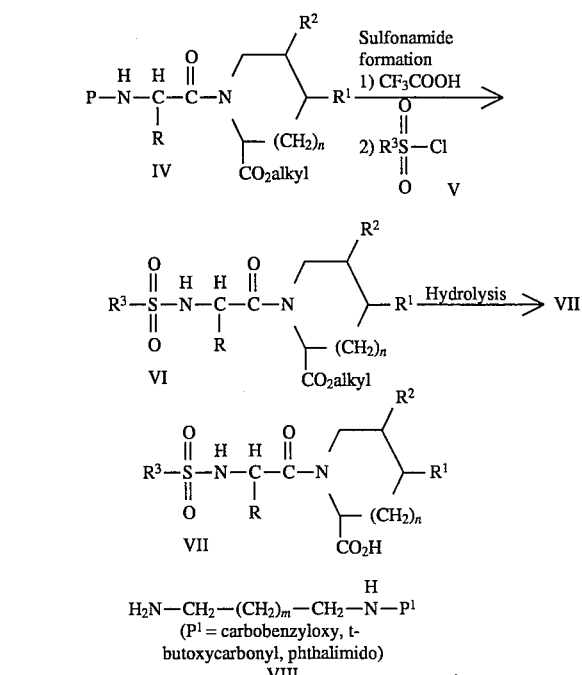
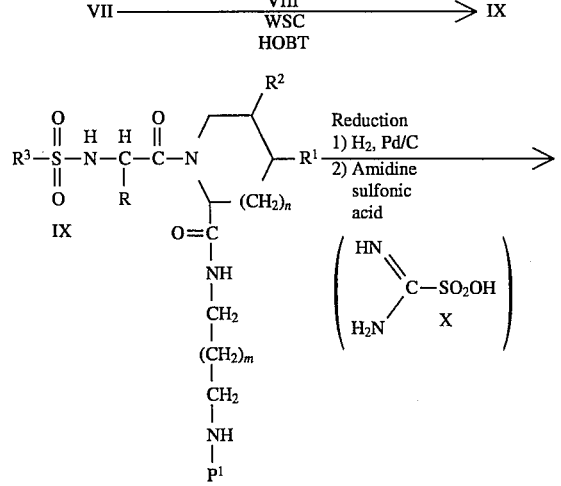
Reaction Sequence I —continued
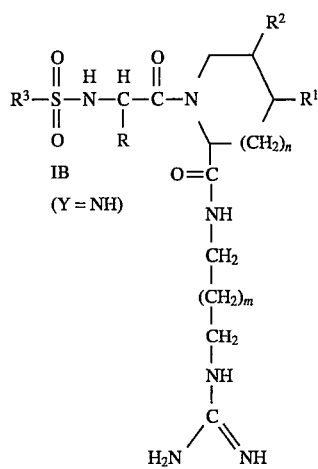
The compounds of formula I of the invention wherein G is
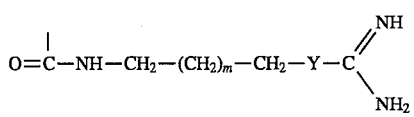
and Y is NH may also be prepared according to the following Reaction Sequence II
Reaction Sequence II
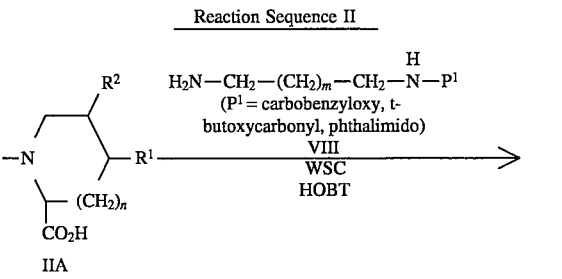
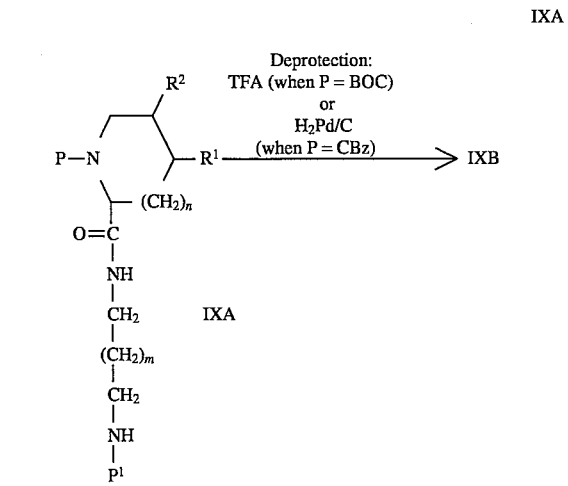

-continued
Reaction Sequence II

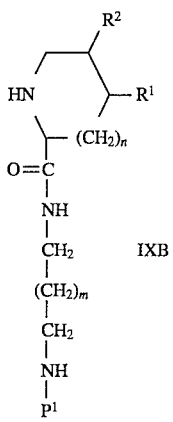

IXB

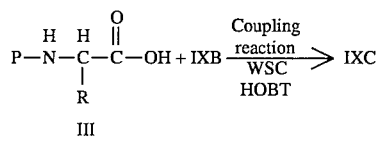

III (P = BOC or CBz)

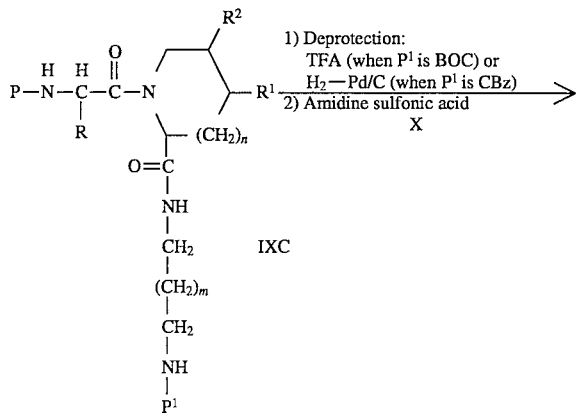

IXC

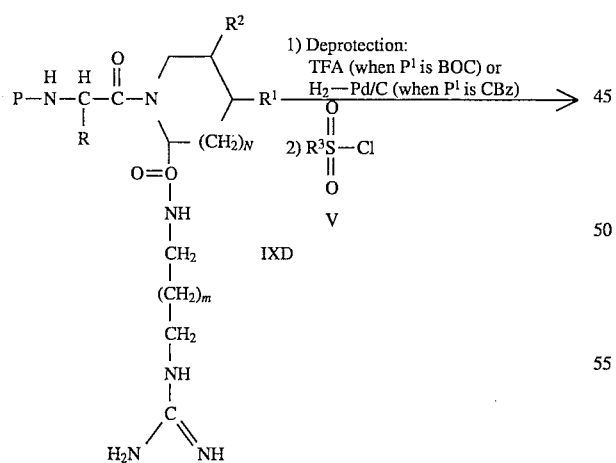

IB

As seen in the above Reaction Sequence I, compounds of formula I wherein Y is —NH—, are prepared as follows. The ester II is made to undergo a carbodiimide coupling reaction with protected amino acid III in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methyl-morpholine (NMM), and in the presence of an inert organic solvent such as dimethylformamide (DMF), THF or N-methylpyrrolidone, to form the amide IV. Amide IV is deprotected by treatment with trifluoroacetic acid with or without the presence of dry inert organic solvent such as dichloromethane, chloroform or THF at temperatures within the range of from about −15° to about 20° C. Sulfonyl chloride V is added followed by organic base such as triethylamine, pyridine or N,N-diisopropylethylamine to form the sulfonamide VI. Sulfonamide VI is hydrolyzed by treatment with alkali metal base such as NaOH or LiOH in the presence of an alcohol solvent such as methanol or ethanol. The reaction mixture is acidified with HCl, KHSO$_4$ or H$_2$SO$_4$, to form acid VII. The acid VII is then subjected to a carbodiimide coupling reaction wherein VII is treated with protected amine VIII in the presence of WSC or DCC, and HOBT, and NMM, in the presence of an inert organic solvent such as dimethylformamide, THF or N-methylpyrrolidone, to form sulfonamide IX. The sulfonamide IX is then dissolved in an alcohol solvent such as ethanol or methanol, to which HCl has been added and the mixture is hydrogenated over Pd—C or Pd(OH)$_2$—C in the case where p$^1$ is carbobenzyloxy. The crude material is separated by conventional procedures and the desired isomers are treated with amidine sulfonic acid X in the presence of an alcohol solvent such as ethanol to form the compound of the invention IB.

In a preferred preparation, compounds of formula IB can be prepared from a compound of formula IX by deprotection of p$^1$ and reaction with 1-(1'-carbobenzyloxy)carboxamidine pyrazole

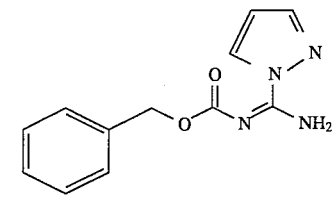

to give the protected guanidine form of IB. The CBZ protecting group can then be removed by hydrogenation.

Compounds of formula IB can also be prepared from a compound of formula VII and a compound of formula

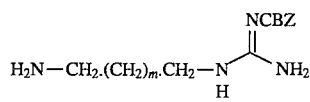

by reaction with a coupling agent such as WSC or DCC and HOBT and a suitable base such as NMM or triethylamine. Hydrogenation over palladium on carbon to remove the CBZ protecting group then affords IB. Further, compounds of formula IB can be prepared by the direct reaction of a compound of formula

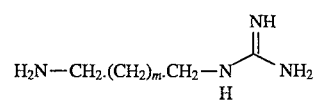

with a coupling reagent such as WSC or DCC and base such as NMM or triethylamine to give IB.

As seen in the above Reaction Sequence II, compounds of formula I wherein Y is —NH—, are prepared as follows. The protected acid IIA is made to undergo a carbodiimide coupling reaction with protected amino acid VIII in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide IXA. Amide IXA is deprotected by treatment with trifluoroacetic acid (TFA) when P is t-butoxycarbonyl (BOC) or $H_2$—Pd/C when P is carbobenzyloxy (CBz), with or without the presence of dry inert organic solvent such as dichloromethane, chloroform or THF, at temperatures within the range of from about –15° to about 20° C. to form amide IXB. The amide IXB is then subjected to a carbodiimide coupling reaction wherein IXB is treated with protected amine III in the presence of WSC or DCC, and HOBT, and NMM, in the presence of an inert organic solvent such as dimethylformamide, THF or N-methylpyrrolidone, to form amide IXC. The amide IXC is then dissolved in an alcohol solvent such as ethanol or methanol, to which HCl has been added and the mixture is hydrogenated over Pd—C or $Pd(OH)_2$—C in the case where $p^1$ is CBz or treated with trifluoroacetic acid when $p^1$ is BOC. The crude material is separated by conventional procedures and the desired isomers are treated with amidine sulfonic acid X in the presence of an alcohol solvent such as ethanol to form IXD. Compound IXD is then deprotected by treatment with TFA when P is BOC or by treatment with $H_2$—Pd/C when P is CBz, as described above, and sulfonyl chloride V is added followed by organic base such as triethylamine, pyridine or N,N-diisopropylethylamine to form the sulfonamide IB.

The compounds of formula I of the invention wherein G is

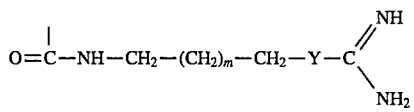

and Y is S may be prepared according to the following Reaction Sequence III.

Reaction Sequence III

VII + $H_2NCH_2(CH_2)_mCH_2OH$

XI

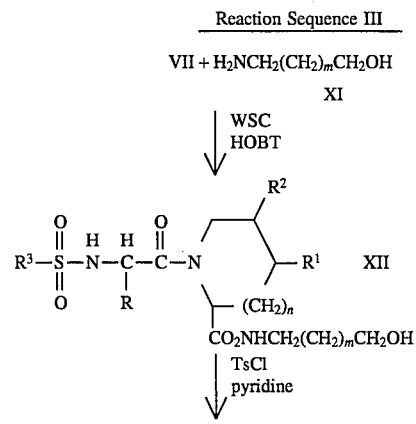

Reaction Sequence III -continued

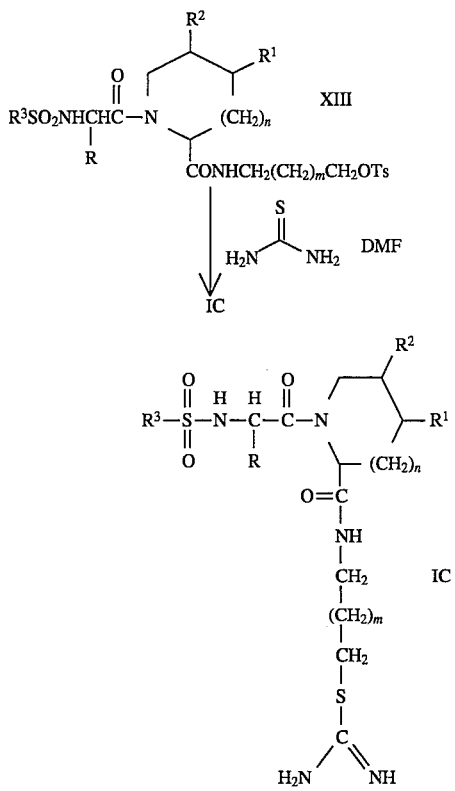

Referring to the above Reaction Sequence III, compounds of formula I wherein Y═S can be prepared as follows. The acid VII is subjected to a carbodiimide coupling reaction wherein VII is treated with an aminoalcohol XI in the presence of WSC or DCC, HOBT, and NMM, in the presence of an inert organic solvent such as dimethylformamide, THF or N-methylpyrrolidone, to form sulfonamide alcohol XII. The sulfonamide alcohol XII is reacted with p-toluenesulfonyl chloride (TsCl) in pyridine, or in a solvent such as methylene chloride or chloroform, with N,N-dimethylaminopyridine to provide toluenesulfonate XIII. The compound IC (Y═S) is prepared by treating XIII with thiourea in a solvent such as DMF or DMSO at temperatures within the range of from about 25° C. to about 100° C.

The compounds of formulae I and IA of the invention wherein G is

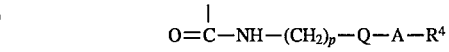

wherein A is azacycloalkyl or azaheteroalkyl, and $R^4$ is amidine, may be prepared according to the following Reaction Sequence IV:

Reaction Sequence IV

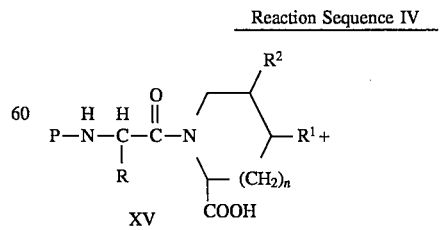

-continued
Reaction Sequence IV
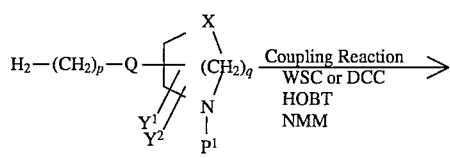
XVI
(where P¹ is a protecting group such as BOC or CBz)
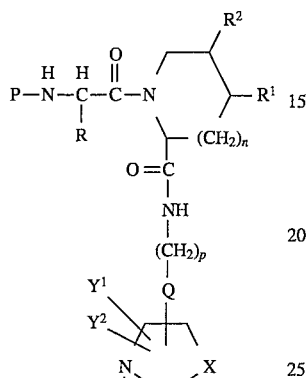
XVII
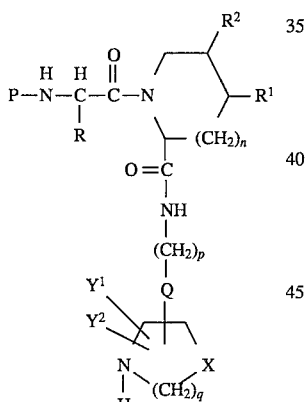
XVIII
XVIII —Amidinesulfonic Acid (X)→
-continued
Reaction Sequence IV
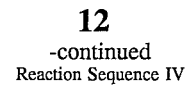
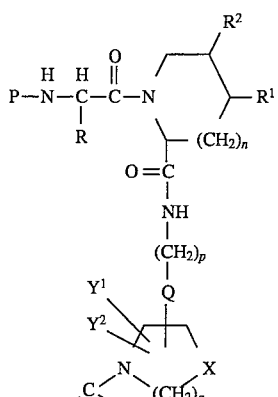
XIX
XIX —Deprotection→
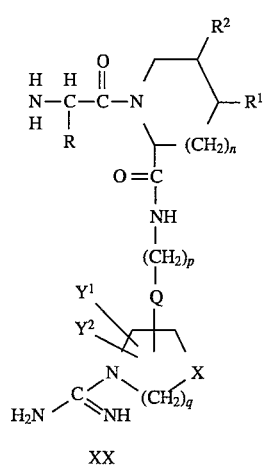
XX
XX —Sulfonation R³SO₂Cl V→
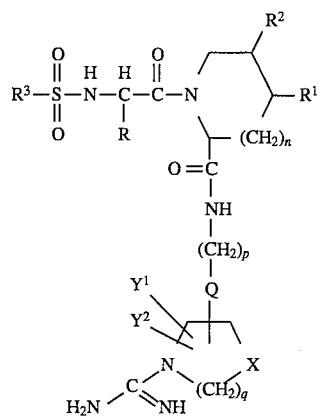
ID As seen in the above Reaction Sequence IV, compounds of formula I wherein G is

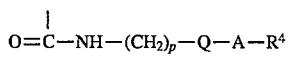

and A is azacycloalkyl or azaheteroalkyl, are prepared as follows. The protected acid XV is made to undergo a carbodiimide coupling reaction with amine XVI in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide XVII. Amide XVII is deprotected by treatment with, for example, $H_2$/Pd—C, if $p^1$ is CBz, to form amine XVIII. Amine XVIII is treated with amidinesulfonic acid x in the presence of alcohol solvent, such as ethanol to form amine XIX. Amine XIX is deprotected by treatment with trifluoroacetic acid (if P=BOC), with or without the presence of dry inert organic solvent such as dichloromethane, chloroform or THF, at temperatures within the range of from about $-15°$ to about $20°$ C. Sulfonyl chloride V is added followed by organic base such as triethylamine, pyridine or N,N-diisopropyl-ethylamine to form the sulfonamide ID of the invention.

Alternatively, the order of steps in reaction sequence IV may be changed. Thus the doubly protected compound of formula XVII is subjected to conditions which remove the protecting group $p^1$ (e.g., trifluoroacetic acid in methylene chloride if $p^1$ is BOC), after which the free amino group is made to undergo a reaction with bis-t-butoxycarbonyl thio-urea as described in the literature (Tet. Lett., 1992, 5933–5936). The product is then subjected to conditions that remove protecting group P (e.g., hydrogenation over Pd—C if P is CBZ), sulfonylated as described, and the BOC protecting groups removed (by e.g., trifluoroacetic acid) to give the compounds of formula ID.

In a preferred embodiment, compounds of formula ID can be prepared from compounds of formula XVII by removal of the P protecting group, followed by sulfonamide formation using $R^3SO_2Cl$. The $p^1$ protecting group of the resulting sulfonamide is then removed, and the product reacted with 1-(1'-carbobenzyloxy)-carboxamidine pyrazole

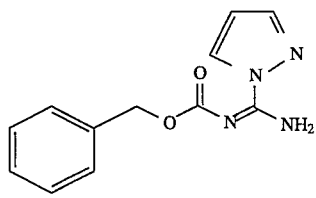

to give the CBZ-protected guanidine. The CBZ group may be removed by hydrogenation to give the guanidine.

Compounds of formula ID can also be prepared from a compound of formula VII and a compound of formula

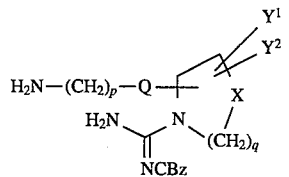

by reaction with WSC or DCC and HOBT and a suitable base such as NMM or triethylamine. Hydrogenation over palladium on carbon to remove the CBZ protecting group then affords ID. Further, compounds of formula ID can be prepared by the direct reaction of compound of formula

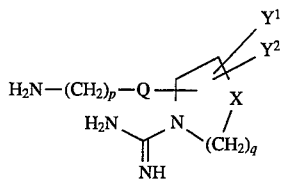

with a coupling reagent such as WSC or DCC and a base such as NMM or triethylamine to give ID.

The starting materials of formula XVI are known in the art or may be prepared by those skilled in the art employing conventional techniques.

The compounds of formulae I and IA of the invention where G is

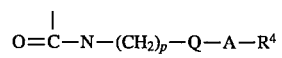

where A is aryl or cycloalkyl and $R^4$ is amidine or guanidine may be prepared according to the following Reaction Sequence V:

Reaction Sequence V

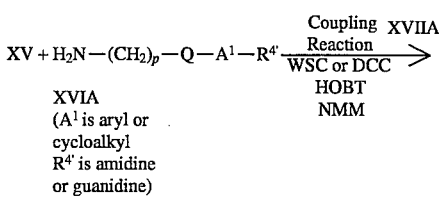

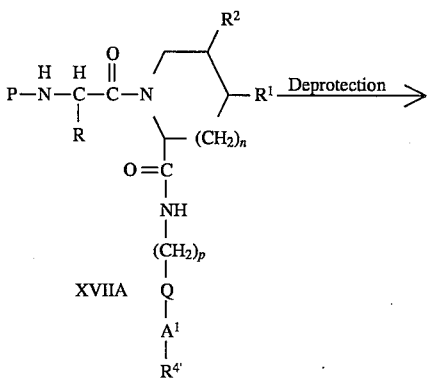

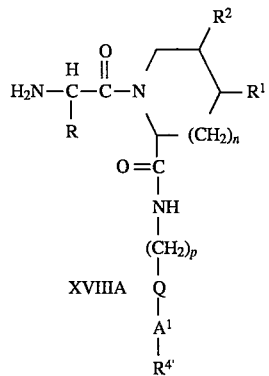

-continued
Reaction Sequence V

XVIIIA $\xrightarrow[\text{R}^3-\text{SO}_2\text{Cl}]{\text{Sulfonation}}$ V

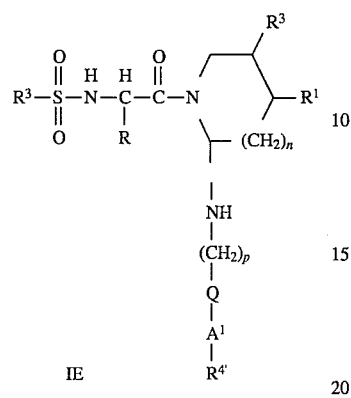

IE

As seen in Reaction Sequence V, compounds of formulae I and IA where G is $$O=\overset{|}{C}-NH-(CH_2)_p-Q-A^1-R^{4'}$$

are prepared as follows. The protected acid XV is subjected to a carbodiimide coupling reaction wherein XV is treated with protected amine XVIA in the presence of WSC or DCC, and HOBT, and NMM, in the presence of an inert organic solvent such as dimethylformamide, THF or N-methylpyrrolidone, to form amide XVIIA. The amide XVIIA is then dissolved in an alcohol solvent such as ethanol or methanol, to which HCl has been added and the mixture is hydrogenated over Pd—C or Pd(OH)$_2$—C in the case where P is carbobenzyloxy. The amide XVIIIA is treated with sulfonyl chloride V followed by base to form the compound of the invention IE.

The starting compound XVIA is known in the art or may be prepared employing conventional procedures.

The compounds of formulae I and IA of the invention wherein G is $$O=\overset{|}{C}-NH-(CH_2)_p-Q-A^1-R^{4'}$$

where A is aryl or cycloalkyl (that is $A^1$) and $R^4$ is aminomethyl (that is $R^{4'}$) may be prepared according to the following Reaction Sequence VI:

Reaction Sequence VI

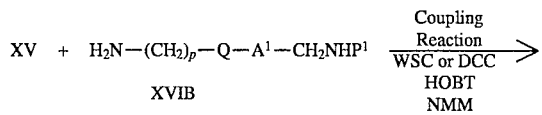

-continued
Reaction Sequence VI

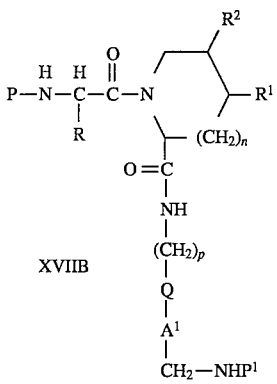
XVIIB

XVIIB $\xrightarrow{\text{Deprotected}}$

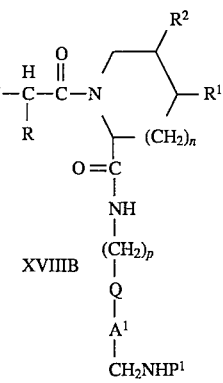
XVIIIB

XVIIIB $\xrightarrow[\text{R}^3\text{SO}_2\text{Cl}]{\text{Sulfonation}}$ V

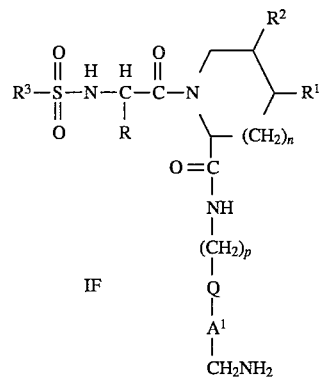
IF

As seen in the above Reaction Sequence VI, compounds of formulae I and IA wherein G is $$O=\overset{|}{C}-NH-(CH_2)_p-Q-A^1-CH_2NH_2$$

are prepared as follows. The protected acid XV is made to undergo a carbodiimide coupling reaction with protected amino acid XVIB in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide XVIIB. Amide XVIIB is deprotected by treatment with trifluoroacetic acid (TFA) when P is t-butoxycarbonyl (BOC) or H$_2$—Pd/C when P is carbobenzyloxy (CBz), with or without the presence of dry inert organic solvent such as dichloromethane, chloroform or THF, at temperatures within the range of from about −15° to about 20° C. to form amide XVIIIB. The amide XVIIIB is then subjected to a sulfonation reaction wherein amide XVIIIB is reacted with sulfonyl chloride V in the presence of organic base such as triethylamine, pyridine or N,N-diisopropylethylamine to form the sulfonamide IF of the invention.

The starting compounds XVIB are known in the art or may be prepared employing conventional procedures.

The starting acid XV may be prepared from ester IV by hydrolyzing ester IV by treating with a base such as NaOH, KOH or LiOH and then neutralizing the resulting alkali metal salt with strong acid such as HCl or oxalic acid.

DESCRIPTION OF THE SECOND EMBODIMENT OF THE INVENTION

In a second aspect or embodiment, the present invention relates to guanidinyl- or amidinyl-substituted heterocyclic thrombin inhibitors which have the structure 1.

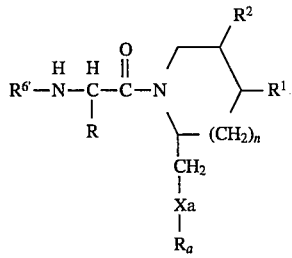

1.

including all stereoisomers thereof, wherein n is 0, 1 or 2;

$X_a$ is S, SO, $SO_2$ or O;

$R_a$ is —$A_1$—$R^{3a}$, where $A_1$ is an alkyl, alkenyl, or alkynyl chain of 2 to 6 carbon atoms and $R^{3a}$ is guanidine, amidine, or amino; or $R_a$ is —$(CH_2)_p$—$A_2$—$R^{2'}$ where $R^{2'}$ is amidine and $A_2$ is an azacycloalkyl ring of 4 to 8 atoms, optionally substituted by alkyl or halo as given by the structure

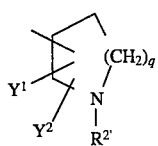

where p is 0, 1 or 2, q is 0, 1, 2, 3 or 4, N and $X_a$ are separated by at least two carbon atoms; and $Y^1$, $Y^2$ are independently H, alkyl, or halo; or $R_a$ is —$(CH_2)_p$—$A_3$—$R^4$, wherein $R^4$ is guanidine, amidine or aminomethyl, and $A_3$ is aryl or cycloalkyl;

R, $R^1$ and $R^2$ are as defined hereinbefore; and $R^{6'}$ is hydrogen,

—$SO_2R^7$ or $CO_2R^7$ (wherein $R^7$ is lower alkyl, aryl, cycloheteroalkyl or heteroaryl);

including pharmaceutically acceptable salts thereof, and all stereoisomers thereof.

Preferred are compounds of formula 1. wherein Xa is S or $SO_2$, n is 0, $R_a$ is —$(CH_2)_p$—$A_2R^{2'}$ or —$CH_2(CH_2)_z$—$R^{3a}$, z is 1, 2, 3 or 4; more preferably $R_a$ is

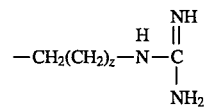

z is 2 or 3, or $R_a$ is

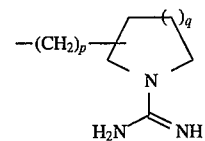

p is 1; q is 1 or 2, $R^1$ and $R^2$ are each H, R is H or —$CH_2OH$, and $R^{6'}$ is

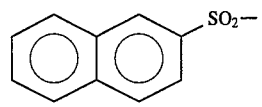

The compounds of formula 1. of the invention (second embodiment) wherein Xa is S, SO, $SO_2$ or O may be prepared according to the following reaction sequences.

Reaction Sequence 1.

(Preparation of 1. where Xa is S and $R_a$ is —$A_1$—$R^{3a}$ and $R^{3a}$ is —$NH_2$)

A.) where $R^{6'} \neq H$:

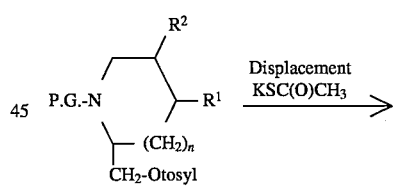

2.

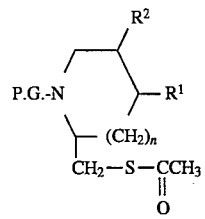

3.

-continued
Reaction Sequence 1.

3. 1) Alkylation NaOCH₃
2) Br—A₁—N (3ᵃ) ⟶

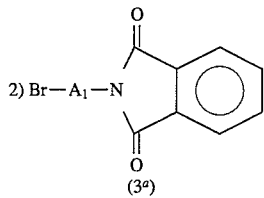

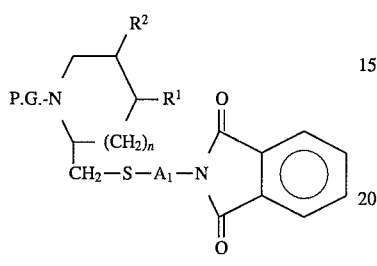

4.

4. 1) Deprotection
2) Coupling
P.G.'-NH—C(R)(H)—CO₂H (4a)
WSC/HOBT ⟶

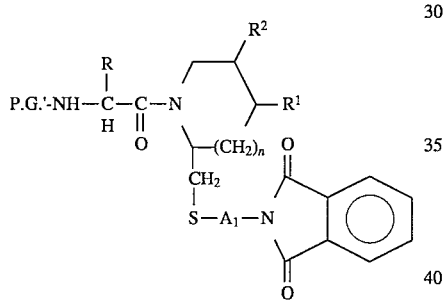

5.

5. Deprotection ⟶

6.

6. Coupling
a) R⁷COOH/WSC/HOBT or
b) R⁷SO₂Cl/(C₂H₅)₃N
or
c) R⁷OCOCl/(C₂H₅)₃N
⟶ 7.

-continued
Reaction Sequence 1.

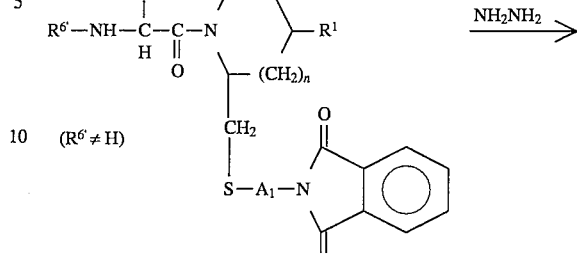

7.

(R⁶' ≠ H)

NH₂NH₂ ⟶

1.A

B.) where R⁶' = H:

6. NH₂NH₂ ⟶

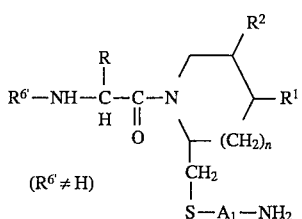

1.A'

Reaction Sequence 2

(Preparation of 1. where Xa is S and Rₐ is —A₁—N(H)—C(=NH)(NH₂))

A.) where R⁶' ≠ H:

1.A Guanylation amidine sulfonic acid ⟶

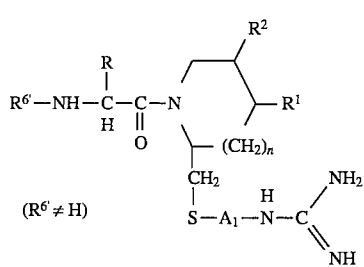

1.B

B.) where R⁶' = H:

5. NH₂NH₂ ⟶

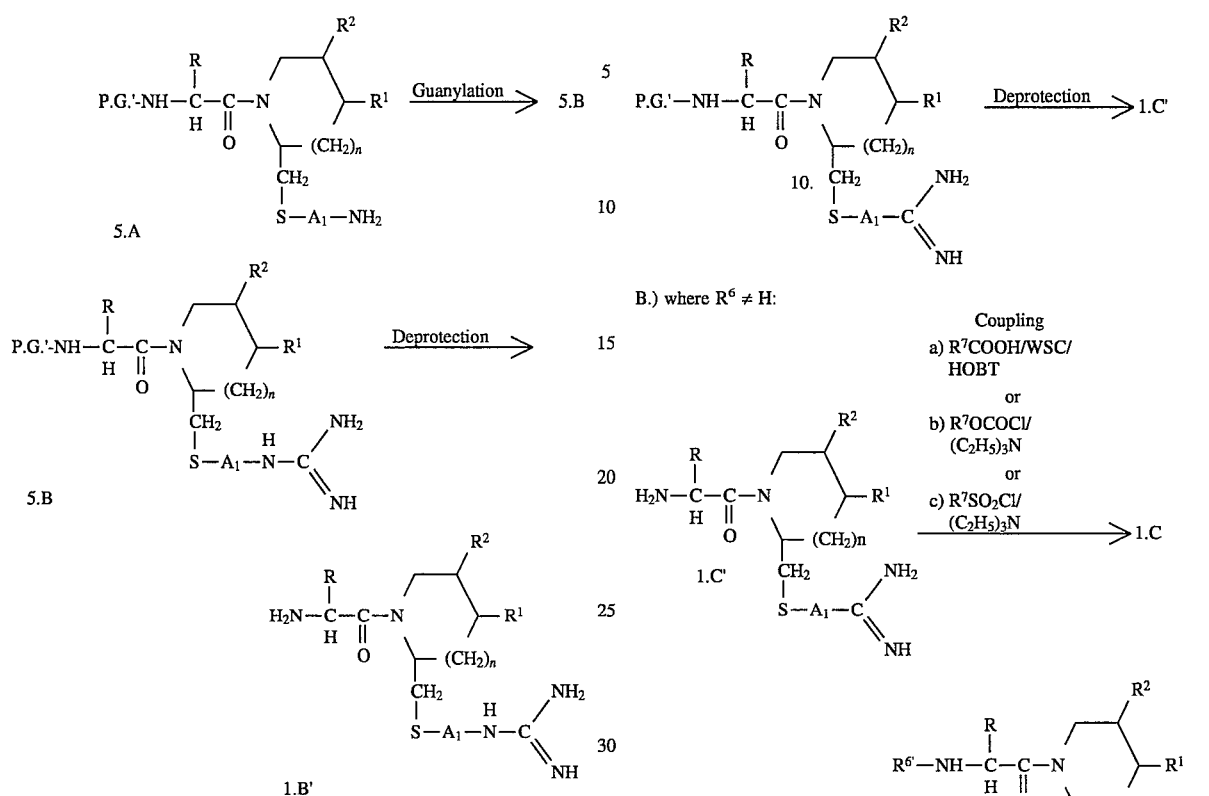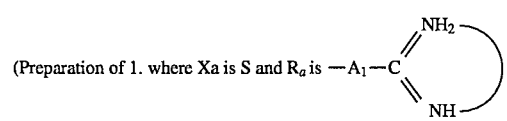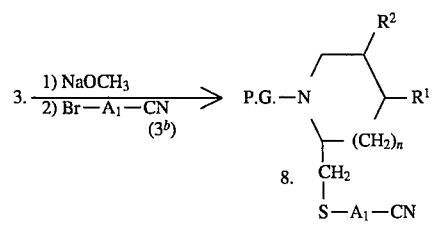

23
-continued
Reaction Sequence 4
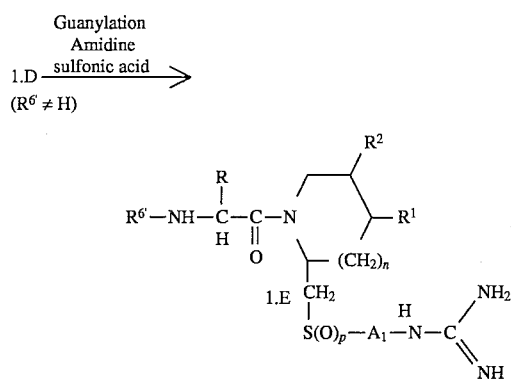
B2.) where $R^{6'}$ is H and $R^{3a}$ is guanidinyl:
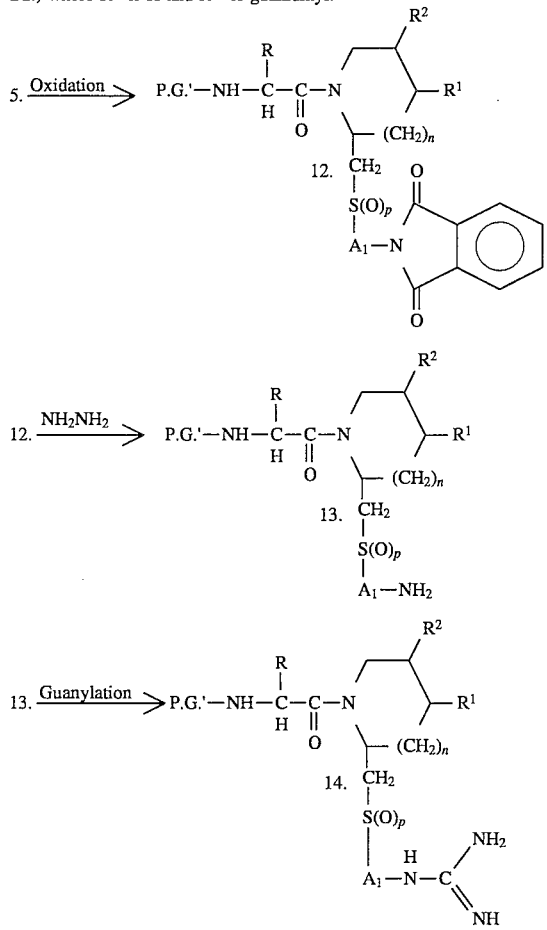
24
-continued
Reaction Sequence 4
C.) where $R^{6'}$ may or may not be H and $R^{3a}$ is amidinyl:
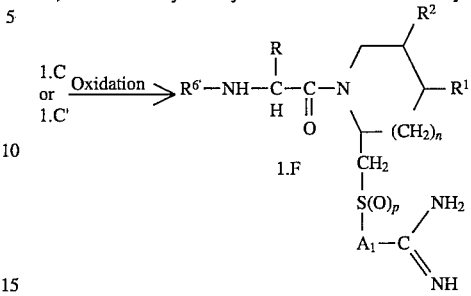
Reaction Sequence 5
(Preparation of 1, where $X_a = S$, $R^{6'} = H$ or $R^{6'} \neq H$, $R_a$ is $-(CH_2)_p-A_2-R^{2'}$, and $R^{2'}$ is amidine)
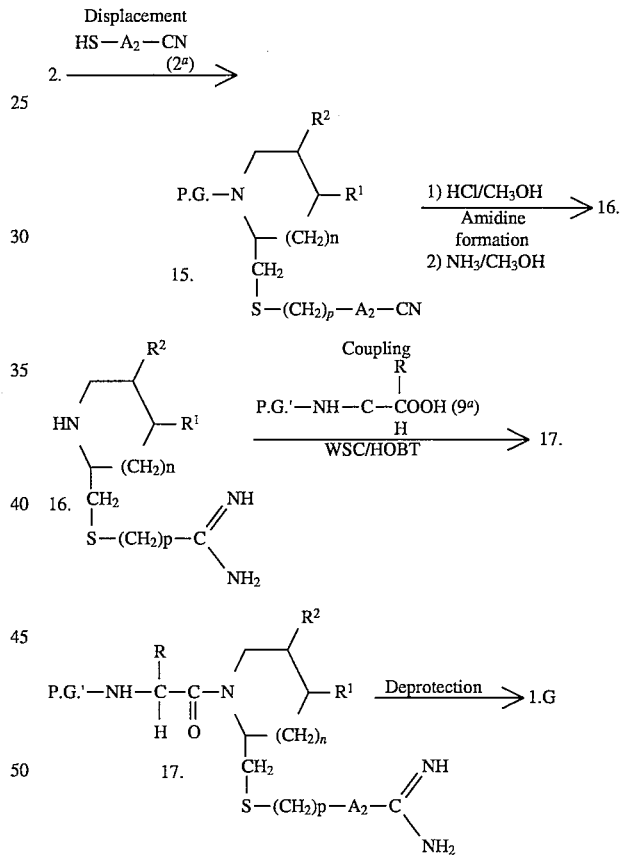
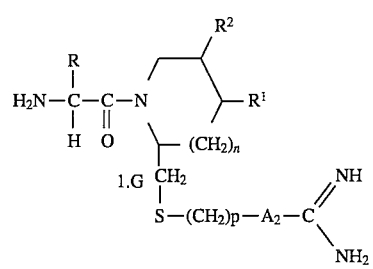

25
-continued
Reaction Sequence 5

Coupling
a) R⁷COOH/WSC/HOBT
or
b) R⁷OCOCl/(C₂H₅)₃N
or
c) R⁷OCOCl/(C₂H₅)₃N

1.G ⟶

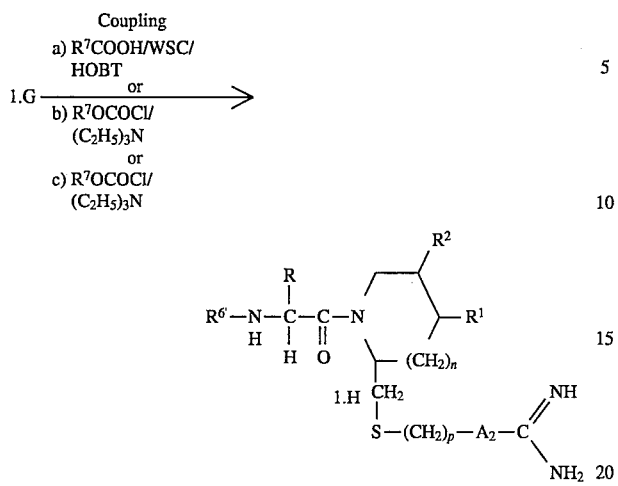

1.H

Reaction Sequence 6.

(Preparation of 1. where Xa = S, $R^{6'}$ = H or $R^{6'}$ ≠ H, Ra is $-(CH_2)_p-A_2-R^{2'}$ and $R^{2'}$ is aminomethyl)

15. ⟶ Reduction LiAlH₄

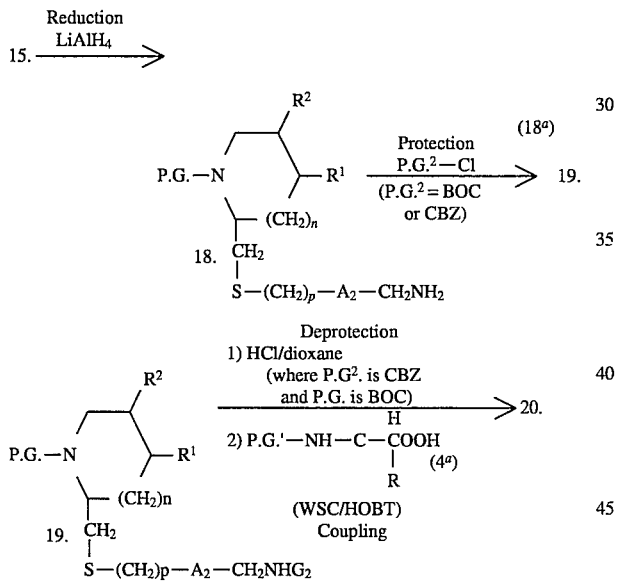

26
-continued
Reaction Sequence 6.

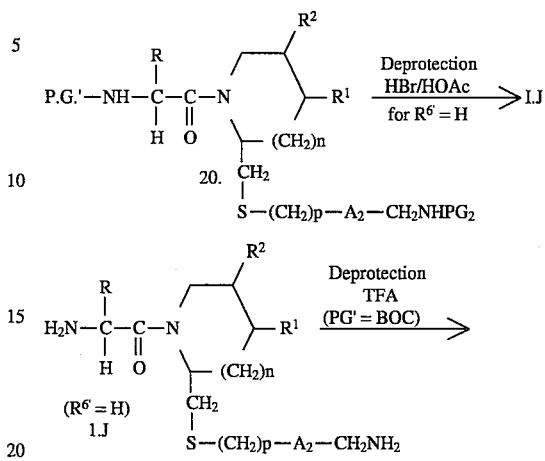

Coupling
a) R⁷COOH/WSC/HOBT
or
b) R⁷OCOCl/(C₂H₅)₃N
or
c) R⁷SO₂Cl/(C₂H₅)₃N

⟶ Deprotection HBr/HOAc ⟶

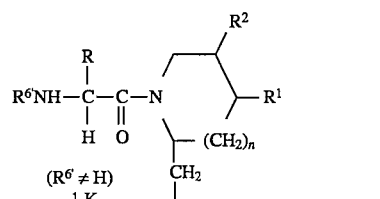

Reaction Sequence 7.

(Preparation of 1. where Xa is S, $R^{6'}$ = H or $R^{6'}$ ≠ H, Ra is $-(CH_2)_p-A_2-R^{2'}$ and $R^{2'}$ is guanidine)

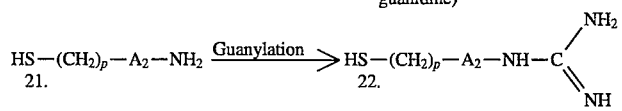

-continued
Reaction Sequence 7.
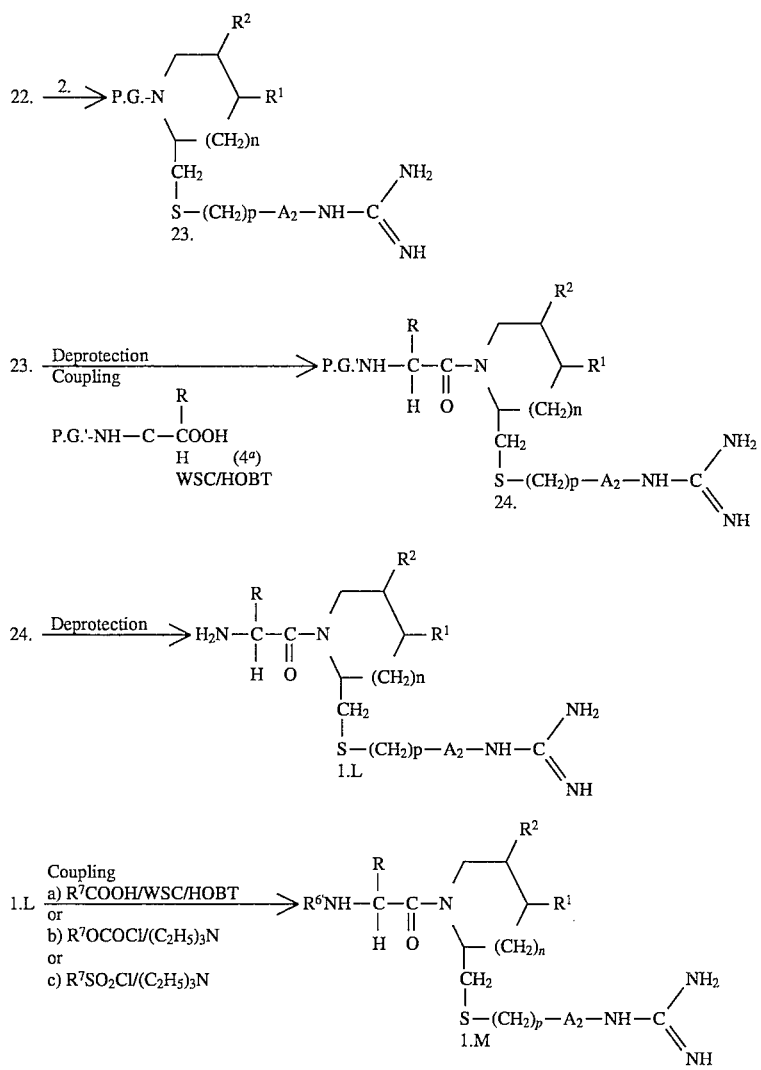
Reaction Sequence 8.
(Preparation of 1. where Xa is SO or $SO_2$ and $R_a$ is $-(CH_2)_p-A_2-R^{2'}$)
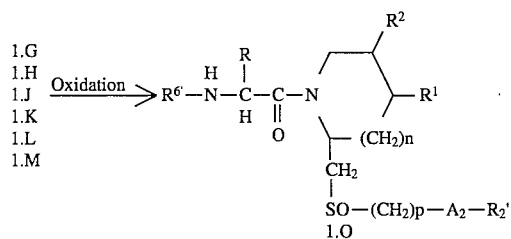
-continued
Reaction Sequence 8.
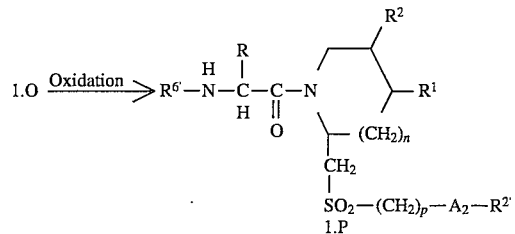

Reaction Sequence 9
(Preparation of 1. where $R_a$ is $-A_2R^{2'}$)
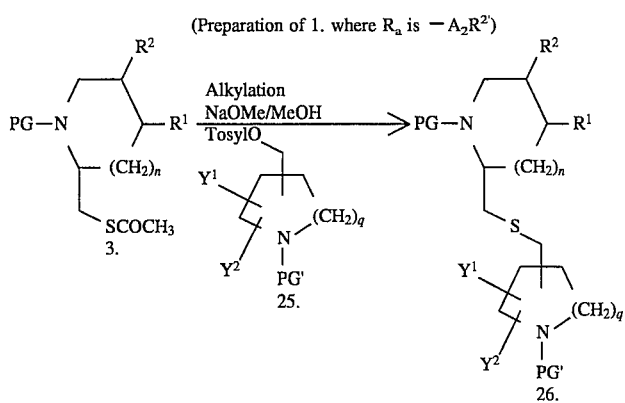
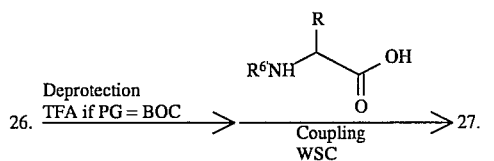
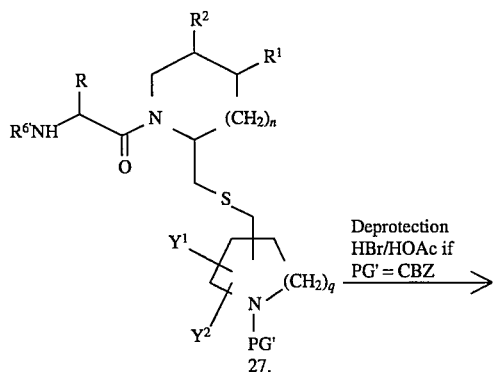
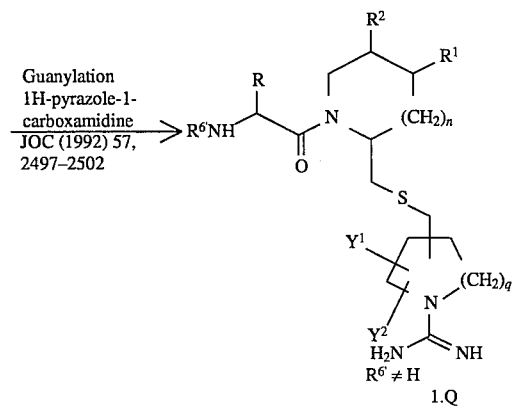

-continued
Reaction Sequence 9

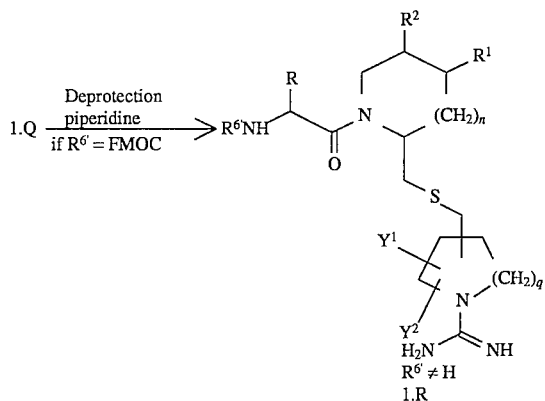

Reaction Sequence 10
(Preparation of 1. where Xa is oxygen)

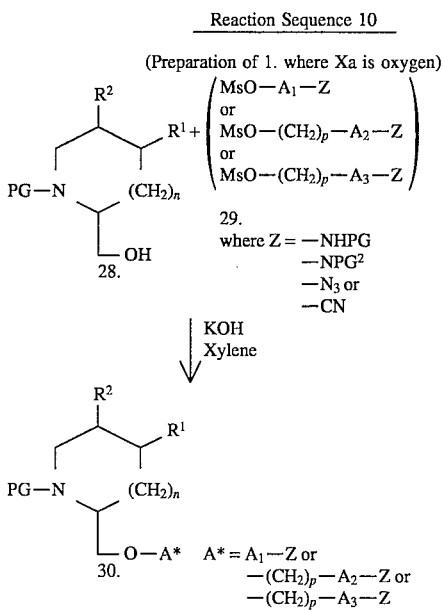

Referring to Reaction Sequence 1. compounds of formula 1. wherein Xa is S and $R_a$ is $-A_1-R^{3a}$ and $R^{3a}$ is amino may be prepared starting with tosylate 2. (prepared as described in J. Med. Chem. 35, 2615 (1992)) (wherein PG in 2. is a protecting group such as

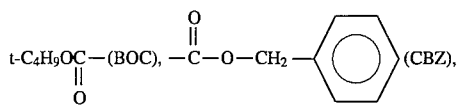

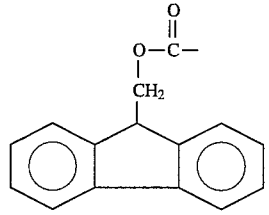

(fluorenylmethoxycarbonyl, FMOC), preferably BOC, which is subjected to a displacement reaction wherein 2. is treated with potassium thioacetate (KSAc) in the presence of an inert organic solvent such as acetone, dimethylformamide (DMF) or tetrahydrofuran (THF), under an inert atmosphere such as argon, at a temperature within the range of from about 0° to about 100° C. to form thioacetate 3. Thioacetate 3. is then alkylated by reacting 3. with an alkali metal alkoxide such as sodium methoxide or potassium t-butoxide in an inert organic solvent such as THF, DMF or diethylether, in the presence of an alcohol solvent such as methanol or ethanol under an inert atmosphere such as argon, at a temperature within the range of from about −30° to about 50° C. To the resulting solution is added N-bromoalkylphthalimide $3^a$ to form the thiophthalimide 4. Thiophthalimide 4. is deprotected by treatment with a deprotecting agent such as trifluoroacetic acid where P.G. is BOC or HBr/acetic acid where P.G. is CBZ, with or without the presence of dry inert organic solvent such as dichloromethane, chloroform or THF, to form a crude amine salt 4'.

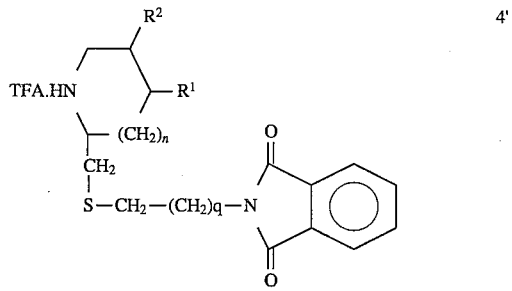

The resulting salt 4' is made to undergo a carbodiimide coupling reaction with protected amino acid $4^a$.

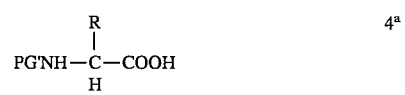

(wherein PG' is a protecting group which may be any of the PG protecting groups) in the presence of 1-hydroxybenzotriazole monohydrate (HOBT), ethyl-3-(3-dimethylamino-)propyl carbodiimide (WSC) or dicyclohexylcarbodiimide (DCC), and N-methylmorpholine (NMM), in the presence of an inert organic solvent such as dimethylformamide (DMF), THF or N-methylpyrrolidone, to form carbamate 5.

Carbamate 5. is deprotected by treatment with trifluoroacetic acid (TFA) or other deprotecting agent such as HBr/HOAc (depending on P.G.'), with or without the presence of dry inert organic solvent such as dichloromethane, chloroform or THF, to give a crude trifluoroacetic acid amine salt 6. (where the deprotecting agent is TFA).

The crude amine salt 6. is then subjected to a coupling reaction wherein it is reacted with a) R⁷COOH in the presence of WSC or DCC, HOBT and NMM, b) R⁷SO₂Cl in the presence of triethylamine or c) R⁷OCOCl in the presence of triethylamine, to form 7.

7. is then reacted with anhydrous hydrazine in the presence of dry solvent such as dichloromethane, chloroform or THF, and an alcohol solvent such as methanol or ethanol, to form thioalkylamine compound 1.A of the invention.

Compounds of formula 1. of the invention where $R^{6'}$ is H, Xa is S and $R_a$ is $-A_1-R^{3a}$ and $R^{3a}$ is $NH_2$ may be prepared as shown in Reaction Sequence 1.B) where amine 6. is reacted with anhydrous hydrazine (as described above in the reaction of 7.) to form 1.A.

Compounds of formula 1. of the invention wherein Xa is S, $R_a$ is $-A_1$-guanidinyl and $R^{6'}$ is not H may be prepared as shown in Reaction Sequence 7.A) wherein 1.A is subjected to a guanylation by reacting 1.A with amidine sulfonic acid or other guanylating agent such as 1H-pyrazole-1-carboxamidine, in the presence of a weak organic base such as triethylamine, pyridine or N-methylmorpholine (NMM) and an alcohol solvent such as ethanol or methanol, to form 1.B.

Compounds of formula 1. of the invention wherein Xa is S, $R_a$ is $-A_1$-guanidinyl and $R^6$ is H may be prepared as outlined in Reaction Sequence 2.B wherein compound 5. is treated with hydrazine (as described above in Sequence 1.A in the reaction of 6.) to form amine 5.A which is subjected to a guanylation reaction (as described above in Sequence 2.A) to form protected guanidine 5.B which is deprotected by treatment with TFA where P.G.' is BOC or using other deprotecting agent as described hereinbefore, to form compound of the invention 1.B'.

Referring to Reaction Sequence 3.A, compounds of formula 1. of the invention wherein Xa is S and $R_a$ is $-A_1$-amidinyl and $R^{6'}$=H are prepared by alkylating 3. by treating 3. with an alkali metal alkoxide and with nitrile (3b) in the presence of methanol or dimethylformamide, at a temperature within the range of from about −60° to about 75° C., to form nitrile 8. which is made to undergo amidine formation by treating nitrile 8. with hydrochloric acid in the presence of an alcohol such as methanol or ethanol, and then with ammonia to form amidine compound 9. Compound 9. is then subjected to a carbodiimide coupling reaction by treating 9. with (4ª) in the presence of WSC and HOBT (as described above in the reaction of 4. to form 5. in Sequence 1.), to form 10. which is deprotected as described hereinbefore to form 1.C'.

Compounds of formula 1. of the invention wherein Xa is S, $R_a$ is $-A_1$-amidinyl and $R^{6'}$ is not H, are prepared as shown in Sequence 3.B where 1.C' is treated with a coupling agent R⁷COOH, R⁷OCOCl or R⁷SO₂Cl (as described above in Sequence 1.A) in the coupling of 6. to form 7.), to thereby form 1.C.

Referring to Reaction Sequence 4., compounds of formula 1. wherein Xa is SO and $R_a$ is $-A_1-R^{3a}$ and $R^{3a}$ is $NH_2$, may be prepared by oxidizing amide 6. or 7. by treating 6. or 7. with an oxidizing agent such as m-chloroperbenzoic acid (MCPBA), oxone or sodium periodate in the presence of an inert organic solvent such as dichloromethane, chloroform or acetonitrile, employing from about 0.9 to about 1.5 moles of oxidizing agent per mole of 6. or 7., to form the corresponding sulfoxide (Xa is SO). The corresponding sulfone (Xa is SO₂) is formed employing from about 2 to about 3 moles of oxidizing agent per mole of 6. or 7. The so-formed sulfoxide or sulfone is then deprotected with hydrazine (as described in Sequence 1.A in the reaction of 6.) to form the corresponding amine 1.D of the invention.

As seen in Sequence 4 B1 where $R^6{\neq}H$ and $R^{3a}$ is guanidine, the resulting amine 1.D is guanylated by reaction with amidine sulfonic acid (as described hereinbefore in forming compounds of formula I where Xa is S) to form compounds of formula 1. where Xa is SO or SO₂ (that is 1.E).

Where $R^{6'}$ is H and $R_a$ is —A1-guanidinyl (Sequence 4.B2) compounds of formula 1. of the invention wherein Xa is SO or SO₂ are formed as follows: compound 5. is oxidized as described above for 6. or 7., to form compound 12. which is then reacted with hydrazine to form 13. which is guanylated and then deprotected to form compound of the invention 1.E' employing procedures described hereinbefore.

Sulfoxides or sulfones of compounds of formula 1. of the invention where $R_a$ is —A₁-amidinyl are prepared as shown in Sequence 4.C) by oxidizing 1.C or 1.C' employing procedures as described above to form compound of the invention 1.F.

Referring to Reaction Sequence 5., compounds of formula 1. wherein Xa is S and $R_a$ is $-A_2R^{2'}$ and $R^{2'}$ is amidinyl, may be prepared starting with tosylate 2. which is subjected to a displacement reaction wherein 2. is treated with nitrile 2ª

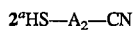

in the presence of a base such as sodium methoxide, triethylamine or pyridine, to form nitrile 15. Nitrile 15. is admixed with strong acid such as hydrochloric acid, and an alcohol solvent such as methanol, or ethanol and made to undergo amidine formation by treatment with ammonia to form the corresponding amidine 16. The resulting amidine compound 16. is then subjected to a carbodiimide coupling reaction with protected amino acid 4ª in the presence of WSC or DCC, and HOBT and NMM, as described with respect to Sequence 1., to form amide 17. Amide 17. is deprotected by treatment with trifluoroacetic acid or other deprotecting agent, as described with respect to Sequence 1., to form compound 1.G of the invention, which may be subjected to a coupling reaction wherein it is reacted with R⁷COOH, R⁷SO²Cl or R⁷OCOCl, as described with respect to Sequence 1., to form compounds of formula 1.H wherein Xa is S and $R_a$ is $-A_2R^{2'}$ and $R^{2'}$ is amidinyl.

Referring to Reaction Sequence 6., compounds of formula 1. of the invention wherein Xa is S, $R_a$ is $-A_2-R^{2'}$ and $R^{2'}$ is aminomethyl, may be prepared by reducing compound 15., for example using a reducing agent such as lithium aluminum hydride, triethylborohydride or diborane, to form amine 18. which is treated with a protecting agent (18ª) such as CBZ-Cl to form 19. Protected amine 19. is then treated with HCl in the presence of an alcohol such as methanol or dioxane and then treated with coupling agent (4ª), as described hereinbefore with respect to Sequence 1., to form compound 20. Compound 20. may be completely deprotected with e.g., HBr/HOAc to give amine 1.J. Alternatively, 20. may be selectively deprotected with e.g., TFA (if PG'= BOC) and then subjected to a coupling reaction by treatment with coupling agent R⁷COOH, R⁷OCOCl or R⁷SO₂Cl, followed by removal of PG² with HBr/HOAc, to form amine 1.K of the invention.

Referring to Reaction Sequence 7., compounds of formula 1. wherein Xa is S, $R_a$ is $-A_2-R^{2'}$ and $R^{2'}$ is guanidinyl may be prepared by guanylating amine 21. to form guanidine 22. which is reacted with 2. to form guanidine 23. Guanidine 23. is deprotected and then made to undergo a coupling reaction with 4ª, as described with respect to Sequence 1., to form 24 which is deprotected to form guanidine 1.L of the invention. Guanidine 1.L may then be reacted with a coupling agent $R^7COOH$, $R^7OCOCl$ or $R^7SO_2Cl$, as described with respect to Sequence 1., to form guanidine 1.M of the invention.

Referring to Reaction Sequence 8., compounds of formula 1. of the invention wherein $R_a$ is —$A_2$—$R^{2'}$ and Xa is SO may be prepared by oxidizing 1.G, 1.H, 1.J, 1.K, 1.L or 1.M by treating same with an oxidizing agent such as m-chloroperbenzoic acid (MCPBA), oxone or sodium periodate in the presence of an inert organic solvent such as dichloromethane, employing from about 0.9 to about 1.5 moles of oxidizing agent per mole of amide, to form the corresponding sulfoxide. The corresponding sulfone may be formed employing from about 2 to about 3 moles of oxidizing agent per mole of amide. The so-formed sulfoxide or sulfone is then deprotected with hydrazine and the resulting amine is guanylated by reaction with amidine sulfonic acid (as described hereinbefore in forming compounds of formula 1. where Xa is S) to form compounds of formula 1. where Xa is SO or $SO_2$.

As seen in Reaction Sequence 9., compounds of formula 1.Q and 1.R may be prepared by treating thioacetate 3. with sodium methoxide, followed by an alkylating agent of formula 25. to provide a compound of formula 26. Deprotection of 26. (by TFA if PG=BOC) and carbodiimide coupling, as described previously, affords compound 27. Removal of the protecting group PG' (by HBr/HOAc if PG'=CBZ) followed by guanylation using 1H-pyrazole-1-carboxamidine (JOC 1992, 57, 2497–2502) then provides a compound of formula 1.Q where $R^{6'}$ is not H. The compound 1.Q can be deprotected by piperidine (if $R^{6'}$= fluorenylmethyloxycarbonyl (FMOC)) to obtain compounds 1.R where $R^{6'}$ =H.

The key step for the preparation of compounds wherein Xa is oxygen is shown in Scheme 10. Treatment of the protected alcohol 28. with KOH and a mesylate (Ms) of formula 29. in xylene (see J. Med. Chem 1986, 29, 2335-2347) will provide the series of compounds 30. Further steps in the preparation of compounds of formula 1. wherein Xa is oxygen may be effected in analogy with the previously described Schemes 1, 2, 3, 5, 6, 7, and 9.

DESCRIPTION OF THE THIRD EMBODIMENT OF THE INVENTION

In a third aspect or embodiment, the present invention relates to guanidinyl- or amidinyl-substituted methylamino heterocyclic thrombin inhibitors which have the structure Ia

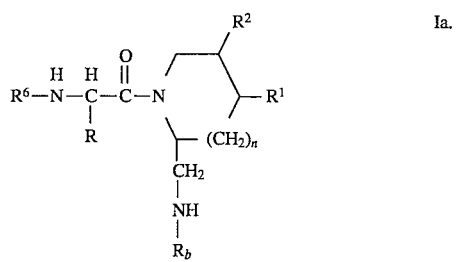

including all stereoisomers thereof wherein n is 0, 1 or 2;

$R_b$ is —$A^1$—$R^{3a}$, —CO—$A^1$—$R^{3a}$ or —$SO_2$—$A^1$—$R^{3a}$; wherein $R^{3a}$ is guanidine, amidine or amino, and $A^1$ is an alkyl, alkenyl or alkynyl chain of 2 to 6 carbons; or $R_b$ is —$(CH_2)_p$—$A_2$—$R^{2'}$ or —$(CH_2)_p$—CO—$A_2$—$R^{2'}$ where p is 0, 1, or 2, $R^{2'}$ is amidine and $A^2$ is an azacycloalkyl, azaheteroalkyl or azaheteroalkenyl ring of 4 to 8 atoms, optionally substituted by alkyl, CO or halo as given by the structure:

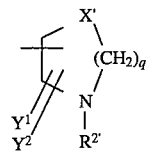

where X' is $CH_2$, O, S or NH;

q=0, 1, 2, 3 or 4 if X'=$CH_2$;

q=2, 3 or 4 if X'=O, S, NH; and $Y^1$, $Y^2$ are independently H, alkyl, or halo; or $R_b$ is —$(CH_2)_p$—$A^3$—$R^4$, —$(CH_2)_p$—CO—$A^3$-$R^4$, or —$(CH_2)_p$—$SO_2$—$A^3$—$R^4$, wherein $R^4$ is guanidine, amidine or aminomethyl, $A^3$ is aryl or cycloalkyl, and p is as defined above;

R, $R^1$ and $R^2$ are as defined hereinbefore;

$R^6$ is hydrogen,

—$SO_2R^{7'}$ or —$CO_2^{R7'}$ (wherein $R^{7'}$ is lower alkyl, aryl or cycloheteroalky);

including pharmaceutically acceptable salts thereof.

Preferred are compounds of formula Ia wherein n is 0, $R_b$ is

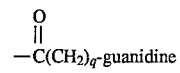

or —$CH_2(CH_2)_q$-guanidine, and q is 3, 4 or 5; and compounds of formula Ia wherein $R_b$ is $A^3$—$R^4$, $A^3$ is phenyl, and $R^4$ is amidine and compounds of formula $I^a$ wherein $R_b$ is —$(CH_2)_p$—$A^2$—$R^{2'}$, or

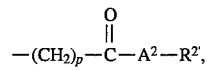

p is 0 or 1, $A^2$ is azacycloalkyl or azacycloalkenyl, and $R^{2'}$ is amidine;

$R^1$ and $R^2$ are each H, R is hydroxymethyl, —$CH_2COOalkyl$, or benzyl and $R^6$ is

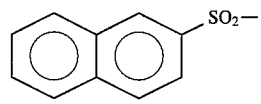

H, BOC or CBZ.

Most preferred are compounds of formula Ia wherein n is 0, $R_b$ is —$(CH_2)_p$—$A_2$—$R^{2'}$ or

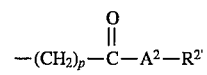

wherein p is 0 or 1, $A^2$ is
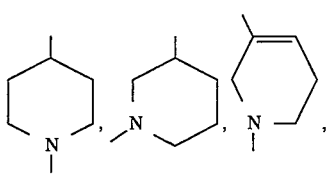
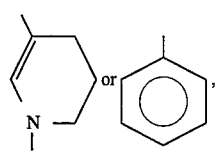
$R^{2'}$ is amidine, $R^1$ and $R^2$ are each H, R is hydroxymethyl, —CH$_2$COOCH$_3$, or benzyl, and $R^6$ is
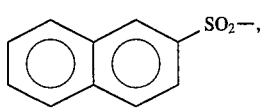
H, BOC or CBZ.
The compounds of formula Ia of the invention (third embodiment) may be prepared according to the following reaction sequences.
Reaction Sequence A
(Preparation of Ia where $R_b$ is —C(=O)—$A^1$—$R^{3a}$, and $R^{3a}$ is guanidine)
A. where $R^6 \neq H$
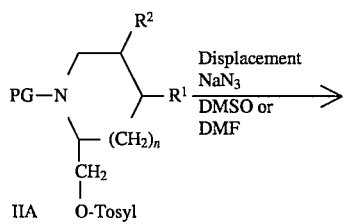
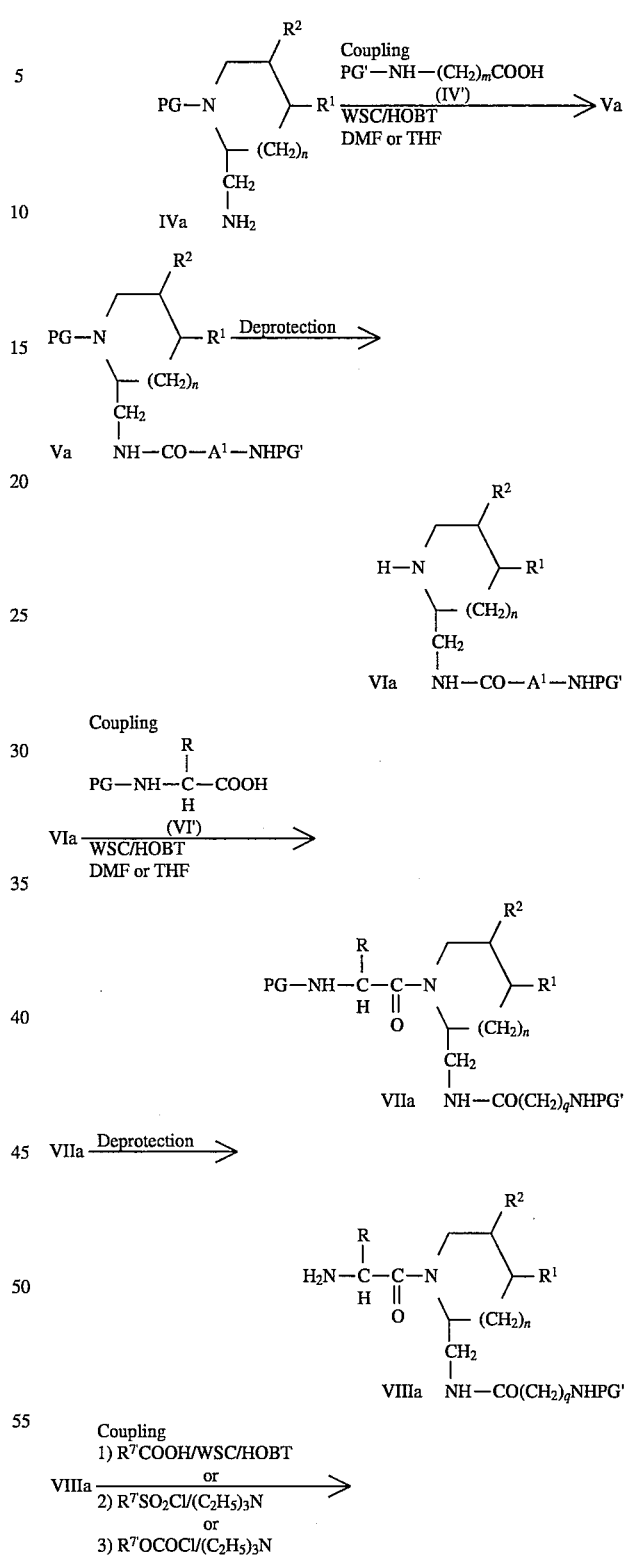

-continued
Reaction Sequence A

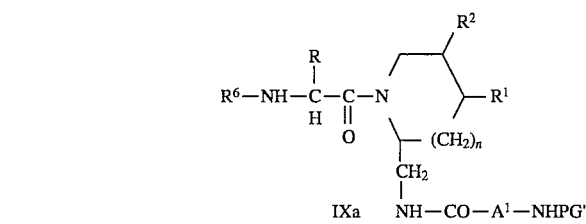

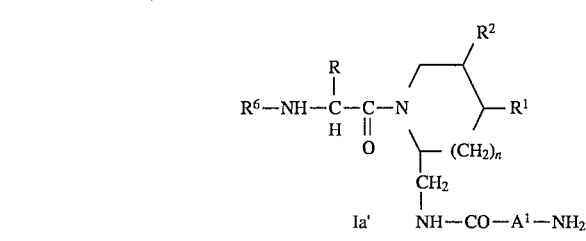

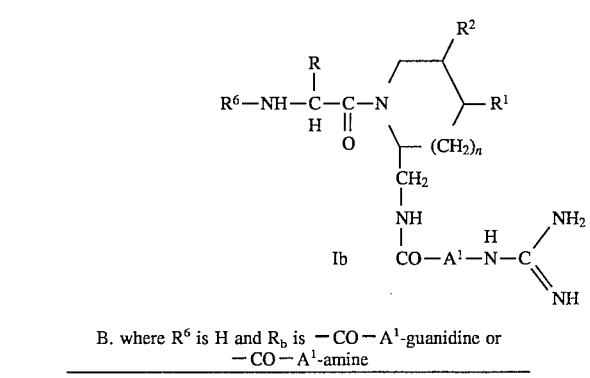

B. where $R^6$ is H and $R_b$ is $-CO-A^1$-guanidine or $-CO-A^1$-amine

1)

VIIa $\xrightarrow{\begin{array}{l}\text{1) Deprotection of PG'}\\\text{TFA (where PG'}\\\text{is BOC)}\\\text{2) Guanylation}\\\text{3) Deprotection of PG}\\\text{H}_2\text{/Pd-C}\\\text{(where PG is CBZ)}\end{array}}$

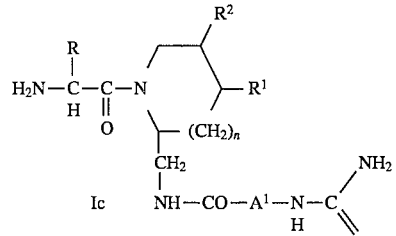

2)

Ia $\xrightarrow{\begin{array}{l}\text{Deprotection}\\\text{TFA (where R}^6\\\text{is BOC)}\\\text{or}\\\text{H}_2\text{/Pd-C}\\\text{(where R}^6\text{ is CBZ)}\end{array}}$

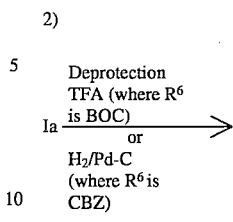

C. where $R_b$ is $CO-A^1$-amidine

IVa $\xrightarrow{\text{HOOC}-A^1-\text{CN}\ (\text{IV}_a')}$

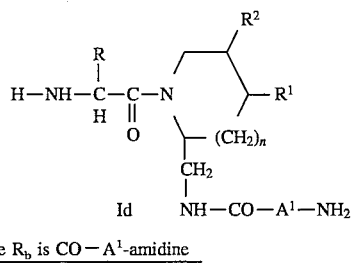

Xa $\xrightarrow{\begin{array}{l}\text{Amidine Formation}\\\text{1) HCl/CH}_3\text{OH}\\\text{2) NH}_3\text{/CH}_3\text{OH}\end{array}}$

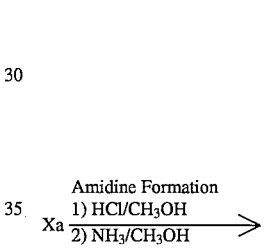

XIa $\xrightarrow{\begin{array}{c}\text{Coupling}\\\text{PG'}-\text{NH}-\overset{R}{\underset{H}{C}}-\text{COOH}\\(VI'')\\\hline\text{WSC/HOBT}\end{array}}$

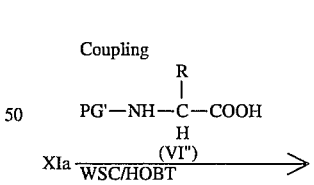

XIIa $\xrightarrow{\text{Deprotection}}$

41
-continued
Reaction Sequence A

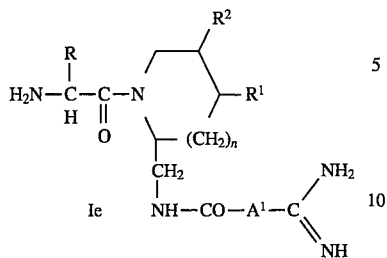

Ie $\xrightarrow{\text{Coupling}}$
1) R$^7$COOH/WSC/HOBT
or
2) R$^7$OCOCl/(C$_2$H$_5$)$_3$N
or
3) R$^7$SO$_2$Cl/(C$_2$H$_5$)$_3$N

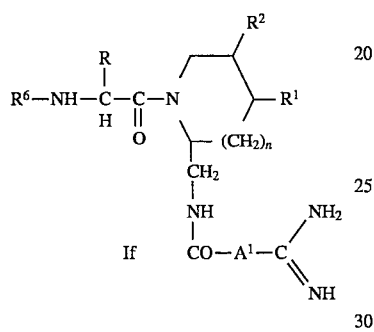

Reaction Sequence B (Preparation of Ia where R$_b$ is —A$^1$—R$^{3a}$,
R$^{3a}$ is amino or guanidine)
A. where R$^6$ ≠ H and R$^{3a}$ is amino or guanidine IVa $\xrightarrow[\text{CF}_3\text{CO}_2\text{COCF}_3]{\text{Acylation}}$

XIIIa $\xrightarrow[\text{DMF or DMSO}]{\substack{\text{Alkylation}\\ \text{1) CsCO}_3\text{ or K}_2\text{CO}_3\text{ or}\\ \text{Na}_2\text{CO}_3}}$

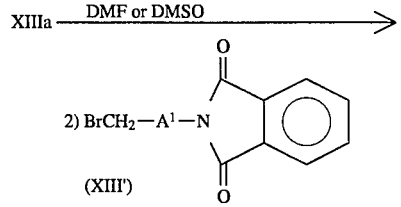

2) BrCH$_2$—A$^1$—N (XIII')

42
-continued
Reaction Sequence B

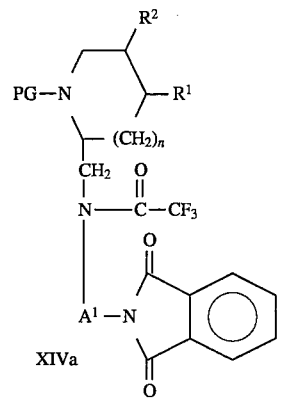

XIVa $\xrightarrow{\text{Deprotection}}$

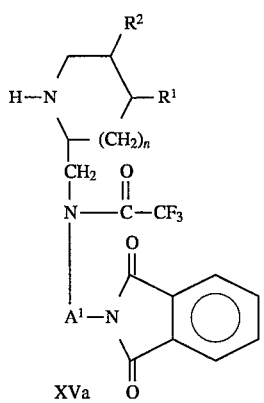

Coupling

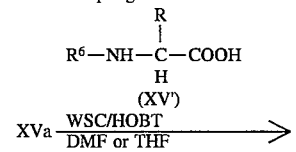

XVa $\xrightarrow[\text{DMF or THF}]{\text{WSC/HOBT}}$

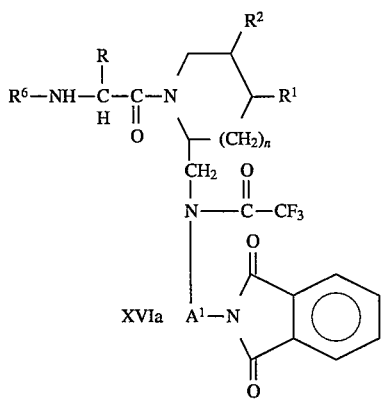

XVIa $\xrightarrow[\text{2) K}_2\text{CO}_3\text{/CH}_3\text{OH}]{\substack{\text{Deprotection}\\ \text{1) CH}_3\text{NHNH}_2}}$ 43
-continued
Reaction Sequence B

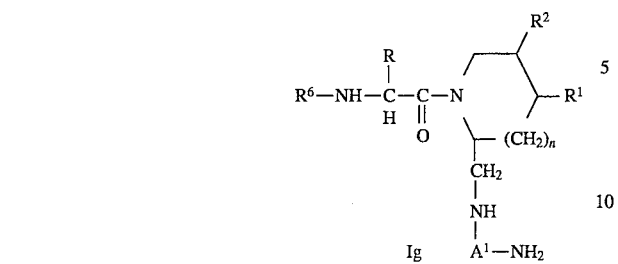
Ig

Ig $\xrightarrow{\text{Guanylation}}$

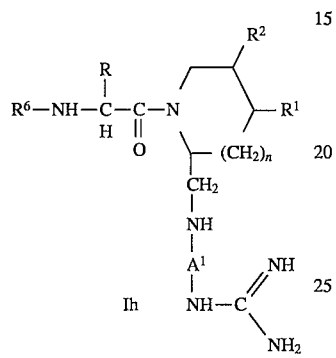
Ih

B. where $R^6$ = H and $R^{3a}$ is guanidine or amine

1)

Ih $\xrightarrow[\text{(where } R^6 \text{ is CBZ)}]{\text{H}_2/\text{Pd-C}}$

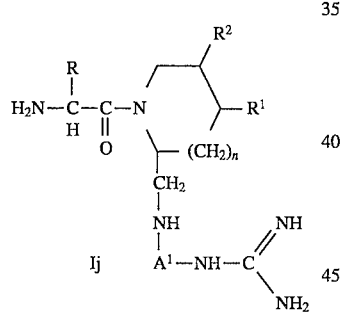
Ij

2)

Ig $\xrightarrow[\text{R}^6 \text{ is BOC})]{\text{Deprotection (where } R^6 = \text{CBZ or}}$

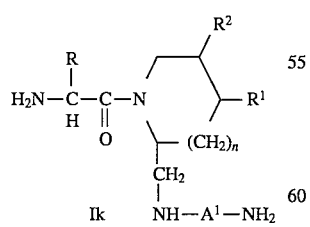
Ik

44
-continued
Reaction Sequence B

C. where $R^{3a}$ is amidine

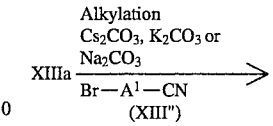

XIIIa $\xrightarrow[\text{Br—A}^1\text{—CN}]{\text{Alkylation Cs}_2\text{CO}_3, \text{K}_2\text{CO}_3 \text{ or Na}_2\text{CO}_3}$ (XIII'')

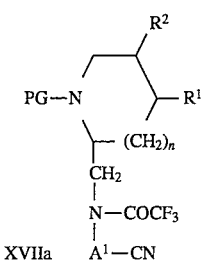
XVIIa

XVIIa $\xrightarrow[\text{WSC/HOBT}]{\begin{array}{l}\text{1) Deprotection}\\\text{TFA}\\\text{2) } R^6-\overset{R}{\underset{H}{N}}-\overset{}{\underset{H}{C}}-\text{COOH}\\\text{(XV')}\end{array}}$

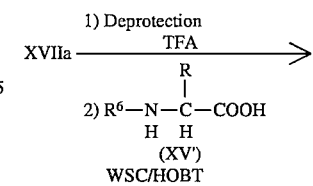
XVIIIa

XVIIIa $\xrightarrow[\text{2) NH}_3/\text{C}_2\text{H}_5\text{OH}]{\begin{array}{l}\text{Amidine Formation}\\\text{1) HCl/C}_2\text{H}_5\text{OH}\end{array}}$

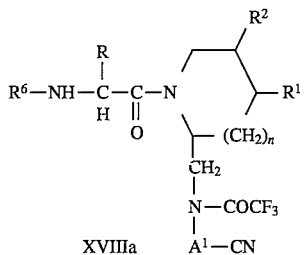

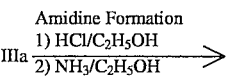

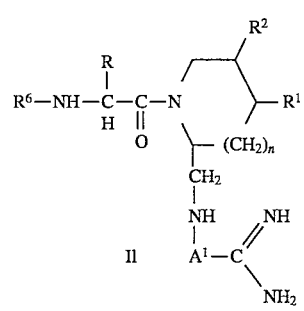
Il ($R^6$ = H if $R^6$ in XVIIIa is BOC)

Reaction Sequence C (Preparation of Ia where $R_b$ is
$-SO_2-A^1-R^{3a}$)
A. where $R^{3a}$ is guanidine

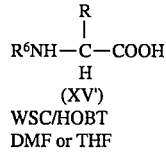

Reduction
XIXa $\xrightarrow[\text{or}]{\begin{array}{c}1)\ H_2/Pd\text{-}C\\\text{or}\\(C_6H_5)_3P/H_2O\\\text{or}\\SnCl_2\ \text{or LAH}\end{array}}$ Sulfonylation
2) $Br-A^1-SO_2Cl$
$\xrightarrow{\quad (XIX')\quad}$ XXA

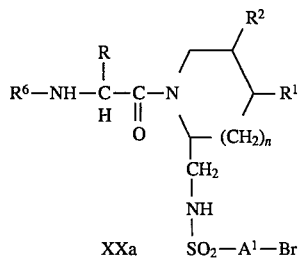

Displacement
$\xrightarrow[\text{DMF or DMSO}]{NaN_3}$ XXIa

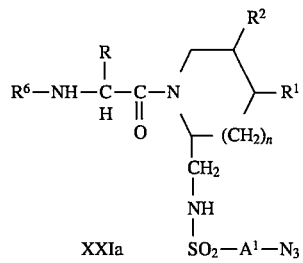

Deprotection
1) TFA (if $R^6$ is CBZ)
or
$H_2/Pd$-C or $SnCl_2$
(if $R^6$ is BOC)
or $(C_6H_5)_3 P/H_2O$
or LAH
2) Guanylation
$\longrightarrow$ Im -continued
Reaction Sequence C

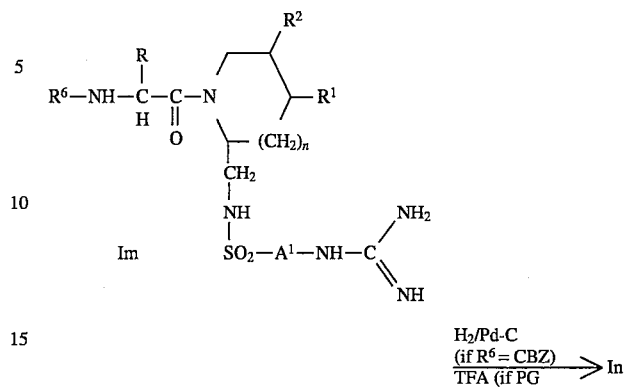

$\xrightarrow[\text{TFA (if PG is BOC)}]{\begin{array}{c}H_2/Pd\text{-}C\\\text{(if } R^6 = CBZ)\end{array}}$ In

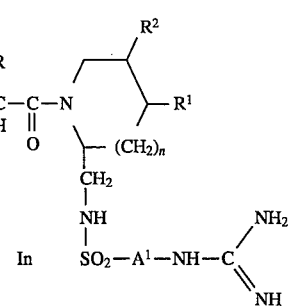

B. where $R^{3a}$ is amine

1. Reduction
(if $R^6$ = CBZ)
XXIa $\xrightarrow[\text{or}]{\begin{array}{c}H_2/Pd\text{-}C\\\text{or}\\(C_6H_5)_3P/H_2O\\\text{or}\\SnCl_2\ \text{or LAH}\end{array}}$

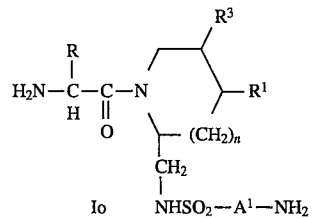

2. 1) Deprotection
(TFA if $R^6$ = BOC)
2) Coupling
$R^7COOH/WSC/HOBT$
XXIa $\xrightarrow[\text{or}]{\begin{array}{c}\text{or}\\R^7SO_2Cl/(C_2H_5)_3N\\\text{or}\\R^7OCOCl/(C_2H_5)_3N\end{array}}$
3) Reduction of azide
$H_2/Pd$-C or
$(C_6H_5)_3P/H_2O$ or LAH

47
-continued
Reaction Sequence C

C. where $R^{3a}$ is amidine

XXA $\xrightarrow{\text{Displacement}}$

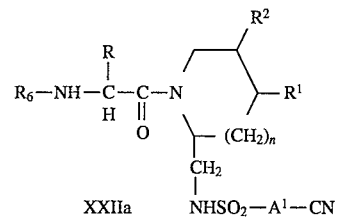

XXIIa

XXIIa $\xrightarrow[\text{2) NH}_3/\text{C}_2\text{H}_5\text{OH}]{\text{1) HCl/C}_2\text{H}_5\text{OH}}$

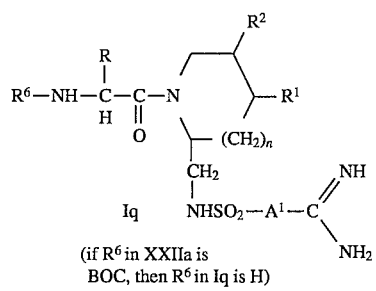

Iq (if $R^6$ in XXIIa is BOC, then $R^6$ in Iq is H)

Reaction Sequence D
(Preparation of Ia where $R_b$ is $-A^3-R^4$)

A. where $R^4$ is amidine

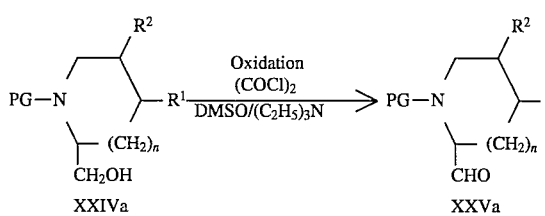

XXIVa → XXVa

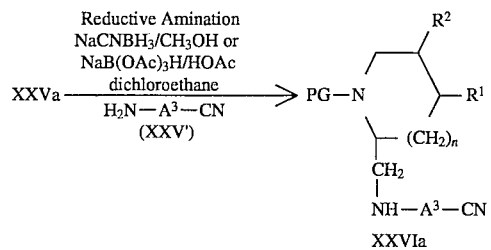
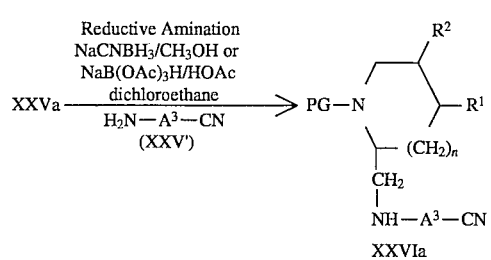

XXVa $\xrightarrow[\substack{\text{dichloroethane} \\ \text{H}_2\text{N}-\text{A}^3-\text{CN} \\ (\text{XXV}')}]{\substack{\text{Reductive Amination} \\ \text{NaCNBH}_3/\text{CH}_3\text{OH or} \\ \text{NaB(OAc)}_3\text{H/HOAc}}}$ XXVIa XXVIa $\xrightarrow[\text{2) NH}_3/\text{C}_2\text{H}_5\text{OH}]{\substack{\text{Amidine formation} \\ \text{1) HCl/C}_2\text{H}_5\text{OH}}}$

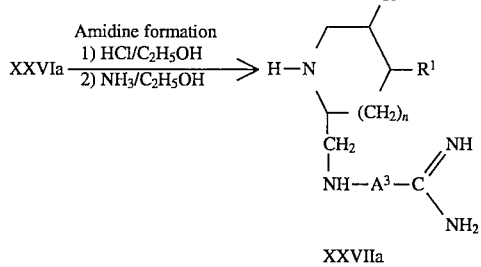

XXVIIa

48
-continued
Reaction Sequence D
(Preparation of Ia where $R_b$ is $-A^3-R^4$)

Coupling

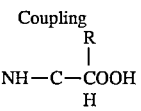

XXVIIa $\xrightarrow[\substack{\text{WSC/HOBT} \\ \text{DMF or THF}}]{(\text{VI}'')}$

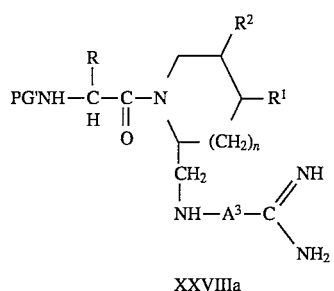

XXVIIIa

XXVIIIa $\xrightarrow[\text{(if PG' is CBZ)}]{\substack{\text{Deprotection} \\ \text{H}_2/\text{Pd}-\text{C}}}$

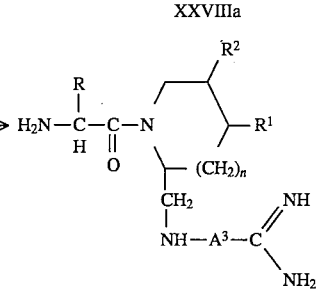

Ir

Coupling
1) $R^7\text{COOH/WSC/HOBT}$
Ir $\xrightarrow[\substack{\text{or} \\ \text{2) } R^7\text{SO}_2\text{Cl}/(\text{C}_2\text{H}_5)_3\text{N} \\ \text{or} \\ \text{3) } R^7\text{OCOCl}/(\text{C}_2\text{H}_5)_3\text{N}}]{}$

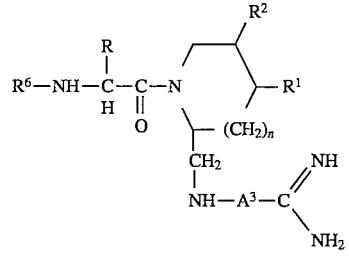

Is

B. where $R^4$ is aminomethyl

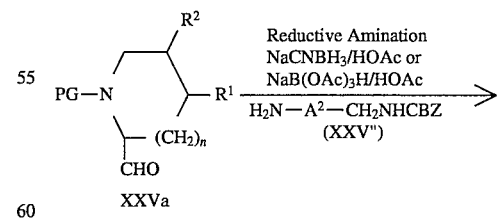

XXVa $\xrightarrow[\substack{\text{H}_2\text{N}-\text{A}^2-\text{CH}_2\text{NHCBZ} \\ (\text{XXV}'')}]{\substack{\text{Reductive Amination} \\ \text{NaCNBH}_3/\text{HOAc or} \\ \text{NaB(OAc)}_3\text{H/HOAc}}}$

-continued
Reaction Sequence D
(Preparation of Ia where $R_b$ is $-A^3-R^4$)
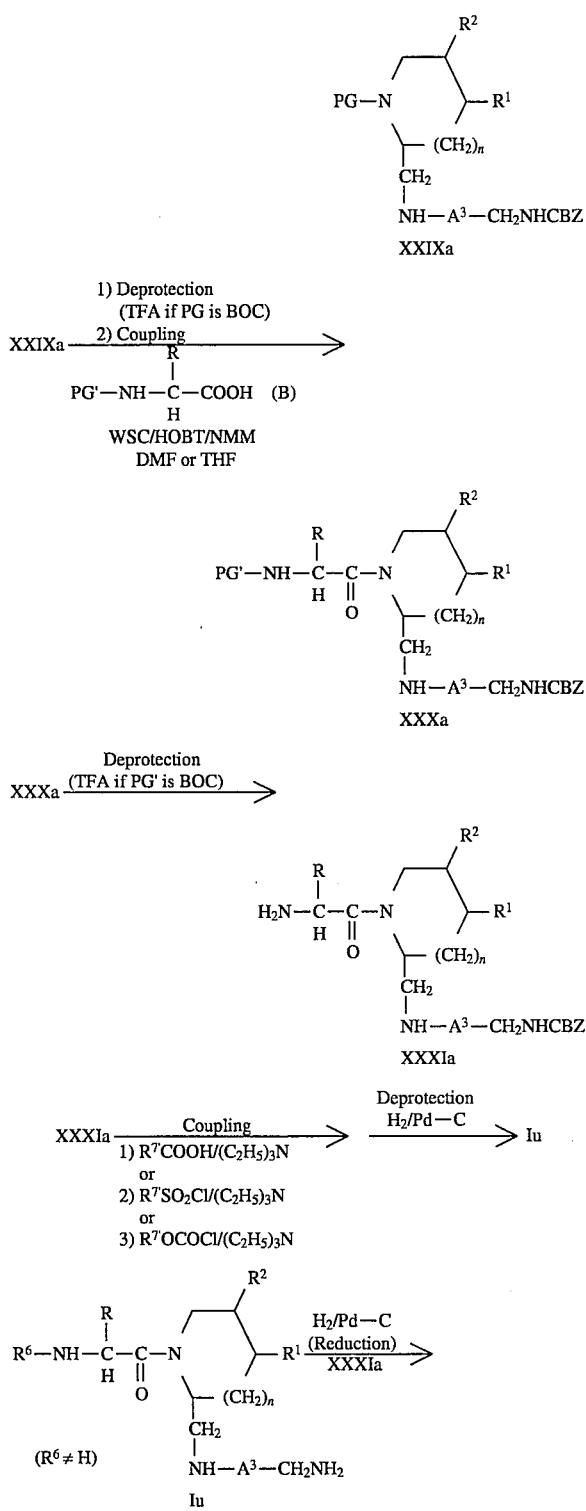
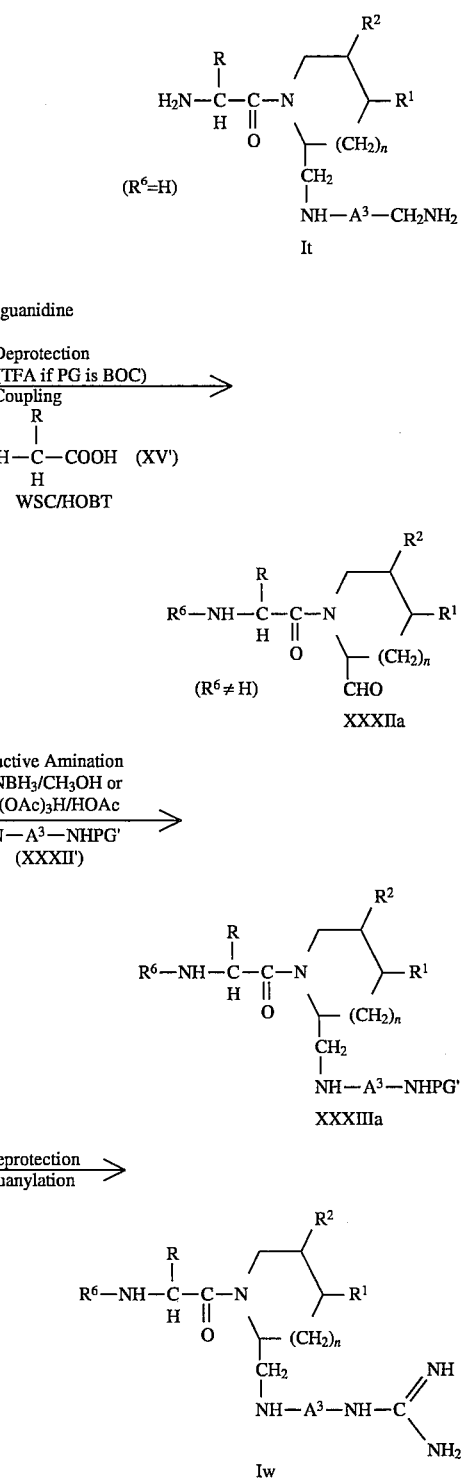

5,583,146

51
-continued
Reaction Sequence D
(Preparation of Ia where $R_b$ is $-A^3-R^4$)

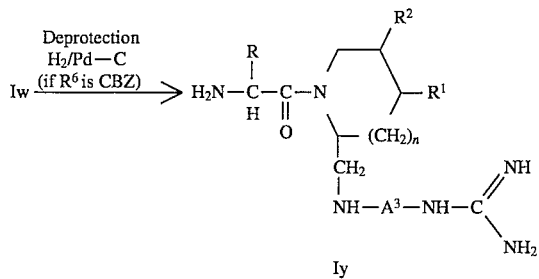

Reaction Sequence E1
(Preparation of Ia where $R_b$ is $-(CH_2)_p-A^2-R^{2'}$, where $R^6$ may or may not be H)

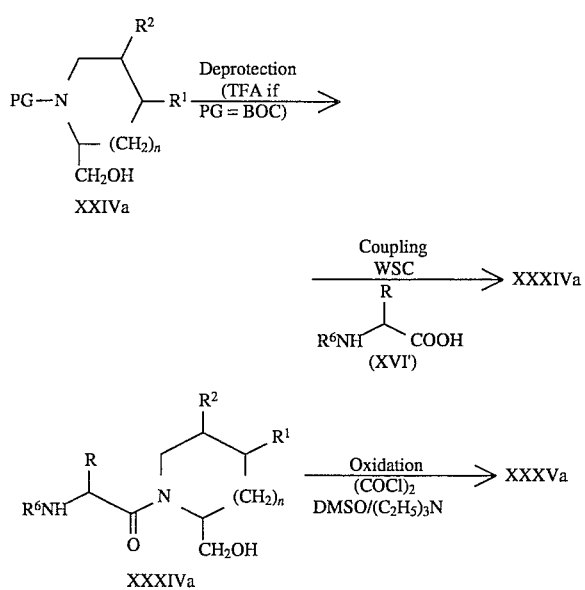

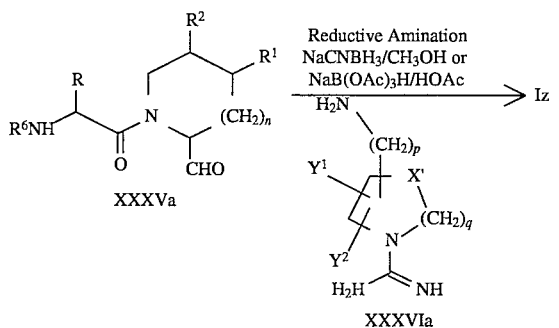

52
-continued
Reaction Sequence E1
(Preparation of Ia where $R_b$ is $-(CH_2)_p-A^2-R^{2'}$, where $R^6$ may or may not be H)

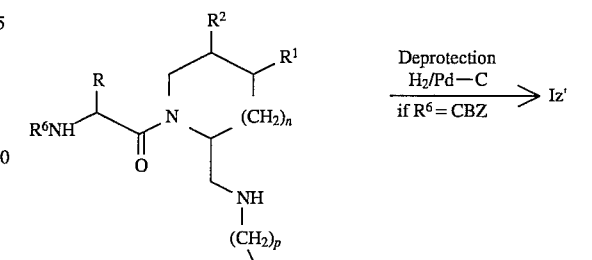

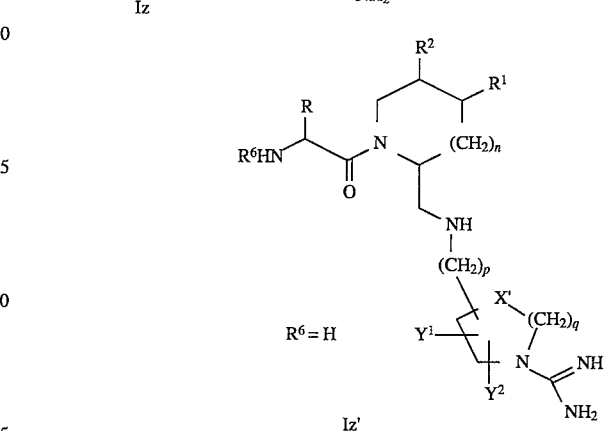

Sequence E2.
(Preparation of Ia where $R_b$ is $-(CH_2)_p-\overset{\overset{O}{\|}}{C}-A^2-R^{2'}$, where $R^6$ may or may not be H)

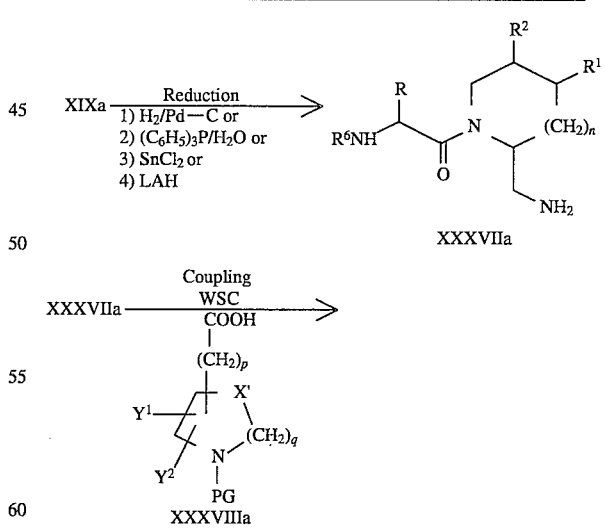

53
-continued
Sequence E2.

(Preparation of Ia where $R_b$ is $-(CH_2)_p-\overset{O}{\underset{\|}{C}}-A^2-R^{2'}$, where $R^6$ may or may not be H)

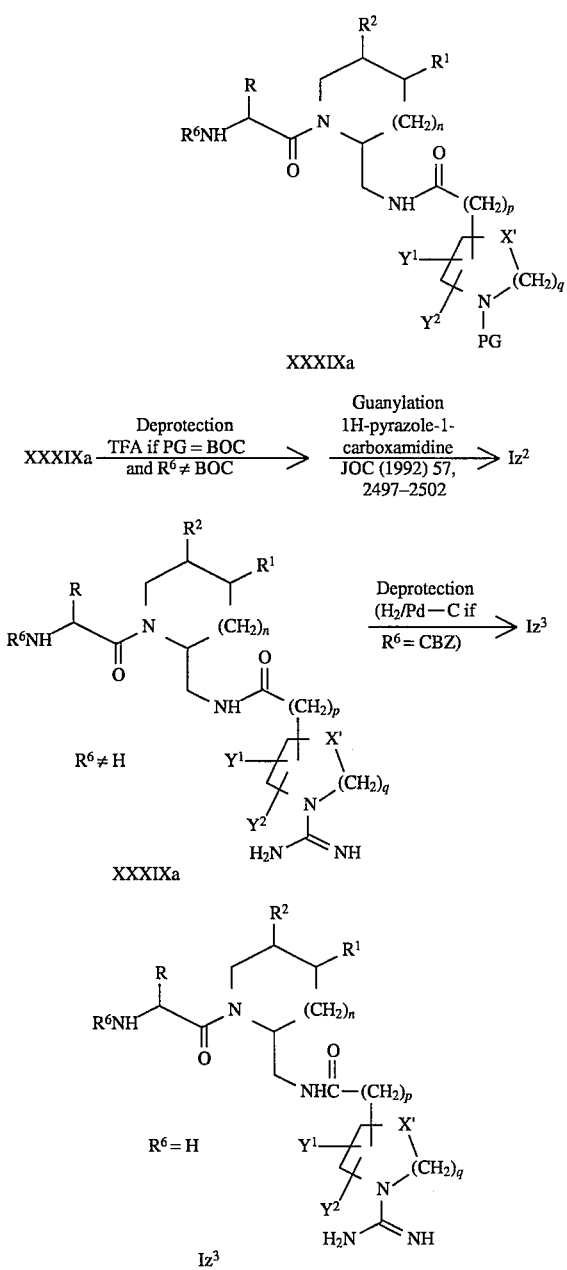

As seen in Reaction Sequence A, Part A, compounds of formula Ia of the invention wherein $R_b$ is

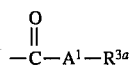

and $R^{3a}$ is guanidine are prepared as follows. Tosylate IIa (prepared as described by J. Das et al, J. Med. Chem., 1992, Vol. 35, 2610) (wherein P.G. represents a protecting group such as t-butyloxy carbonyl (BOC), carbobenzyloxy (CBZ), or fluorenyl-methyloxycarbonyl (FMOC) is made to undergo a displacement reaction with sodium azide in the presence of an inert organic solvent such as dimethylsul-

54 foxide (DMSO) or dimethylformamide (DMF), at a temperature within the range of from about 50 to about 90° C., to form azide IIIa which is reduced by reaction with a reducing agent such as $H_2/Pd$—C or triphenylphospine/$H_2O$, lithium aluminum hydride (LAH) or stannous chloride, to form the corresponding amine IVa.

The amine IVa is made to undergo a carbodiimide coupling reaction with protected amino acid IV' (where PG' is a protecting group such as any of the PG protecting groups set out above) in the presence of ethyl 3-(3-dimethylamino-)propyl carbodiimide hydrochloride (WSC) or dicyclohexylcarbodiimide (DCC), and 1-hydroxybenzotriazole monohydrate (HOBT), and N-methylmorpholine (NMM), in the presence of an inert organic solvent such as dimethylformamide (DMF), THF or N-methylpyrrolidone (NMP), to form the amide Va. Amide Va is deprotected by treatment with trifluoroacetic acid (TFA) (where PG is BOC) or with $H_2/Pd$—C (where PG is CBZ) with or without the presence of dry inert organic solvent such as dichloromethane, chloroform or THF, at temperatures within the range of from about $-15°$ to about 20° C., to form amide VIa. Amide VIa is then made to undergo a carbodiimide coupling reaction with protected amino acid VI' in the presence of WSC or DCC, HOBT and NMM, as described above with respect to amine IVa, to form compound VIIa. The protecting group PG of VIIa is removed by reacting VIIa with TFA where PG is BOC and PG' is other than BOC, to form partially deprotected compound VIIIa. Compound VIIIa is then subjected to a carbodiimide coupling reaction wherein VIIIa is treated with an acid $R^{7'}COOH$ in the presence of WSC or DCC, and HOBT, and NMM, in the presence of an inert organic solvent such as dimethylformamide (DMF), THF or N-methylpyrrolidone, to form compound IXa. Alternatively, VIIIa may be treated with $R^{7'}SO_2Cl$ and triethylamine or $R^{7'}OCOCl$ and triethylamine to form IXa.

Compound IXa is then treated with $H_2/Pd$—C or HBr/acetic acid (HOAc) (where PG' is CBZ) to form compound of the invention Ia'. Ia' is separated by conventional procedures and the desired isomers are guanylated with amidine sulfonic acid, or other guanylation agent such as 1H-pyrazole-1-carboxamidine in the presence of an alcohol solvent such as ethanol to form the compound of the invention Ib.

Referring to Reaction Sequence A, Part B1) compounds of formula Ia of the invention wherein $R^6$ is H and $R_b$ is —CO—A— guanidine may be prepared by deprotecting amide VIIa with TFA where PG' is BOC and PG is not BOC, guanylating the deprotected amide by treatment with amidinesulfonic acid (as described above with regard to Ia') and then removing the remaining protecting group PG by treatment with $H_2/Pd$—C where PG is CBZ, to form compound Ic of the invention.

In Reaction Sequence A, Part B2) compounds of formula Ia of the invention wherein $R^6$ is H and $R_b$ is —CO—A—$NH_2$ are prepared by deprotecting Ia' with TFA (where $R^6$ is BOC) or with $H_2/Pd$—C (where $R^6$ is CBZ) to form compound Id of the invention.

In Reaction Sequence A, Part C, compounds of formula Ia of the invention where Rb is —CO—$A^1$—$R^{3a}$ and $R^{3a}$ is amidine may be prepared by treating amine IVa with acid IV'' in the presence of WSC, HOBT and triethylamine, at a temperature within the range of from about $-30°$ to about 50° C., to form nitrile Xa which is made to undergo amidine formation by treating Xa with HCl in the presence of methanol and then reacting the resulting compound with ammonia in the presence of methanol to form amidine XIa. The protecting group, PG, is removed in this process if PG=BOC. Amidine XIa is then made to undergo a carbodiimide coupling reaction with protected amino acid VI" in the presence of WSC or DCC, and HOBT and NMM (as described above with respect to amide IVa) to form amidine XIIa which is deprotected with TFA (where PG' is BOC) to form compound Ie of the invention where $R^6$ is H.

Amidine Ie may be coupled with coupling agent $R^{7'}COOH$, $R^{7'}OCOCl$, or $R^{7'}SO_2Cl$ (as described above with respect to amide VIIIa) to form amidine compound If of the invention where $R^6$ is not H.

In Reaction Sequence B, Part A compounds of formula Ia of the invention where $R_b$ is —A'—$R^{3a}$ and $R^{3a}$ is amino or guanidine are prepared starting with amine IVa which is acylated by treating amine IVa with trifluoroacetic anhydride in the presence of an inert organic solvent such as dichloromethane, chloroform or ether and a weak organic base such as pyridine, triethylamine or NMM, to form trifluoroacetamide XIIIa which is alkylated by treating XIIIa with bromoalkylphthalimide XIII' in the presence of a base such as an alkali metal carbonate, and an inert organic solvent DMSO or DMF, to form protected phthalimide derivative XIVa. The phthalimide derivative XIVa is deprotected, for example, by treatment with TFA where PG is BOC, to form phthalimide derivative XVa which is coupled with amino acid derivative XV' in the presence of WSC or DCC, and HOBT and NMM as described hereinbefore in Reaction Sequence A with respect to amine IVa, to form phthalimide derivative XVIa. Phthalimide derivative XVIa is then deprotected by treatment with hydrazine or methyl hydrazine in the presence of an alcohol solvent such as ethanol, and then with base such as potassium carbonate or cesium carbonate, and methanol to form amine compound Ig of the invention. Ig may then be guanylated as described hereinbefore in Sequence A, Part A with respect to Ia', to form guanidine compound Ih of the invention.

Compounds of formula Ia of the invention wherein $R^6$ is H and $R_b$ is —$A^1$—$R^{3a}$ and $R^{3a}$ is guanidine or amine are prepared as outlined in Reaction Sequence B, Part B1) and 2), respectively, by deprotecting Ih (where $R^6$ is CBZ) or deprotecting Ig (where $R^6$ is CBZ), with $H_2$/Pd—C to form guanidine compound Ij and amino compound Ik of the invention.

In Reaction Sequence B, Part C, compounds of formula Ia where $R_b$ is —A'—$R^{3a}$ and $R^{3a}$ is amidine are prepared by alkylating compound XIIIa with nitrile xIII" in the presence of a base such as an alkali metal carbonate like cesium carbonate, to form nitrile XVIIa which is deprotected with TFA (where PG is BOC) and then subjected to a carbodiimide coupling reaction with amino acid XV' and WSC or DCC, and HOBT and NMM as described hereinbefore with respect to VIa in Sequence A, Part A, to form nitrile XVIIIa. Nitrile XVIIIa is then treated with HCl and ammonia in the presence of an alcohol solvent such as ethanol to form amidine compound Il of the invention. If in compound XVIIIa, $R^6$ is BOC, then in the final product Il, $R^6$ will be H.

Compounds of formula Ia of the invention wherein $R_b$ is —$SO_2$—$A^1$—$R^{3a}$ and $R^{3a}$ is guanidine are prepared as outlined in Reaction Sequence C, Part A starting with azide IIIa which is deprotected with TFA (where PG is BOC) and then subjected to a carbodiimide coupling reaction by treating the so-formed, deprotected compound with amino acid XV' in the presence of WSC or DCC, and HOBT and NMM (as described in Sequence A for VIa) to form azide XIXa. Azide XIXa is reduced by treating XIXa with $H_2$/Pd—C or other reducing agent as described in Sequence A with respect to the reduction of IIIa) to form the corresponding amine which is sulfonylated by treatment with the sulfonyl chloride XIX' in the presence of dichloromethane or other inert solvent such as chloroform or ether, and a weak organic base such as triethylamine or pyridine, at a temperature of within the range of from about −30° to about 50° C., to form bromosulfonamide XXa. Compound XXa is then reacted with sodium azide in the presence of an inert organic solvent such as DMF or DMSO to form azide XXIa which is deprotected and then guanylated (as described with respect to IXa in Sequence A, Part A) to form guanidine compound Im of the invention. Im may then be deprotected where $R^6$ is CBZ or BOC as shown to form compound In of the invention.

In Reaction Sequence C, Part B1) the preparation of compounds of formula I wherein $R_b$ is —$SO_2$—$A^1$—$NH_2$ and $R^6$ is H is shown starting with azide XXIa which is reduced to form from the amine Io where $R^6$ is H.

In Part B2), compounds of formula Ia wherein $R_b$ is —$SO_2$—$A^1$—$NH_2$ and $R^6$ is other than H is formed starting with azide XXIa which is deprotected and then coupled with $R^{7'}COOH$, $R^{7'}SO_2Cl$ or $R^{7'}OCOCl$ (as described above in Sequence A with respect to VIIIa) to form amine Ip.

Compounds of formula Ia of the invention wherein $R_b$ is —$SO_2$-$A^1$-amidine are prepared as shown in Reaction Sequence C Part C by subjecting compound XXa to a displacement reaction by reacting XXa with cyanide to form nitrile XXIIa which is then amidinated by treatment with HCl and $NH_3$ in the presence of ethanol (as described hereinbefore in Sequence A, Part C with respect to IVa) to form amidine Iq of the invention wherein if $R^6$ in XXIIIa is BOC, then $R^6$ in Iq is H.

Preparation of compounds of formula Ia of the invention wherein $R_b$ is —$A^3$—$R^4$ and $A^4$ is amidine is outlined in Reaction Sequence D, Part A starting with alcohol XXIVa which is oxidized by treatment with, for example, oxalyl chloride or other oxidizing agent such as pyridine.$SO_3$ or pyridinum dichromate, in the presence of an inert organic solvent such as DMSO, ether or methylene chloride, and a weak organic base such as triethylamine to form aldehyde XXVa which is made to undergo reductive amination by treating XXVa with NaCNBH$_3$ in the presence of methanol, or NaB(OAc)$_3$H in the presence of acetic acid and dichloroethylene, and nitrile XXV' to form nitrile XXVIa. Nitrile XXVIa is reacted with HCl and then ammonia in the presence of ethanol to form amidine XXVIIa wherein the protecting group PG is removed if PG=BOC. So-formed amidine XXVIIa is made to undergo a carbodiimide coupling reaction by treating XXVIIa with amino acid coupling agent VI" in the presence of WSC or DCC, and HOBT (as described hereinbefore in Sequence A, Part A with respect to VIa) to form amidine XXVIIIa which is deprotected to form amidine compound Ir of the invention where $R^6$ is H.

Amidine Ir may be subjected to a coupling reaction with $R^{7'}COOH$, $R^{7'}SO_2Cl$ or $R^{7'}OCOCl$ (as described hereinbefore in Sequence A, Part A with respect to VIIIa) to form amidine compound Is of the invention wherein $R^6$ is other than H.

Compounds of formula Ia of the invention wherein $R_b$ is —$A^3$—$CH_2NH_2$ are prepared as shown in Reaction Sequence D, Part B wherein aldehyde XXVa is subjected to a reductive amination employing protected amine XXV" and the procedure as described in Sequence D, Part A with respect to aldehyde XXVa to form protected amine XXIXa which is deprotected and coupled with coupling agent VI" (as described in Sequence A, Part A with respect to VIa) to form protected amine XXXa which is deprotected to form compound XXXIa. Compound XXXIa may then be deprotected to form amine compound It of the invention where $R^6$ is H or XXXIa may be made to undergo a coupling reaction (as described in Sequence A, Part A with respect to VIIIa) to form amine compound Iu of the invention.

In Reaction Sequence D, Part C compounds of formula I wherein $R_b$ is —$A^3$—$R^4$ and $R^4$ is guanidine are prepared starting with XXVa which is deprotected and subjected to a carbodiimide coupling with amino acid XV' (as described hereinbefore in Sequence B, Part C) to form aldehyde XXXIIa. Aldehyde XXXIIa is then made to undergo reductive amination with amine XXXII' (using procedures as described in Sequence D, Part A with respect to XXIa) to form compound XXXIIIa which is deprotected and guanylated (as described in Sequence A, Part A with respect to Ia') to form guanidine compound Iw of the invention. Where $R^6$ in Iw is CBZ, Iw may be reduced with $H_2$/Pd—C to form guanidine compound Iy of the invention.

As seen in Reaction Sequence E1, compounds of formula Iz and Iz' may be prepared by deprotecting previously described alcohol XXIVa and coupling the free amine with a protected amino acid to give compound XXXIVa. The alcohol XXXIVa is oxidized to aldehyde xXXVa as described previously in the preparation of compound XXVa. The aldehyde is coupled with a compound of formula XXXVIa using the reductive amination methodology described in the preparation of compound XXIXa to give compound Iz. In the case where $R^6$ =H, Iz can be deprotected (Pd—C/$H_2$ if $R^6$=CBZ) to provide compound Iz'. Compounds of formula $Iz^2$ and $Iz^3$ can be prepared by reduction of azide XIXa as described in Reaction Sequence C Part A to give the amine XXXVIIa. This amine is coupled to an acid of formula XXXVIIIa using standard carbodiimide coupling methodology described in the preparation of Va to give a compound of formula XXXIXa. Compound XXXIXa is deprotected (TFA if PG=BOC) and guanylated with a reagent such as 1H-pyrazole-1-carboxamidine to provide a compound of formula $Iz^2$. In the case where $R^6$=CBZ, the compounds of formula $Iz^2$ can be deprotected to give a compound of formula $Iz^3$ where $R^6$=H.

DESCRIPTION OF THE FOURTH EMBODIMENT OF THE INVENTION

In a fourth aspect or embodiment, the present invention relates to heterocyclic thrombin inhibitors of the invention have the structure A.

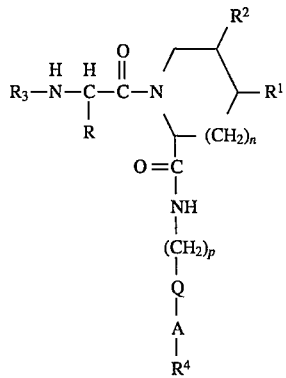

including all stereoisomers thereof, and including all pharmaceutically acceptable salts thereof;

wherein n is 0, 1 or 2;

p is 0, 1 or 2;

Q is a single bond or

A is aryl or cycloalkyl, or an azacycloalkyl ring $\underline{A}$ of 4 to 8 members in the ring or an azaheteroalkyl ring $\underline{A}$ of 4 to 8 members in the ring, as given by the structure

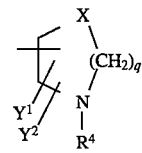

X is $CH_2$, O, S or NH;

q=0, 1, 2, 3 or 4 if X=$CH_2$;

q=2, 3 or 4 if X=O, S, NH; and $Y^1$ and $Y^2$ are independently H, alkyl or halo;

$R^4$ is guanidine, amidine or aminomethyl;

R, $R^1$ and $R^2$ are as defined hereinbefore; and $R_3$ is hydrogen,

or —$CO_2R^{7'}$ (wherein $R^{7'}$ is lower alkyl, aryl, arylalkyl or cycloheteroalkyl);

with the provisos that where A is aryl or cycloalkyl, $R^4$ is guanidine, amidine or aminomethyl;

where A is azacycloalkyl or azaheteroalkyl, $R^4$ is amidine;

where X is a hetero atom (that is A is azaheteroalkyl), then there must be at least a 2-carbon chain between X and any N atom in the ring $\underline{A}$ or outside the ring $\underline{A}$.

Examples of the $\underline{A}$ ring (azacycloalkyl or azaheteroalkyl) which may be employed herein include

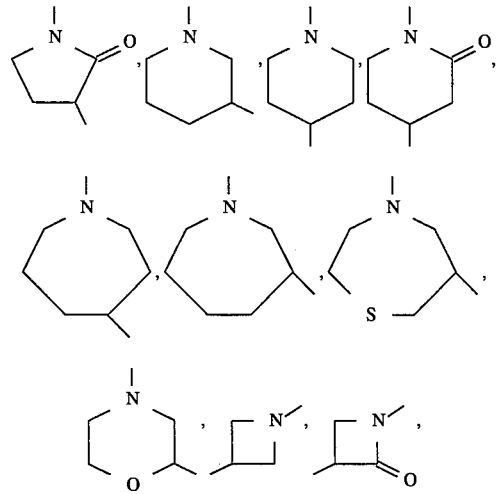

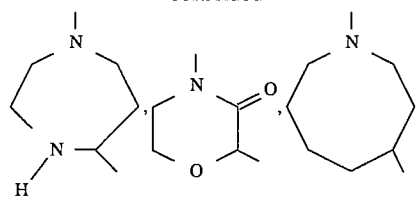

and the like. Preferred are compounds of formula I wherein
n is 0 or 1,
R₃ is H; R is aralkyl or hydroxyalkyl,
R¹ and R² are each H, p is 0 or 1,
Q is a single bond, A is an azacycloalkyl ring

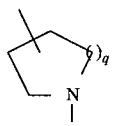

where q is 1 or 2; R⁴ is amidine.

Most preferred are compounds of formula I wherein R₃ is H, n is 0, R¹ and R² are each H,
R is aralkyl such as benzyl,
p is 1, Q is a single bond, AR⁴ is

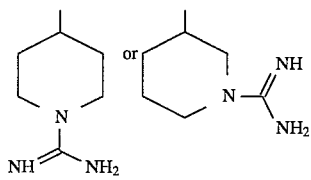

The compounds of formula A of the invention (fourth embodiment) may be prepared according to the following reaction sequences.

The compounds of formula A of the invention wherein A is azacycloalkyl or azaheteroalkyl and R⁵ is amidine may be prepared according to the following Reaction Sequence a.

The compounds of formula B or C are known in the art or may be prepared by those skilled in the art employing conventional preparatory techniques.

Reaction Sequence a.

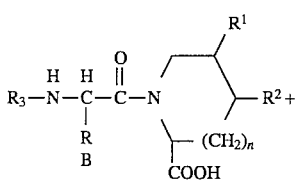

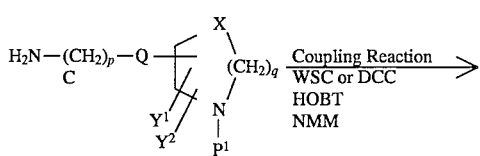

(where P¹ is a protecting group such as BOC or CBz)

-continued
Reaction Sequence a.

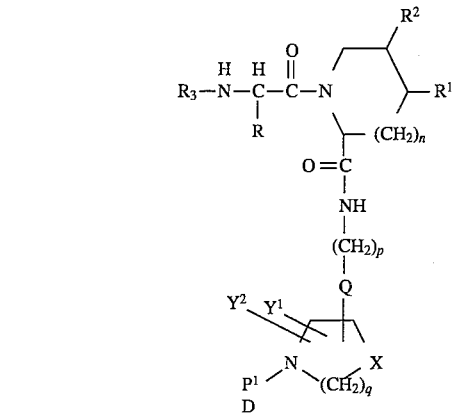

Deprotection of P¹
(Hydrogenation with H₂/Pd—C if P¹ is CBz)

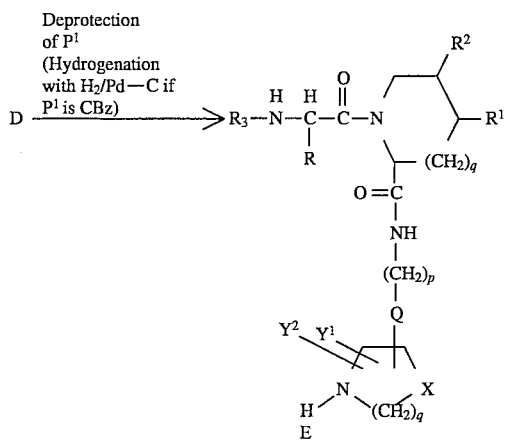

Amidinesulfonic Acid

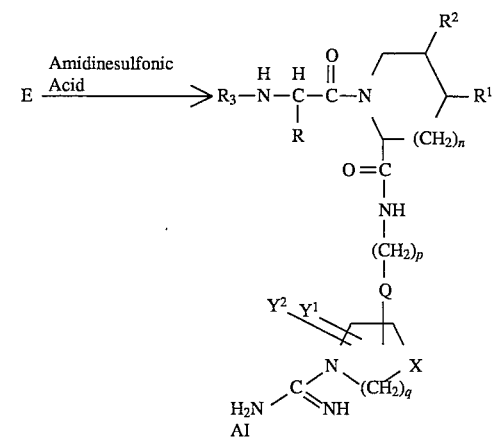

-continued
Reaction Sequence a.

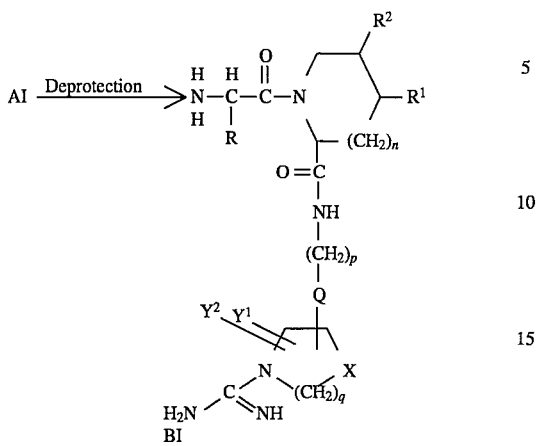

As seen in the above Reaction Sequence a., compounds of formula I wherein A is azacycloalkyl or azaheteroalkyl, are prepared as follows. The protected acid B is made to undergo a carbodiimide coupling reaction with amine C in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide D. Amide D is deprotected by treatment with, for example, $H_2$/Pd—C if $p^1$ is CBz, to form amine E. Amine E is treated with amidinesulfonic acid in the presence of alcohol solvent, such as ethanol to give cyclic guanidine AI. Guanidine AI is deprotected by treatment with trifluoroacetic acid (if $R^3$=BOC) with or without the presence of dry inert organic solvent such as dichloromethane, chloroform or THF at temperatures within the range of from about −15° to about 20° C. to form amidine compound of the invention BI.

The compounds of the invention where A is aryl or cycloalkyl and $R^4$ is amidine or guanidine may be prepared according to the following Reaction Sequence b.:

Reaction Sequence b.

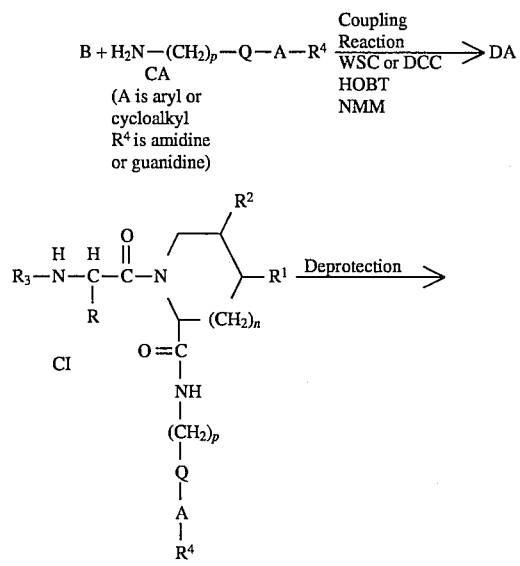

-continued
Reaction Sequence b.

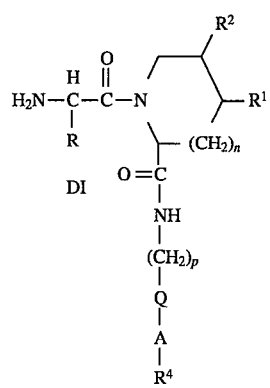

As seen in Reaction Sequence b., compounds of formula A. where A is aryl or cycloalkyl and $R^4$ is amidine or guanidine are prepared as follows. The protected acid B is subjected to a carbodiimide coupling reaction wherein B is treated with protected amine CA in the presence of WSC or DCC, and HOBT, and NMM, in the presence of an inert organic solvent such as dimethylformamide, THF or N-methylpyrrolidone, to form amide CI. The amide CI is then dissolved in an alcohol solvent such as ethanol or methanol, to which HCl has been added and the mixture is hydrogenated over Pd—C or Pd(OH)$_2$—C in the case where $R_3$ is carbobenzyloxy, to form compound DI of the invention.

The compounds of formula A. of the invention wherein A is aryl or cycloalkyl and $R^4$ is aminomethyl may be prepared according to the following Reaction Sequence c.:

Reaction Sequence c.

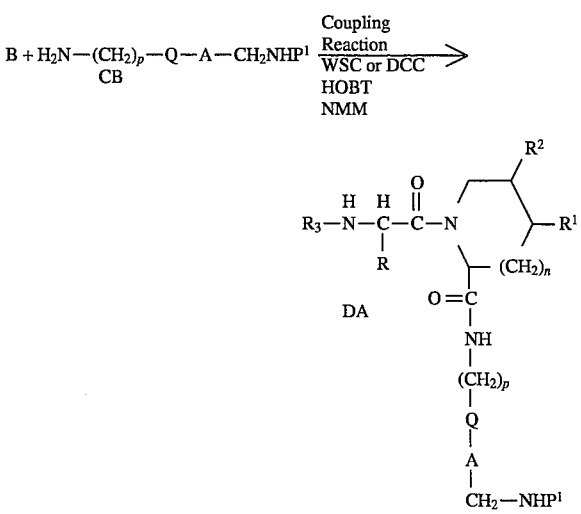

-continued
Reaction Sequence c.

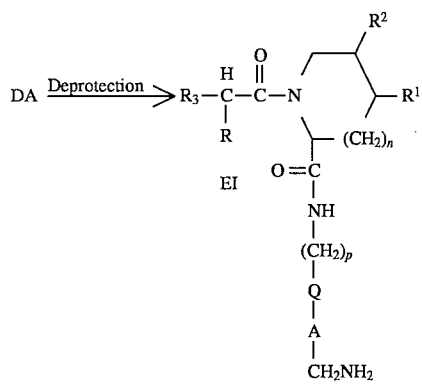

As seen in the above Reaction Sequence c. compounds of formula A wherein A is aryl or cycloalkyl and $R^4$ is aminomethyl are prepared as follows. The protected acid $\underline{B}$ is made to undergo a carbodiimide coupling reaction with protected amino acid $\underline{CB}$ in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide $\underline{DA}$. Amide $\underline{DA}$ is deprotected by treatment with trifluoroacetic acid (TFA) when $p^1$ is t-butoxycarbonyl (BOC) or $H_2$—Pd/C when $p^1$ is carbobenzyloxy (CBz), with or without the presence of dry inert organic solvent such as dichloromethane, chloroform or THF, at temperatures within the range of from about $-15°$ to about $20°$ C. to form amide EI of the invention.

The starting acid $\underline{B}$ may be prepared according to the following reaction sequence:

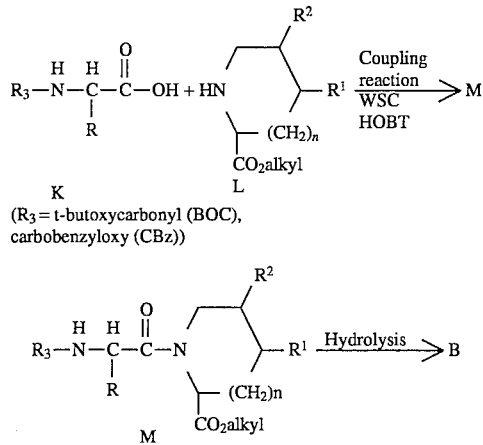

As seen in the above reaction sequence, compounds of formula $\underline{B}$ are prepared as follows. The ester $\underline{L}$ is made to undergo a carbodiimide coupling reaction with protected amino acid $\underline{K}$ in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide $\underline{M}$. Amide $\underline{M}$ is hydrolyzed by treatment with base such as NaOH, KOH or LiOH to form an alkali metal salt which is neutralized with strong acid such as HCl or oxalic acid to form $\underline{B}$.

DESCRIPTION OF THE FIFTH EMBODIMENT OF THE INVENTION

In a fifth aspect or embodiment, the present invention relates to alkylsulfonamido heterocyclic thrombin inhibitors invention having the structure (i)

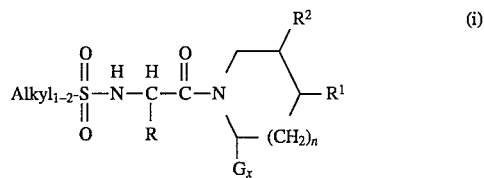

wherein $G_x$ is an amido moiety which is

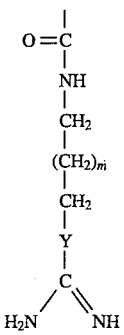

including all stereoisomers thereof; and including all pharmaceutically acceptable salts thereof;

wherein $Alkyl_{1-2}$ is methyl or ethyl and

R, $R^1$, $R^2$, n, m and Y are as defined hereinbefore with respect to the formula I compound (first embodiment of the invention).

Preferred are compounds of formula (i) wherein n is 0 or 1; m is 2; $Alkyl_{1-2}$ is methyl; R is arylalkyl; $R^1$ and $R^2$ are independently hydrogen or lower alkyl such as methyl or ethyl; and Y is —NH—.

The compounds of formula (i) of the invention wherein Y is NH may be prepared according to the following Reaction Sequence (i).

Reaction Sequence (i)
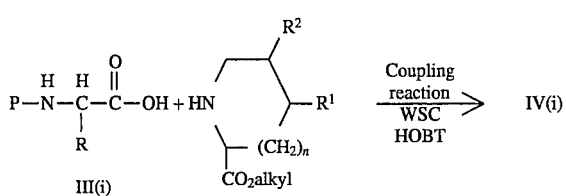
(P = t-butoxycarbonyl (BOC), carbobenzyloxy (CBz))
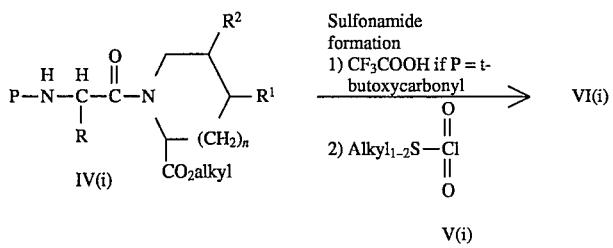
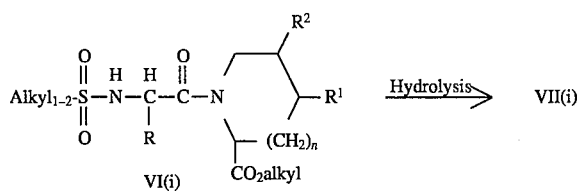
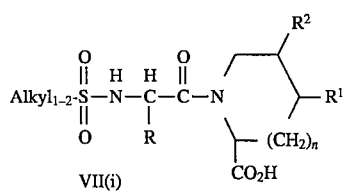
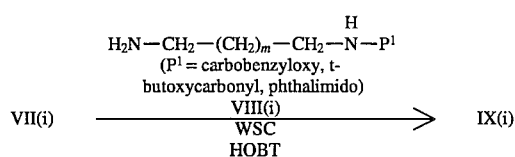
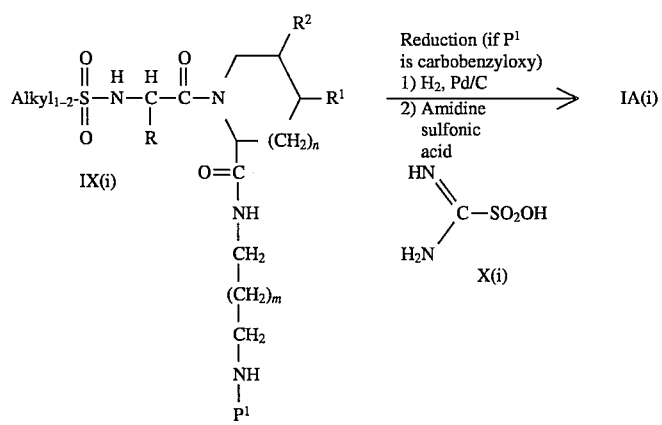

-continued
Reaction Sequence (i)
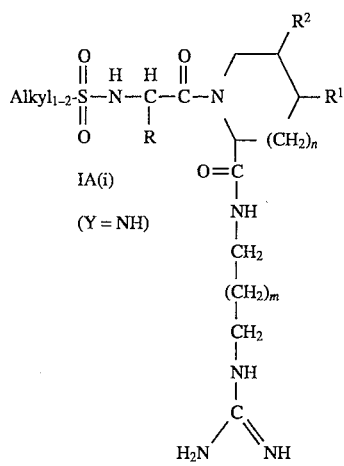
IA(i)
(Y = NH)
The compounds of formula I of the invention wherein Y is NH may also be prepared according to the following Reaction Sequence (ii)
Reaction Sequence (ii)
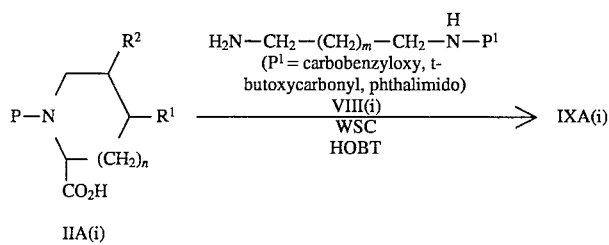
IIA(i)
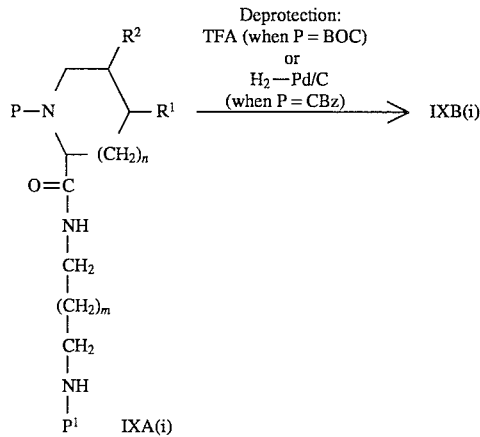

-continued
Reaction Sequence (ii)

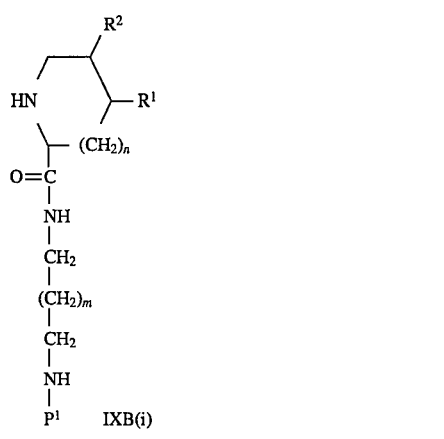

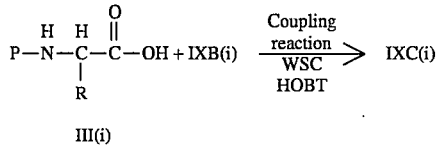

(P = BOC or CBz)

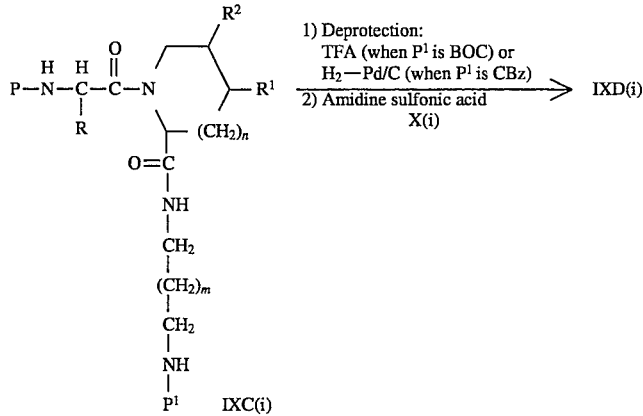

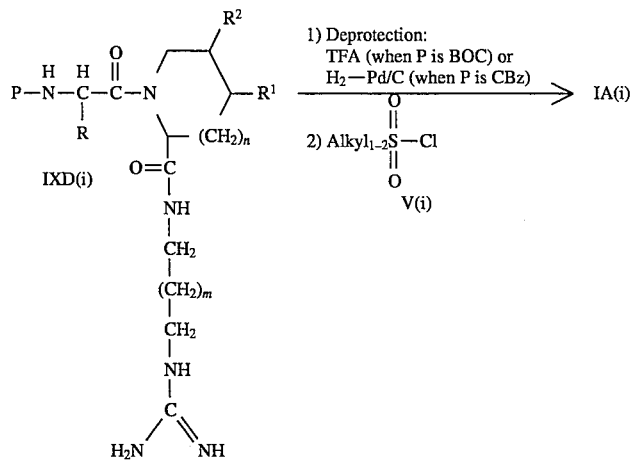

As seen in the above Reaction Sequence (i), compounds of formula I(i) wherein Y is —NH—, are prepared as follows. The ester II(i) is made to undergo a carbodiimide coupling reaction with protected amino acid III(i) in the presence of ethyl 3-(3-dimethyl-amino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide IV(i). Amide IV(i) is deprotected by treatment with trifluoroacetic acid with or without the presence of dry inert organic solvent such as dichloromethane, chloroform or THF at temperatures within the range of from about −15° to about 20° C. Sulfonyl chloride v(i) is added followed by organic base such as triethylamine, pyridine or N,N-diisopropylethylamine to form the sulfonamide VI(i). Sulfonamide VI(i) is hydrolyzed by treatment with alkali metal base such as NaOH or LiOH in the presence of an alcohol solvent such as methanol or ethanol. The reaction mixture is acidified with HCl, KHSO$_4$ or H$_2$SO$_4$, to form acid VII(i). The acid VII(i) is then subjected to a carbodiimide coupling reaction wherein VII(i) is treated with protected amine VIII(i) in the presence of WSC or DCC, and HOBT, and NMM, in the presence of an inert organic solvent such as dimethylformamide, THF or N-methylpyrrolidone, to form sulfonamide IX(i). The sulfonamide IX(i) is then dissolved in an alcohol solvent such as ethanol or methanol, to which HCl has been added and the mixture is hydrogenated over Pd—C or Pd(OH)$_2$—C in the case where p$^1$ is carbobenzyloxy. The product is then treated with amidine sulfonic acid X(i) in the presence of an alcohol solvent such as ethanol to form the compound of the invention IA(i).

As seen in the above Reaction Sequence (ii), compounds of formula I(i) wherein Y is —NH—, are also prepared as follows. The protected acid IIA(i) is made to undergo a carbodiimide coupling reaction with protected diamine VIII(i) in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide IXA(i). Amide IXA(i) is deprotected by treatment with trifluoroacetic acid (TFA) when P is t-butoxycarbonyl (BOC) or H$_2$—Pd/C when P is carbobenzyloxy (CBz), with or without the presence of dry inert organic solvent such as dichloromethane, chloroform or THF, at temperatures within the range of from about −15° to about 20° C. to form amide IXB(i). The amide IXB(i) is then subjected to a carbodiimide coupling reaction wherein IXB(i) is treated with protected amine III(i) in the presence of WSC or DCC, and HOBT, and NMM, in the presence of an inert organic solvent such as dimethylformamide, THF or N-methylpyrrolidone, to form amide IXC(i). The amide IXC(i) is then dissolved in an alcohol solvent such as ethanol or methanol, to which HCl has been added and the mixture is hydrogenated over Pd—C or Pd(OH)$_2$—C in the case where p$^1$ is CBz or treated with trifluoroacetic acid when p$^1$ is BOC. The product is then treated with amidine sulfonic acid X(i) in the presence of an alcohol solvent such as ethanol to form IXD(i). Compound IXD(i) is deprotected by treatment with TFA when P is BOC or by treatment with H$_2$—Pd/C when P is CBz, as described above, and sulfonyl chloride V(i) is added followed by organic base such as triethyl-amine, pyridine or N,N-diisopropylethylamine to form the sulfonamide IA(i).

The compounds of formula I of the invention wherein Y is S may be prepared according to the following Reaction Sequence (iii).

Reaction Sequence (iii)

VII(i) + H$_2$NCH$_2$(CH$_2$)$_m$CH$_2$OH

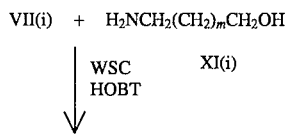

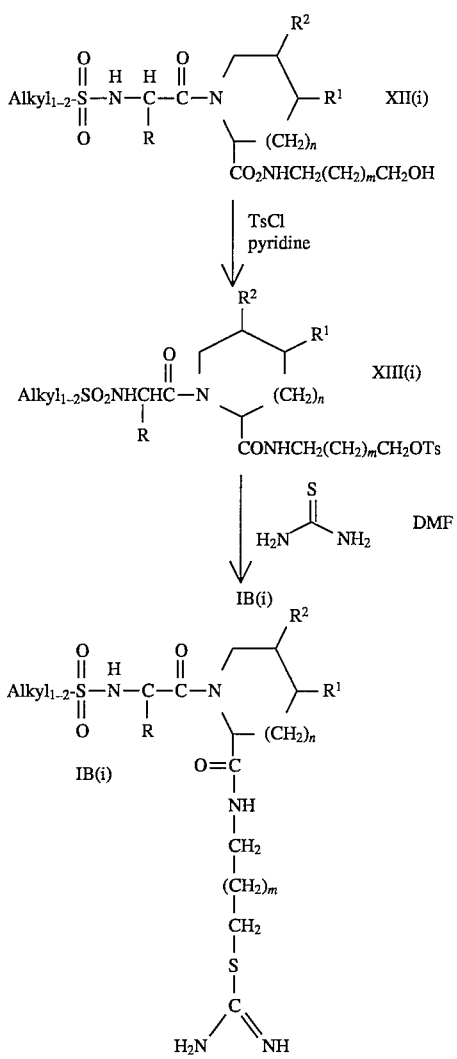

Referring to the above Reaction Sequence (iii), compounds of formula I(i) wherein Y=S can be prepared as follows. The acid VII(i) is subjected to a carbodiimide coupling reaction wherein VII(i) is treated with an aminoalcohol XI(i) in the presence of WSC or DCC, HOBT, and NMM, in the presence of an inert organic solvent such as dimethylformamide, THF or N-methylpyrroli-done, to form sulfonamide alcohol XII(i). The sulfonamide alcohol XII(i) is reacted with p-toluene-sulfonyl chloride (TsCl) in pyridine, or in a solvent such as methylene chloride or chloroform, with N,N-dimethylaminopyridine to provide toluene-sulfonate XIII(i). The compound IB(i) (Y=S) is prepared by treating XIII(i) with thiourea in a solvent such as DMF or DMSO at temperatures within the range of from about 25° C. to about 100° C.

In General

The term "lower alkyl" or "alkyl" as employed herein by itself or as part of another group includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents (for example, to form CF$_3$ or CF$_3$CH$_2$) and/or 1 or 2 of the following substituents: an aryl substituent (for example, to form benzyl or phenethyl), an alkyl-aryl substituent, a haloaryl substituent, a cycloalkyl substituent, an alkylcycloalkyl substituent, an alkenyl substituent, an alkynyl substituent, hydroxy or a carboxy substituent. It will be appreciated that the same "alkyl" group may be substituted with one or more of any of the above substituents.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy, and/or hydroxy groups.

The term "aryl" or "Ar" as employed herein by itself or as part of another group refers to monocyclic or bicyclic aromatic groups containing from 6 to 10 carbons in the ring portion, such as phenyl, or naphthyl. Aryl (or Ar), phenyl or naphthyl may include substituted aryl, substituted phenyl or substituted naphthyl, which may include 1 or 2 substituents on either the Ar, phenyl or naphthyl such as lower alkyl, cyano, amino, alkylamino, dialkylamino, nitro, carboxy, carboalkoxy, trifluoromethyl, halogen (Cl, Br, I or F), lower alkoxy, arylalkoxy, hydroxy, alkylthio, alkylsulfinyl, alkylsulfonyl, arylthio, arylsulfinyl and/or arylsulfonyl.

In a separate embodiment of the invention, where R$^3$ in formula I is phenyl, the phenyl group may include 3, 4 or 5 substituents such as alkyl, for example, pentamethyl and 2,4,6-tri-isopropyl, and halo, for example, pentafluoro.

The term "aralkyl", "aryl-alkyl" or "aryllower alkyl" as used herein by itself or as part of another group refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein by itself or as part of another group refers to chlorine, bromine, fluorine or iodine with chlorine being preferred.

The term "lower alkenyl" or "alkenyl" as employed herein by itself or as part of another group includes a carbon chain of up to 16 carbons, preferably 3 to 10 carbons, containing one double bond which will be separated from "N" by at least one saturated carbon moiety such as —(CH$_2$)$_q$— where q can be 1 to 14, such as 2-propenyl, 2-butenyl, 3-butenyl, 2-pentenyl, 4-pentenyl and the like, and may include a halogen substituent such as I, Cl, or F.

The term "lower alkynyl" or "alkynyl" as employed herein by itself or as part of another group includes a carbon chain of up to 16 carbons, preferably 3 to 10 carbons, containing one triple bond which will be separated from "N" by at least one saturated carbon moiety such as —(CH$_2$)$_{q'}$— where q' can be 1 to 14, such as 2-propynyl, 2-butynyl, 3-butynyl and the like.

The term "heteroaryl" or heteroaromatic by itself or as part of another group refers to a 5- to 10-membered aromatic ring(s) which includes 1, 2, 3 or 4 hetero atoms such as nitrogen, oxygen or sulfur, such as

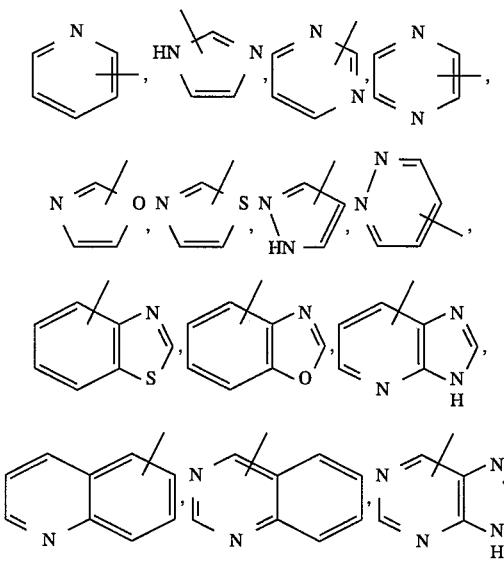

and the like. The heteroaryl rings may optionally be fused to aryl rings defined previously. The heteroaryl rings may optionally include 1 or 2 substituents such as halogen (Cl, Br, F or CF$_3$), lower alkyl, lower alkoxy, carboxy, amino, lower alkylamino and/or dilower alkylamino.

The term "cycloheteroalkyl" as used herein refers to a 5-, 6- or 7-membered saturated ring which includes 1 or 2 hetero atoms such as nitrogen, oxygen and/or sulfur, such as

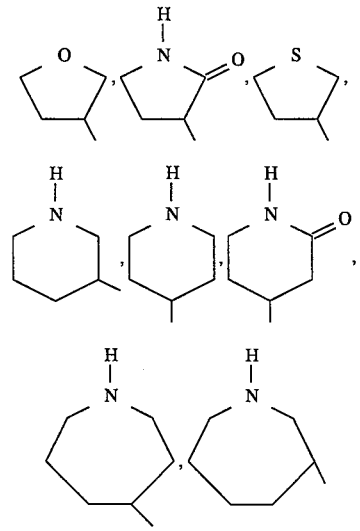

and the like.

The term "azaheteroalkenyl" as used herein refers to a 4- to 8-membered ring which includes 1 or 2 hetero atoms such as nitrogen, oxygen and/or sulfur, such as

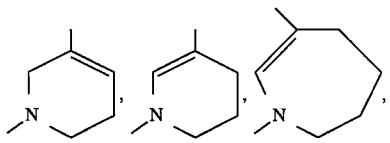

-continued

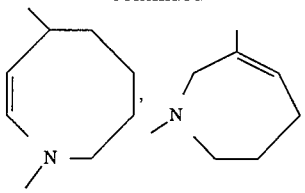

The term "amino acid side chain" refers to any of the known alpha-amino acids such as arginine, histidine, alanine, glycine, lysine, glutamine, leucine, valine, serine, homoserine, allothreonine, naphthylalanine, isoleucine, phenylalanine and the like.

The compounds of formulae I, 1., Ia, A and (i) of the invention can be obtained as pharmaceutically acceptable acid addition salts by reacting a free base with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like.

The compounds of the present invention are serine protease inhibitors, and in particular may inhibit thrombin, Factor Xa, and/or trypsin. The compounds of the present invention are useful for the treatment or prophylaxis of those processes which involve the production and/or action of thrombin. This includes a number of thrombotic and prothrombotic states in which the coagulation cascade is activated which include, but are not limited to, deep vein thrombosis (DVT), disseminated intravascular coagulopathy (DIC), Kasabach-Merritt syndrome, pulmonary embolism, myocardial infarction, stroke, thromboembolic complications of surgery (such as hip replacement and endarterectomy) and peripheral arterial occlusion. In addition to its effects on the coagulation process, thrombin has been shown to activate a large number of cells (such as neutrophils, fibroblasts, endothelial cells, smooth muscle cells). Therefore, the compounds of the present invention may also be useful for the treatment or prophylaxis of adult respiratory distress syndrome, septic shock, septicemia, inflammatory responses which include, but are not limited to, edema, acute or chronic atherosclerosis, and reperfusion damage.

The compounds of the invention may also be useful in treating neoplasia/metastasis (in particular those which utilize fibrin) and neurodegenerative diseases such as Alzheimer's disease and Parkinson's disease. In addition, the compounds of the present invention may be useful to prevent restenosis following arterial injury induced by endogenous (rupture of an atherosclerotic plaque) or exogenous (invasive cardiological procedure) events.

The compounds of the present invention may also be used as an anticoagulant in extracorpeal blood circuits, such as those necessary in dialysis and surgery (such as coronary artery bypass surgery).

The compounds of the present invention may also be used in combination with thrombolytic agents, such as tissue plasminogen activator (natural or recombinant), streptokinase, urokinase, prourokinase, anisolated streptokinase plasminogen activator complex (ASPAC), animal salivary gland plasminogen activators, and the like. The compounds of the present invention may act in a synergistic fashion to prevent reocclusion following a successful thrombolytic therapy and/or reduce the time to reperfusion. The compounds of the present invention may also allow for reduced doses of the thrombolytic agent to be used and therefore minimize potential hemorrhagic side-effects.

The compounds of the present invention may also be used in combination with other antithrombotic or anticoagulant drugs such as thromboxane receptor antagonists, prostacyclin mimetics, phosphodiesterase inhibitors, fibrinogen antagonists, and the like.

Compounds of the present invention that inhibit trypsin may also be useful for the treatment of pancreatitis.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I, 1., Ia or A. They may be compounded in conventional matter with a physiologically acceptable vehicle or carrier, excipient, binder, preservative, stabilizer, flavor, etc., as called for by accepted pharmaceutical practice.

The following Examples represent preferred embodiments of the first embodiment of the present invention. Unless otherwise indicated, all temperatures are expressed in degrees Centigrade.

EXAMPLE 1

[1(S), 2α, 4β]-N-[4-[(Aminoiminomethyl)amino]butyl]-1-[3-hydroxy-2-[(2-naphthalenylsulfonyl)amino]-1-oxo-propyl]-4-methyl-2-piperidinecarboxamide, trifluoroacetate (1:1) salt A. (2R-trans)-1-[(Phenylmethoxy)carbonyl]-4-methyl-2-piperidinecarboxylic acid, ethyl ester A(1). 4-Methyl-2-piperidinecarbonitrile To 500 g of sodium hypochlorite solution (5% in Cl, Aldrich) cooled in an ice bath was added dropwise 33.6 g (340 mmol, Aldrich) of 4-methylpiperidine, over 40 minutes. The reaction mixture was stirred for 20 minutes then poured into a separatory funnel and extracted with two-400 mL portions of ether. The extracts were combined, dried (sodium sulfate) and concentrated in vacuo to give ~44 g of N-chloro intermediate as a yellow liquid.

To a solution of 19.1 g (340 mmol) of potassium hydroxide in 140 mL of 95% ethanol heated to 80° was added dropwise over 40 minutes the solution of crude N-chloropiperidine from above in 20 mL of 95% ethanol. The addition was mildly exothermic and a precipitate formed. The reaction mixture was stirred for 10 minutes, cooled to room temperature, concentrated in vacuo, and to the residue was added 85 mL of 2N aqueous NaOH solution. The resulting mixture was extracted with three 75 mL portions of ether. The ether extracts were combined, dried (sodium sulfate) and concentrated in vacuo to give the crude imine as a viscous yellow oil.

To a solution of 110 g (1.7 mol, Mallinckrodt) of potassium cyanide in 400 mL of water cooled in an ice-bath was added over ~1 h 183 mL (2.20 mol) of concentrated HCl, followed by the crude imine from above. The reaction mixture was stirred between 10°–20° C. for 4 h then cooled in an ice-bath and basified to pH 12 by addition of ~80 g of potassium hydroxide pellets. the resulting solution was poured into a separatory funnel and extracted with three-300 mL portions of ether. The ether layers were combined, dried (sodium sulfate) and concentrated in vacuo to give a yellow oil. The crude material was purified by simple distillation at reduced pressure to afford 13.2 g (106 mmol, 31%) of title nitrile as a clear liquid, bp 72°–74° (3 mm).

A(2). 4-Methyl-2-piperidinecarboxylic acid, ethyl ester

To 250 mL of 6N aqueous HCl solution was added 13.0 g (105 mmol) of Part A(1) nitrile at room temperature. The reaction mixture was heated to reflux (bath temp 145°) for 6 h then cooled to room temperature and concentrated in vacuo to give the crude acid hydrochloride as a solid.

To 250 mL of absolute ethanol cooled in an ice-bath was added dropwise 40 mL (550 mmol) of thionyl chloride over 30 minutes. The solution was stirred for an additional 15 minutes then added to the crude acid hydrochloride from above. The resulting slurry was heated to reflux for 4 h then cooled to room temperature and filtered to remove solids. The filtrate was concentrated in vacuo to give the crude ester amine hydrochloride as brown oil. The oil was partitioned between 150 mL of saturated aqueous potassium carbonate solution and 150 mL of chloroform. The aqueous layer was separated and extracted with two-100 mL portions of chloroform. The organic extracts were combined, dried (sodium sulfate) and concentrated to give crude title ester as a brown oil. The crude material was purified by distillation through a 10 cm packed column (glass helices, 3 mm) at reduced pressure to afford 11.0 g (64.3 mmol, 61%) of title amine as a colorless liquid, bp 37°–38° (0.4 mm). The trans/cis ratio was determined as ~6:1 by 270 MHz $^1$H NMR.

A(3). (2R-trans)-1-[(Phenylmethoxy)carbonyl]-4-methyl-2-piperidinecarboxylic acid, ethyl ester To a solution of 10.0 g (58.5 mmol) of Part A(2) amine in 100 mL of methylene chloride cooled to 0° was added 9.8 mL (70 mmol, distilled from calcium hydride) of triethylamine in one portion then dropwise 11.9 g (70 mmol, Aldrich) of benzyl chloroformate over 20 minutes. The reaction mixture was stirred for 30 minutes then washed with 100 mL of 1N aqueous HCl, 100 mL of saturated aqueous sodium bicarbonate solution, 50 mL of brine, dried (magnesium sulfate) and then concentrated in vacuo to give an oil. The crude oil was purified by flash chromatography (Merck silica, 30×10 cm, 600 g, 1:9 EtOAc/hexane) to afford 12.7 g (41.6 mmol, 71%) of title compound (trans isomer) as a colorless oil. In addition 2.95 g (9.67 mmol, 17%) of a ~1:1 mixture of trans/cis isomers was obtained as a colorless oil.

B. (2R-trans)-4-Methylpiperidinecarboxylic acid, ethyl ester

Part A racemic CBZ ester (2.36 g, 7.73 mmol) was dissolved in absolute ethanol (50 mL) and hydrogenated over Pd—C (10%, 250 mg) at RT and 1 atm. After 6 hrs additional catalyst (50 mg) was added, the reaction continued for 2 hours, filtered, and evaporated in vacuo to provide the title free amine (1.22 g, 7.13 mmol, 92%).

C. (2R-trans)-1-[N-[(1,1-Dimethylethoxy)carbonyl]-O-(phenylmethyl)-L-seryl]-4-methyl-2-piperidinecarboxylic acid, ethyl ester Part B pipecolic ester (1.22 g, 7.13 mmol) and BOC-Ser(OBn)—OH (2.36 g, 8.0 mmol) were dissolved in DMF (15 mL) at RT. HOBT (1.08 g, 8.0 mmol), WSC (1.54 g, 8.0 mmol) and N-methyl morpholine (NMM) (0.88 mL, 8.0 mmol) were added. The pH was ca 8.5. The reaction was stirred for 90 min, partitioned between ethyl acetate and 10% KHSO$_4$, the aqueous layer back-extracted, and the organic layers combined. The combined organic layers were washed with saturated NaHCO$_3$ (2×), saturated NaCl, dried over magnesium sulfate and stripped in vacuo to provide title ester as an oil (2.99 g, 6.67 mmol, D. (2R-trans)-1-[N-(2-Naphthalenylsulfonyl)-O-(phenylmethyl)-L-seryl]-4-methyl-2-piperidinecarboxylic acid, ethyl ester Part C BOC-Ser-pipecolic ester (2.80 g, 6.25 mmol) was dissolved in trifluoroacetic acid (TFA) at 0° C., and allowed to warm to RT over 60 min. The TFA was evaporated in vacuo for two hours to provide the TFA salt as an oil (4.2 g). The crude TFA salt was dissolved in dichloromethane (15 mL) and 2-naphthylsulfonyl chloride (Aldrich, 1.58 g, 7.0 mmol) was added, followed by triethylamine (3.5 mL, 25 mmol). A vigorous exotherm developed, and the reaction was put into an ice bath for 10 min, then warmed to RT. After 6 hr the dichloromethane was evaporated, the reaction mixture partitioned between ethyl acetate and 10% KHSO$_4$ (2×), washed with saturated NaHCO$_3$ (2×), dried over magnesium sulfate and evaporated to provide crude title ester (3.18 g). The crude product was chromatographed on silica gel (1:3==>1:2 ethyl acetate (EtOAc):hexanes to provide the two diastereomers as an oil (2.29 g, 4.25 mmol, 68% over two steps).

E. (2R-trans)-1-[N-(2-Naphthalenylsulfonyl)-O-(phenylmethyl)-L-seryl]-4-methyl-2-piperidinecarboxylic acid The Part D ester was dissolved in methanol (MeOH) (30 mL) and treated with 1N NaOH (10 mL, 10 mmol). The reaction was stirred for 12 hr, and additional NaOH (5 mL) was added. After 24 hr the reaction was acidified with HCl (50 mL, 1N), extracted with ethyl acetate (2×), and dried in vacuo to give title free acid (1.99 g, 3.90 mmol, 99%).

F. (4-Aminobutyl)carbamic acid, phenylmethyl ester 1,4-butanediamine dihydrochloride (5.96 g, 37 mmol) was dissolved in water (15 mL), and DMF (50 mL) was added. With rapid stirring, CBZ-Cl (1.0 mL, 7.0 mmol) was added dropwise over 2 minutes. The cloudy solution had pH~2.8. The pH was adjusted to 9.0 with 5N NaOH, (clear solution) and stirred for 2 hr. The reaction mixture was acidified to pH=1.25, extracted with ether (2×), made basic (pH>10) with 5N NaOH, and extracted with dichloromethane (2×). The dichloromethane fractions were combined and washed with water (2×), dried and evaporated in vacuo to provide the crude mono-CBZ amine (0.72 g, 3.24 mmol, 46%) which was used as is in the next step.

G. (2R-trans)-1-[N-(2-Naphthalenylsulfonyl)-O-(phenylmethyl)-L-seryl]-N-[4-[[(phenylmethoxy)carbonyl]amino]butyl]-4-methyl-2-piperidinecarboxamide To a solution of Part E mono-CBZ amine (400 mg, 1.8 mmol) and Part E acid (640 mg, 1.25 mmol) in DMF (5 mL) was added HOBT (170 mg, 1.25 mmol), WSC (0.25 g, 1.3 mmol), and NMM (138 µL, 1.3 mmol). The pH was ~8.5. The reaction was stirred for two hr (complete by HPLC), partitioned between ethyl acetate and 10% KHSO$_4$, back-extracted, and the combined organic layers washed with 10% KHSO$_4$, saturated NaHCO$_3$ (2×), saturated NaCl, and evaporated to provide the crude product in quantitative yield. The crude product was chromatographed on silica gel (2:1:EtOAc:hexanes) to provide a mixture of the title two diastereomers (671 mg, 0.94 mmol, 75%).

H. [1(S),2α,4β]-N-[4-[(Aminoiminomethyl)amino]butyl]-1-[3-hydroxy-2-[(2-naphthalenylsulfonyl)amino]-1-oxopropyl]-4-methyl-2-piperidinecarboxamide, trifluoroacetate (1:1) salt The Part G O-benzyl CBZ derivative was dissolved in ethanol (20 mL) to which acetyl chloride had been added (0.71 mL, 10 mmol, gives a 0.5M solution of HCl), and the mixture hydrogenated over Pd—C (10%, 150 mg) at 1 atm and reflux temperature. After 5 hr the reaction mixture was filtered, stripped and fresh ethanol and catalyst added. The reaction was determined to be ca 80% complete after an additional 2 hr, whereupon it was filtered and stripped to provide the crude amine (412 mg). The crude material was purified by preparative HPLC (80:20=>50:50) to provide the des-benzyl, des-CBZ diastereomers (281 mg, 0.57 mmol, 71%) and the O-benzyl, des-CBZ compounds (69 mg, 0.12 mmol, 15%).

The des-benzyl, des-CBZ material above (208 mg, 0.46 mmol) was dissolved in ethanol (5 mL), to which amidinesulfonic acid (78 mg, 0.65 mmol) and triethyl amine (176 μL, 1.26 mmol) were added. After 20 hr the solvent was evaporated and the material purified by preparative HPLC (80:20=>50:50). Fractions containing the two major components were combined and lyophilized to provide title compound as a 40:60 mixture of isomers A:B (255 mg, 78%). Purity ≧98%.

$[\alpha]_D$ (c=1.0, MeOH)=−11.7°.

Analysis calc'd for 1.30 TFA+0.80 $H_2O$: C, 47.68; H, 5.64; N, 12.09; F, 10.66. Found: C, 47.68; H, 5.34;, N, 11.97; F, 10.83.

EXAMPLE 2

[1(S), 2α,4β]-N-[4-[(Aminoiminomethyl)amino]butyl]-4-methyl-1-[2-[(2-naphthalenylsulfonyl)amino]-1-oxo-3-(phenylmethoxy)propyl]-2-piperidinecarboxamide, trifluoroacetate (1:1) salt The O-benzyl, des-CBZ compound described in Example 1 Part H (69 mg, 0.099 mmol) was dissolved in ethanol (2 mL), to which amidinesulfonic acid (22 mg, 0.18 mmol, prepared as described in Synthesis (1986) 777–779), and triethyl amine (50 μL, 0.36 mmol) were added. After 20 hr the solvent was evaporated and the material purified by preparative HPLC (80:20=>50:50). Fractions containing the two major components were combined and lyophilized to provide title compound as a 1:3 mixture of isomers A:B (76 mg, 100%). Purity≧98%.

$[\alpha]_D$ (c=1.0, MeOH)=−5.6°.

Analysis calc'd for 1.10 TFA+0.30 $H_2O$: C, 54.51; H, 5.84; N, 11.15; F, 8.32. Found: C, 54.19; H, 5.84;, N, 11.04; F, 8.29.

EXAMPLE 3

[2R-[1(S*), 2α, 4β]-N-[4-[(Aminoiminomethyl)amino]butyl]-1-[3-hydroxy-2- [(2-naphthalenylsulfonyl)amino ]-1-oxopropyl]-4-methyl-2-piperidinecarboxamide, trifluoroacetate (1:1) salt Example 1 compound (ca 220 mg) was dissolved in water (15 mL) and chromatographed on a YMC S-10 20 mm×500 mm ODS column, using an 80:20=>50:50 gradient. After lyophilization, the first peak to elute (isomer A) comprised 95 mg. The stereochemistry (2R, 4R) was assigned by comparison to a sample prepared form non-racemic starting material.

$[\alpha]D$ (c=1.00, MeOH)+11.0°.

Analysis calc'd for 1.16 $H_2O$+1.07 TFA: C, 48.25; H, 5.88; N, 12.44; F, 9.03; S, 4.75. Found: C, 48.25; H, 5.61; N, 12.25; F, 9.25; S, 5.19.

EXAMPLE 4

[2S-[1(R*), 2α, 4β]-N-[4-[(Aminoiminomethyl)amino]butyl]-1-[3-hydroxy-2-[(2-naphthalenylsulfonyl)amino)-1-oxopropyl]-4-methyl-2-piperidinecarboxamide, trifluoroacetate (1:1) salt Example 1 compound (ca 220 mg) was dissolved in water (15 mL) and chromatographed on a YMC S-10 20 mm×500 mm ODS column, using an 80:20=>50:50 gradient (acetonitrile:water). After lyophilization, the second peak to elute (isomer B) comprised 103 mg. The stereochemistry (2S, 4S) was assigned by comparison of the two isomers. $[\alpha]D$ (c=1.00, MeOH) −29.0°.

Analysis calc'd for 1.39 $H_2O$+1.17 TFA: C, 47.52; H, 5.83; N, 12.16; F, 9.65; S, 4.64. Found: C, 47.52; H, 5.49; N, 11.96; F, 9.60; S, 5.25.

High resolution MS shows $(M+H)^+$=533.2546 ($C_{25}H_{37}O_5N_6S$).

EXAMPLE 5

(2S-trans)-N-[4-[(Aminoiminomethyl)amino]butyl]-4-methyl-1-[[[(1,2,3,4-tetrahydro-3-methyl-8-quinolinyl)sulfonyl]amino]acetyl]-2-piperidinecarboxamide, trifluoroacetate salt A. (2S-trans)-4-Methyl-2-piperidinecarboxylic acid, ethyl ester To a solution of dry EtOH (65 mL) and acetyl chloride (6.52 mL added dropwise at 0° C.) was added (2S, 4S)-4-methyl pipecolic acid (2.8 g, 19.6 mmol) at room temperature. The reaction was stirred at room temperature for 16 hrs and then concentrated in vacuo to give the title compound, (3.01 g, 90%).

B. (2S-trans)-1-[[[(1,1-Dimethylethoxy)carbonyl]amino]acetyl]-4-methyl-2-piperidinecarboxylic acid, ethyl ester To a solution of L-Boc-Glycine (0.4 g, 2.25 mmol) and HOBT (0.31 g, 2.25 mmol) in 7 mL DMF was added WSC (0.44 g, 2.25 mmol) and Part A ethyl ester (0.35 g, 2.04 mmol), followed by NMM (240 μl, 2.25 mmol) to adjust the pH of the solution to 8. The reaction was stirred at room temperature for 16 hrs and worked up by washing with a saturated solution of $NaHCO_3$, a saturated solution of $KHSO_4$, brine, dried over $Na_2SO_4$ and evaporated to give the title compound (0.60 g, 89%).

$(M+H)^+$@329

C. (2S-trans)-1-[[[(1,1-Dimethylethoxy)carbonyl]amino]acetyl]-4-methyl-2-piperidinecarboxylic acid To a solution of Part B (560 mg, 1.71 mmol) in 6.5 mL EtOH was added 1N NaOH (6.5 mL) at 0° C. The reaction was stirred at room temperature for 16 hrs and concentrated in vacuo. The reaction was acidified with 1N HCl to pH 2 and extracted with EtOAc. Then the EtOAc was washed with a saturated solution of KHSO4, brine, dried over $Na_2SO_4$ and concentrated to give the title compound (512 mg, quantitative).

$(M+H)^+$@301

D. (4-Aminobutyl)carbamic acid, phenylmethyl ester

To a solution of 1,4-diaminopentane (25 g, 155 mmol) in 100 mL DMF/$H_2O$ (1:1) was added 5N NaOH to adjust the pH to 9. CBZ-Cl (3.7 mL, 26 mmol) was added as one portion and stirred at room temperature for 16 hrs. The reaction was acidified to pH 1.25 and washed with diethyl ether. The pH of the reaction was then adjusted to 9.5 and the reaction extracted with EtOAc. The organic layer was washed with $H_2O$, brine, dried over $Na_2SO_4$ and evaporated to give title compound (1.57 g, 30%).

E. (2S-trans)-1-[[[(1,1-Dimethylethoxy)carbonyl]amino]acetyl]-4-methyl-N-[4-[[(phenylmethoxy)carbonyl]amino]butyl]-2-piperidinecarboxamide To a solution of Part C compound (516 mg, 1.72 mmol) and HOBT (256 mg, 1.89 mmol) in 10 mL DMF was added WSC (363 mg, 1.89 mmol) and Part D CBZ amine, (381 mg, 1.72 mmol), followed by NMM (198 μl, 1.89 mmol) to adjust the pH of the solution to 8. The reaction was stirred at room temperature for 16 hrs. The reaction was worked up by pouring into a saturated solution of $NaHCO_3$ and extracting with EtOAc. The EtOAc layer was washed with a saturated solution of $KHSO_4$, brine, dried over $Na_2SO_4$ and concentrated in vacuo to give the title compound (900 mg, quantitative).

F. (2S-trans)-1-(Aminoacetyl)-4-methyl-N-[4-[[(phenylmethoxy)carbonyl]amino]butyl]-2-piperidinecarboxamide hydrochloride To a solution of Part E compound (0.76 g, 1.51 mmol) in 5 mL MeOH was added 4.5 mL of 4N HCl/dioxane at 0° C. After 2 hrs at room temperature, the reaction was worked up by adding Et$_2$O to precipitate the title compound (0.70 g, quantitative).

G. (2S-trans)-4-Methyl-1-[[[(3-methyl-8-quinolinyl)sulfonyl]amino]acetyl]-N-[4-[[(phenylmethoxy)carbonyl]amino]butyl]-2-piperidinecarboxamide To a solution of Part F compound (500 mg, 1.13 mmol) in 11 mL CHCl$_3$ was added Et$_3$N (475 ml, 3.39 mmol) at 0° C. After 5 minutes, 6-methyl-8-quinolinesulfonyl chloride, (273 mg, 1.13 mmol) was added. The reaction was stirred at 0° C. for another 5 minutes then stirred at room temperature for 3 hrs. The reaction was washed with a saturated solution of NaHCO$_3$, a saturated solution of KHSO$_4$, brine, dried over Na$_2$SO$_4$ and evaporated to give the crude product which was purified by a silica gel column, using CH$_2$Cl$_2$: MeOH eluting solvent to give the title compound (150 mg, 22%).

H. (2S-trans)-N-(4-Aminobutyl)-4-methyl-1-[[[(1,2,3,4-tetrahydro-3-methyl-8-quinolinyl)sulfonyl]amino]acetyl]-2-piperidinecarboxamideo hydrochloride A solution of Part G compound (140 mg, 0.23 mmol) and 230 µl 1N HCl in 5 mL EtOH was hydrogenated at 1 atm over 10% Pd / C (40 mg). After 16 hrs, the suspension was filtered through Celite and concentrated in vacuo to give the title free amine, (130 mg, quantitative).

I. (2S-trans)-N-[4-[(Aminoiminomethyl)amino]butyl]-4-methyl-1-[[[(1,2,3,4-tetrahydro-3-methyl-8-quinolinyl)sulfonyl]amino]acetyl]-2-piperidinecarboxamide To a solution of Part H compound (80 mg, 0.145 mmol) in 0.8 mL EtOH was added Et$_3$N (60 ml, 0.43 mmol), followed by amidinesulfonic acid (27 mg, 0.22 mmol). After 16 hrs at room temperature, the reaction was concentrated in vacuo and was subjected to preparative HPLC using an 80:20 to 50:50 gradient (H$_2$O: CH$_3$CN) over 50 minutes to give the title compound (40 mg, 50%).

(M+H)+@522

Anal Calc'd for C$_{24}$H$_{39}$N$_7$O$_4$S.1.2 TFA.1.1 H$_2$O C, 43.54; H, 6.04; N, 13.46; F, 9.39 Found C, 43.87; H, 5.72; N, 13.09; F, 9.33.

$[\alpha]_D$=–6.7 (c=0.51, methanol)

EXAMPLE 6 trans-N-[4-[(Aminoiminomethyl)amino]butyl]-4-(methylthio)-1-[[(2-naphthalenylsulfonyl)amino]acetyl]-L-prolinamide, trifluoroacetate salt A. cis-4-Hydroxy-1-[(phenylmethoxy)carbonyl]-L-proline, methyl ester N-CBZ-L-keto proline was dissolved in methanol (150 mL), cooled to 0° to 5° C. and treated dropwise with a solution of NaBH$_4$ (2.875 g) in water (10 mL). The mixture was kept at 0° to 5° C. for 19 h. The methanol was removed in vacuo and the residue was treated with 75 mL of 3N NaOH and stirred at room temperature for 40 min. After cooling in an ice bath, the mixture was acidified with conc HCl. The product was extracted into ethyl acetate (3×50 mL). The combined extracts were washed with brine (2×40 mL), dried (MgSO$_4$) and freed of solvent in vacuo to give the cis-hydroxy acid. This was converted to the methyl ester by dissolving in methanol (75 mL), treating with acetyl chloride (7.5 mL), and stirring overnight at room temperature. The solvent was removed. The residue was dissolved in ethyl acetate (75 mL), washed with sodium bicarbonate solution (2×25 mL), dried (MgSO$_4$) and freed of solvent in vacuo to give title compound as a viscous oil (4.315 g, 81%).

B. cis-4-[[(4-Methylphenyl)sulfonyl]oxy]-1-[(phenylmethoxy)carbonyl]-L-proline, methyl ester The Part A alcohol (4.315 g, 16.84 mmol) was dissolved in dry pyridine (23 mL), cooled in an ice bath and treated with tosyl chloride (6.8 g). The mixture was allowed to warm slowly to room temperature and left stirring 60 h. After cooling, cold 2N HCl was added and the mixture was left at 0° to 5° C. for 4 h. The solid was collected by filtration and dissolved in dichloromethane. This solution was washed with 1N HCl soln and brine, dried (MgSO$_4$) and freed of solvent in vacuo leaving title compound as a crystalline material.

C. 4-(Methylthio)-1-[(phenylmethoxy)carbonyl]-L-proline, methyl ester

Part B tosylate (2.09g, 4.8 mmol) was dissolved in absolute ethanol (20 mL) and acetone (20 mL), under an atmosphere of argon, and treated with sodium thiomethoxide (1.39 g, 19.9 mmol). The mixture was heated under reflux 1 h, cooled and most of the solvent was removed in vacuo. The residue was partitioned between 1N HCl and ethyl acetate. The ethyl acetate layer was washed with water, dried (MgSO$_4$), and freed of solvent in vacuo. NMR and TLC indicated the material was mainly the free acid. It was converted to the methyl ester by dissolving in methanol (20 mL), adding acetyl chloride (2 mL) and stirring at room temperature for two hours. After removal of the solvent, the product was purified by chromatography on silica gel, eluting with ethyl acetate:hexane (1:2) to give the title thiomethyl compound (1.364 g, 99%).

D. 4-(Methylthio)-L-proline, methyl ester, hydrobromide

Part C compound (945 mg, 3.3 mmol) was treated with 30% HBr in HOAc (8 mL) for 1 h and then concentrated in vacuo. Trituration of the residue with ether gave a solid which was harvested by filtration and washed with more ether leaving the title deprotected amine (749 mg, 89%).

E. trans-1-[[[(1,1-Dimethylethoxy)carbonyl]amino]acetyl]-4-(methylthio)-L-proline, methyl ester
and F. cis-1-[N-[(1,1-Dimethylethoxy)carbonyl)glycyl]-4-(methylthio)-L-proline, methyl ester Part D L-proline derivative (1.012 g, 3.95 mmol) and BOC-glycine (900 mg, 5.1 mmol) were dissolved in DMF (20 mL) at RT. HOBT (688 mg, 5.1 mmol), WSC (974 mg, 5.1 mmol) and NMM (1.0 mL, 9.1 mmol) were added. The reaction was stirred for 16 h, partitioned between ethyl acetate (50 mL) and 10% KHSO$_4$ (100 mL). The aqueous layer was extracted with ethyl acetate (2×50 mL), and the organic layers were combined. The combined organic layers were washed with saturated NaHCO$_3$, saturated NaCl, dried over magnesium sulfate and concentrated in vacuo to provide an oil. TLC indicated this was two major products. The crude material was purified by chromatography on silica gel. Elution with ethyl acetate:hexanes(1:2 followed by 1:1) gave the major product (tentatively assigned the trans configuration of the title compound, 603 mg, 46%) and the minor product (tentatively assigned the cis configuration of the title compound, 204 mg, 16%) as well as some mixed fractions (438 mg, 33%).

G. trans-4-(Methylthio)-1-[[(2-naphthalenylsulfonyl)amino]acetyl]-L-proline, methyl ester The Part E BOC derivative (600 mg, 1.8 mmol) was dissolved in trifluoroacetic acid (TFA) (15 mL) and stirred at RT 1 h. The TFA was removed by distillation under reduced pressure and by coevaporation with toluene. The crude TFA salt was dissolved in dichloromethane (20 mL), cooled in an ice bath, and 2-napthylsulfonyl chloride (Aldrich, 450 mg, 2.0 mmol) was added, followed by triethylamine (1.5 mL). The solution was warmed to RT and stirred 1.5 h before diluting with dichloromethane (75 mL). This solution was washed with potassium hydrogen sulfate solution(2×40 mL) and saturated NaHCO$_3$ (2×40 mL), dried over magnesium sulfate, and evaporated to provide crude title compound. The crude product was chromatographed on silica gel and eluted with 50% EtOAc in hexanes to provide title sulfonamide as a foam (700 mg, 92% overall in two steps).

H. trans-4-(Methylthio)-1-[[(2-naphthalenylsulfonyl)amino]acetyl]-L-proline

A solution of Part G methyl ester (700 mg, 1.65 mmol) in methanol (20 mL) was treated with 1$\underline{N}$ NaOH solution (8 mL) and stirred at room temperature for three h. After acidification with 1$\underline{N}$ HCl solution, the product was extracted into dichloromethane (2×50 mL), dried over magnesium sulfate and freed of solvent in vacuo to give title compound as a white foam (687 mg, 100%).

I. trans-4-(Methylthio)-1-[[(2-naphthalenylsulfonyl)amino]acetyl]-N-[4- [[(phenylmethoxy)carbonyl]amino]butyl]-L-prolinamide To a solution of mono-CBZ butyl diamine (484 mg, 2.18 mmol) and Part H acid (687 mg, 1.65 mmol) in DMF (25 mL) was added HOBT (230 mg, 1.7 mmol), WSC (325 mg, 1.7 mmol), and NMM (373 µL, 3.4 mmol). The reaction was stirred at RT for 20 h, partitioned between ethyl acetate (50 mL) and KHSO$_4$ solution (50 mL), back-extracted with ethyl acetate (2×50 mL), and the combined organic layers were washed with saturated NaHCO$_3$ and brine, dried (MgSO$_4$), filtered and concentrated. The crude product was chromatographed on silica gel and eluting with 50–67% EtOAc in hexanes followed by EtOAc to provide title compound (577 mg, 58%).

J. trans-N-(4-Aminobutyl)-4-(methylthio)-1-[[(2-naphthalenylsulfonyl)amino]acetyl]-L-prolinamide, hydrobromide The CBZ group was removed from Part I compound (577 mg, 0.96 mmol) by treating with 30% HBr in HOAc (10 mL) for 1.5 h and then concentrated in vacuo. Trituration of the residue with ether gave a solid which was harvested by filtration and washed with more ether leaving the title deprotected amine (100%).

K. trans-N-[4-[(Aminoiminomethyl)amino]butyl]-4-(methylthio)-1-[[(2-naphthalenylsulfonyl)amino]acetyl]-L-prolinamide, trifluoroacette salt The Part J compound (0.96 mmol) was dissolved in ethanol (20 mL), to which amidinesulfonic acid (173 mg, 1.4 mmol) and triethyl amine (375 µL, 2.7 mmol) were added. After 4 h the mixture was filtered through a pad of Celite, washed with ethanol and the filtrate was concentrated to dryness. The crude material was purified by preparative HPLC (YMC S-10 ODS 50×500 mm column, eluting with 54% methanol in water, containing 0.1% TFA). Fractions containing pure title compound were combined and lyophilized to provide a white solid (279 mg, 44%), Purity≧98%.

$[\alpha]_D = -12.7°$, (c=0.7, MeOH).

Analysis calcd for 1.10TFA+0.90 H$_2$O: C, 45.70; H, 5.31; N, 12.69; F, 9.68; S, 9.47. Found: C, 45.65; H, 5.09; N, 12.51; F, 9.74; S, 9.37.

EXAMPLE 7

N-[4-[(Aminoiminomethyl)amino]butyl]-1-[N-(2-naphthalenylsulfonyl)-D-phenylalanyl]-L-prolinamide, trifluoroacetate salt, hemihydrate A. N-[4-[[(1,1-Dimethylethoxy)carbonyl]amino]butyl]-L-prolinamide, hydrochloride A(1). (4-Aminobutyl)carbamic acid, 1,1-dimethylethyl ester To a stirred solution of 1,4-diaminobutane (50 g, 567 mmol) in 195 mL of dioxane under argon at room temperature was added dropwise a solution of Di-t-butyl dicarbonate (15.7 g, 71.9 mmol) in 195 mL of dioxane over 3.5 h. Some white precipitate appeared during the addition. The mixture was stirred at room temperature for 22 h and concentrated in vacuo. The residue was diluted with 320 mL of water and the precipitate was filtered off. The aqueous filtrate was extracted with methylene chloride (3×300 mL). The combined methylene chloride extracts were washed with water (2×200 ml) and brine (1×200 mL). The organic layer was dried (MgSO$_4$), filtered and concentrated in vacuo to give 9.79 g (72%) of title mono-BOC.amine.

TLC: silica gel, 2%NH$_4$OH in 10%CH$_3$OH/CH$_2$Cl$_2$, Rf 0.30, Ninhydrin.

A(2). N-[4-[[(1,1-Dimethylethoxy)carbonyl]amino]butyl]-1-[(phenylmethoxy)carbonyl]-L-prolinamide To a stirred solution of N-CBZ-L-proline (12.7 g, 50.9 mmol), 1-hydroxybenzotriazole monohydrate (6.49 g, 50.9 mmol) and Part A(1) BOC amine (9.57 g, 50.9 mmol) in 250 mL of DMF was added in order 4-methylmorpholine (11.2 mL, 102 mmol) and ethyl-3-(3-dimethylamino)propyl carbodiimide hydrochloride (9.76 g, 50.9 mmol). The reaction solution was stirred at room temperature for 22 h and concentrated under pump vacuum at 50° C. The residue was diluted with 600 mL of EtOAc and washed with 1N HCl solution (2×250 mL), saturated NaHCO$_3$ solution (2×250 mL) and brine (1×250 mL). The EtOAc layer was dried (MgSO$_4$), filtered and concentrated in vacuo to give 20.7 g (97%) of title CBZ amine.

TLC: silica gel, 4%CH$_3$OH/CH$_2$Cl$_2$, Rf 0.44, UV, Ce(SO$_4$)$_2$.

A(3). N-[4-[[(1,1-Dimethylethoxy)carbonyl]amino]butyl]-L-prolinamide, hydrochloride To a stirred solution of Part A(2) CBZ amine (20.2 g, 48.2 mmol) in 250 mL of methanol under argon was added 20%Pd(OH)$_2$/C (4.04 g, 20% based on the weight of Part A(2) compound). The atmosphere was replaced by hydrogen with several vacuum-fill cycles. The reaction mixture was stirred at room temperature for 21 h. The catalyst was filtered off through a 4 µM polycarbonate film and rinsed with methanol (3×50 mL). The filtrate was concentrated in vacuo. The oily residue was dissolved in 200 mL of ether and treated with 1N HCl solution in ether (53.0 mL, 53.0 mmol). The solution was concentrated in vacuo. The residue was mixed with 200 mL of toluene and 30 mL of methanol and concentrated in vacuo to give title amine hydrochloride in quantitative yield (15.5 g) as an oil.

B. N-[4-[[(1,1-Dimethylethoxy)carbonyl]amino]butyl]-1-[N-[(phenylmethoxy)carbonyl]D-phenylalanyl]-L-prolinamide A stirred solution of N-α-CBZ-D-phenylalanine (0.56 g, 1.9 mmol) in 6.5 mL of DMF at room temperature under argon was treated with 1-hydroxybenzotriazole (0.29 g, 1.9 mmol) and ethyl-3-(3-dimethylamino)propyl carbodiimide hydrochloride (0.36 g, 1.9 mmol). After 20 minutes, Part A compound was added (0.50 g, 1.6 mmol) and stirring was carried out for 16 hours. The reaction was quenched by the addition of 75 mL of 0.25M KHSO$_4$ solution. The suspension was washed with EtOAc (2×40 mL), the combined EtOAc layers were washed with 0.25M KHSO$_4$ solution (2×40 mL), saturated aqueous KHCO$_3$ solution (2×40 mL), brine, dried (Na$_2$SO$_4$), and concentrated to yield 1.07 g of a white taffy, which by TLC analysis appeared to contain unreacted N-α-CBZ-D-phenylalanine. The crude product was redissolved in 60 mL of EtOAc, washed with saturated aqueous KHCO$_3$ solution (3×40 mL), brine, dried (Na$_2$SO$_4$), concentrated, co-evaporated several times with ether and hexane and triturated with 50 mL of hexane to yield title compound (0.78 g, 88%) as a white solid.

C. N-[4-[[(1,1-Dimethylethoxy)carbonyl]amino]butyl]-1-D-phenylalanyl-L-prolinamide A solution of Part B compound (0.58 g, 1.0 mmol) with 0.12 g of Pd(OH)$_2$/carbon in 5.0 mL of methanol was hydrogenated at 1 atm for 3.75 hours. The catalyst was removed by filtration through a porous membrane (Whatman 0.2 μ Nylon Autovial), and the filtrate was concentrated to yield title compound (0.39 g, 88%) as a white, hygroscopic solid.

D. N-[4-[[(1,1-Dimethylethoxy)carbonyl]amino]butyl]-1-[N-(2-naphthalenylsulfonyl)-D-phenylalanyl]-L-prolinamide Triethylamine (0.25 mL, 1.8 mmol) was added dropwise to a stirred 0° C. solution of Part C compound (0.39 g, 0.90 mmol) and 2-naphthalenesulfonyl chloride (0.21 g, 0.95 mmol) in 7.0 mL of CH$_2$Cl$_2$. The reaction was carried out at room temperature for 45 minutes. Dichloromethane was removed under vacuum, the residue was partitioned between EtOAc (50 mL) and aqueous 0.25M KHSO$_4$ solution (15 mL), the EtOAc layer was washed with 0.25M KHSO$_4$ solution (3×15 mL), brine, dried (Na$_2$SO$_4$), and concentrated to yield 0.61 g of a colorless glass. Trituration with 50 mL of hexane yielded title compound (0.52 g, 93%) as a white solid.

E. N-(4-Aminobutyl)-1-[N-(2-naphthalenylsulfonyl)-D-phenylalanyl]-L-prolinamide, trifluoroacetate salt Trifluoroacetic acid (5.0 mL) was added to ice-cooled Part D compound (0.48 g, 0.77 mmol). The reaction solution was stirred at room temperature for 45 minutes. Trifluoroacetic acid was removed under vacuum and co-evaporated several times with ether and hexane until title compound was obtained as a white solid (0.51 g, ca. 100%).

F. N-[4-[(Aminoiminomethyl)amino]butyl]-1-[N-(2-naphthalenylsulfonyl)-D-phenylalanyl]-L-prolinamide, trifluoroacetate salt, hemihydrate A solution of Part E compound (0.49 g, 0.77 mmol) in 6.0 mL of absolute ethanol was treated with amidine sulfonic acid (0.14 g, 1.2 mmol) followed by triethylamine (3.2 mL, 2.3 mmol). Within several minutes reaction time, a precipitate appeared. After 5 hours reaction time, TLC analysis of the reaction mixture (silica, 3:1:1 nBuOH:HOAc:H$_2$O) indicated a small amount of unconsumed Part E compound. An additional portion of amidine sulfonic acid (0.05 g) and triethylamine (0.53 mL) were introduced, and the reaction was continued for 16 hours. TLC analysis as above indicated complete consumption of Part E compound. The reaction mixture was concentrated, dissolved in 25 mL of CH$_3$OH, and filtered through a porous membrane (Gelman Acrodisc CR PFTE, 0.45μ). Preparative HPLC of the filtered solution (25%B to 100%B, 30 minute gradient) and subsequent lyophilization of the pooled fractions yielded title compound, (258 mg, 48%) as a colorless solid. mp 100°–120° C. with foaming.

[α]$_D$=+19.4° (c=0.5, CH$_3$OH).

TLC: Rf=0.70 (silica, 3:1:1 nBuOH; HOAc;H$_2$O).

Anal. Calc'd for C$_{31}$H$_{37}$N$_6$O$_6$F$_3$S.1.1 C$_2$HF$_3$O$_2$.0.50 H$_2$O: C, 53.60; H, 5.49; N, 12.02; F, 8.97; S, 4.59 Found: C, 53.61; H, 5.50; N, 11.81; F, 9.03; S, 4.36

EXAMPLE 8

N-[4-[(Aminoiminomethyl)amino]butyl]-1-[N-(2-naphthalenylsulfonyl)-D-glutaminyl]-L-prolinamide A. N-[4-[[(1,1-Dimethylethoxy)carbonyl]amino]butyl]-1-[N-[(phenylmethoxy)carbonyl]-D-glutaminyl]-L-prolinamide To a stirred solution of Example 7 Part A amine hydrochloride (0.56 g, 1.74 mmol), 1-hydroxybenzotriazole monohydrate (0.29 g, 1.74 mmol) and N-CBZ-D-glutamine (0.49 g, 1.74 mmol) in 15 mL of DMF was added 4-methylmorpholine (0.57 mL, 5.23 mmol) followed by ethyl-3-(3-dimethylamino)propyl carbodiimide hydrochloride (0.33 g, 1.74 mmol). The solution was stirred at room temperature for 19 h and concentrated under pump vacuum at 45° C. The oily residue was diluted with 160 mL of EtOAc and washed with 1N HCl solution (2×60 mL), saturated NaHCO$_3$ solution (2×60 mL) and brine (1×60 mL). The EtOAc layer was dried (MgSO$_4$), filtered and concentrated in vacuo to give 0.75 g (77%) of title CBZ amine.

TLC: silica gel, 6%CH$_3$OH/CH$_2$Cl$_2$, Rf 0.22, Ce(SO$_4$)$_2$.

B. N-[4-[[(1,1-Dimethylethoxy)carbonyl]amino]butyl]-1-[N-(2-naphthalenylsulfonyl)-D-glutaminyl]-L-prolinamide To a stirred solution of Part A CBZ amine (0.73 g, 1.33 mmol) in 12 mL of methanol under argon was added Pd(OH)$_2$/C (146 mg, 20% based on the weight of Part A compound). The atmosphere was replaced by hydrogen with several vacuum-fill cycles. The reaction solution was stirred at room temperature for 22 h and the catalyst was filtered off through a 4 μM polycarbonate film. The solid was rinsed with methanol (2×20 mL). The filtrate was concentrated in vacuo to give 0.54 g of the intermediate amine. To a stirred solution of this amine (0.44 g, 1.07 mmol) and 2-naphthalenesulfonyl chloride (0.27 g, 1.18 mmol, in 10 mL of dry methylene chloride under argon at 0° C. was added Et$_3$N (0.33 mL, 2.34 mmol). The reaction solution was stirred at room temperature for 2 h and diluted with 180 mL of EtOAc. This solution was washed with 1N HCl solution (2×60 mL), saturated NaHCO$_3$ solution (1×60 mL) and brine (1×60 mL). The organic layer was dried (MgSO$_4$), filtered and concentrated in vacuo. Purification was effected by flash chromatography on 30 g of Merck silica gel 60 using 240 mL of 4%CH$_3$OH/CH$_2$Cl$_2$ and 480 mL of 6%CH$_3$OH/CH$_2$Cl$_2$ as eluants to give pure title sulfonamide (310 mg, 48%).

TLC: silica gel, 4%CH$_3$OH/CH$_2$Cl$_2$, Rf 0.20, UV, I$_2$.

C. N-[4-[(Aminoiminomethyl)amino]butyl]-1-[N-(2-naphthalenylsulfonyl)-D-glutaminyl]-L-prolinamide To a stirred solution of Part B sulfonamide (310 mg, 0.51 mmol) in 5 mL of dry methylene chloride was added 0° C. 4N HCl in dioxane (6.00 mL, 24.0 mmol). The solution was stirred at room temperature for 2 h and diluted with 120 mL of ether. The solid was filtered off and rinsed with ether (2×30 mL). The solid was dissolved in 60 mL of methanol and concentrated in vacuo to give the intermediate amine hydrochloride. To a stirred mixture of this amine hydrochloride and Et$_3$N (0.39 mL, 2.31 mmol) in 5 mL of absolute EtOH under argon was added aminoiminomethanesulfonic acid (204 mg, 1.64 mmol). The mixture was stirred at room temperature for 5 h and concentrated in vacuo. The reaction mixture was purified by preparative HPLC, eluting isocratically with a 37% composition of water:methanol (90:10 and 10:90) containing 0.2% H$_3$PO$_4$. The fractions were concentrated in vacuo and lyophilized to give 260 mg (93%) of title compound.

m.p. 72°–74° C.

[α]$_D$=+5.80 (c=0.69, methanol).

Anal. Calc'd for C$_{25}$H$_{35}$N$_7$O$_5$S.1.60 TFA.1.0 H$_2$O: C, 45.40; H, 5.21; N, 13.14; S, 4.30; F, 12.22 Found: C, 45.45; H, 4.98; N, 12.95; S, 4.32; F, 11.90

Following the procedures of Examples 1 to 8 and those outlined above, the following additional examples may be prepared.

|  | Melting Point °C., Optical Rotation and/or Elemental Analysis (where available). |
|---|---|
| 9. 2R-[1(S*), 2α, 4β)]-N-[3-[(Aminoiminomethyl)amino]propyl]-1-[4-hydroxy-3-[(2-naphthalenylsulfonyl)amino]-1,2-dioxobutyl]-2-piperidinecarboxamide, trifluoroacetate (1:1) salt<br>Anal. Calc'd for $C_{24}H_{34}N_6O_5S.1.1$ TFA.1.34 $H_2O$: | $[\alpha]_D = +11.0$ (c = 1.09 MeOH) |

C, 47.10; H, 5.70; N, 12.58; S, 4.80; F, 9.38
Found:  C, 47.39; H, 5.41; N, 12.29; S, 5.21; F, 9.56

| 10. N-[4-[(Aminoiminomethyl)amino]butyl]-1-[N-(2-naphthalenylsulfonyl)-L-seryl]-L-prolinamide<br>Anal. Calc'd for $C_{23}H_{32}N_6O_5S.1.15$ TFA.0.5 $H_2O$: | $[\alpha]_D = -70.2$ (c = 0.5, MeOH) |

C, 47.13; H, 5.34; N, 13.03; S, 4.97; F, 10.17
Found:  C, 46.83; H, 5.28; N, 12.84; S, 5.14; F, 10.43

| 11. N-[4-[(Aminoiminomethyl)amino]butyl]-1-[N-(2-naphthalenylsulfonyl)-L-seryl]-D-prolinamide, trifluoroacetate (1:1) salt<br>Anal. Calc'd for $C_{23}H_{32}N_6O_5S.1.15$ TFA.1.6 $H_2O$: | $[\alpha]_D = -14.8$ (c = 0.5, MeOH) |

C, 45.73; H, 5.51; N, 12.65; S, 4.82; F, 9.86
Found:  C, 45.58; N, 5.19; N, 12.41; S, 5.14; F, 10.01

| 12. (2R-trans)-N-[4-[(Aminoiminomethyl)amino]butyl]-4-methyl-1-[[(2-naphthalenylsulfonyl)amino]acetyl]-2-piperidinecarboxamide, trifluoroacetate salt, hydrate<br>Anal. Calc'd for $C_{24}H_{34}N_6O_4S.1.35$ TFA.0.85 $H_2O$: | $[\alpha]_D = +33.0$ (c = 1.08 MeOH) |

C, 47.73; H, 5.56; N, 12.51; S, 4.77; F, 11.45
Found:  C, 47.73; H, 5.51; N, 12.13; S, 4.95; F, 11.42

| 13. [2R-[1(S*)2α, 4β]]-N-[4-[(Aminoiminomethyl)amino]butyl]-1-[3-hydroxy-2-[(2-naphthalenylsulfonyl)amino]-1-oxopropyl]-4-methyl-2-piperidinecarboxamide, trifluoroacetate salt, hydrate<br>Anal. Calc'd for $C_{26}H_{38}N_6O_5S.1.36$ TFA.1.00 $H_2O$: | $[\alpha]_D = +18.8$ (c = 1.06 MeOH) |

C, 47.93; H, 5.79; N, 11.68; S, 4.45; F, 10.77
Found:  C, 47.92; H, 5.66; N, 11.53; S, 4.89; F, 10.75

| 14. [1(S)]-N-[4-[(Aminoiminomethyl)amino]butyl]-1,2,3,4-tetrahydro-2-[3-hydroxy-2-[(2-naphthalenylsulfonyl)amino]-1-oxopropyl]-3-isoquinolinecarboxamide, isomer A, trifluoroacetate salt, hydrate<br>Anal. Calc'd for $C_{28}H_{34}N_6O_5S.1.25$ TFA.1.0 $H_2O$: | $[\alpha]_D = -30.9$ (c = 0.5, MeOH) |

C, 50.37; H, 5.16; N, 11.56; S, 4.41; F, 9.80
Found:  C, 50.31; H, 5.05; N, 11.58; S, 4.44; F, 9.65

| 15. [1(S)]-N-[4-[(Aminoiminomethyl)amino]butyl]-1,2,3,4-tetrahydro-2-[3-hydroxy-2-[(2-naphthalenylsulfonyl)amino]-1-oxopropyl]-3-isoquinolinecarboxamide, isomer B, trifluoroacetate salt, hydrate<br>Anal. Calc'd for $C_{28}H_{34}N_6O_5S.1.25$ TFA.1.0 $H_2O$: | $[\alpha]_D = -22.8$ (c = 0.6, MeOH) |

C, 50.15; H, 5.13; N, 11.47; S, 4.37; F, 10.11
Found:  C, 50.04; H, 4.95; N, 11.36; S, 4.51; F, 10.17

| 16. (4S*)-N-(4-[(Aminoiminomethyl)amino]butyl]-4-hydroxy-1-[N-(2-naphthalenylsulfonyl)-L-seryl]-L-prolinamide, trifluoroacetate (1:1) salt<br>Anal. Calc'd for $C_{23}H_{32}N_6O_6S.1.15$ TFA.1.0 $H_2O$: | $[\alpha]_D = -29.0$ (c = 0.6, MeOH) |

C, 45.25; H, 5.31; N, 12.51; S, 4.77; F, 9.76
Found:  C, 45.28; H, 4.98; N, 12.52; S, 4.86; F, 9.86

| 17. (4S*)-N-[4-[(Aminoiminomethyl)amino]butyl]-4-methoxy-1-[N-(2-naphthalenylsulfonyl)-L-seryl]-L-prolinamide, trifluoroacetate (1:1) salt<br>Anal. Calc'd for $C_{24}H_{34}N_6O_6S.1.1$ TFA.1.3 $H_2O$: | $[\alpha]_D = -24.5$ (c = 0.6, MeOH) |

C, 46.04; H, 5.56; N, 12.30; S, 4.69; F, 9.17
Found:  C, 46.04; H, 5.48; N, 12.16; S, 4.78; F, 9.22

| 18. N-[4-[(Aminoiminomethyl)amino]butyl]-1-[N-(2-naphthalenylsulfonyl)-L-phenylalanyl]-L-prolinamide, trifluoroacetate (1:1) salt<br>Anal. Calc'd for $C_{31}H_{37}N_6O_6F_3S.1.2$ $C_2HF_3O_2.0.80$ $H_2O$: | m.p. 172–178° C. with foaming<br>$[\alpha]_D = -27.0$ (c = 0.5, $CH_3OH$) |

C, 52.68; H, 5.46; N, 11.74; F, 9.55; S, 4.48
Found:  C, 52.71; H, 5.35; N, 11.50; F, 9.33; S, 4.26

| 19. (2S-trans)-N-[4-[(Aminoiminomethyl)amino]butyl]-4-methyl-1-[[(2-naphthalenylsulfonyl)amino]acetyl]-2-piperidinecarboxamide<br>Anal. Calc'd for $C_{26}H_{35}N_6O_6S.0.25$ TFA.1.20 $H_2O$: | $[\alpha]_D = -36.4$ (c = 0.98, MeOH) |

C, 47.74; H, 5.69; N, 12.60; F, 10.68; S, 4.81
Found:  C, 47.75; H, 5.51; N, 12.62; F, 10.86; S, 4.95

| 20. N-[4-[(Aminoiminomethyl)amino]butyl]-1-[N-(2-naphthalenylsulfonyl)-L-glutaminyl]-L-prolinamide, trifluoroacetate (1:1) salt<br>Anal. Calc'd for $C_{25}H_{35}N_7O_5S.1.27$ TFA.1.57 $H_2O$: | $[\alpha]_D = -48.1$ (c = 0.68, methanol) |

C, 46.02; H, 5.53; N, 13.64; S, 4.46; F, 10.07
Found:  C, 46.02; H, 5.18; N, 13.33; S, 4.86; F, 10.06

| 21. N-[4-[(Aminoiminomethyl)amino]butyl]-1-[N-(2-naphthalenylsulfonyl)-L-threonyl]-L-prolinamide, trifluoroacetate (1:1) salt<br>Anal. Calc'd for $C_{24}H_{34}N_6O_5S.1.25$ TFA.1.20 $H_2O$: | m.p. 68–78° C.<br>$[\alpha]_D = -72.6$ (c = 0.69, methanol) |

C, 46.62; H, 5.56; N, 12.31; S, 4.70; F, 10.43
Found:  C, 46.75; H, 5.50; N, 12.08; S, 4.82; F, 10.40

| 22. N-[4-[(Aminoiminomethyl)amino]butyl]-1-[N-(2-naphthalenylsulfonyl)-L-allothreonyl]-L-prolinamide, trifluoroacetate (1:1) salt<br>Anal. Calc'd for $C_{24}H_{34}N_6O_5S.1.16$ TFA.0.97 $H_2O$: | m.p. 85–96° C.<br>$[\alpha]_D = -70.8$ (c = 0.76, methanol) |

C, 47.30; H, 5.59; N, 12.57; S, 4.80; F, 9.89
Found:  C, 47.30; H, 5.16; N, 12.39; S, 5.19; F, 9.48

| 23. (S)-N-[4-[(Aminoiminomethyl)amino]butyl]-4-(methylthio)-1-[N-(2-naphthalenylsulfonyl)glycyl]-L-prolinamide, trifluoroacetate (1:1) salt<br>Anal. Calc'd for $C_{23}H_{32}N_6O_5S_2.1.10$ TFA.1.0 $H_2O$: | $[\alpha]_D = +13.4$ (c = 0.6, MeOH) |

C, 45.58; H, 5.33; N, 12.65; S, 9.44; F, 9.66
Found:  C, 45.52; H, 5.11; N, 12.46; S, 9.49; F, 9.65

| 24. (R)-N-[4-[(Aminoiminomethyl)amino]butyl]-4-(methylthio)-1-[N-(2-naphthalenylsulfonyl)glycyl]-L-prolinamide, trifluoroacetate (1:1) salt<br>Anal. Calc'd for $C_{23}H_{32}N_6O_4S_2.1.10$ TFA.0.9 $H_2O$: | $[\alpha]_D = -12.7$ (c = 0.7, MeOH) |

C, 45.70; H, 5.31; N, 12.69; S, 9.47; F, 9.68
Found:  C, 45.65; H, 5.09; N, 12.51; S, 9.37; F, 9.74

25. N-[4-[(Aminoiminomethyl)amino]butyl]-1-[[(2-naphthalenyl-

89
-continued

| | Melting Point °C., Optical Rotation and/or Elemental Analysis (where available). |
|---|---|
| sulfonyl)amino]acetyl]-2-piperidinecarboxamide | |
| High Resolution Mass Spectrum: $(M + H)^+ = 489.2287$. | |
| 26. N-[4-[(Aminoiminomethyl)amino]butyl]-1-[N-(2-naphthalenylsulfonyl)-D-tryptophyl]-L-prolinamide, trifluoroacetate (1:1) salt | m.p. 100–160° C. foam/dec $[\alpha]_D = +44.4$ (c = 0.5, $CH_3OH$) |
| Anal. Calc'd for $C_{31}H_{37}N_7O_4S.1.06$ $C_2HF_3O_2.1.35$ $H_2O$: | |

C, 53.12; H, 5.49; N, 13.09; F, 8.07; S, 4.28
Found: C, 53.51; H, 5.35; N, 12.73; F, 8.10; S, 4.28

| 27. (2S-trans)-N-[4-[(Aminoiminomethyl)amino]butyl]-4-methyl-1-[[[(3-methyl-8-quinolinyl)sulfonyl]amino]acetyl]-2-piperidinecarboxamide, trifluoroacetate salt | $[\alpha]_D = -24.1$ (c = 0.99 MeOH) |
|---|---|
| Anal. Calc'd for $C_{24}H_{35}N_7O_4S.1.37$ TFA.1.00 $H_2O$: | |

C, 46.42; H, 5.59; N, 14.17; F, 11.29; S, 4.63
Found: C, 46.51; H, 5.32; N, 14.06; F, 11.28; S, 4.55

| 28. N-[4-[(Aminoiminomethyl)amino]butyl]-1-[[(8-quinolinylsulfonyl)amino]acetyl]-2-piperidinecarboxamide, trifluoroacetate salt | |
|---|---|
| Anal. Calc'd for $C_{22}H_{31}N_7O_6S.2C_2HF_3O_2.2.20$ $H_2O$: | |

C, 41.21; H, 5.04; N, 12.84; F, 14.93; S, 4.20
Found: C, 41.34; H, 4.69; N, 12.39; F, 14.91; S, 4.55

| 29. N-[4-[(Aminoiminomethyl)amino]butyl]-1-[N-(2-naphthalenylsulfonyl)-D-α-glutamyl]-L-prolinamide, trifluoroacetate (1:1) salt | $[\alpha]_D = $ (c = 0.60, methanol) |
|---|---|
| Anal. Calc'd for $C_{25}H_{34}N_6O_6S.1.35$ TFA.1.13 $H_2O$: | |

C, 46.42; H, 5.31; N, 12.16; S, 4.35; F, 10.43
Found: C, 46.42; H, 5.33; N, 11.84; S, 4.66; F, 10.50

EXAMPLE 29

N-[4-[(Aminoiminomethyl)amino]butyl]-1-[N-(methylsulfonyl)-D-phenylalanyl]-L-prolinamide, trifluoroacetate (1:1) salt.

A. N-[4-[(Aminoiminomethyl)amino]butyl]-1-D-phenylalanyl-L-prolinamide, trifluoroacetate salt A(1). N-[4-(Aminobutyl)]-1-[N-[(phenylmethoxy)carbonyl]-D-phenylalanyl-L-prolinamide, trifluoroacetate The title compound of Example 7, Part B (0.78 g, 1.38 mmol) was dissolved in trifluoroacetic acid (3.2 mL)). After 3 hours the solvent was evaporated and then co-evaporated with hexane/ether five times, and dried 16 hours in vacuo to provide a colorless taffy which was used in the next step.

A(2). N-[4-[(Aminoiminomethyl)amino]butyl]-1-[N-[(phenylmethoxy)carbonyl]-D-phenylalanyl-L-prolinamide, trifluoroacetate The Part A(1) compound (0.80 g, 1.38 mmol) was dissolved in absolute ethanol (10.9 mL) and treated with amidinesulfonic acid (0.26 g, 1.5 eq), followed by triethylamine (0.58 mL, 3 eq). After stirring for two hours the solvent was evaporated and the crude product purified on reverse phase HPLC to provide a colorless solid (414 mg, 45%).

A(3). N-[4-[(Aminoiminomethyl)amino]butyl]-1-D-phenylalanyl-L-prolinamide, trifluoroacetate salt The title compound of Part A(2) (0.20 g, 0.30 mmol) was dissolved in methanol (1.5 mL) and hydrogenated at 1 atmosphere and room temperature for 3 hours with $Pd(OH)_2$ (40 mg of 20% catalyst). The catalyst was removed by filtration, and the solvent stripped to provide an oil. The oil was dissolved in methanol, acidified with trifluoroacetic acid (0.2 mL) and evaporated to dryness, then dissolved in water and lyophilized to provide the title compound (152 mg).

Optical rotation:=−75.8° (c=0.5, $CH_3$ OH).

Anal. Calc'd for $C_{19}H_{30}N_6O_2.2.07$ $C_2HF_3O_2.0.90$ $H_2O$): C, 44.35; H, 5.45; N, 13.41; F, 18.82 Found: C, 44.52; H, 5.01; N, 13.26; F, 18.52.

B. N-[4-[(Aminoiminomethyl)amino]butyl]-1-[N-(methylsulfonyl)-D-phenylalanyl]-L-prolinamide, trifluoroacetate (1:1) salt To a stirred solution of Part A amine (550 mg, 0.80 mmol) in 15 mL of dry $CH_2Cl_2$ and 15 mL of dry THF under argon was added in order triethylamine ($Et_3N$) (0.44 mL, 3.20 mmol) and methanesulfonyl chloride (68.0 μL, 0.88 mmol). This turbid mixture was stirred at room temperature for 3 h and diluted with 0.50 mL of water. The mixture was stirred at room temperature for 10 min and concentrated in vacuo. The residue was diluted with 30 mL of methanol, concentrated in vacuo and purified by preparative HPLC. The fractions were concentrated in vacuo and lyophilized to give 300 mg (75%) of title compound.

Opt. rot.: $[\alpha]_D$=−68.7° (c=1.00, methanol).

Elemental Analysis (%) Calc'd: C, 43.59; H, 5.31; N, 13.09; S, 4.99; F, 14.65 Found: C, 43.59; H, 5.33; N, 13.08; S, 4.80; F, 14.69

EXAMPLE 30

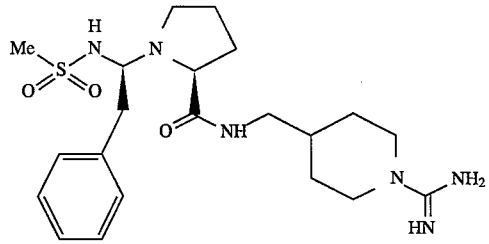

N-[[1-(Aminoiminomethyl)-4-piperidinyl]methyl]-1-[N-(methylsulfonyl)-D-phenylalanyl]-L-prolinamide A. 4-(Aminomethyl)-N,N'-bis[(1,1-dimethylethoxy)carbonyl]-1-piperidinecarboximidamide To a stirred solution of 4-aminomethylpiperidine (0.72 g, 6.31 mmol) in 40 mL of toluene was added benzaldehyde (0.78 mL, 6.94 mmol). The reaction solution was refluxed for 18 h and water was removed by a Dean Stark trap. The reaction solution was cooled to room temperature at which time bis-Boc amidinopyrazole (1.96 g, 6.31 mmol) was added. The reaction solution was stirred at room temperature for 48 h and concentrated in vacuo. The oily residue was diluted with 15 mL of 1M (aq) $KHSO_4$ solution and stirred at room temperature for 5 h. This aqueous solution was washed with ether (2×20 mL) and basified to pH 12 by the addition of 1N NaOH solution. This basic solution was then saturated with NaCl and extracted with dichloromethane (3×60 mL). The combined dichloromethane extracts were dried ($MgSO_4$), filtered and concentrated in vacuo to give 2.10 g (93%) of title amine which was used for the next transformation without further purification.

B. (S*)-N-[[1-[[[(1,1-Dimethylethoxy)carbonyl]amino][(1,1-dimethylethoxy)carbonyl]imino]methyl]-4-piperidinyl]methyl]-1-[1-[[(1,1-dimethylethoxy)carbonyl]amino]-2-phenylethyl]-L-prolinamide To a stirred solution of N-Boc-D-Phe-L-Pro-OH (0.73 g, 2.02 mmol), Part A amine (0.72 g, 2.02 mmol) and 1-hydroxybenzotriazole monohydrate (0.34 g, 2.02 mmol) in 30 mL of DMF was added in order 4-methylmorpholine (0.66 mL, 6.05 mmol) and ethyl-3-(3-dimethylamino)propyl carbodiimide hydrochloride (0.39 g, 2.02 mmol). The reaction solution was stirred at room temperature for 19 h and concentrated under pump vacuum at 45° C. The residue was diluted with 100 mL of saturated NaHCO₃ solution and extracted with dichloromethane (4×100 mL). The combined dichloromethane extracts were dried (MgSO₄), filtered and concentrated in vacuo. This was chromatographed on silica gel to give 0.70 g (50%) of title bis-Boc guanidine.

C. N-[[1-(Aminoiminomethyl)-4-piperidinyl]methyl]-1-D-phenylalanyl-L-prolinamide To a stirred solution of Part B bis-Boc guanidine (0.68 g, 0.97 mmol) in 6.0 mL of dichloromethane was added trifluoroacetic acid (TFA) (6.00 mL, 77.9 mmol). The reaction solution was stirred at room temperature for 3 h and concentrated in vacuo. This was purified by prep HPLC to give 310 mg (45%) of title compound.

D. N-[[1-(Aminoiminomethyl)-4-piperidinyl]methyl]-1-[N-(methylsulfonyl)-D-phenylalanyl]-L-prolinamide To a stirred solution of Part C guanidine (275 mg, 0.68 mmol) in 4.0 mL of dichloromethane and 2.0 mL of THF under argon at 0° C. was added Et₃N (0.38 mL, 2.74 mmol) and methanesulfonyl chloride (69 μL) in order. The reaction mixture was stirred at room temperature for 2.5 h and diluted with 2.0 mL of water. The mixture was concentrated in vacuo, and purified by prep HPLC to give 160 mg (37%) of title compound.

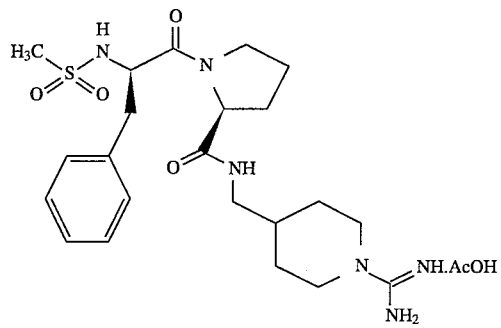

EXAMPLE 30a

Alternate Route for Preparation of N-[[1-(Aminoiminomethyl)-4-piperidinyl]methyl]-1-[N-(methylsulfonyl)-D-phenylalanyl]-L-prolinamide To a suspension of N-methylsulfonyl-D-phenylalanyl-proline (497 mg, 1.46 mmol), 4-(aminomethyl)-1-piperidinecarboximidamide (470 mg, 1.9 mmol) and HOBt (217 mg, 1.6 mmol) in 1:1 v/v isopropyl alcohol/water (4.5 mL) was added NMM (0.32 mL, 2.9 mmol). The homogeneous solution was cooled to 0° C. and ethyl-3-(3-dimethylamino)-propylcarbodiimide.hydrochloride salt (EDAC.HCl) (308 mg, 1.6 mmol) was added. After 18 hr the reaction was concentrated in vacuo, dissolved in water (10 mL) and washed with ether (2×75 mL). Aqueous NaOH (1N, 3.8 mL) was added until the aqueous layer attained pH 9.7, the aqueous layer was washed with ether (75 mL) and the process repeated. Aqueous HCl (1N, 3.8 mL) was added until the pH reached 2.0, the aqueous layer was washed with ethyl acetate (3×75 mL), concentrated in vacuo, dissolved in water, and lyophilized to give a foam which was subjected to chromatography on HP-20 polystyrene resin to provide the title compound (629 mg, 84%).

EXAMPLE 30b

N-[[(1-Aminoiminomethyl)-4-piperidinyl]methyl]-1-[N-(methylsulfonyl)-D-phenylalanyl]-L-prolinamide, acetate (1:1)

A. [[4-(Aminomethyl)-1-piperidinyl]imino-methylcarbamic acid, phenylmethyl ester

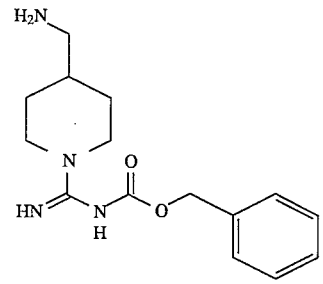

A(1).

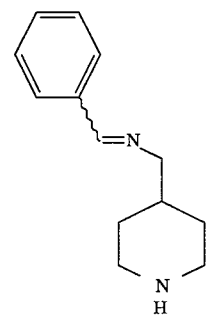

A 500-mL, round-bottomed flask equipped with Dean-Stark trap was sequentially charged with 4-aminomethylpiperidine (14.84 g, 129.96 mmole), toluene (250 mL), and benzaldehyde (14.98 g, 141.16 mmole). The mixture was heated to reflux under an argon atmosphere and stirred overnight (18 h). The reaction was cooled to room temperature and the toluene was removed in vacuo. Residual toluene was removed under high vacuum to provide 28.14 g of the title compound as an orange oil (quantitative yield). The crude product was carried directly into the next step.

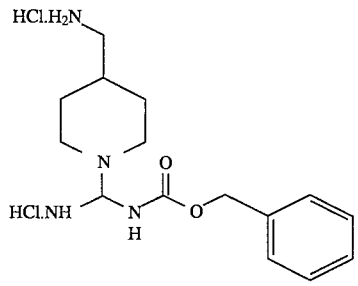

A(2).

A 500-mL, round-bottomed flask was sequentially charged with Part A(1) Schiff base (21.20 g, 104.8 mmole), acetonitrile (200 mL), [imino(1H-pyrazol-1-yl)methyl]carbamic acid, phenylmethyl ester (31.50 g, 128.96 mmole) and 1,8-diazabicyclo[5.4.0]undec-7-ene (DBU) (18 mL, 120.36 mmole). After stirring for five minutes, the solution became clear yellow. The reaction was heated to 50° C. and stirred under a nitrogen atmosphere for 16 h. After the reaction had cooled to room temperature, 12N hydrochloric acid (36 mL, 432 mmole, reaction mixture reached pH 1) was added over 20 minutes (exotherm to 40° C.). The reaction was stirred for 2.5 h at room temperature. The mixture was concentrated in vacuo to a yellow oil and isopropanol (35 mL) was added. With stirring, acetonitrile (250 mL) was added resulting in the separation of an oil. The mixture was heated to 40° C. providing a clear solution which was seeded. Within five minutes a white solid crystallized from solution. The slurry was stirred for an additional 40 minutes at 40° C. and then cooled to room temperature and stirred overnight. The product was collected by filtration and washed with 1:1 ethyl acetate/hexane (1×100 mL), 1:3 ethyl acetate/hexane (1×100 mL), and hexane (3×100 mL). Residual solvents were removed under high vaccuum to provide 29.95 g of an 11:1 mixture of [imino(1H-pyrazol-1-yl)methyl]carbamic acid, phenylmethyl ester, dihydrochloride salt: 4-aminomethyl piperidine, dihydrochloride salt as a white solid (79%).

A(3). [[4-(Aminomethyl)-1-piperidinyl]iminomethyl]carbamic acid, phenylmethyl ester Sodium hydroxide (4.45 g, 111.25 mmole) was dissolved in 150 mL of deionized water. The mixture of [imino(1H-pyrazol-1-yl)methyl]carbamic acid, phenylmethyl ester, dihydrochloride salt and 4-aminomethyl piperidine, dihydrochloride salt (prepared above, 16.18 g, 44.54 mmole) was added (pH of the cloudy solution was 13) and the mixture was extracted with dichloromethane (1×200 mL and 2×100 mL). The organic layers were combined and washed with brine (1×200 mL), dried (MgSO$_4$), filtered and concentrated in vacuo to provide the title compound as a white foam (12.29 g, 95%).

B. [N-(Methylsulfonyl)-D-phenylalanyl]-L-proline

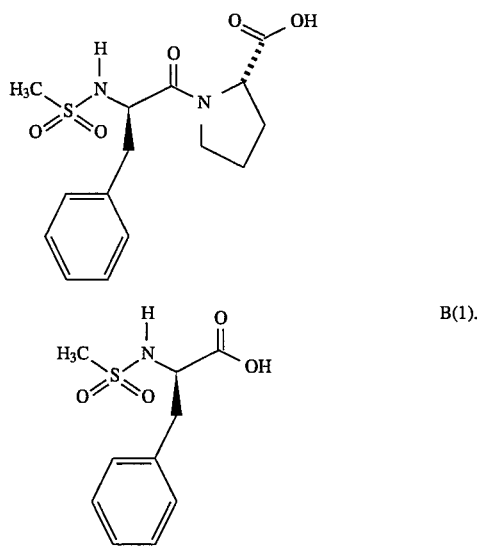

B(1).

D-Phenylalanine (15.01 g, 90.865 mmol) was weighed into a 250-mL, 5-necked, round-bottomed flask equipped with thermocouple, pH probe, overhead stirrer and two addition funnels (one a constant-rate funnel to ensure even addition of methanesulfonyl chloride). Sodium hydroxide (3.642 g, 91.05 mmol) was dissolved in 90 mL of deionized water and added to the reaction flask. With stirring, the mixture became a clear solution. The internal temperature was brought to −2° C. (pH 12.3). With rapid stirring, methanesulfonyl chloride (5.0 mL, 64.60 mmol) was added via the constant-rate addition funnel. Once pH 11 was reached, 6N NaOH was added dropwise to maintain the pH at 10.9 ±0.2. A second portion of methanesulfonyl chloride (4.2 mL, 54.26 mmol) was then added while maintaining the pH at 10.5±0.2 (internal temperature <8°) by dropwise addition of 6N sodium hydroxide. Once the pH had stabilized at 10.5, HPLC analysis of an aliquot showed a 9:1 mixture of the title compound to D-phenylalanine. A third portion of methanesulfonyl chloride (1.2 mL, 15.5 mmol) was then added at 0° over 5 minutes while maintaining the pH at 10.5±0.2. After the addition was complete and the pH had stabilized at 10.4, the reaction mixture was brought to pH 13 with 6N sodium hydroxide, allowed to warm to 15° C. over 2 hr, and then washed with methyl isobutylketone (2×100 mL). The aqueous layer was acidified to pH 1 with 6N hydrochloric acid and extracted with ethyl acetate (1×200 mL and 2×150 mL). The ethyl acetate layers were combined and washed with brine (1×150 mL), dried over MgSO$_4$, and concentrated in vacuo to yield a yellow oil (18.36 g, 83%). HPLC analysis of the oil showed a 7:1 mixture of the title compound to [N-methylsulfonyl-D-phenylalanine]-D-phenylalanine. This material was carried into the next step without further purification.

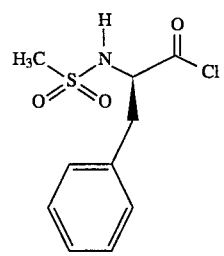

B(2).

The Part B(1) mixture of N-methylsulfonyl-D-phenylalanine and [N-methylsulfonyl-D-phenylalanine]-D-phenylalanine (18.36 g, 75.47 mmol) was dissolved in 250 mL of dichloromethane under an argon atmosphere. Heating to reflux and stirring for about 15 minutes was necessary to completely dissolve the material. After the solution had cooled to room temperature, DMF (0.23 mL, 2.97 mmol) was added and the internal temperature was further lowered to 3° C. (ice bath). Oxalyl chloride (7.4 mL, 84.85 mmol) was added in a steady stream over 2 minutes. After the addition was complete, the reaction was allowed to warm to room temperature over 3 hours and then stirred at room temperature for one hour. The mixture was concentrated in vacuo to a yellow oil, toluene (100 mL) was added and the solution was concentrated to a yellow oily solid (19.89 g, 101%). This material was stored in a refrigerator overnight under an argon atmosphere and was carried into the next step without further purification.

B(3). [N-(Methylsulfonyl)-D-phenylalanyl]-L-proline

The crude Part B(2) acid chloride prepared above was dissolved in 120 mL of toluene, with heating to 40° C., and then cooled to room temperature under an argon atmosphere. L-proline (13.11 g, 113.87 mmol) was weighed into a 500-mL, 5-necked flask equipped with two addition funnels, thermocouple, pH probe and overhead stirrer. Sodium hydroxide (2.68 g, 67 mmol) was dissolved in 120 mL of deionized water and added to the reaction flask. The proline readily dissolved with stirring to give a clear solution which was cooled to 0° C. The initial pH was 12.15. The acid chloride-toluene solution was added dropwise to the rapidly stirring proline solution until the pH reached 11.0 (internal temperature maintained at <5° C.). The remainder of the acid chloride was added dropwise over 25 minutes while maintaining the internal temperature below 5° C. and the pH at 11.0±0.2 by dropwise addition of 4N sodium hydroxide (23 mL total). The acid chloride was washed in with 20 mL of toluene. After the addition was complete and the pH had stabilized to 11.1, the icebath was removed and the reaction was allowed to warm to 12° C. over 30 minutes. The aqueous and organic layers were separated and the basic aqueous layer was washed with ethyl acetate (1×100 mL, discard). Ethyl acetate (350 mL) was added to the basic aqueous solution and while stirring vigorously, the mixture was acidified with 6N hydrochloric acid to pH 1. The organic and aqueous layers were separated and the acidic aqueous was extracted with ethyl acetate (2×150 mL). The combined ethyl acetate layers from the acidic extractions were washed with brine (1×150 mL), dried (MgSO$_4$), filtered, and concentrated in vacuo to a total weight of 260 g, providing a slurry of the title compound in the ethyl acetate. With stirring, 260 mL of hexane was added and the slurry was stirred for 4 h at room temperature. The white crystalline solid was collected by filtration, washed with hexane/ethyl acetate (2:1, 2×100 mL) followed by hexane (2×100 mL). Drying in vacuo provided the title compound (20.84 g, 84%) as a white crystalline solid.

C. N-[[1-(Aminoiminomethyl)-4-piperidinyl]methyl]-1-[N-(methylsulfonyl)-D-phenylalanyl]-L-prolinamide, acetate (1:1)

C(2). N-[[1-(Aminoiminomethyl)-4-piperidinyl]methyl]-1-[N-(methylsulfonyl)-D-phenylalanyl]-L-prolinamide, acetate (1:1)

A solution of Part C(1) CBZ-protected compound (13.22 g, 21.58 mmole) in MeOH (150 mL) was purged with argon for ten minutes. Palladium hydroxide on carbon (1.32 g) was added and the mixture was again purged with argon for ten minutes. The solution was then purged with hydrogen and the reaction was stirred under a hydrogen atmosphere for 2.5 hours. After the reaction was complete by HPLC, the mixture was purged with argon, filtered through celite and the celite washed with methanol (2×100 mL). Acetic acid was added and the solution was concentrated in vacuo to an oil. Isopropanol (100 mL) was added and the solution concentrated in vacuo to 45 g. The thick solution was seeded. With stirring, 180 mL of acetonitrile was added over 20 minutes. Within three hours, a white solid crystallized from solution and the resulting slurry was allowed to stir overnight at room temperature. The solid was collected by filtration and washed with acetonitrile (1×50 mL), 1:1 hexane/ethyl acetate (1×60 mL), and hexane (2×50 mL). The product was dried in vacuo to yield the title compound as a white crystalline solid (8.83 g, 76%).

C(1).

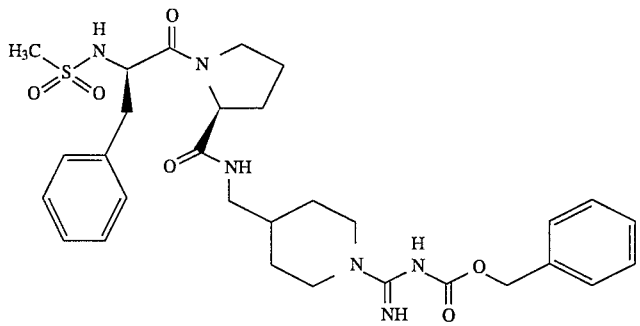

A 500-mL, round-bottomed flask was sequentially charged with Part A compound (10.41 g, 35.84 mmole), isopropanol (60 mL), deionized water (60 mL), and Part B compound (10.00 g, 29.38 mmole). Under an argon atmosphere, the clear yellow solution was brought to 10° C. and 1-hydroxybenzotriazole hydrate (4.40 g, 32.56 mmole) was added. The mixture was further cooled to 4° C. and 1-(3-dimethylaminopropyl)-3-ethlycarbodiimide hydrochloride (6.53 g, 34.06 mmole) was added. The resulting clear solution was stirred between 1° and 4° C. for 3 hours and then slowly warmed to 20° C. over 14 hours. A portion of the solvent (62 g) was removed in vacuo. Ethyl acetate (250 mL) was added. With stirring, deionized water (465 mL) and 6N hydrochloric acid (40 mL) were added. The aqueous and organic layers were separated and the aqueous layer was washed with ethyl acetate (1×100 mL). The combined ethyl acetate layers were concentrated to 100 g and extracted with 0.5N hydrochloric acid (2×60 mL). The combined acidic aqueous layers were brought to pH 6 with 12N sodium hydroxide and extracted with dichloromethane (1×250 mL and 2×150 mL). The dichloromethane layers were combined and washed with deionized water (1×150 mL) and brine (1×150 mL), dried (MgSO$_4$), filtered and concentrated in vacuo. The residual solvents were removed under high vacuum to provide title CBZ-protected compound as a white foam (15.44 g, 83% yield, corrected for ethyl acetate in $^1$H NMR). The crude product was carried directly into the next step.

EXAMPLE 31

N-[[1-(Aminoiminomethyl)-3-piperidinyl]methyl]-1-[N-(methylsulfonyl)-D-phenylalanyl]-L-prolinamide A. N-Boc-3-hydroxymethylpiperidine To a stirred solution of 3-hydroxymethylpiperidine (15.1 g, 131 mmol) and Et$_3$N (21.9 mL, 158 mmol) in 100 mL of dichloromethane was added dropwise a solution of di-t-butyl dicarbonate (31.5 g, 144 mmol) in 100 mL of dichloromethane over 1 h. The reaction was stirred at room temperature for 18 h and then diluted with 200 mL of dichloromethane. The resulting solution was washed with 1N HCl solution (3×100 mL), saturated NaHCO$_3$ solution (2×100 mL) and brine (1×100 mL). The organic layer was dried (MgSO$_4$), filtered and concentrated in vacuo to give N-Boc-3-hydroxymethylpiperidine (27.0 g, 96%).

B. 3-(Azidomethyl)-1-piperidinecarboxylic acid, 1,1-dimethylethyl ester

To a stirred solution of Part A N-Boc-3-hydroxymethylpiperidine (27.0 g, 126 mmol) in 150 mL of dry dichloromethane under argon at 0° C. was added in order triethylamine (22.7 mL, 163 mmol) and methanesulfonyl chloride (11.7 mL, 151 mmol). The reaction was stirred at room temperature for 1.5 h and diluted with 450 mL of dichloromethane. The reaction was washed with 0° C. 1N HCl solution (2×100 mL) and brine (1×100 mL). The dichloromethane layer was dried (Na$_2$SO$_4$), filtered and concentrated in vacuo. The residue was dissolved in 200 mL of DMF and combined with sodium azide (24.5 g, 377 mmol). The mixture was stirred at room temperature for 33 h and the solid was filtered off. The filtrate was concentrated under pump vacuum at 45° C. The residue was partitioned between 400 mL of EtOAc and 10% sodium thiosulfate solution (2×100 mL) and brine (1×100 mL). The EtOAc layer was dried (MgSO$_4$), filtered and concentrated in vacuo. Purification was effected by a flash column chromatography on silica gel to give 19.5 g (65%) of title azide.

C. 3-(Aminomethyl)-1-piperidinecarboxylic acid, 1,1-dimethylethyl ester

To a stirred solution of Part B azide (19.0 g, 79.2 mmol) in 250 mL of methanol under argon was added 10%Pd/C (3.80 g, 20% based on the weight of Part B azide). The atmosphere was replaced with hydrogen by several vacuum-fill cycles. The mixture was stirred at room temperature for 15 h. The catalyst was filtered through a 4 μM polycarbonate film and rinsed with methanol (4×30 mL). The filtrate was concentrated in vacuo to give 16.3 g (96%) of title amine.

D. N-[[1-[(1,1-Dimethylethoxy)carbonyl]-3-piperidinyl]methyl]-1-[N-[(phenylmethoxy)carbonyl]-D-phenylalanyl]-L-prolinamide To a stirred solution of Part C amine (2.00 g, 9,35 mmol), N-Cbz-D-Phe-L-Pro (3.70 g, 9.35 mmol), 1-hydroxybenzotriazole monohydrate (1.58 g, 9.35 mmol) and 4-methylmorpholine (3.07 mL, 28.0 mmol) was added ethyl-3-(3-dimethylamino)propyl carbodiimide hydrochloride (1.79 g, 9.35 mmol). The reaction solution was stirred at room temperature for 17 h and concentrated under pump vacuum at 45° C. The residue was dissolved in 360 mL of EtOAc and washed with 1N HCl solution (2×120 mL), saturated NaHCO$_3$ solution (1×120 mL) and brine (1×120 mL). The EtOAc layer was dried (MgSO$_4$), filtered, concentrated in vacuo and chromatographed on silica gel to give 1.30 g (23%) of title carbamate.

E. N-[[1-(Aminoiminomethyl)-3-piperidinyl]methyl]-1-[N-[(phenylmethoxy)carbonyl]-D-phenylalanyl]-L-prolinamide To a stirred solution of Part D carbamate (2.30 g, 3.89 mmol) in 10 mL of dry dichloromethane was added 0° C. 4N HCl in dioxane (15.0 mL, 60.0 mmol). The solution was stirred at room temperature for 3 h and diluted with 300 mL of ether. The precipitate was filtered off and rinsed with ether (3×30 mL). The precipitate was dried under pump vacuum at room temperature and purified by prep HPLC to give 1.39 g (59%) of intermediate amine.TFA salt. To a stirred solution of the intermediate amine.TFA salt (500 mg, 0.83 mmol) and diisopropylethyl amine (0.35 mL, 1.98 mmol) in 2.0 mL of DMF was added 1H-pyrazole-1-carboxamidine (133 mg, 0.91 mmol). The reaction solution was stirred at room temperature for 6 h and diluted with 100 mL of ether. The desired oily precipitate was separated from the ether solution and purified by prep HPLC to give 250 mg (47%) of title Cbz-carbamate.

F. N-[[1-(Aminoiminomethyl)-3-piperidinyl]methyl]-1-D-phenylalanyl-L-prolinamide To a stirred solution of Part E Cbz-carbamate (240 mg, 0.37 mmol) in 10 mL of methanol under argon was added 20%Pd(OH)$_2$/C (48 mg, 20% based on the weight of Part E Cbz-carbamate). The atmosphere was replaced with hydrogen by several vacuum-fill cycles. The reaction mixture was stirred at room temperature for 24 h. The catalyst was filtered off and rinsed with methanol (4×20 mL). The filtrate was concentrated in vacuo. The residue was dissolved in 50 mL of a solution of 0.1%TFA in water and lyophilized to give 220 mg (82%) of title compound.

G. N-[[1-(Aminoiminomethyl)-3-piperidinyl]methyl]-1-[N-(methylsulfonyl)-D-phenylalanyl]-L-prolinamide Following the procedure of Example 30 Part D except substituting the Part F amidine for the Example 30 Part C amidine, the title compound is obtained.

EXAMPLE 32

N-[[1-(Aminoiminomethyl)-4-piperidinyl]methyl]-1-[N-[(phenylmethyl)sulfonyl]-D-alanyl]-L-prolinamide, trifluoroacetate (1:1) salt A. N-[[(Phenylmethoxy)-carbonyl]-D-alanyl]-L-proline methyl ester To a solution of N-CBZ-D-alanine (28.1 g, 0.149 mol) in DMF (250 mL) at 0° C., was added L-proline-methylester-.HCl (24.6 g, 0.149 mmol), 1-hydroxybenzotriazole hydrate (22.2 g, 0.164 mmol), ethyl-3-(3-dimethylamino)-propyl carbodiimide.HCl (31.4 g, 0.164 mmol) and 4-methylmorpholine (22.6 g, 0.224 mmol). The reaction mixture was stirred for 12 h while allowing the reaction to warm to room temperature. The reaction mixture was poured in water (750 mL) and extracted with ethyl acetate (2×150 mL). The combined organic extracts were washed as follows: KHSO$_4$ (0.25M, 2×50 mL), water (1×50 mL), saturated aqueous NaHCO$_3$ (2×50 mL) and saturated NaCl (1×50 mL). The organic layer was dried over MgSO$_4$, filtered and the solvent removed in vacuo to give the title compound, 41.16 g (92%), as an oil. MS (M+H)$^+$=301$^+$.

B. N-[[[(Phenylmethyl)sulfonyl]carbonyl]-D-alanyl]-L-proline methyl ester

A solution of Part A compound (1.56 g, 5.2 mmol) in trifluoroacetic acid (3 mL) was stirred at 0° C. for 1.5 hr and concentrated in vacuo to give the corresponding TFA salt. This salt was dissolved in chloroform (10 mL), and triethylamine (2.2 mL, 15.6 mmol) and benzylsulfonyl chloride (1.48, 7.8 mmol) at 0° C. were added to it. The reaction mixture was stirred to room temperature overnight. After 25 h, the reaction mixture was poured into EtOAc (50 mL), washed with 0.25M aqueous KHSO$_4$ (2×20 mL), H$_2$O (1×20 mL) and saturated aqueous NaHCO$_3$ (2×20 mL), successively; dried over MgSO$_4$, filtered and concentrated in vacuo to give title compound as an oil (1.56 g, 85%): MS (M+H)$^+$ =355$^+$.

C. N-[[[(Phenylmethyl)sulfonyl]carbonyl]-D-alanyl]-L-proline

To a solution of Part B compound (1.33 g, 3.75 mmole) in THF (10 mL) at 0° C. was added aqueous NaOH (1.0N, 9.5 mL). After 30 min the reaction mixture was warmed to room temperature and stirring continued for an additional 4 h. The organic solvent was removed in vacuo. The aqueous layer was acidified to pH of 2–3 and extracted with ethyl acetate (3×10 mL). The combined extracts were dried over MgSO$_4$, filtered and the solvent removed in vacuo to give title compound, 1.21 g (94%), as a white solid.

MS (M+H)$^+$=341$^+$.

D. N-[[[1-(1,1-Dimethylethoxy)carbonyl]-4-piperidinyl]methyl]-1-[N-[(phenylmethyl)sulfonyl]-D-alanyl]-L-prolinamide To a solution of Part C compound (1.09 g, 3.2 mmol) in DMF (15 mL) at 0° C. were added N-1,1-[(dimethylethoxy)carboxyl]-4-methylaminopiperidine (prepared in Example 33 Part A) (0.685 g, 3.2 mmol), 1-hydroxybenzotriazole hydrate (0.476 g, 3.5 mmol), ethyl-3-(3-dimethylamino)-propyl carbodiimide.HCl (0.675 g, 3.5 mmol) and 4-methylmorpholine until basic by pH paper. The reaction mixture was stirred for 12 h while allowing the reaction to warm to room temperature. The reaction mixture was poured into 0.25M aqueous KHSO$_4$ (50 mL) and extracted with EtOAc (2×20 mL). The organic layers were combined and washed with 0.25M aqueous KHSO$_4$ (1×30 mL), water (1×25 mL), saturated aqueous NaHCO$_3$ (2×25 mL) and water (1×20 mL). The organic layer was dried over MgSO$_4$, filtered and the solvent removed in vacuo to give title compound, 1.67 g (9%), as an oil.

MS (M+H)⁺=537⁺.

E. N-[[1-(Aminoiminomethyl)-4-piperidinyl]methyl]-1-[N-[(phenylmethyl)sulfonyl]-D-alanyl]-L-prolinamide, trifluoroacetate (1:1) salt A solution of Part D compound (1.17 g, 2.2 mmol) in trifluoroacetic acid (10.0 mL) was stirred at 0° C. for 5 h. The reaction mixture was concentrated in vacuo to give the corresponding TFA salt. To a solution of this salt (2.2 mmol), 1H-pyrazole-1-carboxamidine hydrochloride (0.474 g, 3.3 mmol) and N,N-diisopropylethylamine (1.1 mL, 6.5 mmol) in DMF (3.0 mL) were added and stirred for 3 days. The reaction mixture was concentrated in vacuo and purified by preparative HPLC (CH₃CN/H₂O with TFA buffer using a C-18 silica gel column). The appropriate fractions were combined, concentrated in vacuo, dissolved in H₂O and lyophilized to yield title compound (0.486 g, 38%) as a white solid:

$[a]_D$=+1.4 (c 1.0, MeOH)

MS (M+H)⁺=479⁺

Anal. Calc'd for $C_{22}H_{34}N_6O_4S$.1.3 TFA.0.7 H₂O: C, 46.21; H, 5.78; N, 13.14; S, 5.01; F, 11.59 Found: C, 46.42; H, 5.83; N, 12.88; S, 4.97; F, 11.82

EXAMPLE 33

N-[[1-(Aminoiminomethyl)-4-piperidinyl]methyl]-1-[N-[(2,2,2-trifluoroethyl)sulfonyl]-D-phenylalanyl]-L-prolinamide, trifluoroacetate (1:1) salt A. N-1,1-[(Dimethylethoxy)carbonyl]-4-methylamino piperidine Benzaldehyde (14.6 g, 0.138 mmol), 4-(aminomethyl)-piperdine (14.29 g, 0.125 mmol) and toluene (250 mL) were combined and heated at reflux for 4.5 h with removal of water. The reaction mixture was cooled to −25° C. and di-t-butyl dicarbonate (28.7 g, 0.131) was added. The reaction mixture was allowed to warm to room temperature and stirred an additional 8 h. To this reaction mixture was added aqueous KHSO₄ (1.0M, 120 mL) and stirred for 3 h. The organic layer was removed and the remaining aqueous layer was extracted with ether (3×75 mL). The aqueous layer was made basic through the addition of aqueous NaOH (1.0M, 130 mL) and extracted with ether (3×75 mL). The combined organic extracts were dried over NaSO₄ filtered, and the solvent removed in vacuo to give title compound, 24.4 g (9%), as a white solid.

B. N-[[(Phenylmethoxy)-carbonyl]-D-phenylalanyl]-L-proline methyl ester

To a solution of N-CBZ-D-phenylalanine (47.3 g, 0.158 mmol) in DMF (300 mL) at 0° C., was added L-proline-methylester.HCl (25.0 g, 0.151 mmol), 1-hydroxybenzotriazole hydrate (20.28 g, 0.166 mmol), ethyl-3-(3-dimethylamino)-propyl carbodiimide.HCl (31.8 g, 0.166 mmol) and 4-methylmorpholine (16.0 g, 0.159 mmol). The reaction mixture was stirred for 8 h while allowing the reaction to warm to room temperature. The reaction mixture was poured in water (1.2 L) and extracted with ethyl acetate (3×300 mL). The combined organic extracts were washed as follows: KHSO₄ (0.25M, 2×200 ml), water (1×200 mL), saturated aqueous NaHCO₃ (2×200 ml) and saturated NaCl (1×200 mL). The organic layer was dried over MgSO₄, filtered and the solvent removed in vacuo to give title compound, 60.9 g (98%), as an oil.

MS (M+H)⁺=411⁺.

C. N-[[(Phenylmethoxy)-carbonyl]-D-phenylalanyl]-L-proline

To a solution of Part B compound (57.8 g, 0.141 mol) in MeOH (180 mL) and THF (60 mL) at 0° C. was added aqueous NaOH (1.0N, 183 mL). After 30 min the reaction mixture was warmed to room temperature and stirring continued for an additional 4 h. Aqueous HCl (1.0N, 42 mL) was added and the organic solvents removed in vacuo. The resulting aqueous layer was acidified to pH of 2–3 and extracted with ethyl acetate (2×300 mL). The combined extracts were dried over MgSO₄, filtered and the solvent removed in vacuo to give title compound, 45.53 g (97%), as a white solid. MS (M+H)⁺=397⁺.

D. N-[[[1-(1,1-Dimethylethoxy)carbonyl]-4-piperidinyl]methyl]-1-[N-[(phenylmethoxy)carbonyl]-D-phenylalanyl]-L-prolinamide To a solution of Part C compound (19.39 g, 48.90 mmol) in DMF (120 mL) at 0° C., was added Part A compound (9.98 g, 46.57 mmol), 1-hydroxybenzotriazole hydrate (6.26 g, 51.23 mmol) and ethyl-3-(3-dimethylamino)-propyl carbodiimide.HCl (9.82 g, 51.23 mmol). The reaction mixture was stirred for 12 h while allowing the reaction to warm to room temperature. The reaction mixture was poured in water (500 mL) and extracted with ethyl acetate (3×100 mL). The combined organic extracts were washed as follows: KHSO₄ (0.25M, 2×50 mL), water (1×75 mL), saturated aqueous NaHCO₃ (2×75 mL) and saturated NaCl (1×50 mL). The organic layer was dried over MgSO₄, filtered and the solvent removed in vacuo to give title compound, 23.4 g (85%), as an oil. MS (M+H)⁺=593⁺.

E. N-[[[[1-(1,1-Dimethylethoxy)carbonyl]-4-piperidinyl]methyl]-1-D-phenylalanyl]-L-prolinamide To a stirred solution of Part D compound (15.00 g, 25.3 mmol) in MeOH (150 mL) was added Pd/C (1.50 g) and the reaction mixture was placed under 1 atmosphere of hydrogen. An additional Pd/C (2.5 g) was added after stirring for 2 h. The reaction was complete after stirring 8 more hours. The reaction mixture was filtered and the solvent removed in vacuo to give title compound, 11.41 g (91%), as a white solid. MS (M+H)⁺=459⁺.

F. N-[[[1-(1,1-Dimethylethoxy)carbonyl]-4-piperidinyl]methyl]-1-[N-[(2,2,2-trifluoroethyl)sulfonyl]-D-phenylalanyl]-L-prolinamide To a solution of Part E compound (1.71 g, 3.5 mmol) and triethylamine (2.5 mL, 17.9 mmol) in chloroform (10 mL) at 0° C. under argon was added trifluoroethylsulfonyl chloride (0.5 mL, 4.5 mmol). The reaction mixture was stirred to room temperature overnight. After 24 hr, triethylamine (2.0 mL, 14.3 mmol) and trifluoroethylsulfonyl chloride (0.5 mL, 4.5 mmol) were added at 0° C. The ice-water bath was removed, and the reaction was stirred for 6 h. The mixture was diluted with 0.25M aqueous KHSO₄ and EtOAc. After separation of the two layers, the organic layer was washed with 0.25M aqueous KHSO₄, H₂O, saturated aqueous NaHCO₃, and H₂O, successively; dried over NaSO₄, filtered and concentrated in vacuo to give title compound, (1.60 g, 75%):MS (M+H)⁺=605⁺.

G. N-[[1-(Aminoiminomethyl)-4-piperidinyl]methyl]-1-[N-[(2,2,2-trifluoroethyl)sulfonyl]-D-phenylalanyl]-L-prolinamide, trifluoroacetate (1:1)

To a solution of Part F compound (1.60 g, 2.6 mmol) in dichloromethane (4.4 mL) at 0° C. under argon was added trifluoroacetic acid (3.0 mL, 38.9 mmol). After 5.5 h, the reaction mixture was concentrated in vacuo to give the corresponding TFA salt. To a solution of this salt (1.3 mmol) and 1H-pyrazole-1-carboxamidine hydrochloride (0.311 g, 2.1 mmol) in DMF (1.3 mL) under argon was added N,N-diisopropylethylamine (0.7 mL, 4.0 mmol). After 2 days, 1H-pyrazole-1-carboxamidine hydrochloride (0.150 g, 1.0 mmol) and N,N-diisopropylethylamine (0.5 mL, 2.9 mmol) were added. After 1 day, 1H-pyrazole-1-carboxamidine hydrochloride (0.150 g, 1.0 mmol) and N,N-diisopropylethylamine (0.5 mL, 2.9 mmol) were added. After 2 days, the reaction mixture was concentrated in vacuo and purified by preparative HPLC (CH$_3$CN/H$_2$O with TFA buffer using a C-18 silica gel column). The appropriate fractions were combined, concentrated in Vacuo, dissolved in H$_2$O and lyophilized to yield title compound (0.256 g, 29%) as a white solid:

[a]$_D$=−56.0 (c 0.50, MeOH)
MS (M+H)$^+$=547$^+$
Anal. Calc'd for C$_{23}$H$_{33}$N$_6$O$_4$SF$_3$·1.22 TFA·1.14 H$_2$O: C, 43.26; H, 5.21; N, 11.90; S, 4.54; F, 17.92 Found: C, 42.82; H, 4.87; N, 11.48; S, 4.98; F, 17.52

EXAMPLE 34

N-[[1-(Aminoiminomethyl)-4-piperidinyl]methyl]-1-[N-[(phenylmethyl)sulfonyl]-L-alanyl]-L-prolinamide, trifluoroacetate (1:1) salt A. N-[[(t-Butoxy)-carbonyl]-L-alanyl]-L-proline methyl ester To a solution of N-BOC-L-alanine (150 mmol) in DMF (250 mL) at 0° C., is added proline methyl ester. HCl (150 mmol), 1-hydroxybenzotriazole hydrate (22.2 g, 0.164 mmol), ethyl-3-(3-dimethylamino)propyl carbodiimide.HCl (31.4 g, 0.164 mmol) and 4-methylmorpholine (22.6 g, 0.224 mmol). The reaction mixture is stirred for 12 h while allowing the reaction to warm to room temperature. The reaction mixture is poured in water (750 mL) and extracted with ethyl acetate (2×150 mL). The combined organic extracts are washed as follows: KHSO$_4$ (0.25M, 2×50 mL), water (1×50 mL), saturated aqueous NaHCO$_3$ (2×50 mL) and saturated NaCl (1×50 mL). The organic layer is dried over MgSO$_4$, filtered and the solvent removed in vacuo to give title compound.

B. N-[[(Phenylmethyl)sulfonyl]carbonyl]-L-alanyl]-L-proline methyl ester

A solution of Part A compound (5.2 mmol) in trifluoroacetic acid (3 mL) is stirred at 0° C. for 1.5 hr and concentrated in vacuo to give the corresponding TFA salt. This salt is dissolved in chloroform (10 mL), and triethylamine (2.2 mL, 15.6 mmol) and benzylsulfonyl chloride (1.48, 7.8 mmol) at 0° C. are added to it. The reaction mixture is stirred to room temperature overnight. After 25 h, the reaction mixture is poured into EtOAc (50 mL), washed with 0.25M aqueous KHSO$_4$ (2×20 mL), H$_2$O (1×20 mL) and saturated aqueous NaHCO$_3$ (2×20 mL), successively; dried over MgSO$_4$, filtered and concentrated in vacuo to give title compound.

C. N-[[(Phenylmethyl)sulfonyl]carbonyl]-L-alanyl]-L-proline

To a solution of Part B compound (3.75 mmole) in THF (10 mL) at 0° C. is added aqueous NaOH (1.0N, 9.5 mL). After 30 min the reaction mixture is warmed to room temperature and stirring continued for an additional 4 h. The organic solvent is removed in vacuo, the aqueous layer acidified to pH of 2–3 and extracted with ethyl acetate (3×10 mL). The combined extracts are dried over MgSO$_4$, filtered and the solvent removed in vacuo to give title compound.

D. N-[[[1-(1,1-Dimethylethoxy)carbonyl]-4-piperidinyl]methyl]-1-[N-[(phenylmethyl)sulfonyl]-L-alanyl]-L-prolinamide To a solution of Part C compound (3.2 mmol) in DMF (15 mL) at 0° C. is added N1-BOC-4-methylamino piperidine (3.2 mmol), 1-hydroxybenzotriazole hydrate (0.476 g, 3.5 mmol), ethyl-3-(3-dimethylamino)-propyl carbodiimide-.HCl (0.675 g, 3.5 mmol) and 4-methylmorpholine until basic by pH paper. The reaction mixture is stirred for 12 h while allowing the reaction to warm to room temperature. The reaction mixture is poured into 0.25M aqueous KHSO$_4$ (50 mL) and extracted with EtOAc (2×20 mL). The organic layers are combined and washed with 0.25M aqueous KHSO$_4$ (1×30 mL), water (1×25 mL), saturated aqueous NaHCO$_3$ (2×25 mL) and water (1×20 mL), the organic layer dried over MgSO$_4$, filtered and the solvent removed in vacuo to give title compound.

E. N-[[1-(Aminoiminomethyl)-4-piperidinyl]methyl]-1-[N-[(phenylmethyl)sulfonyl]-L-alanyl]-L-prolinamide, trifluoroacetate (1:1) salt A solution of Part D compound (2.2 mmol) in trifluoroacetic acid (10.0 mL) is stirred at 0° C. for 5 h. The reaction mixture is concentrated in vacuo to give the corresponding TFA salt. To a solution of this salt (2.2 mmol), 1H-pyrazole-1-carboxamidine hydrochloride (0.474 g, 3.3 mmol) and N,N-diisopropylethylamine (1.1 mL, 6.5 mmol) in DMF (3.0 mL) are added and stirred for 3 days. The reaction mixture is concentrated in vacuo and purified by preparative HPLC (CH$_3$CN/H$_2$O with TFA buffer using a C-18 silica gel column). The appropriate fractions are combined, concentrated in vacuo, dissolved in H$_2$O and lyophilized to yield title compound.

EXAMPLE 35

N-[[1-(Aminoiminomethyl)-4-piperidinyl]methyl]-1-[N-[(phenylmethyl)sulfonyl]-glycyl]-L-prolinamide, trifluoroacetate (1:1) salt A. N-[[(t-Butoxy)-carbonyl]-glycyl]-L-proline methyl ester To a solution of N-BOC-glycine (150 mmol) in DMF (250 mL) at 0° C., is added proline methyl ester. HCl (150 mmol), 1-hydroxybenzotriazole hydrate (22.2 g, 0.164 mmol), ethyl-3-(3-dimethylamino)propyl carbodiimide.HCl (31.4 g, 0.164 mmol) and 4-methylmorpholine (22.6 g, 0.224 mmol). The reaction mixture is stirred for 12 h while allowing the reaction to warm to room temperature. The reaction mixture is poured in water (750 mL) and extracted with ethyl acetate (2×150 mL). The combined organic extracts are washed as follows: KHSO$_4$ (0.25M, 2×50 mL), water (1×50 mL), saturated aqueous NaHCO$_3$ (2×50 mL) and saturated NaCl (1×50 mL). The organic layer is dried over MgSO$_4$, filtered and the solvent removed in vacuo to give title compound.

B. N-[[[(Phenylmethyl)sulfonyl]carbonyl]glycyl]-L-proline methyl ester

A solution of Part A compound (5.2 mmol) in trifluoroacetic acid (3 mL) is stirred at 0° C. for 1.5 hr and concentrated in vacuo to give the corresponding TFA salt. This salt is dissolved in chloroform (10 mL), and triethylamine (2.2 mL, 15.6 mmol) and benzylsulfonyl chloride (1.48, 7.8 mmol) at 0° C. are added to it. The reaction mixture is stirred to room temperature overnight. After 25 h, the reaction mixture is poured into EtOAc (50 mL), washed with 0.25M aqueous KHSO$_4$ (2×20 mL), H$_2$O (1×20 mL) and saturated aqueous NaHCO$_3$ (2×20 mL), successively; dried over MgSO$_4$, filtered and concentrated in vacuo to give title compound.

C. N- [[[(Phenylmethyl)sulfonyl]carbonyl]glycyl]-L-proline

To a solution of Part B compound (3.75 mmole) in THF (10 mL) at 0° C. is added aqueous NaOH (1.0N, 9.5 mL). After 30 min the reaction mixture is warmed to room temperature and stirring continued for an additional 4 h. The organic solvent is removed in vacuo, the aqueous layer acidified to pH of 2–3 and extracted with ethyl acetate (3×10 mL). The combined extracts are dried over MgSO$_4$, filtered and the solvent removed in vacuo to give title compound.

D. N-[[[1-(1,1-Dimethylethoxy)carbonyl]-4-piperidinyl]methyl]-1-[N-[(phenylmethyl)sulfonyl]-glycyl]-L-prolinamide To a solution of Part C compound (3.2 mmol) in DMF (15 mL) at 0° C. is added N1-BOC-4-methylamino piperidine (3.2 mmol), 1-hydroxybenzotriazole hydrate (0.476 g, 3.5 mmol), ethyl-3-(3-dimethylamino)-propyl carbodiimide-.HCl (0.675 g, 3.5 mmol) and 4-methylmorpholine until basic by pH paper. The reaction mixture is stirred for 12 h while allowing the reaction to warm to room temperature. The reaction mixture is poured into 0.25M aqueous KHSO$_4$ (50 mL) and extracted with EtOAc (2×20 mL). The organic layers are combined and washed with 0.25M aqueous KHSO$_4$ (1×30 mL), water (1×25 mL), saturated aqueous NaHCO$_3$ (2×25 mL) and water (1×20 mL), the organic layer dried over MgSO$_4$, filtered and the solvent removed in vacuo to give title compound.

E. N-[[1-(Aminoiminomethyl)-4-piperidinyl]methyl]-1-[N-[(phenylmethyl)sulfonyl]glycyl]-L-prolinamide, trifluoroacetate (1:1) salt A solution of Part D compound (2.2 mmol) in trifluoroacetic acid (10.0 mL) is stirred at 0° C. for 5 h. The reaction mixture is concentrated in vacuo to give the corresponding TFA salt. To a solution of this salt (2.2 mmol), 1H-pyrazole-1-carboxamidine hydrochloride (0.474 g, 3.3 mmol) and N,N-diisopropylethylamine (1.1 mL, 6.5 mmol) in DMF (3.0 mL) are added and stirred for 3 days. The reaction mixture is concentrated in vacuo and purified by preparative HPLC (CH$_3$CN/H$_2$O with TFA buffer using a C-18 silica gel column). The appropriate fractions are combined, concentrated in vacuo, dissolved in H$_2$O and lyophilized to yield title compound.

EXAMPLES 36 to 53

Following the procedures of Examples 30 to 33, the following examples of compounds of the invention may be prepared.

TABLE

| Example No. | R$^3$ | R | R$^2$ | R$^1$ | n | p | o | A | R$^4$ |
|---|---|---|---|---|---|---|---|---|---|
| 36 | CH$_3$ | CH$_2$OH(S) | H | CH$_3$ | 1 | 0 | — | piperidinyl | H$_2$N—C(=NH)— |
| 37 | C$_6$H$_5$ | H | OH | H | 0 | 1 | CO | morpholinone | H$_2$N—C(=NH)— |
| 38 | pyridinyl | —CH$_2$C$_6$H$_5$(R) | OCH$_3$ | CH$_3$ | 0 | 2 | — | azetidinone | H$_2$N—C(=NH)— |
| 39 | imidazolyl | —CH$_2$C$_6$H$_5$(S) | | | | | | | |

TABLE-continued $$R^3-\underset{\underset{O}{\overset{O}{\|}}}{S}-\overset{H}{N}-\underset{R}{\overset{H}{C}}-\overset{O}{\underset{\|}{C}}-N\begin{pmatrix}CH_2-\overset{R^2}{\underset{|}{C}H}-R^1\\(CH_2)_n\end{pmatrix}$$
$$O=C-NH-(CH_2)_p-Q-A-R^4$$

| Example No. | $R^3$ | R | $R^2$ | $R^1$ | n | p | o | A | $R^4$ |
|---|---|---|---|---|---|---|---|---|---|
| 40 | pyrazin-2-yl | —CH₂CH₂CONH₂(S) | H | H | 1 | 0 | — | 1,4-phenylene | —CH₂NH₂ |
| 41 | C₆H₅ | —CH₂CH₂CONH₂(R) | H | CH₃ | 1 | 1 | CO | 1,4-cyclohexylene | —CH₂NH₂ |
| 42 | 4-pyridyl | —CH(OH)CH₃(S—Thr) | —CHCH₂CH₂CH— | | 0 | 2 | — | 1,4-phenylene | —NH—C(=NH)NH₂ |
| 43 | 4-methyloxazol-2-yl | CH(OH)CH₃(S-alloThr) | CH₃ | H | 1 | 2 | CO | 1-methyl-3-methyl-2-oxopyrrolidinyl | —C(=NH)NH₂ |
| 44 | 4-methylthiazol-2-yl | 3-indolylmethyl (R) | SCH₃ | CH₃ | 1 | 1 | — | 1-methyl-3-piperidyl | —C(=NH)NH₂ |
| 45 | quinolin-6-yl | —CH₂CH₂CO₂H(R) | H | CH₃ | 0 | 0 | CO | 1-azetidin-3-yl | —C(=NH)NH₂ |
| 46 | C₂H₅ | CH₂OCH₂Ph(R) | H | H | 1 | 0 | — | 2-morpholinyl | —C(=NH)NH₂ |
| 47 | C₆H₅CH₂ | CH₂CH₂Ph(S) | H | H | 1 | 1 | — | 1-methyl-3-piperidyl | —C(=NH)NH₂ |

TABLE-continued

Structure:

$$R^3-\underset{\underset{O}{\|}}{\overset{\overset{O}{\|}}{S}}-N-\underset{R}{\overset{H}{C}}-\overset{O}{\overset{\|}{C}}-N\begin{pmatrix}CH_2-\underset{R^1}{\overset{R^2}{CH}}\\ (CH_2)_n\\ |\\ O=C\\ |\\ NH\\ |\\ (CH_2)_p\\ |\\ Q\\ |\\ A\\ |\\ R^4\end{pmatrix}$$

| Example No. | R³ | R | R² | R¹ | n | p | o | A | R⁴ |
|---|---|---|---|---|---|---|---|---|---|
| 48 | 1,2,3,4-tetrahydroquinolin-3-ylmethyl | (1-methylpiperidin-4-yl)methylamino | H | H | 1 | 2 | — | 1-methylpiperidin-3-yl | —C(=NH)NH₂ |

EXAMPLE 49

N-[[1-(Aminoiminomethyl)-4-piperidinyl]methyl]-1-[N-(ethylsulfonyl)-D-phenylalanyl]-L-prolinamide, trifluoroacetate (1:1) salt $[\alpha]_D = -49.2$ (c 1.08, MeOH)
MS (M+H)⁺=493⁺

Anal. Calc'd for $C_{23}H_{36}N_6O_4S \cdot 1.4$ TFA$\cdot 1.0$ H₂O: C, 46.23; H, 5.92; N, 12.54; S, 4.78; F, 11.90 Found: C, 46.23; H, 6.08; N, 12.39; S, 4.71; F, 11.98

EXAMPLE 50

N-[[1-(Aminoiminomethyl)-4-piperidinyl]methyl]-1-[N-(propylsulfonyl)-D-phenylalanyl]-L-prolinamide, trifluoroacetate (1:1) salt $[\alpha]_D = -47.0$ (c 1.02, MeOH)
MS (M+H)⁺=507⁺

Anal. Calc'd for $C_{24}H_{38}N_6O_4S \cdot 1.15$ TFA$\cdot 1.2$ H₂O: C, 47.91; H, 6.35; N, 12.74; S, 4.86; F, 9.94 Found: C, 47.90; H, 6.21; N, 12.50; S, 4.82; F, 10.06

EXAMPLE 51

N-[[1-(Aminoiminomethyl)-4-piperidinyl]methyl]-1-[N-[(phenylmethyl)sulfonyl]-D-phenylalanyl]-L-prolinamide, trifluoroacetate (1:1) salt $[\alpha]_D = -44.6$ (c 0.8, MeOH)
MS (M+H)⁺=555⁺

Anal. Calc'd for $C_{28}H_{38}N_6O_4S \cdot 1.55$ TFA$\cdot 0.67$ H₂O: C, 50.31; H, 5.42; N, 11.32; S, 4.32; F, 11.90 Found: C, 50.31; H, 5.69; N, 11.24; S, 4.26; F, 11.97

EXAMPLE 52

N-[[1-(Aminoiminomethyl)-4-piperidinyl]methyl]-1-[N-(phenylsulfonyl)-D-phenylalanyl]-L-prolinamide, trifluoroacetate (1:1) salt $[\alpha]_D = +10.1$ (c 1.0, MeOH)
MS (M+H)⁺=541⁺

Anal. Calc'd for $C_{27}H_{36}N_6O_4S \cdot 1.3$ TFA$\cdot 0.83$ H₂O: C, 50,51; H, 5.58; N, 11.94; S, 4.55; F, 10.53 Found: C, 50.51; H, 5.47; N, 11.83; S, 4.71; F, 10.52

EXAMPLE 53

N-[[1-(Aminoiminomethyl)-4-piperidinyl]methyl]-1-[N-[(1-methylethyl)sulfonyl]-D-phenylalanyl]-L-prolinamide, trifluoroacetate (2:3) salt $[\alpha]_D = -43.1$ (c 1.10, MeOH)
MS (M+H)⁺=507⁺

Anal. Calc'd for $C_{24}H_{38}N_6O_4S \cdot 1.5$ TFA$\cdot 1.35$ H₂O: C, 46.20; H, 6.06; N, 11.97; S, 4.57; F, 12.18 Found: C, 46.61; H, 5.86; N, 11.95; S, 4.44; F, 12.02

EXAMPLE 54

N-[[1-(Aminoiminomethyl)-4-piperidinyl]methyl]-1-[N-((±)-10-camphorsulfonyl)-D-phenylalanyl]-L-prolinamide, trifluoroacetate (1:1) salt

A.

[Structure: Cbz-HN-CH(CH₂Ph)-C(=O)-N(pyrrolidine)-C(=O)-NH-CH₂-(4-piperidinyl)-N-C(=N-Boc)-NH-Boc]

N-[[1-[[[1,1,-Dimethylethoxy)carbonyl]amino[[1,1,-dimethylethoxy)carbonyl]imino]methyl]-4-piperidinyl]methyl]-1-[(N-carbobenzyloxy)-D-phenylalanyl]-L-prolinamide To a stirred solution of N-[[1-(1,1-dimethylethoxycarbonyl)-4-piperidinyl]methyl]-1-[N-(carbobenzyloxy)-D-phenylalanyl]-L-prolinamide (10.0 g, 16.9 mmol) in 10 mL of dry dichloromethane was added a solution of 4N HCl in dioxane (25 mL, 100 mmol). The reaction solution was stirred at room temperature for 2.5 h and concentrated in vacuo to give the intermediate hydrochloride salt. To a stirred solution of this salt, bis-t-butoxycarbonyl thiourea (5.12 g, 18.5 mmol) and triethyl amine (8.21 mL, 59.0 mmol) in 40 mL of DMF under argon at 0° C. was added HgCl₂ (5.04 g, 18.5 mmol). The reaction mixture was stirred at 0° C. for 1 h and at room temperature for 30 min at which time another batch of triethyl amine (2.00 mL, 14.4 mmol), bis-t-butoxycarbonyl thiourea (2.56 g, 9.25 mmol) and HgCl₂ (2.52 g, 9.25 mmol) was added. The reaction mixture was stirred at room temperature for 1 h and diluted with 0.5 L of EtOAc, filtered through a 3" pad of Celite, the pad rinsed with EtOAc and the filtrate washed with 5%KHSO₄ solution and brine. The EtOAc layer was dried (MgSO₄), filtered and concentrated in vacuo to give the part A compound.

B.

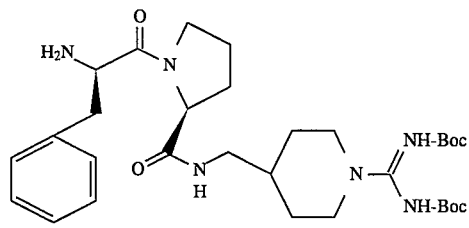

N-[[1-[[[1,1,-Dimethylethoxy]carbonyl]amino[[1,1,-dimethylethoxy]carbonyl]iminomethyl]-4-piperidinyl]methyl]-D-phenylalanyl-L-prolinamide To a stirred solution of part A carbamate (3.60 g, 4.90 mmol) in 100 mL of methanol under argon was added 20%Pd(OH)₂/C (0.72 g). The atmosphere was replaced with hydrogen, the mixture stirred at room temperature for 20 h, the catalyst filtered off through a 4 mM polycarbonate film, rinsed with methanol and concentrated in vacuo to give 2.41 g (82%) of part B amine.

C.

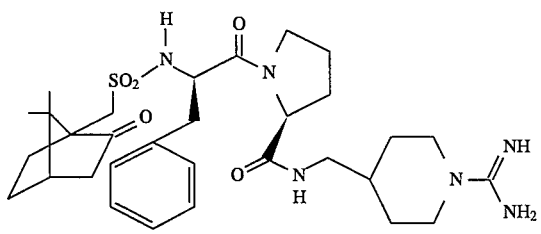

N-[[1-(Aminoiminomethyl)-4-piperidinyl]methyl]-1-[N-((±)-10-camphorsulfonyl)-D-phenylalanyl]-L-prolinamide, trifluoroacetate (1:1) salt To a stirred solution of part B amine (600 mg, 1.00 mmol) and triethyl amine (0.14 mL, 3.00 mmol) in 5 mL of chloroform under argon was added (±)-10-camphorsulfonyl chloride (376 mg, 1.50 mmol). The solution was stirred at room temperature for 2 h at which time 0.20 mL (1.44 mmol) of triethyl amine was added. The solution was stirred at room temperature for 25 h and diluted with EtOAc, washed with KHSO₄ solution, saturated NaHCO₃ solution, and brine. The organic layer was dried (MgSO₄), filtered and concentrated in vacuo. To this bis-Bocguanidine (280 mg, 0.34 mmol) at 0° C. was added TFA (3.00 mL, 38.9 mmol). The solution was stirred at 0° C. for 1 h and at room temperature for 1 h, concentrated in vacuo and purified by preparative HPLC to give 240 mg (93%) of N-[[1-(aminoiminomethyl)-4-piperidinyl]methyl]-1-[N-((±)-10-camphorsulfonyl)-D-phenylalanyl]-L-prolinamide, trifluoroacetate (1:1) salt.

$[\alpha]_D$=−28.3° (c=0.59, MeOH)

Anal. Calc'd for $C_{31}H_{46}N_6O_5S.1.2$ TFA: C, 53.37; H, 6.33; N, 11.18; S, 4.27; F, 9.10 Found: C, 53.16; H, 6.39; N, 10.93; S, 4.24; F, 8.98

EXAMPLE 55

N-[[1-(Aminoiminomethyl)-4-piperidinyl]methyl]-1-[N-(pentafluorophenylsulfonyl)-D-phenylalanyl]-L-prolinamide, trifluoroacetate (1:1) salt

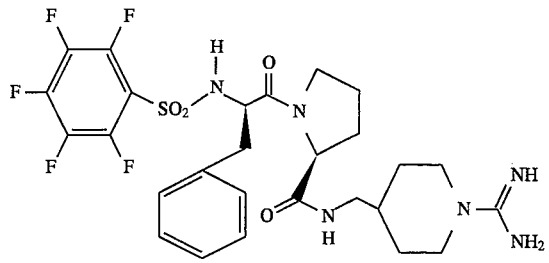

By substituting pentafluorophenyl sulfonyl chloride in the Example 1, Part B reaction sequence there was obtained N-[[1-(aminoiminomethyl)-4-piperidinyl]methyl]-1-[N-(pentafluorophenylsulfonyl)-D-phenylalanyl]-L-prolinamide.

$[\alpha]_D$=−18.4° (c=0.63, MeOH)

Anal. Calc'd for $C_{27}H_{31}N_6O_4SF_5.1.00$ TFA.1.00 H₂O: C, 45.67; H, 4.49; N, 11.02; S, 4.20; F, 19.93 Found: C, 45.71; H, 4.24; N, 10.72; S, 4.38; F, 20.04

EXAMPLES 56 to 63

Following the methods described above the following compounds were prepared.

EXAMPLE 56

N-[[1-(Aminoiminomethyl)-4-piperidinyl]methyl]-1-[N-(pentamethylphenylsulfonyl)-D-phenylalanyl]-L-prolinamide, trifluoroacetate (1:1) salt $[\alpha]_D$=+3.5° (c=0.5, MeOH)

Anal. Calc'd for $C_{32}H_{46}N_6O_4S.1.40$ TFA.0.70 H₂O: C, 53.38 H, 6.28; N, 10.73; S, 4.09; F, 10.19 Found: C, 53.39; H, 6.00; N, 10.41; S, 4.07; F, 9.93

EXAMPLE 57

N-[[1-(Aminoiminomethyl)-4-piperidinyl]methyl]-1-[N-(2,4,6-isopropylphenylsulfonyl)-D-phenylalanyl]-L-prolinamide, trifluoroacetate (1:1) salt $[\alpha]_D$=+21.7° (c=0.5, MeOH)

Anal. Calc'd for $C_{36}H_{54}N_6O_4S.1.40$ TFA.0.40 H₂O: C, 55.89; H, 6.79; N, 10.08; S, 3.85; F, 9.57 Found: C, 55.91; H, 6.94; N, 10.19; S, 3.97; F, 9.48

EXAMPLE 58

N-[[1-(Aminoiminomethyl)-4-piperidinyl]methyl]-1-[N-(4-carboxyphenylsulfonyl)-D-phenylalanyl]-L-prolinamide, trifluoroacetate (1:1) salt $[\alpha]_D$=+21.5° (c=0.79, MeOH)

Anal. Calc'd for $C_{28}H_{36}N_6O_4S.1.00$ TFA.0.73 H₂O: C, 50.62; H, 5.45; N, 11.80; S, 4.50; F, 8.01 Found: C, 50.83; H, 5.31; N, 11.59; S, 4.66; F, 8.15

EXAMPLE 59

N-[[1-(Aminoiminomethyl)-4-piperidinyl]methyl]-1-[N-2,2,5,7,8-(pentamethylchroman-6-sulfonyl)-D-phenylalanyl]-L-prolinamide, trifluoroacetate (1:1) salt $[\alpha]_D$=+18.3° (c=0.6, MeOH)

Anal. Calc'd for $C_{35}H_{50}N_6O_5S \cdot 1.18$ TFA $\cdot 0.22$ $H_2O$: C, 55.72; H, 6.46; N, 10.43; S, 3.98; F, 8.35 Found: C, 55.71; H, 6.57; N, 10.27; S, 4.07; F, 8.36

EXAMPLE 60

N-[[1-(Aminoiminomethyl)-4-piperidinyl]methyl]-1-[N-(3-trifluoromethylphenylsulfonyl)-D-phenylalanyl]-L-prolinamide, trifluoroacetate (1:1) salt $[\alpha]_D = +3.3°$ (c=0.44, MeOH)

Anal. Calc'd for $C_{28}H_{35}N_6O_4SF_3 \cdot 1.05$ TFA $\cdot 0.70$ $H_2O$: C, 49.36; H, 5.02; N, 11.48; S, 4.38; F, 15.95 Found: C, 49.36; H, 4.76; N, 11.24; S, 4.47; F, 15.98

EXAMPLE 61

N-[[1-(Aminoiminomethyl)-4-piperidinyl]methyl]-1-[N-(methylsulfonyl)-D-leucyl]-L-prolinamide, trifluoroacetate (1:1) salt $[\alpha]_D = -19°$ (c=0.21, MeOH)

Anal. Calc'd for $C_{19}H_{36}N_6O_4S \cdot 1.31$ TFA $\cdot 3.34$ $H_2O$: C, 44.43; H, 5.44; N, 13.55; S, 5.17; F, 13.51 Found: C, 44.61; H, 5.28; N, 12.66; S, 4.98; F, 13.82

EXAMPLE 62

N-[[1-(Aminoiminomethyl)-4-piperidinyl]methyl]-1-[N-(methylsulfonyl)-D-phenylalanyl]-L-pipecolinamide, trifluoroacetate (1:1) salt $[\alpha]_D = -60.1°$ (c=0.7, MeOH)

Anal. Calc'd for $C_{23}H_{36}N_6O_4S \cdot 1.30$ TFA $\cdot 01.00$ $H_2O$: C, 46.67 H, 6.01; N, 12.76; S, 4.87; F, 11.25 Found: C, 46.42; H, 5.58; N, 12.52; S, 4.59; F, 11.02

EXAMPLE 63

N-[[1-(Aminoiminomethyl)-4-piperidinyl]methyl]-1-[N-(3-carboxyphenylsulfonyl)-D-phenylalanyl]-L-prolinamide, trifluoroacetate (1:1) salt $[\alpha]_D = +8.3°$ (c=0.84, MeOH)

Anal. Calc'd for $C_{28}H_{36}N_6O_6S \cdot 1.03$ TFA $\cdot 0.71$ $H_2O$: C, 50.50; H, 5.42; N, 11.76; S, 4.48; F, 8.21 Found: C, 50.50; H, 5.16; N, 11.65; S, 4.60; F, 8.24

The following Examples represent preferred embodiments of the second embodiment of the present invention. Unless otherwise indicated, all temperatures are expressed in degrees Centigrade.

EXAMPLE I

[S-(R*,R*)]-N-[2-[2-[[[4-[(Aminoiminomethyl)amino]butyl]thio]methyl]-1-pyrrolidinyl]-1-(hydroxymethyl)-2-oxoethyl]-2-naphthalenesulfonamide, trifluoroacetate (1:1) salt A. (S)-2-[[[4-(1,3-Dihydro-1,3-dioxo-2H-isoindol-2-yl)butyl]thio]methyl]-1-pyrrolidinecarboxlic acid, 1,1-dimethylethyl ester To a stirred solution of (S)-2-[[[(4-methylphenyl)sulfonyl]oxy]methyl]-1-pyrrolidinecarboxylic acid, 1,1-dimethylethyl ester (reported in Journal of Med. Chemistry, p2615, 1992) (10.0 g, 28.2 mmol) in 100 mL of acetone under argon was added potassium thioacetate (3.91 g, 34.2 mmol). The reaction solution was refluxed for 18 h at which time another batch of potassium thioacetate (3.22 g, 28.2 mmol) was added. This mixture was refluxed for 24 h and cooled to room temperature. The precipitate was filtered off through a 2" pad of Celite and rinsed with acetone (2×30 mL). The filtrate was concentrated in vacuo. The residue was dissolved in 300 mL of ether and washed with water (2×50 mL) and brine (1×50 mL). The organic layer was dried ($Na_2SO_4$), filtered and concentrated in vacuo to give 6.75 g of the intermediate thioacetate. To a stirred solution of this thioacetate (3.27 g, 12.6 mmol) in 100 mL of methanol under argon at 0° C. was added a solution of 1M t-$C_4H_9$OK in tetrahydrofuran (THF) (12.6 mL, 12.6 mmol). This reaction solution was then sparged with argon for 15 min. To this solution was added N-(4-bromobutyl)phthalimide (3.56 g, 12.6 mmol). The reaction solution was stirred at room temperature for 3 h and quenched at 0° C. by dropwise addition of 20 mL of saturated $NH_4Cl$ solution. The mixture was concentrated in vacuo. The residue was diluted with 600 mL of EtOAc and washed with saturated $NaHCO_3$ solution (2×200 ml) and brine (1×200 mL). The EtOAc layer was dried ($MgSO_4$), filtered and concentrated in vacuo. Purification was effected by flash chromatography on 180 g of Merck silica gel 60 using 29% ether in hexane as eluant to give 3.16 g (55%) of title thioether.

B. [S-(R*,R*)]-[2-[2-[[[4-(1,3-Dihydro-1,3-dioxo-2H-isoindol-2-yl)butyl]thio]methyl]-1-pyrrolidinyl]-1-(hydroxymethyl)-2-oxoethyl]carbamic acid, 1,1-dimethylethyl ester To a stirred solution of Part A thioether (3.28 g, 7.85 mmol) in 10 mL of dry dichloromethane was added 10 mL of trifluoroacetic acid (TFA). The solution was stirred at room temperature for 1.5 h and diluted with 100 mL of ether. The solution was concentrated in vacuo to give a crude TFA.amine salt. To a stirred solution of this salt, 1-hydroxybenzotriazole monohydrate (HOBT) (1.33 g, 7.85 mmol) and N-Boc-L-serine (1.70 g, 7.85 mmol) in 40 mL of dimethylformamide (DMF) was added in order N-methylmorpholine (NMM) (2.58 mL, 23.5 mmol) and ethyl-3-(3-dimethylamino)propyl carbodiimide hydrochloride (1.50 g, 7.85 mmol). This reaction solution was sparged with argon for 10 min and stirred at room temperature for 18 h. The mixture was concentrated under pump vacuum at 45° C. The residue was dissolved in 200 mL of EtOAc and washed with 1N HCl solution (2×80 mL), saturated $NaHCO_3$ solution (1×80 mL) and brine (1×80 mL). The EtOAc layer was dried ($MgSO_4$), filtered and concentrated in vacuo to give 3.65 g (90%) of title carbamate.

C. [S-(R*,R*)]-N-[2-[2-[[[4-(1,3-Dihydro-1,3-dioxo-2H-isoindol-2-yl)butyl]thio]methyl]-1-pyrrolidinyl]-1-(hydroxymethyl)-2-oxoethyl]-2-naphthalenesulfonamide To a stirred solution of Part B carbamate (3.65 g, 7.06 mmol) in 15 mL of dry dichloromethane was added 15 mL of TFA. The solution was stirred at room temperature for 1.5 h and diluted with 200 mL of ether. The solution was concentrated in vacuo to give a crude TFA.amine salt. To a stirred solution of this salt and triethyl amine (2.95 mL, 21.2 mmol) in 60 mL of dry dichloromethane at 0° C. was added 2-naphthalenesulfonyl chloride (1.76 g, 7.77 mmol). The reaction solution was stirred at room temperature for 4.5 h and diluted with 140 mL of dichloromethane. The solution was washed with 1N HCl solution (2×60 mL), saturated $NaHCO_3$ solution (2×60 mL) and brine (1×60 mL). The organic layer was dried ($MgSO_4$), filtered and concentrated in vacuo. This was chromatographed on 120 g of Merck silica gel 60 using 2% $CH_3OH/CH_2Cl_2$ as eluant to give 2.62 g (61%) of title sulfonamide.

D. [S-(R*,R*)]-N-[2-[2-[[[(4-Aminobutyl)thio]methyl]-1-pyrrolidinyl]-1-(hydroxymethyl)-2-oxoethyl]-2-naphthalenesulfonamide To a stirred solution of Part C sulfonamide (0.77 g, 1.27 mmol) in 20 mL of dry dichloromethane under argon was added anhydrous hydrazine (0.24 g, 7.61 mmol). The reaction mixture was stirred at room temperature for 2.5 h and concentrated in vacuo. The residue was combined with 30 mL of methanol and 60 mL of toluene. The mixture was concentrated in vacuo. This co-evaporation with methanol and toluene was repeated three times. The residue was dissolved in 80 mL of methanol and the solution was heated to reflux for 17 h. The mixture was then cooled to room temperature and acidified to pH 1 by the addition of 1N HCl in ether. The mixture was cooled in an acetone dry ice bath for 5 min and the precipitate was filtered off, the solid was rinsed with methanol (2×10 mL), and the filtrate was concentrated in vacuo. The product was purified by prep HPLC and lyophilized to give 290 mg (39%) of title amine.TFA.

E. [S-(R*,R*)]-N-[2-[2-[[[4-[(Aminoiminomethyl)amino]butyl]thio]methyl]-1-pyrrolidinyl]-1-(hydroxymethyl)-2-oxoethyl]-2-naphthalenesulfonamide, trifluoroacetate (1:1) salt To a stirred mixture of Part D amine.TFA (280 mg, 0.47 mmol) and Et$_3$N (0.36 mL, 2.61 mmol) in 4 mL of absolute EtOH under argon was added aminoiminomethanesulfonic acid (206 mg, 1.66 mmol). The mixture was stirred at room temperature for 3 h and concentrated in vacuo. This was purified by prep HPLC to give 180 mg (57%) of title compound.

Opt. Rotation: [α]$_D$=−54.7° (c=0.70, MeOH).

Analysis calc'd for 0.33 H$_2$O+1.35 TFA: C, 46.24; H, 5.29; N, 10.49; S, 9.61; F, 11.53 Found: C, 46.24; H, 5.22; N, 10.47; S, 9.92; F, 11.47.

EXAMPLE II

[S-(R*,R*)]-N-[4-[[[1-(2-Amino-1-oxo-3-phenylpropyl)-2-pyrrolidinyl]methyl]thio]butyl]guanidine, trifluoroacetate (2:5) salt A. [S-(R*,S*)]-[2-[2-[[[4-(1,3-Dihydro-1,3-dioxo-2H-isoindol-2-yl)butyl]thio]methyl]-1-pyrrolidinyl]-2-oxo-1-(phenylmethyl)ethyl]carbamic acid, 1,1-dimethylethyl ester To a stirred solution of TFA-amine (prepared in Example I, Part B) (3.11 g, 7.20 mmol), 1-hydroxybenzotriazole monohydrate (1.22 g, 7.20 mmol) and N-Boc-D-phenylalanine (1.91 g, 7.20 mmol) in 60 mL of DMF was added in order 4-methylmorpholine (3.16 mL, 28.8 mmol) and ethyl-3-(3-dimethylamino)propyl carbodiimide hydrochloride (1.38 g, 7.20 mmol). This reaction solution was sparged with argon for 20 min and stirred at room temperature for 18 h. The mixture was concentrated under pump vacuum at 45° C. The residue was dissolved in 400 mL of EtOAc and washed with 1N HCl solution (2×100 mL), saturated NaHCO$_3$ solution (2×100 mL) and brine (1×100 mL). The EtOAc layer was dried (MgSO$_4$), filtered and concentrated in vacuo. Purification was effected by flash chromatography to give 2.74 g (68%) of title carbamate.

B. [S-(R*,S*)]-[2-[2-[[(4-Aminobutyl)thio]methyl]-1-pyrrolidinyl]-2-oxo-1-(phenylmethyl)ethyl]carbamic acid, 1,1-dimethylethyl ester To a stirred solution of Part A carbamate (1.01 g, 1.79 mmol) in 25 mL of methanol under argon was added anhydrous hydrazine (1.00 mL, 31.9 mmol). The reaction solution was heated at 50° C. for 3 h and concentrated in vacuo. The residue was combined with 50 mL of methanol and 20 mL of toluene. The mixture was concentrated in vacuo. The residue was diluted with 40 mL of 1N NaOH solution and extracted with EtOAc (3×70 mL). The combined organic extracts were dried (MgSO$_4$), filtered and concentrated in vacuo to give 700 mg (89%) of title amine.

C. [S-(R*,S*)]-[2-[2-[[[4-[(Aminoiminomethyl)-amino]butyl]thio]methyl]-1-pyrrolidinyl]-2-oxo-1-(phenylmethyl)ethyl]carbamic acid, 1,1-dimethylethyl ester To a stirred mixture of Part B amine (680 mg, 1.56 mmol) and triethylamine (Et$_3$N) (0.76 mL, 5.47 mmol) in 7 mL of absolute EtOH under argon was added aminoimino-methanesulfonic acid (485 mg, 3.91 mmol). The mixture was stirred at room temperature for 2 h concentrated in vacuo, and purified by prep HPLC to give 780 mg (92%) of title BOC.amine.

D. [S-(R*,R*)]-N-[4-[[[1-(2-Amino-1-oxo-3-phenylpropyl)-2-pyrrolidinyl]methyl]thio]butyl]guanidine, trifluoroacetate (2:5) salt To Part C BOC.amine (410 mg, 0.69 mmol) at 0° C. was added 4 mL of TFA. The reaction solution was stirred at room temperature for 30 min and diluted with 20 mL of methanol. The solution was concentrated in vacuo and purified by prep HPLC to give 130 mg (28%) of title aminoguanidine.

Opt. rotation: [α]$_D$=−73.3° (c=0.54, MeOH).

Analysis calc'd for 1.03 H$_2$O+2.30 TFA: C, 43.06; H, 5.41; N, 10.64; S, 4.87; F, 19.91 Found: C, 43.06; H, 5.14; N, 10.40; S, 5.22; F, 20.00.

EXAMPLE II

[S-(R*,R*)]-N-[2-[2-[[[4-[(Aminoiminomethyl)amino]butyl]sulfonyl]methyl]-1-pyrrolidinyl]-1-(hydroxymethyl)-2-oxoethyl]-2-naphthalenesulfonamide, trifluoroacetate (1:1) salt A. [S-(R*,R*)]-N-[2-[2-[[[4-(1,3-Dihydro-1,3-dioxo-2H-isoindol-2-yl)butyl]sulfonyl]methyl]-1-pyrrolidinyl]-1-(hydroxymethyl)-2-oxoethyl]-2-naphthalenesulfonamide To a stirred solution of the thioether prepared in Example I, Part C (1.00 g, 1.65 mmol) in 50 mL of dichloromethane was added m-chloroperbenzoic acid (MCPBA) (1.14 g, 3.29 mmol). The reaction solution was stirred at room temperature for 10 min and quenched by the addition of 10% sodium bisulfite solution until the KI-starch paper test was negative. The mixture was diluted with 300 mL of EtOAc and washed with saturated NaHCO$_3$ solution (2×150 mL) and brine (1×150 mL). The organic layer was dried (MgSO$_4$), filtered and concentrated in vacuo to give 1.20 g (97%) of title sulfone.

B. [S-(R*,R*)]-N-[2,[2-[[(4-Aminobutyl)sulfonyl]methyl]-1-pyrrolidinyl]-1-(hydroxymethyl)-2-oxoethyl]-2-naphthalenesulfonamide To a stirred solution of Part A sulfone (1.20 g, 1.96 mmol) in 30 mL of methanol under argon was added anhydrous hydrazine (0.63 g, 19.6 mmol). The reaction solution was heated to reflux for 2.5 h and concentrated in vacuo. The residue was combined with 40 mL of methanol and 80 mL of toluene. The mixture was concentrated in vacuo, the residue was diluted with 40 mL of 1N NaOH solution and extracted with EtOAc (2×80 mL) and 10% isopropyl alcohol (IPA) in dichloromethane (3×80 mL). The combined organic extracts were dried (MgSO$_4$), filtered, concentrated in vacuo and purified by prep HPLC to give 350 mg (30%) of title amine.TFA.

C. [S-(R*,R*)]-N-[2-[2-[[[4-[(Aminoiminomethyl)amino]butyl]sulfonyl]methyl]-1-pyrrolidinyl]-1-(hydroxymethyl)-2-oxoethyl]-2-naphthalenesulfonamide, trifluoroacetate (1:1) salt To a stirred mixture of Part B amine.TFA (340 mg, 0.57 mmol) and Et$_3$N (0.32 mL, 2.29 mmol) in 6 mL of absolute EtOH under argon was added aminoiminomethanesulfonic acid (177 mg, 1.43 mmol). The mixture was stirred at room temperature for 4 h concentrated in vacuo, and purified by prep HPLC to give 370 mg (92%) of title compound.

Opt. rotation: [α]$_D$=−53.3° (c=0.95, MeOH).

Analysis calc'd for 0.16 H$_2$O+1.40 TFA: C, 44.13; H, 4.98; N, 9.97; S, 9.13; F, 11.36 Found: C, 44.13; H, 4.87; N, 9.97; S, 9.05; F, 11.48.

EXAMPLE IV

[S-(R*,R*)]-N-[2-[2-[[[3-[(Aminoiminomethyl)amino]propyl]thio]methyl]-1-pyrrolidinyl]-1-(hydroxymethyl)-2-oxoethyl]-2-naphthalenesulfonamide, trifluoroacetate (1:1) salt A. (S)-2-[[[3-(1,3-Dihydro-1,3-dioxo-2H-isoindol-2-yl)propyl]thio]methyl]-1-pyrrolidinecarboxylic acid, 1,1-dimethylethyl ester To a stirred solution of the tosylate employed as a starting material in Example I, Part A (10.0 g, 28.2 mmol) in 120 mL of acetone under argon was added potassium thioacetate (4.14 g, 36.2 mmol). The reaction solution was sparged with argon for 10 min. This mixture was refluxed for 4 h and cooled to room temperature. The precipitate was filtered off through a 3" pad of Celite and rinsed with acetone (3×30 mL). The filtrate was concentrated in vacuo. The residue was dissolved in 400 mL of ether and washed with cold water (1×100 mL) and brine (1×100 mL). The organic layer was dried (Na$_2$SO$_4$), filtered and concentrated in vacuo to give 7.20 g (99%) of the intermediate thioacetate. To a stirred solution of this thioacetate (7.20 g, 27.8 mmol) in 250 mL of methanol under argon at 0° C. was added a solution of 1M t-BuOK in THF (27.8 mL, 27.8 mmol). This reaction solution was then sparged with argon for 15 min. To this solution was added N-(3-bromopropyl)-phthalimide (7.45 g, 27.8 mmol). The reaction solution was stirred at room temperature for 4 h and quenched at 0° C. by dropwise addition of 40 mL of saturated NH$_4$Cl solution. The mixture was concentrated in vacuo, the residue diluted with 400 mL of EtOAc and washed with saturated NaHCO$_3$ solution (2×100 mL) and brine (1×100 mL). The EtOAc layer was dried (MgSO$_4$), filtered and concentrated in vacuo. Purification was effected by flash chromatography on to give 6.11 g (54%) of title thioether.

B. [S-(R*,R*)]-2-[2-[[[3-(1,3-Dihydro-1,3-dioxo-2H-isoindol-2-yl)propyl]thio]methyl]-1-pyrrolidinyl-1-(hydroxymethyl)-2-oxoethyl]carbamic acid, 1,1-dimethylethyl ester To a stirred solution of Part A thioether (6.00 g, 14.9 mmol) in 10 mL of dry dichloromethane was added 15 mL of TFA. The solution was stirred at room temperature for 1.5 h and diluted with 150 mL of ether. The solution was concentrated in vacuo to give a crude TFA,amine salt. To a stirred mixture of this TFA-amine salt in 100 mL of dry dichloromethane was added a solution of 1N HCl in ether (20.0 mL, 20.0 mmol). The mixture was concentrated in vacuo to give the amine.HCl salt in a quantitative yield. To a stirred solution of this HCl salt (4.05 g, 9.19 mmol), 1-hydroxybenzotriazole monohydrate (1.55 g, 9.19 mmol) and N-Boc-L-serine (2.00 g, 9.19 mmol) in 40 mL of DMF was added in order 4-methylmorpholine (4.04 mL, 36.8 mmol) and ethyl-3-(3-dimethylamino)propyl carbodiimide hydrochloride (1.76 g, 9.19 mmol). This reaction solution was sparged with argon for 10 min and stirred at room temperature for 22 h. The mixture was concentrated under pump vacuum at 45° C. The residue was dissolved in 300 mL of EtOAc and washed with 1N HCl solution (2×100 mL), saturated NaHCO$_3$ solution (1×100 mL) and brine (1×100 mL). The EtOAc layer was dried (MgSO$_4$), filtered and concentrated in vacuo to give 3.88 g (84%) of title carbamate.

C. [S-(R*,R*)]-N-[2-[2-[[[3-(1,3-Dihydro-1,3dioxo-2H-isoindol-2-yl)propyl]thio]methyl]-1-pyrrolidinyl]-1-(hydroxymethyl)-2-oxoethyl]-2-naphthalenesulfonamide.

To a stirred solution of Part B carbamate (2.04 g, 4.06 mmol) in 10 mL of dry dichloromethane was added at 0° C. a solution of 4N HCl in dioxane (15.0 mL, 60.0 mmol). The solution was stirred at room temperature for 1.5 h and diluted with 200 mL of ether. The solution was concentrated in vacuo to give a crude HCl.amine salt. To a stirred solution of this salt and triethyl amine (1.69 mL, 12.2 mmol) in 60 mL of dry dichloromethane at 0° C. was added 2-naphthalenesulfonyl chloride (1.01 g, 4.46 mmol). The reaction solution was sparged with argon for 5 min and stirred at room temperature for 3 h. The reaction solution was diluted with 240 mL of dichloromethane. The solution was washed with 1N HCl solution (3×60 mL), saturated NaHCO$_3$ solution (2×60 mL) and brine (1×100 mL). The organic layer was dried (MgSO$_4$), filtered and concentrated in vacuo. The residue was washed with hexane (2×60 mL) and the solid was chromatographed on 120 g of Merck silica gel 60 using 3%CH$_3$OH/CH$_2$Cl$_2$ as eluant to give 1.69 g (70%) of title sulfonamide.

D. [S-(R*,R*)]-N-[2-[2-[[[3-[(Aminoiminomethyl)amino]propyl]thio]methyl]-1-pyrrolidinyl]-1-(hydroxymethyl)-2-oxoethyl]-2-naphthalenesulfonamide, trifluoroacetate (1:1) salt To a stirred solution of Part C sulfonamide (1.59 g, 1.68 mmol) in 40 mL of methanol under argon was added anhydrous hydrazine (0.54 g, 16.8 mmol). The reaction mixture was heated at 45° C. for 5 h and concentrated in vacuo. The residue was combined with 60 mL of methanol and 100 mL of toluene. The mixture was concentrated in vacuo to give 1.07 g (85%) of the intermediate amine. To a stirred mixture of this amine (1.05 g, 2.25 mmol) and Et$_3$N (1.09 mL, 7.87 mmol) in 50 mL of absolute EtOH under argon was added aminoiminomethanesulfonic acid (698 mg, 5.62 mmol). The mixture was stirred at room temperature for 4 h, concentrated in vacuo and purified by prep HPLC to give 350 mg (25%) of title compound.

Opt. rotation: [α]$_D$=−63.1° (c=1.12, MeOH).

Analysis calc'd for 0.30 H$_2$O+1.07 TFA: C, 46.69; H, 5.30; N, 11.28; S, 10.32; F, 9.82 Found: C, 46.64; H, 5.24; N, 11.12; S, 10.37; F, 9.85.

EXAMPLE V

[S-(R*,R*)]-N-[2-[2-[[[[1-(Aminoiminomethyl)-4-piperidinyl]methyl]thio]methyl]-1-pyrrolidinyl]-1-hydroxymethyl)-2-oxoethyl]-2-naphthalenesulfonamide, trifluoroacetate (1:1) salt A. (S)-4-[[[[1-[(1,1-Dimethylethoxy)carbonyl]-2-pyrrolidinyl]methyl]thio]methyl]-1-piperidinecarboxylic acid, phenylmethyl ester To a solution of the thioacetate intermediate prepared in Example I, Part A,

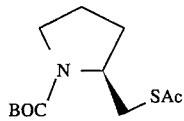

and 4-tosyloxymethyl-N-carbobenzyloxy piperidine, 1.5 g, 3.86 mmol) in 35 mL DMF was added NaOMe (0.88 mL, 15.44 mmol) at 0° C. After the reaction stirred for 10 minutes and the ice bath was removed, the reaction was stirred at room temperature for 2 hrs. NaOMe (0.6 mL) was added and the reaction stirred for another 30 minutes. The reaction mixture was concentrated and partitioned between EtOAc and H$_2$O, the EtOAc layer washed with brine, dried over Na$_2$SO$_4$ and concentrated in vacuo to give the crude product which then was purified by a silica gel column (EtOAc:hexane=1:4) (87% yield).

B. N-(2-Naphthalenylsulfonyl)-L-serine

To a solution of 2-naphthalene sulfonyl chloride (3 g, 13.23 mmol) and serine benzylester (3.07 g, 13.23 mmol) in 120 mL CH$_2$Cl$_2$ was added Et$_3$N (5.53 mL, 13.23 mmol) at 0° C. The reaction was stirred at room temperature for 1 hr and washed with a saturated (sat.) solution of KHSO$_4$, brine, and dried over Na$_2$SO$_4$. The organic layer was concentrated in vacuo to give the naphthylsulfonamide (93%).

To a solution of the naphthylsulfonamide (1 g, 2.59 mmol) and Pd/C (10%, 50 mg) in 25 mL EtOAc was added 2.6 mL of 1N HCl, followed by H$_2$. The reaction was stirred at room temperature for 16 hrs and the catalyst was removed by filtration. The filtrate was concentrated in vacuo to give (89% yield).

C. [S-(R*,R*)]-N-[1-(Hydroxymethyl)-2-oxo-2-[[[[1-[(phenylmethoxy)carbonyl]-4-piperidinyl]methyl]thio]methyl]-1-pyrrolidinyl]ethyl ]-2-naphthalenesulfonamide To a solution of Part A compound (1.39 g, 3.10 mmol) in 2 mL CH$_2$Cl$_2$ was added 9.3 mL trifluoroacetic acid (TFA) at 0° C. The ice bath was removed and the reaction was stirred at room temperature for 30 minutes. The reaction mixture was concentrated in vacuo and co-evaporated with Et$_2$O to give the TFA salt (70% yield).

To a solution of Part B compound (0.638 g, 2.16 mmol) and HOBT (0.321 g, 2.37 mmol) in 10 mL DMF was added WSC (0.46 g, 2.37 mmol) and the TFA salt (100 g, 2.16 mmol), followed by NMM (0.264 mL, 2.37 mmol). The reaction was stirred at room temperature for 16 hrs and partitioned between EtOAc and a sat. solution of NaHCO$_3$. The organic layer was further washed with a sat. solution of KHSO$_4$, brine, dried over Na$_2$SO$_4$ and concentrated in vacuo to give (81% yield).

D. [S-(R*,R*)]-N-[1-[(Acetyloxy)methyl]-2-oxo-2-[2-[[(4-piperidinylmethyl)thio]methyl]-1-pyrrolidinyl]ethyl]-2-naphthalenesulfonamide To a solution of Part C compound (1.1 g, 2.08 mmol) in 1 mL CH$_2$Cl$_2$ was added 6.24 mL HBr in HOAc (30%) at 0° C. The ice bath was removed and stirred at room temperature for 1 hr. The reaction mixture was concentrated in vacuo and triturated with Et$_2$O to give title compound.

E. [S-(R*,R*)]-N-[1-[(Acetyloxy)methyl]-2-[2-[[[[1-(aminoiminomethyl)-4-piperidinyl]methyl]thio]methyl]-1-pyrrolidinyl]-2-oxoethyl]-2-naphthalenesulfonamide To a solution of Part D (1.47 g, 2.57 mmol) and H-pyrazole-1-carboxamidine (0.42 g, 2.83 mmol) in 8 mL DMF was added diisopropylethylamine (0.898 mL, 5.14 mmol). The reaction was stirred at room temperature for 16 hrs and purified by a preparative HPLC to give title compound (25% yield).

F. [S-(R*,R*)]-N-[2-[2-[[[[1-(Aminoiminomethyl)-4-piperidinyl]methyl]thio]methyl]-1-pyrrolidinyl]-1-(hydroxymethyl)-2-oxoethyl]-2-naphthalenesulfonamide, trifluoroacetate (1:1) salt To a solution of Part E compound (0.33 g, 0.57 mmol) in 2 mL MeOH was added 1N NaOH (1.72 mL, 1.72 mmol) at 0° C. The ice bath was removed and stirred at room temperature for 1.5 hrs. The reaction mixture was concentrated in vacuo and purified on a preparative HPLC to give title compound (56% yield).

Anal. Calc'd for C$_{25}$H$_{35}$N$_5$O$_4$S$_2$.1.2 TFA-1.2 H$_2$O: C, 47.55; H, 5.62; N, 10.12; S, 9.26 Found: C, 47.60; H, 5.36; N, 9.99; S, 10.08.

[α]$_D$=−164.9 (c=3.04, CD$_3$OD).

EXAMPLE VI

[S-(R*,R*)]-N-[2-[2-[[[1-(Aminoiminomethyl)-4-piperidinyl]methoxy]methyl]-1-pyrrolidinyl]-1-(hydroxymethyl)-2-oxoethyl]-2-naphthalenesulfonamide A. (S)-4-[[[1-[(1,1-Dimethylethoxy)carbonyl]-2-pyrrolidinyl]methoxy]methyl]-1-piperidinecarboxylic acid, phenylmethyl ester To BOC-L-prolinol (10 mmol) in xylene (10 mL) was added KOH (20 mmol), 4-tosyloxymethyl-N-carbobenzyloxy piperidine (11 mmol) and the reaction was heated to reflux for 3 hours. The reaction mixture was stirred at room temperature for 16 hours, quenched with NH$_4$Cl, extracted with ethyl acetate and purified by column chromatography to provide the title ether.

B. [S-(R*,R*)]-4-[[[1-[3-Hydroxy-2-[(2-naphthalenylsulfonyl)amino]-1-oxopropyl]-2-pyrrolidinyl]methoxy]methyl]-1-piperidinecarboxylic acid, phenylmethyl ester The Part A ether (9 mmol) was dissolved in trifluoroacetic acid (10 mL) at 0° C. After stirring for 30 min, the TFA was evaporated in vacuo and the trifluoracetate salt precipitated with ether. The TFA salt was dissolved in DMF (10 mL) and reacted with N-2-napthylsulfonyl-serine (9 mmol) in the presence of WSC (9 mmol), HOBT (9 mmol) and NMM (9 mmol). After stirring for 12 hours, the reaction mixture was diluted with ethyl acetate (50 mL), washed with sat'd KHSO$_4$ (3×), sat'd NaHCO$_3$, sat'd NaCl, and dried in vacuo to provide the title naphthylsulfonyl serine derivative.

C. [S-(R*,R*)]-N-[2-[2-[[[1-(Aminoiminomethyl)-4-piperidinyl]methoxy]methyl]-1-pyrrolidinyl]-1-(hydroxymethyl)-2-oxoethyl]-2-naphthalenesulfonamide The Part B compound (8 mmol) was dissolved in HBr/HOAc at 0° C. for 30 min. The reaction mixture was then made basic with NaOH and extracted with ethyl acetate. The free base derived from the ethyl acetate layer was treated with 1H-pyrazolecarboxamidine in ethanol at 40° C. for 3 hours, the reaction mixture stripped and purified by preparative HPLC to provide the title compound.

EXAMPLE VII

[S-(R*,S*)]-N-[2-[2-[[[4-[(Aminoiminomethyl)amino]butyl]thio]methyl]-1-pyrrolidinyl]-2-(hydroxymethyl)-2-oxoethyl]-2-naphthalenesulfonamide The title compound was prepared employing a procedure similar to that described in Example I except substituting (R)-2-[[[(4-methylphenyl)sulfonyl]oxy]methyl]-1-pyrrolidine carboxylic acid, 1,1-dimethylethyl ester for the corresponding (S)-isomer (140 mg, 40% yield).

Anal. Calc'd for C$_{23}$H$_{33}$N$_5$O$_4$S$_2$.1.1 TFA.0.04 H$_2$O: C, 47.81, H, 5.43; N, 11.06; S, 10.13; F, 9.90 Found: C, 47.75; H, 5.35; N, 10.93; S, 10.14; F, 9.78

EXAMPLE VIII

[S-[R*,R*-(E)]]-N-[2-[2-[[(4-Amino-2-butenyl)thio ]methyl]-1-pyrrolidinyl]-1-(hydroxymethyl)-2-oxoethyl]-2-naphthalenesulfonamide A. (S,Z)-2-[4-[(2-Pyrrolidinylmethyl)thio]-2-butenyl]-1H-isoindole-1,3(2H)-dione, hydrochloride To a solution of (S,Z)-2-[4-[[[1-[(1,1-dimethylethoxy)carbonyl]-2-pyrrolidinyl]methyl]thio]-2-butenyl]-1H-isoindole-1,3(2H)-dione, (prepared as in Example I, Part A, except substituting 4-bromo-2-butenyl phthalimide for the corresponding phthalimide) (3.60 mmol)) in 2 mL of CH$_2$Cl$_2$ was added 18 mL of 4N HCl/dioxane at 0° C. The ice bath was removed and the reaction was stirred at room temperature for 3 hrs. The reaction mixture was concentrated in vacuo to give title compound (92% yield).

B. [S-[R*,R*-(Z)]]-N-[2-[2-[[[4-(1,3-Dihydro-1,3-dioxo-2H-isoindol-2-yl)-2-butenyl]thio]methyl]-1-pyrrolidinyl]-2-(hydroxymethyl)-2-oxoethyl]-2-naphthalenesulfonamide To a solution of Example V, Part B compound (650 mg, 2.20 mmol) and HOBT (327 mg, 2.42 mmol) in 14 mL of DMF was added WSC (464 mg, 2.42 mmol), followed by the Part A amine salt (818 mg, 2.20 mmol). The pH was adjusted to 8 by NMM (0.27 mL, 2.42 mmol) and the reaction was stirred at room temperature for 16 hrs. The reaction mixture was partitioned between H$_2$O and EtOAc and EtOAc was washed with a sat. solution of NaHCO$_3$, a sat. solution of KHSO$_4$, brine and dried over MgSO$_4$. The organic layer was concentrated in vacuo to give title compound (86% yield).

C. [S-[R*,R*-(E)]]-N-[2-[2-[[(4-Amino-2-butenyl)thio]-methyl]-1-pyrrolidinyl]-1-(hydroxymethyl)-2-oxoethyl]-2-naphthalenesulfonamide To a solution of Part B compound (800 mg, 1.34 mmol) in 34 mL CH$_3$OH was added hydrazine (0.42 mL, 13.4 mmol) at room temperature and the reaction was stirred at 40°–50° C. for 3 hrs. The reaction mixture was concentrated in vacuo and partitioned between EtOAc and 1N NaOH; the aqueous layer was salted out with NaCl and extracted with EtOAc. The organic layers were combined and concentrated in vacuo to give the crude product which was crystallized in EtOAc (71% yield).

Anal. Calc'd for C$_{22}$H$_{29}$N$_3$O$_4$S$_2$.1.00 HCl.0.14 H$_2$O: C, 52.57; H, 6.07; N, 8.36; S, 12.76; Cl 7.05 Found: C, 52.84; H, 6.01; N, 8.09; S, 12.57; Cl, 7.14

$[\alpha]_D$=−36.8 (c=0.50, MeOH).

EXAMPLE IX

[S- [R*,R*-(E)]]-N-[2-[[[[4-[(Aminoiminomethyl)amino]-2-butenyl]thio]methyl]-1-pyrrolidinyl]-1-(hydroxymethyl)-2-oxoethyl]-2-naphthalenesulfonamide, trifluoroacetate (1:) salt To a solution of Example VIII title compound (0.4 g, 0.86 mmol) and amidinesulfonic acid (161 mg, 1.29 mmol) in 5 mL EtOH was added Et$_3$N (0.364 mL, 2.59 mmol). The reaction was stirred at room temperature for 1 hr. The reaction mixture was concentrated in vacuo and purified by preparative HPLC to give title compound (60% yield).

Anal. Calc'd for C$_{23}$H$_{31}$N$_5$O$_4$S$_2$.1.20 TFA.0.28 H$_2$O: C, 47.11; H, 5.10; N, 10.82; S, 9.90; F, 10.56 Found: C, 47.12; H, 4.92; N, 10.56; S, 9.48; F, 10.23

$[\alpha]D$=−26.6 (c=0.50, MeOH).

EXAMPLE X

[S-(R*,R*)]-N-[2-[2-[[[[1-(Aminoiminomethyl)-3-piperidinyl]methyl]thio]methyl]-1-pyrrolidinyl]-1-(hydroxymethyl)-2-oxoethyl]-2-naphthalenesulfonamide, trifluoroacetate (1:1) salt The title compound was prepared in a manner similar to that described in Example V, except substituting 3-tosyloxymethyl-N-carbobenzyloxy piperidine for 4-tosyloxymethyl-N-carbobenzyloxy piperidine, to provide the desired product.

Anal. Calc'd for C$_{25}$H$_{35}$N$_5$O$_4$S$_2$.1.2 TFA.1.01 H$_2$O: C, 47.78; H, 5.59; N, 10.17; S, 9.31 Found: C, 47.78; H, 5.46; N, 9.97; S, 9.37

$[\alpha]D$=−57.7 (c=2.01, DMSO).

EXAMPLE XI

[S-(R*,R*)]-N-[2-[2-[[[5-[(Aminoiminomethyl)amino]pentyl]thio]methyl]-1-pyrrolidinyl]-1-(hydroxymethyl)-2-oxoethyl]-1-naphthalenesulfonamide, trifluoroacetate (1:1) salt The title compound was prepared as described in Example I, except N-(5-bromopentyl)phthalimide was substituted for the N-(4-bromobutyl)phthalimide.

Anal. Calc'd for C$_{24}$H$_{35}$N$_5$O$_4$S.1.16 TFA.0.92 H$_2$O: C, 47.15; H, 5.71; N, 10.44; S, 9.56 Found: C, 47.15; H, 5.42; N, 10.36; S, 9.91

$[\alpha]_D$=−263.7 (c=4.51, CD$_3$OD).

EXAMPLE XII

[S-(R*,R*)]-N-[2-[[2-[[[6-[(Aminoiminomethyl)amino] hexyl]thio]methyl]-1-pyrrolidinyl]-1-(hydroxymethyl)-2-oxoethyl]-2-naphthalenesulfonamide, trifluoroacetate (1:1) salt A. 6-Phthalimido-1-bromohexane A solution of phthalic anhydride (32.0 g, 0.21 mol) and 6-aminohexanol (25.0 g, 0.21 mol) in 180 mL dry toluene was heated to reflux for 3 hrs. When the intermediate phthalimide was formed, PBr$_3$ (18.2 mL, 0.58 mol in 20 mL toluene) was added dropwise and the reaction was stirred at 100° C. for 1.5 hrs. The reaction mixture was filtered thru a microfiber filter and the filtrate was concentrated in vacuo to give the crude product which then crystallized from toluene to give 6-phthalimido-1-bromohexane. (86% yield).

B. N-Boc-2-pyrrolidinethio-6-hexaphthalimide

To a solution of the Example I Part A tosylate (8 g, 22.53 mmol) in 150 mL acetone was added KSAc (3.34 g, 29.3 mmol). The reaction was heated to reflux for 16 hrs. The precipitate was removed by filtration and the filtrate was concentrated in vacuo. The crude product was isolated by a silica gel column using a mixture of EtOAc and hexane (2 to 1 ratio) as an eluting solvent to give N-Boc-2-pyrrolidinethio-acetate (43% yield).

(M+H)$^+$@260.

To a solution of N-Boc-2-pyrrolidinethioacetate (0.9 g, 3.47 mmol) and 6-phthalimido-1-bromohexane (1.08 g, 3.47 mmol) in 10 mL MeOH and 1 mL of DMF was added NaOMe (0.8 mL, 3.47 mmol) under argon at 0° C. After the reaction was stirred at 0° C. for 30 minutes, the ice bath was removed; the reaction was stirred at room temperature for 16 hrs and was concentrated in vacuo. The crude product was purified on a silica gel column using EtOAc/Hexane (1 to 4 ratio) to give title compound (35% yield).

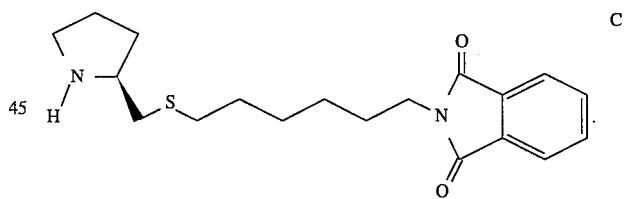

C

To a solution of N-Boc-2-pyrrolidine thio-6-hexaphthalimide (0.5 g, 11.2 mmol) in 3 mL of CH$_2$Cl$_2$ was added 4N HCl (3.5 mL, 3.5 mmol) at 0° C. The ice bath was removed and the reaction was stirred at room temperature for 1 hr. The reaction mixture was concentrated in vacuo to give the title HCl salt (89% yield).

D.

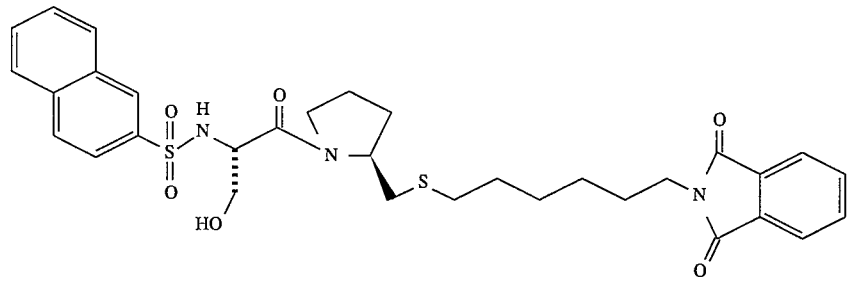

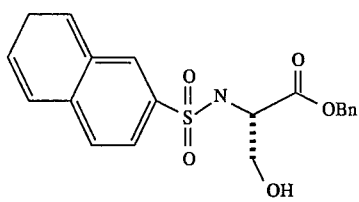

To a solution of 2-naphthalene sulfonyl chloride (3 g, 13.23 mmol) and serine benzylester (3.07 g, 13.23 mmol) in 120 mL $CH_2Cl_2$ was added $Et_3N$ (5.53 mL, 13.23 mmol) at 0° C. The reaction was stirred at room temperature for 1 hr and washed with a sat. solution of $KHSO_4$, brine over $Na_2SO_4$. The organic layer was concentrated in vacuo to give title compound (93% yield). $(M+H)^+@386$.

D(2). 2-Naphthalenesulfonyl-serine

To a solution of Part D(1) compound (1 g, 2.59 mmol) and Pd/C (10%, 50 mg) in 25 mL EtOAc was added 2.6 mL of 1N HCl, followed by $H_2$. The reaction was stirred at room temperature for 16 hrs and the catalyst was removed by filtration. The filtrate was concentrated in vacuo to give 2-naphthalene sulfonylserine (89% yield). $(M+H)^+@296$.

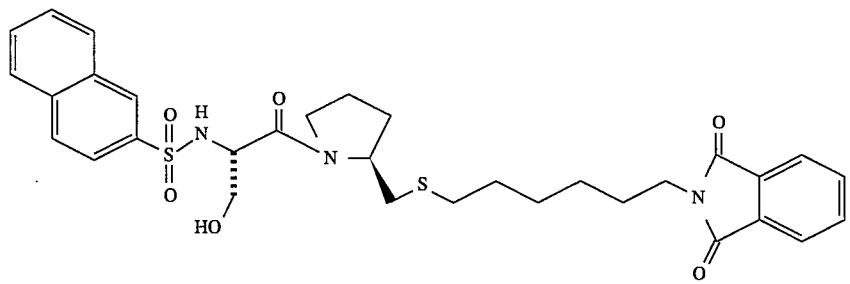

To a solution of 2-naphthalene sulfonyl-serine (293 mg, 0.99 mmol) and HOBT (1.47 g, 1.09 mmol) in 10 mL DMF was added WSC (209 mg, 1.09 mmol) and Part C compound (380 mg, 0.99 mmol), followed by NMM (0.3 mL, 2.18 mmol). The reaction was stirred at room temperature for 16 hrs. The reaction mixture was partitioned between EtOAc and a sat. solution of $NaHCO_3$ and the organic layer was washed with a sat. solution of $KHSO_4$, brine, dried over $Na_2SO_4$., and EtOAc was concentrated in vacuo to give title compound (83% yield).

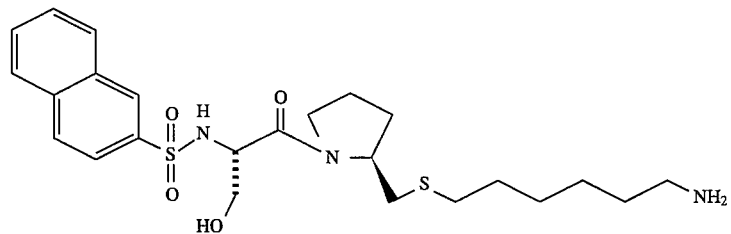

To a solution of Part D compound (510 mg, 0.82 mmol) in 10 mL MeOH was added hydrazine (0.26 mL, 8.2 mmol) at room temperature. The reaction was stirred at 40°–50° C. for 4 hrs. The reaction mixture was concentrated in vacuo and partitioned between EtOAc and 1N NaOH, dried over $Na_2SO_4$. The organic layer concentrated in vacuo to give title compound (74% yield).

D(1).

F. [S-(R*,R*)]-N-[2-[[2-[[[6-[(Aminoiminomethyl)amino]hexyl]thio]methyl]-1-pyrrolidinyl]-1-(hydroxymethyl)-2-oxoethyl]-2-naphthalenesulfonamide, trifluoroacetate (1:1) salt To a solution of Part E amine (300 mg, 0.61 mmol) and amidinesulfonic acid (113 mg, 0.91 mmol) in 10 mL EtOH was added $Et_3N$ (0.26 mL, 1.83 mmol). The reaction stirred at room temperature for 16 hrs. The reaction mixture was concentrated in vacuo and purified by a preparative HPLC to give title compound (34% yield).

Elemental Analysis: $C_{25}H_{37}N_5O_4S$.1.15 TFA.0.52 $H_2O$ Calc.: C, 47.15; H, 5.71; N, 10.44; S, 9.56 Found: C, 47.15; H, 5.42; N, 10.36; S, 9.91.

$[\alpha]_D = -91.0$ (c=2.00, $CH_3OH$).

D(3).

EXAMPLE XIII

[3R-[3R*,3(S*,S*)]]-N-[2-[2-[[[[1-(Aminoiminomethyl)-3-piperidinyl]methyl]thio]methyl]-1-pyrrolidinyl]-1-(hydroxymethyl)-2-oxoethyl]-2-naphthalenesulfonamide, trifluoroacetate (1:1) salt A. N-Carbobenzyloxy-3-piperidinemethanol To a solution of 3(R)-N-carbobenzyloxy-3-carboxypiperidine (2.0 g, 7.6 mmol) in 15 mL THF was added $BH_3.Me_2S$ dropwise at 0° C. and the ice bath was removed.

E.

The reaction was stirred at room temperature for 2 hrs. The reaction mixture was quenched with HOAc, MeOH, then 1N 7.6 mL NaOH and was stirred at room temperature for 2 hrs. The reaction mixture was concentrated in vacuo and extracted with EtOAc. The EtOAc layer was washed with 1N NaOH and concentrated in vacuo to give N-carbobenzyloxy-3-piperidinemethanol.

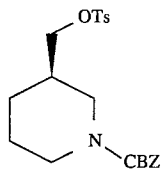

To a solution of Part A compound (2.0 g, 8.03 mmol) and TsCl (3.06 g, 16.06 mmol) in 35 mL CH$_2$Cl$_2$ was added Et$_3$N (3.39 mL, 24.09 mmol) at 0° C. The ice bath was removed and the reaction was stirred at room temperature for 16 hrs. The reaction mixture was washed with H$_2$O and was concentrated in vacuo to give the crude which was purified by a silica gel column using a mixed solvent (EtOAc:hexane=1:2 ratio) to obtain title compound (70% yield).

C.

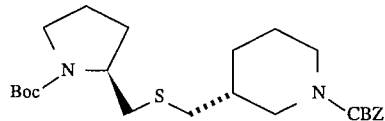

To a solution of N-Boc-2-pyrrolidinethioacetate (Example XII Part B) (1.0 g, 3.86 mmol) in 30 mL DMF was added NaOMe (0.88 mL, 15.44 mmol) under argon at 0° C. The reaction was stirred at 0° C. for 5 minutes and Part B compound (1.5 g, 3.86 mmol) was added at 0° C. The ice bath was removed and stirred at room temperature for 2 hrs. The reaction mixture was partitioned between EtOAc and H$_2$O and the EtOAc was washed with brine, dried over Na$_2$SO$_4$, concentrated in vacuo to give title compound (79% yield).

D.

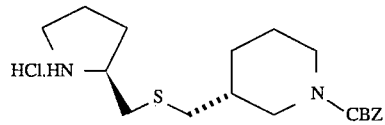

To a solution of Part C compound (1.2 g, 2.46 mmol) in 2 mL CH$_2$Cl$_2$ was added 4N HCl (7.4 mL, 7.4 mmol) at 0° C. The ice bath was removed and the reaction was stirred at room temperature for 2 hrs. The reaction was concentrated in vacuo to give title compound.

E.

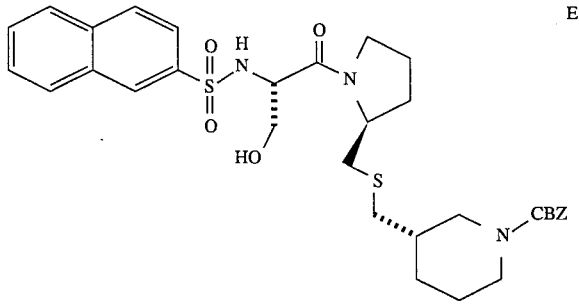

To a solution of 2-naphthalene sulfonyl-serine (prepared in Example XII Part D) (0.78 g, 2.67 mmol) and HOBT (0.4 g, 2.93 mmol) in 11 mL DMF was added WSC (0.56 g, 2.93 mmol), followed by Part D compound (1.03 g, 2.67 mmol). After 5 minutes, NMM (0.82 mL, 5.86 mmol) was added to adjust the pH to 7.5–8.0 and the reaction stirred at room temperature for 16 hrs. The reaction mixture was partitioned between EtOAc and a sat. solution of NaHCO$_3$ and the EtOAc layer was washed with a sat. solution of KHSO$_4$, brine, dried over Na$_2$SO$_4$. The organic layer was concentrated in vacuo to give title compound (87% yield).

F.

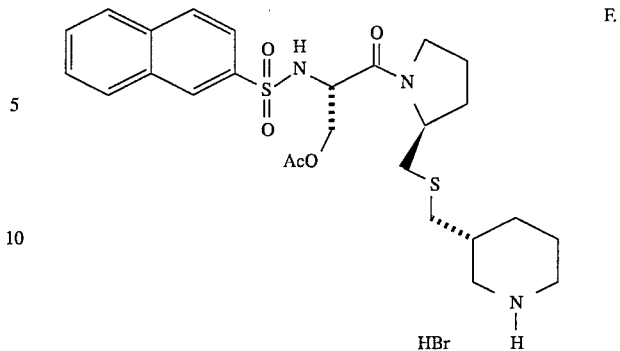

To a solution of Part E compound (1.3 g, 2.08 mmol) in 3 mL CH$_2$Cl$_2$ was added HBr (6.3 mL, 6.3 mmol) at 0° C. The ice bath was removed and the reaction was stirred at room temperature for 1 hr. The reaction mixture was concentrated in vacuo to give the title HBr salt (98% yield).

G.

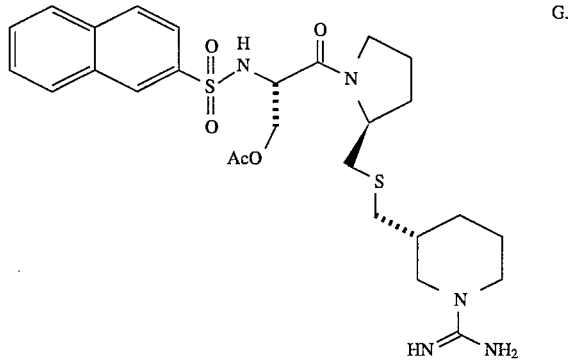

To a solution of the Part F piperidine HBr salt (1.08 g, 2.04 mmol) and H-pyrazole-1-carboxamidine.HCl (490 mg, 3.34 mmol) in 10 mL DMF was added diisopropylethylamine (DIEA) (1.06 mL, 6.08 mmol) and the reaction was stirred at room temperature for 72 hrs. The reaction mixture was purified by a preparative HPLC to give title compound (27% yield).

H. [3R-[3R*,3(S*,S*)]]-N-[2-[2-[[[[1-(Aminoiminomethyl)-3-piperidinyl]methyl]thio]methyl]-1-pyrrolidinyl]-1-(hydroxymethyl)-2-oxoethyl]-2-naphthalenesulfonamide, trifluoroacetate (1:1) salt

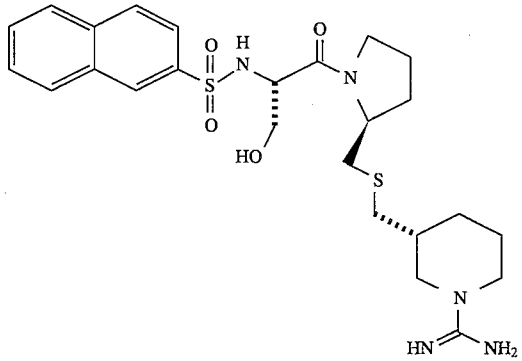

To a solution of Part G compound (0.31 g, 0.54 mmol) in 3 mL MeOH was added 1N NaOH (1.62 mL, 1.62 mmol) at 0° C. The ice bath was removed and the reaction was stirred at room temperature for 2 hrs. The reaction mixture was concentrated in vacuo and purified by preparative HPLC to give title compound (97% yield).

EXAMPLE XIV

[3S-[3R*,3(R*,R*)]]-N-[2-[2-[[[[1-(Aminoiminomethyl)-3-piperidinyl]methyl]thio]methyl]-1-pyrrolidinyl]-1-(hydroxymethyl)-2-oxoethyl]-2-naphthalenesulfonamide, trifluoroacetate (1:1) salt

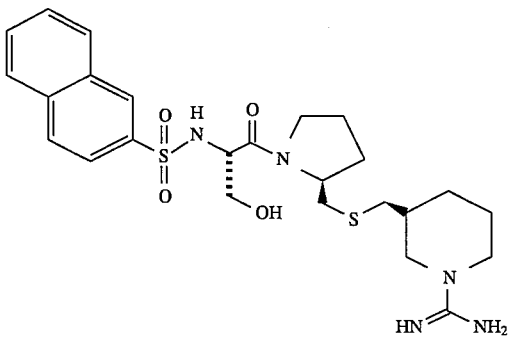

Elemental Analysis: $C_{25}H_{35}N_5O_4S_2$.1.4 TFA.1.25 $H_2O$
Calc.: C, 46.64; H, 5.48; N, 9.78; S, 8.96; F, 11.15 Found: C, 46.64; H, 5.28; N, 9.77; S, 8.77; F, 11.16.
$[\alpha]_D = -49.3°$ (c=4.1, $CD_3OD$).

Following the procedure of Example XIII, except substituting 3(S)-N-carbobenzyloxy-3-carboxypiper-idine for the 3(R) isomer used in Part A of Example XIII, the title compound was obtained.

Elemental Analysis: $C_{25}H_{35}N_5O_4S_2$.1.15 TFA.1.20$H_2O$
Calc.: C, 47.77; H, 5.66; N, 10.20; S, 9.34; F, 9.55 Found: C, 47.77; H, 5.37; N, 10.31; S, 8.99; F, 9.57.
$[\alpha]_D = -21.0°$ (c=4.08, DMSO).

Examples of additional compounds which may be prepared following the procedures set out in Examples I to XIV and in the specification are set out below.

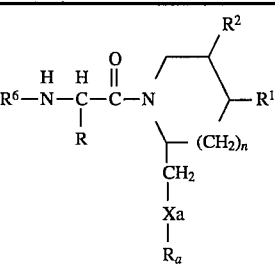

| Example | R6' | R | R2 | R1 | Xa | Ra | n |
|---|---|---|---|---|---|---|---|
| XV | 2-naphthyl-SO2— | HOCH2 | H | CH3 | S | —(CH2)4—NH—C(NH2)=NH | 0 |
| XVI | 2-naphthyl-SO2— | PhCH2—O—CH2— | H | CH3 | SO | —(CH2)4—NH—C(NH2)=NH | 1 |
| XVII | C2H5C(O)— | H | CH3S | H | SO2 | Ph-CH2NH2 | 2 |
| XVIII | H | PhCH2— | CH3O | cyclohexyl | S | —(CH2)4—C(NH2)=NH | 2 |
| XIX | 3-methylquinolin-8-yl-SO2— | NH2COCH2CH2— | OH | phenyl | SO | —(CH2)3—NH—C(NH2)=NH | 0 |

| Example | R6' | R | R2 | R1 | Xa | Ra | n |
|---|---|---|---|---|---|---|---|
| XX | quinolin-8-yl-SO2— | CH3CH(OH)— | H | —CH=O | SO2 | cyclohexyl-N(H)—C(NH2)=NH | 1 |
| XXI | phenyl-CO2— | HO2CCH2CH2— | H | NH2 | S | —(CH2)2—C(NH2)=NH | 1 |
| XXII | C4H9—CO2 | cyclohexylmethyl | H | (2-methylphenyl) | SO | phenyl-N(H)—C(NH2)=NH | 2 |

The following Examples represent preferred embodiments of the third embodiment of the present invention. Unless otherwise indicated, all temperatures are expressed in degrees Centigrade.

EXAMPLE 1a

[S-(R*,R*)]-4-Amino-N-[[1-[3-hydroxy-2-[(2-naphthalenylsulfonyl)amino]-1-oxopropyl]-2-pyrrolidinyl]methyl]butanamide, hydrochloride A. (S)-2-(Azidomethyl)-1-pyrrolidinecarboxylic acid, 1,1-dimethylethyl ester (S)-2-[[[(4-Methylphenyl)sulfonyl]oxy]methyl]-1-pyrrolidinecarboxylic acid, 1,1-dimethylethyl ester (3.55 g, 10 mmol, see J. Das et al, J. Med Chem, 1992, Vol.35,2610 for preparation) was dissolved in dimethyl sulfoxide (DMSO) (40 mL) and treated with sodium azide (980 mg, 15 mmol). The mixture was heated at 70° C. for 5 hours, then cooled and diluted with ether. After washing with water (3×50 mL), the ether layer was dried (MgSO4) and freed of solvent in vacuo to give title compound as a colorless oil (2.05 g, 91%) which was used without further purification.

B. N-BOC-L-Proline Methylamine

The Part A azide (1.45 g, 6.4 mmol) was dissolved in absolute ethanol (50 mL), and treated with 10% palladium on carbon (290 mg). The flask was equipped with a hydrogen filled balloon via a three way stopcock. Air inside the flask was evacuated under reduced pressure and the flask was then filled with hydrogen from the balloon. This process was repeated three times. The mixture was stirred overnight in the hydrogen atmosphere. The catalyst was then removed by filtration through a pad of MgSO4 and the pad was washed with more ethanol. The solvent was removed in vacuo to give title compound as a colorless oil (1.19 g, 93%).

C. (S)-2-[[[1-Oxo-4-[[(phenylmethoxy)carbonyl]amino]butyl]amino]methyl]-1-pyrrolidinecarboxylic acid, 1,1-dimethyl-ethyl ester Part B N-BOC-L-proline methylamine (1.04 g, 5.2 mmol) and N-CBZ-4-aminobutyric acid (1.24 g, 5.2 mmol) were dissolved in dimethyl formamide (DMF) (20 mL) at room temperature (RT). HOBT (702 mg, 5.2 mmol), WSC (995 mg, 5.2 mmol) and NMM (570 µL, 5.2 mmol) were added. The reaction was stirred for 16 hours (h), partitioned between ethyl acetate(50 mL) and 10% KHSO4 (100 mL). The aqueous layer was extracted with ethyl acetate (2×50 mL), and the organic layers were combined. The combined organic layers were washed with saturated NaHCO3 (50 mL) and saturated NaCl (50 mL), dried over magnesium sulfate and concentrated in vacuo to provide an oil. The crude material was purified by chromatography on silica gel. Elution with ethyl acetate:hexanes(2:1) followed by ethyl acetate gave title compound, (1.809 g, 83%) as a viscous oil which was characterized by NMR and used in the next step.

D. (S)-4-[[(Phenylmethoxy)carbonyl]amino]-N-(2-pyrrolidinylmethyl)butanamide, trifluoroacetate salt Part C BOC derivative (915 mg, 2.19 mmol) was dissolved in trifluoroacetic acid (TFA) (15 mL) and stirred at RT 80 min. The TFA was removed by distillation under reduced pressure and by coevaporation with toluene to give title amine.

E. [S-(R*,R*)]-[2-Oxo-2-[2-[[[1-oxo-4-[[(phenylmethoxy)carbonyl]amino]butyl]amino]methyl]-1-pyrrolidinyl]-1-[(phenylmethoxy)methyl]ethyl]carbamic acid, 1,1-dimethylethyl ester The Part D crude TFA salt (2.19 mmol) and BOC-Ser(OBn)-OH (710 mg, 2.41 mmol) were dissolved in DMF (10 mL) at RT. HOBT (326 mg, 2.41 mmol), WSC (463 mg, 2.41 mmol) and NMM (570 µL) were added. The reaction was stirred for 18 h, partitioned between ethyl acetate (50 mL) and saturated KHSO4 solution (50 mL). The aqueous layer was reextracted with ethyl acetate (2×50 mL) and the organic layers were combined. The combined organic layers were washed with saturated NaHCO3 (30 mL) and saturated NaCl, dried over magnesium sulfate and concentrated in vacuo. The remaining yellow oil was purified by chromatography on silica gel. Elution with ethyl acetate gave title compound, (611 mg, 47%) which was characterized by NMR.

F. [S-(R*,R*)]-N-[[1-[2-[(2-Naphthalenylsulfonyl)amino]-1-oxo-3-(phenylmethoxy)propyl]-2-pyrrolidinyl]methyl]-4-[[(phenylmethoxy)carbonyl]amino]butanamide Part E BOC derivative (610 mg, 1.02 mmol) was dissolved in TFA (15 mL) and stirred at RT 100 min. The TFA was removed by distillation under reduced pressure and by coevaporation with toluene. The crude TFA salt was dissolved in dichloromethane (15 mL), cooled in an ice bath, and 2-naphthylsulfonyl chloride (Aldrich, 254 mg, 1.12 mmol) was added, followed by triethylamine (855 µL, 6.12 mmol). The solution was warmed to RT and stirred 1.75 h before diluting with dichloromethane (50 mL). This solution was washed with potassium hydrogen sulfate solution (2×30 mL) and saturated $NaHCO_3$ (2×30 mL), dried over magnesium sulfate, and evaporated to provide crude title compound. The crude product was chromatographed on silica gel and eluted with EtOAc:hexanes (2:1) followed by EtOAc followed by 5%MeOH in $CH_2Cl_2$ to provide title sulfonamide as a foam (384 mg, 72% overall in two steps).

G. [S-(R*,R*)]-4-Amino-N-[[1-[3-hydroxy-2-[(2-naphthalenylsulfonyl)amino]-1-oxopropyl]-2-pyrrolidinyl]methyl]butanamide, hydrochloride Part F compound (480 mg, 0.71 mmol) was dissolved in ethanol (60 mL) to which acetyl chloride (1.4 mL) had been added and the mixture was hydrogenated over 10%Pd—C (150 mg) at 55 psi. After 17 h, additional catalyst (100 mg) and acetyl chloride (0.5 mL) were added. After an additional 18 h, the reaction mixture was filtered and the residual catalyst was washed with EtOH. The filtrate was concentrated in vacuo to obtain title des-benzyl, des-CBZ product.

EXAMPLE 2a

[S-(R*,R*)]-4-[(Aminoiminomethyl)amino]-N-[[1-[3-hydroxy-2-[(2-naphthalenylsulfonyl)amino]-1-oxopropyl]-2-pyrrolidinyl]methyl]butanamide, trifluoroacetate (1:1) salt Example 1a compound (0.71 mmol) was dissolved in ethanol (20 mL), to which amidinesulfonic acid (124 mg, 1.0 mmol) and triethylamine (270 µL, 1.9 mmol) were added. After 2.5 h the mixture was filtered through a pad of celite, washed with ethanol and the filtrate was concentrated to dryness. The crude material was purified by preparative HPLC to provide a white solid (218 mg, 47% overall yield from Example 1, Part F), Purity≧98%.

$[\alpha]_D$=−37.2° (c=0.9, MeOH)

Analysis calcd for 1.25 TFA+0.60 $H_2O$: C, 46.55; H, 5.28; N, 12.77; F, 10.83; S, 4.87. Found: C, 46.54; H, 5.56; N, 12.69; F, 10.80; S, 4.93.

EXAMPLE 3a

[R-(R*,S*)]-[2-[2-[[(4-Aminobutyl)amino]methyl]-1-pyrrolidinyl]-2-oxo-1-(phenylmethyl)ethyl]carbamic acid, phenylmethyl ester A. (S)-2-[[(Trifluoroacetyl)amino]methyl]-1-pyrrolidinecarboxylic acid, 1,1-dimethylethyl ester A solution of Example 1a, Part B N-BOC-L-prolinemethylamine compound (2.64 g, 13.27 mmol) in dichloromethane (50 mL) and pyridine (10 mL) was cooled to 0° C. and treated dropwise with trifluoroacetic anhydride (3.78 mL, 26.55 mmol). The reaction was allowed to warm slowly to room temperature and left stirring overnight. The mixture was diluted with ethyl acetate (150 mL) and washed with satd. copper sulfate solution (5×50 mL) and brine (3×30 mL), dried ($MgSO_4$) and freed of solvent in vacuo to give title compound as a yellow oil (3.516 g, 84%) which was used without further purification.

B. (S)-2-[[[4-(1,3-Dihydro-1,3-dioxo-1H-isoindol-2-yl)butyl](trifluoroacetyl)amino]methyl]-1-pyrrolidinecarboxylic acid, 1,1-dimethylethyl ester The Part A trifluoroacetamide (3.514 g, 11.12 mmol) and N-(4-bromobutyl)-phthalimide (3.136 g, 11.12 mmol) were dissolved in DMF (60 mL), and treated with cesium carbonate (7.25 g, 22.24 mmol). The reaction was heated in an oil bath maintained at 55° C. for 22 hours, cooled to room temperature and partioned between ethyl acetate (150 mL) and water (100 mL). The layers were separated, and the aqueous layer was reextracted with ethyl acetate (50 mL). The combined organic layers were dried over magnesium sulfate and concentrated in vacuo. The crude material was purified by chromatography on silica gel (Merck, 400 mL), eluting with 20–40% ethyl acetate in hexane to give title compound (2.773 g, 50%) as a viscous foam.

C. [R-(R*,S*)]-[2-[2-[[[4-(1,3-Dihydro-1,3-dioxo-2H-isoindol-2-yl)butyl](trifluoroacetyl)amino]methyl]-1-pyrrolidinyl]-2-oxo-1-(phenylmethyl)ethyl]carbamic acid, phenylmethyl ester Part A BOC derivative (2.27 g, 4.567 mmol) was dissolved in dichloromethane (10 mL) and TFA (30 mL) and stirred at RT 2.5 hours. The TFA was removed by distillation under reduced pressure and by coevaporation with toluene to give the TFA salt of the amine. This and Z-D-phenylalanine (1.50 g, 5.02 mmol)were dissolved in DMF (20 mL) at RT. HOBT (680 mg, 5.02 mmol), WSC (965 mg, 5.02 mmol) and NMM (1.1 mL, 10 mmol) were added. The reaction was stirred for 16 h, partitioned between ethyl acetate (70 mL) and 10% $KHSO_4$ (70 mL). The aqueous layer was extracted with ethyl acetate (2×70 mL), and the organic layers were combined. The combined organic layers were washed with saturated $NaHCO_3$ (50 mL) and saturated NaCl (50 mL), dried over magnesium sulfate and concentrated in vacuo to provide a viscous oil. The crude material was purified by chromatography on silica gel. Elution with ethyl acetate-:hexanes(1:1) followed by ethyl acetate gave title phthalimide, (2.43 g, 78%) as a viscous oil which was characterized by NMR.

D. [R-(R*,S*)]-[2-[2-[[(4-Aminobutyl)amino]methyl]-1-pyrrolidinyl]-2-oxo-1-(phenylmethyl)-ethyl]carbamic acid, phenylmethyl ester Part C phthalimide (1.79 g, 2.63 mmol) was dissolved in ethanol (12 mL) and treated with methyl hydrazine (2 mL). The mixture was heated under reflux for 2 hours at which time the HPLC indicated that no starting material remained, but showed a mixture of products. The solvent was removed in vacuo and by co-evaporation with toluene. The residue was dissolved in methanol (50 mL) and water (15 mL) and treated with potassium carbonate (2 g). The mixture was left stirring overnight at room temperature to complete the removal of the trifluoroacetamide group. 1N HCl solution was added to acidify the mixture and non-basic organics were removed by extracting with dichloromethane (70 mL). The dichloromethane layer was extracted with 1N HCl (50 mL). The combined aqueous layers were basified with NaOH solution and the desired amine was extracted into dichloromethane (3×70 mL), dried over magnesium sulfate and concentrated in vacuo to provide title compound as an oil (1.065 g, 90%).

EXAMPLE 4a

[R-(R*,S*)]-[2-[2-[[[4-[(Aminoiminomethyl)amino]butyl]amino]methyl]-1-pyrrolidinyl]-2-oxo-1-(phenylmethyl) ethyl]carbamic acid, phenylmethyl ester, trifluoroacetate (1:2) salt Example 3a compound (1.069 g, 2.356 mmol) was dissolved in ethanol (60 mL), to which amidinesulfonic acid (352 mg, 2.84 mmol) and triethylamine (550 μL, 3.94 mmol) were added. After 3.5 h the mixture was filtered through a pad of celite, washed with ethanol and the filtrate was concentrated to dryness. The crude material was purified by preparative HPLC to provide a white solid (1.225 g, 69%), Purity≧98%.

$[\alpha]_D = -2.9°$ (c=0.5 MeOH)

Analysis calcd for 2.20 TFA+0.70 $H_2O$: C, 49.75; H, 5.53; N, 11.09; F, 16.54. Found: C, 49.71; H, 5.48; N, 11.09; F, 16.57.

EXAMPLE 5a (2S)-N-[4-[[[1-(D-Phenylalanyl)-2-pyrrolidinyl]methyl]amino]butyl]guanidine, trifluoroacetate (1:2) salt Example 4a compound (540 mg, 0.712 mmol) was dissolved in methanol (30 mL) and treated with Periman's catalyst (Pd(OH)$_2$) (125 mg). The flask was equipped with a hydrogen filled balloon via a three-way stopcock. Air inside the flask was removed under reduced pressure and replaced with hydrogen from the balloon. This process was repeated three times. The mixture was stirred under the hydrogen atmosphere for 2.5 hours. The catalyst was removed by filtration and the filter pad was washed with additional methanol. The filtrate was freed of solvent in vacuo to give title compound which was dissolved in water (30 mL), passed through a millipore membrane and lyophilized to provide title compound as a white solid (429 mg, 93%), Purity≧98%.

Analysis calcd for 2.50 TFA+0.20 $H_2O$: C, 44.41; H, 5.72; N, 12.95; F, 21.95. Found: C, 44.49; H, 5.70; N, 12.86; F, 21.91.

EXAMPLE 6a

[R-(R*,S*)]-[2-[2-[[[(4-Aminobutyl)sulfonyl]amino]methyl]-1-pyrrolidinyl]-2-oxo-1-(phenylmethyl)ethyl]carbamic acid, 1,1-dimethylethyl ester A. 4-Bromobutylsulfonylchloride A stirred suspension of anhydrous sodium bromide (1.13 g, 11 mmol) and 1,4-butane sultone (1.36 g, 10 mmol) in DMF (10 mL) was heated in a bath maintained at 80° C. for 2 hours. The clear solution was cooled to room temperature and a white solid precipitated. The mixture was diluted with ethyl acetate and filtered. The white solid collected was washed five times with ether and dried in vacuo to give the sodium salt of 4-bromobutyl sulfonic acid (2.18 g). Solid phosphorous pentachloride (3.12 g, 15 mmol) was added to the sodium salt in several portions with mixing. After addition, the solid mixture was triturated with a spatula. An exothermic reaction ensued, the mixture became colored and became fluid. After stirring at room temperature for 30 min., the mixture was diluted with dichloromethane and treated slowly with ice water. The layers were separated and the dichloromethane solution was dried (MgSO$_4$), filtered and the solvent was removed in vacuo. The crude colorless oil was purified on silica gel (Merck) eluting with 50% ethyl acetate in hexane to give title compound as a colorless oil (1.69 g, 72%).

B. [R-(R*,S*)]-[2-[2-(Aminomethyl)-1-pyrrolidinyl]-2-oxo-1-(phenylmethyl)ethyl]carbamic acid, 1,1-dimethylethyl ester (1) [R-(R*,S*)]-[2-[2-(Azidomethyl)-1-pyrrolidinyl]-2-oxo-1-(phenylmethyl)ethyl]carbamic acid, 1,1-dimethylethyl ester Example 1a, Part A azide (4.52 g, 20 mmol) was dissolved in dichloromethane (5 mL) and trifluoroacetic acid (10 mL) and stirred at RT 2 hours. The TFA was removed by distillation under reduced pressure and by coevaporation with toluene to give the amine as a TFA salt. This and t-BOC-D-phenylalanine (5.3 g, 20 mmol) were dissolved in DMF (30 mL). HOBT (2.7 g, 20 mmol), WSC (4 g, 20 mmol) and NMM (8 mL) were added. The reaction was stirred for 24 h, diluted with ethyl acetate (75 mL) and washed with 10% KHSO$_4$ (2×), saturated sodium bicarbonate solution (2×) and 10% lithium chloride solution (2×). The ethyl acetate layer was dried over magnesium sulfate and concentrated in vacuo to provide title compound (7.4 g, 99%) as an oil which was used without further purification.

(2) [R-(R*,S*)]-[2-[2-(Aminomethyl)-1-pyrrolidinyl]-2-oxo-1-(phenylmethyl)ethyl]carbamic acid, 1,1-dimethylethyl ester The Part (1) azide (2.25 g, 6.0 mmol) was dissolved in absolute ethanol (40 mL), and treated with 10% palladium on carbon (200 mg). The flask was equipped with a hydrogen filled balloon via a three way stopcock. Air inside the flask was evacuated under reduced pressure and the flask was then filled with hydrogen from the balloon. This process was repeated three times. The mixture was stirred overnight in the hydrogen atmosphere. The catalyst was then removed by filtration through a pad of MgSO$_4$ and the pad was washed with more ethanol. The solvent was removed in vacuo to give title amine as a white foam (2.15 g, Quant).

C. [R-(R*,S*)]-[2-[2-[[[(4-Bromobutyl)sulfonyl]amino]methyl]-1-pyrrolidinyl]-2-oxo-1-(phenylmethyl)ethyl]carbamic acid, 1,1-dimethylethyl ester A solution of Part A 4-bromobutyl sulfonyl chloride (942 mg, 4 mmol) in dichloromethane (3 mL) was added dropwise to a cooled (−10° C.) stirred solution of Part B amine (868 mg, 2.5 mmol) and triethyl amine (1.2 mL, 8 mmol) in dichloromethane (10 mL). After a few minutes, a precipitate formed. The suspension was stirred at −10° C. for 2 hours, diluted with dichloromethane (25 mL) and washed with 1 N HCl solution (2×15 mL). The dichloromethane solution was dried (MgSO$_4$), filtered and the solvent was removed in vacuo. The crude oil was purified on silica gel (Merck) eluting with 30%, 50%, and 70% ethyl acetate in hexane to give title compound as a white foam (910 mg, 67%).

D. [R-(R*,S*)]-[2-[2-[[[(4-Azidobutyl)sulfonyl]amino]methyl]-1-pyrrolidinyl]-2-oxo-1-(phenylmethyl)ethyl]carbamic acid, 1,1-dimethylethyl ester A solution of Part C bromo sulfonamide (800 mg, 1.46 mmol) in DMSO (5 mL) was treated with sodium azide (143 mg, 2.2 mmol) and the mixture was heated in an oil bath maintained at 60° C. for 3.5 hours. After cooling, the mixture was partitioned between ether (50 mL) and water (25 mL). The ether layer was washed with water (2×10 mL), dried (MgSO$_4$), filtered and the solvent was removed in vacuo. The crude oil was purified on silica gel (Merck) eluting with 50% ethyl acetate in hexane to give title compound as an oil (733 mg, 98%).

E. [R-(R*,S*)]-[2-[2-[[[(4-Aminobutyl)sulfonyl]amino]methyl]-1-pyrrolidinyl]-2-oxo-1-(phenylmethyl)ethyl]carbamic acid, 1,1-dimethylethyl ester Part D compound (730 mg, 1.437 mmol) was dissolved in ethanol (20 mL) and treated with 10% palladium on carbon (180 mg). The flask was equipped with a hydrogen filled balloon via a three-way stopcock. Air inside the flask was removed under reduced pressure and replaced with hydrogen from the balloon. This process was repeated three times. The mixture was stirred under the hydrogen atmosphere for 18 hours. The catalyst was removed by filtration and the filter pad was washed with additional ethanol. The filtrate was taken to dryness in vacuo leaving title compound as a colorless oil (758 mg, Quant.).

EXAMPLE 7a

[R-(R*,S*)]-4-[(Aminoiminomethyl)amino]-N-[[1-(2-amino-1-oxo-3-phenylpropyl)-2-pyrrolidinyl]methyl]butanesulfonamide, trifluoroacetate (1:2) salt Example 6a amine (1.437 mmol) was dissolved in ethanol (30 mL), to which amidinesulfonic acid (250 mg, 2.0 mmol) and triethyl amine (280 µL, 2.0 mmol) were added. After 3 h, the mixture was filtered through a pad of celite, washed with ethanol and the filtrate was concentrated to dryness. The residue was treated with TFA (5 mL) for 3 hours and then freed of excess TFA by coevaporation with toluene. The crude material was purified by preparative HPLC to provide a white solid (523 mg, 55% from Example 6, Part D compound), Purity≧98%.

$[\alpha]_D = -63.3°$ (c=0.6, MeOH).

Analysis calcd for 2.2 TFA+0.2 $H_2O$: C, 41.39; H, 5.14; N, 12.38; F, 18.47; S, 4.72. Found: C, 41.44; H, 5.16; N, 11.89; F, 18.41; S, 4.56.

EXAMPLE 8a

[R-(R*,S*)]-2-[2-[[[(3-Aminopropyl)sulfonyl]amino]methyl]-1-pyrrolidinyl]-2-oxo-1-(phenylmethyl)ethyl]carbamic acid, 1,1-dimethylethyl ester A. 3-Bromopropyl sulfonyl chloride A stirred suspension of anhydrous sodium bromide (1.60 g, 15.5 mmol) and 1,3-propane sultone (1.83 g, 15 mmol) in DMF (15 mL) was heated in a bath maintained at 80° C. for 2 hours, during this time material precipated. The mixture was cooled to room temperature, dilited with ethyl acetate and filtered. The white solid collected was washed five times with ether and dried in vacuo to give the sodium salt of 3-bromopropyl sulfonic acid (3.11 g). Solid phosphorous pentachloride (4.68 g, 22.5 mmol) was added to the sodium salt, in several portions, with mixing. After addition, the solid mixture was triturated with a spatula. An exothermic reaction ensued, the mixture became colored and became fluid. After stirring at room temperature for 30 min., the mixture was diluted with dichloromethane and treated slowly with ice water. The layers were separated and the dichloromethane solution was dried ($MgSO_4$), filtered and the solvent was removed in vacuo. The crude colorless oil was purified on silica gel (Merck) eluting with 30% ethyl acetate in hexane to give title compound as a colorless oil (2.544 g, 76%).

B. [R-(R*,S*)]-2-[2-[[[(3-Bromopropyl)sulfonyl]amino]methyl]-1-pyrrolidinyl]-2-oxo-1-(phenylmethyl)ethyl]carbamic acid, 1,1-dimethylethyl ester A solution of Part A 3-bromopropyl sulfonyl chloride (1.06 g, 4.8 mmol) in dichloromethane (5 mL) was added dropwise to a cooled (−10° C.) stirred solution of Example 6a, Part B amine (1.05 g, 3.02 mmol) and triethyl amine (1.44 mL, 9.6 mmol) in dichloromethane (15 mL). After a few minutes, a precipitate formed. The suspension was stirred at −10° C. for 2.5 hours, diluted with dichloromethane (35 mL) and washed with 1N HCl solution (2×15 mL). The dichloromethane solution was dried ($MgSO_4$), filtered and the solvent was removed in vacuo. The crude oil was purified on silica gel (Merck, 150 mL) eluting with 50% ethyl acetate in hexane to give title compound as a white foam (1.160 g, 72%).

C. [R-(R*,S*)]-2-[2-[[[(3-Azidopropyl)sulfonyl]amino]methyl]-1-pyrrolidinyl]-2-oxo-1-(phenylmethyl)ethyl]carbamic acid, 1,1-dimethylethyl ester A solution of Part B bromo sulfonamide (1.10 g, 2.06 mmol) in DMSO (8 mL) was treated with sodium azide (202 mg, 3.1 mmol) and the mixture was heated in an oil bath maintained at 60° C. for 3.75 hours. After cooling, the mixture was partitioned between ether (60 mL) and water (30 mL). The ether layer was washed with water (2×15 mL), dried ($MgSO_4$), filtered and the solvent was removed in vacuo. The crude oil was purified on silica gel (Merck, 150 mL) eluting with 50% ethyl acetate in hexane to give title compound as a white foam (872 mg, 86%).

D. [R-(R*,S*)]-2-[2-[[[(3-Aminopropyl)sulfonyl]amino]methyl]-1-pyrrolidinyl]-2-oxo-1-(phenylmethyl)ethyl]carbamic acid, 1,1-dimethylethyl ester Part C compound (870 mg, 1.76 mmol) was dissolved in ethanol (25 mL) and treated with 10% palladium on carbon (200 mg). The flask was equipped with a hydrogen filled balloon via a three-way stopcock. Air inside the flask was removed under reduced pressure and replaced with hydrogen from the balloon. This process was repeated three times. The mixture was stirred under the hydrogen atmosphere for 18 hours. The catalyst was removed by filtration and the filter pad was washed with additional ethanol. The filtrate was taken to dryness in vacuo leaving title compound as a colorless oil.

EXAMPLE 9a

[R-(R*,S*)]-2-[2-[[[3-[(Aminoiminomethyl)amino]propyl]sulfonyl]amino]methyl]-1-pyrrolidinyl]-2-oxo-1-(phenylmethyl)ethyl]carbamic acid, 1,1-dimethylethylethyl ester, trifluoroacetate (1:1) salt Example 8a amine (1.76 mmol) was dissolved in ethanol (35 mL) and amidinesulfonic acid (306 mg, 2.46 mmol) and triethylamine (345 µL, 2.5 mmol) were added. After 3 hours, the mixture was filtered through a pad of celite, washed with ethanol and the filtrate was concentrated to dryness. The crude material was purified by preparative HPLC to provide a white solid (820 mg, 71% from Example 8a, Part C compound), Purity≧98%.

$[\alpha]_D = -38.4°$ (c=0.9, MeOH). Analysis calcd for 1.25 TFA+0.2 $H_2O$: C, 46.63; H, 6.09; N, 12.80; F, 10.85; S, 4.88. Found: C, 46.87; H, 6.12; N, 12.60; F, 10.83; S, 4.92.

EXAMPLE 10a

[R-(R*,S*)]-3-[(Aminoiminomethyl)amino]-N-[[1-(2-amino-1-oxo-3-phenylpropyl)-2-pyrrolidinyl]methyl]propanesulfonamide, trifluoroacetate (1:2) salt Example 9a compound (500 mg, 0,76 mmol) was treated with TFA (5 mL) for 1.5 hours and then freed of excess TFA in vacuo. The residue was dissolved in water (20 mL) and passed through a Millipore filtration membrane. The aqueous solution was frozen and lyophillized to give a dense solid. This was again dissolved in water (20 mL) and relyophillized to give title compound as a fluffy white solid (479 mg, 93%), Purity≧98%.

$[\alpha]_D = -60.2°$ (c=0.6, MeOH).

Analysis calcd for 2.2 TFA+0.4 $H_2O$: C, 40.24; H, 4.98; N, 12.57; F, 18.75; S, 4.80. Found: C, 40.21; H, 5.10; N, 12.35; F, 18.94; S, 4.81.

EXAMPLE 11a

[R-(R*,S*)]-2-Amino-1-[2-[[[4-(aminomethyl)phenyl]amino]methyl]-1-pyrrolidinyl]-3-phenyl-1-propanone, trifluoroacetate (1:3) salt A. [(4-Aminophenyl)methyl]carbamic acid, phenylmethyl ester To a solution of 4-aminobenzenemethanamine (1.5 g, 12.3 mmol) in 20 mL $CH_2Cl_2$ was added benzylchloroformate (1.57 mL, 11 mmol), followed by triethylamine ($Et_3N$)

(1.5 mL, 11 mmol) at room temperature. White percipitates was observed immediately. The reaction was stirred at room temperature for 10 minutes and removed Et$_3$N salt by filtration. The reaction mixture was concentrated in vacuo and partitioned between EtOAc and H$_2$O. The EtOAc layer was washed with a sat. solution of KHSO$_4$, a sat. solution of NaHCO$_3$, concentrated in vacuo and subjected to a silica-gel column using CHCl$_3$/CH$_3$OH=25/1 ratio as an eluting solvent to give title compound (43% yield).

B. (S)-[[4-[[[1-[(1,1-Dimethylethoxy)carbonyl]-2-pyrrolidinyl]methyl]amino]phenyl]methyl]carbamic acid, phenylmethyl ester To a solution of Example 16a, Part A aldehyde (0.36 g, 1.79 mmol) and Part A compound (0.46 g, 1.79 mmol) in 3 mL CH$_2$Cl$_2$CH$_2$Cl$_2$ was slowly added acetic acid (AcOH) (140 µl, 2.33 mmol) at 0° C., followed by NaB(AcO)$_3$H. The reaction stirred at room temperature for 115 minutes and partitioned between EtOAc/hexane (1:1 ratio) and H$_2$O. The organic layer was washed with H$_2$O, brine, dried over Na$_2$SO$_4$ and concentrated in vacuo to give title compound (98% yield).

C. (S)-[[4-[(2-Pyrrolidinylmethyl)amino]phenyl]methyl] carbamic acid, phenylmethyl ester, trifluoroacetate (1:1) salt To a solution of Part B compound (0.8 g, 1.82 mmol) in 5 mL CH$_2$Cl$_2$ was added trifluoroacetic acid (TFA) (5.5 mL, 5.46 mmol) at 0° C. The ice bath was removed and stirred at room temperature for 1 hr. The reaction mixture was concentrated in vacuo and treated with a sat. HCl/Et$_2$O to give title compound (quant. yield).

D. [R-(R*,S*)]-2-[[(1,1-Dimethylethoxy)carbonyl] amino]-3-phenyl-1-[2-[[[4-[[[(phenylmethoxy)amino]methyl]phenyl]amino]methyl]-1-pyrrolidinyl]-1-propanone To a solution of Boc-D-Phenylalanine (0.55 g, 2.05 mmol) and HOBT (0.28 g, 2.05 mmol) in 4 mL DMF was added WSC (0.39 g, 2.05 mmol), followed by Part C compound (0.7 g, 1.87 mmol). NMM (226 ml, 2.05 mmol) was used to adjust the pH to 7.5–8.0. The reaction stirred at room temperature for 16 hrs and partitioned between EtOAc and H$_2$O. The EtOAc layer was further washed with a sat. solution of NaHCO$_3$, a sat. solution of KHSO$_4$, brine, dried over Na$_2$SO$_4$ and concentrated in vacuo to give title compound (41% yield).

E. [R-(R*,S*)]-2-Amino-1-[2-[[[4-(aminomethyl)phenyl] amino]methyl]-1-pyrrolidinyl]-3-phenyl-1-propanone, trifluoroacetate (1:3) salt To a solution of Part D compound (0.2 g, 0.34 mmol) in 1 mL HOAc was added slowly 30% HBr in HOAc (1 mL, 1.12 mmol) at 0° C. The ice bath was removed and the reaction was stirred at room temperature for 1 hr. The reaction mixture was concentrated in vacuo and added Et$_2$O with stirred to formed white percipitates which was filtered to give title compound (59% yield).

Elemental Analysis: C$_{21}$H$_{28}$N$_4$O.3.10 TFA.0.60 H$_2$O Calc.: C, 45.58; H, 4.54; N, 7.82; F, 24.65 Found: C, 45.59; H, 4.29; N, 8.09; F, 24.80.

EXAMPLE 12a

[R-(R*,S*)]-N-[2-[2-[[[4-(Aminomethyl)phenyl]amino] methyl]-1-pyrrolidinyl]-2-oxo-1-(phenylmethyl)ethyl]-2-naphthalenesulfonamide, trifluoroacetate (2:3) salt A. [S-(R*,S*)]-2-Amino-3-phenyl-1-[2-[[[4-[[[(phenylmethoxy)amino]methyl]phenyl]amino]methyl]-1-pyrrolidinyl]-1-propanone To a solution of Example 1a, Part D compound (0.2 g, 0.34 mmol) in 2 mL CH$_2$Cl$_2$ was added TFA (1 mL, 1.12 mmol) at 0° C. The ice bath was removed and the reaction was stirred at room temperature for 1.5 hrs. The reaction mixture was concentrated in vacuo to give title compound (97% yield).

B. [R-(R*,S*)]-N-[2-[2-[[[4-[[[(Phenylmethyl)carbonyl] amino]methyl]phenyl]amino]methyl]-1-pyrrolidinyl]-2-oxo-1-(phenylmethyl)ethyl]-2-naphthalenesulfonamide To a solution of Part C compound (0.17 g, 0.28 mmol) in 3 mL CH$_2$Cl$_2$ was added 2-naphthalene sulfonyl chloride (0.07 g, 0.31 mmol), followed by Et$_3$N (86 ml, 0.62 mmol). Additional Et$_3$N (20 ml, 0.14 mmol) was added after 1 hr. The reaction was stirred at room temperature for 1 more hr and partitioned between CH$_2$Cl$_2$ and H$_2$O. The CH$_2$Cl$_2$ layer was washed with a sat. solution of KHSO$_4$, a sat. solution of NaHCO$_3$, brine, dried over Na$_2$SO$_4$ and concentrated in vacuo to give title compound (83% yield).

C. [R-(R*,S*)]-N-[2-[2-[[[4-(Aminomethyl)phenyl] amino]methyl]-1-pyrrolidinyl]-2-oxo-1-(phenylmethyl) ethyl]-2-naphthalenesulfonamide, trifluoroacetate (2:3) salt To a solution of Part B compound (0.16 g, 0.24 mmol) in 1 mL HOAc was added 30% HBr in HOAc (0.8 mL, 0.71 mmol) at 0° C. The ice bath was removed and the reaction was stirred at room temperature for 4 hrs. The reaction mixture was concentrated in vacuo and subjected to a prep. HPLC using 35 to 90% B over 40 minutes gradient to give title compound (49% yield).

Elemental Analysis Calcd for C$_{31}$H$_{34}$N$_4$O$_3$S.1.60 TFA: C, 56.65; H, 4.95; N, 7.73; F, 12.58; S, 4.42 Found: C, 56.66; H, 4.93; N, 7.79; F, 12.56; S, 4.20.

[α]$_D$=−35.1 (c=0.51, MeOH).

EXAMPLE 13a

[R, (R*,S*)]-2-Amino-1-[2-[3-[(aminoiminomethyl)amino] propyl]-1-pyrrolidinyl]-2-phenyl-1-propanone, trifluoroacetate (1:3) salt A. (S)-2-[[[3-(1,3-Dihydro-1,3-dioxo-1H-isoindol-2-yl) propyl](trifluoroacetyl)amino]methyl]-1-pyrrolidinecarboxylic acid, 1,1-dimethylethyl ester A solution of Example 3a, Part A trifluoroacetamide (1.26 g, 4 mmol) and N-(3-bromopropyl)phthalimide (1.7 g, 6 mmol) in DMF (40 mL) was treated with cesium carbonate (2.61 g, 8 mmol). The reaction was heated in an oil bath maintained at 55° C. for 24 hours, cooled to room temperature and partitioned between ethyl acetate (75 mL) and water. The layers were separated. The organic layer was dried over magnesium sulfate and concentrated in vacuo. The crude material was purified by chromatography on silica gel (Merck, 400 mL), eluting with 10–30% ethyl acetate in hexane to give title compound (1.07 g, 53%) as a colorless oil.

B. [R-(R*,S*)]-[2-[2-[[[3-(1,3-Dihydro-1,3-dioxo-2H-isoindol-2-yl)propyl](trifluoroacetyl)amino]methyl]-1-pyrrolidinyl]-2-oxo-1-(phenylmethyl)ethyl]carbamic acid, phenylmethyl ester.

Part A BOC derivative (974 mg, 2.0 mmol) was dissolved in dichloromethane (2 mL) and TFA (4 mL) and stirred at RT 2 hours. The TFA was removed by distillation under reduced pressure and by coevaporation with toluene to give the TFA salt of the amine as an oil. This and Z-D-phenylalanine (600 mg, 2 mmol) were dissolved in DMF (15 mL) at RT. HOBT (270 mg, 2 mmol), WSC (382 mg, 2 mmol) and NMM (0.6 mL, 6 mmol) were added. The reaction was stirred for 16 h, diluted with ethyl acetate (75 mL) and washed with KHSO$_4$ (20 mL, 2×) and saturated NaHCO$_3$ (20 mL, 2×). The ethyl acetate extract was dried over magnesium sulfate and concentrated in vacuo to provide an oil. The crude material was purified by chromatography on silica gel.

Elution with 20, 30, and 50% ethyl acetate in hexanes gave title compound, (1.06 g, 80%) as a white foam.

C. [R-(R*,S*)]-[2-[2-[[(3-Aminopropyl)amino]methyl]-1-pyrrolidinyl]-2-oxo-1-(phenylmethyl)ethyl]carbamic acid, phenylmethyl ester Part B phthalimide (1 g, 1.51 mmol) was dissolved in absolute ethanol (15 mL) and treated with methyl hydrazine (1.2 mL). The mixture was heated under reflux for 2 hours. The solvent was removed in vacuo and by co-evaporation with toluene (10 mL) and dichloromethane (10 mL×2). The residue was dissolved in methanol (30 mL) and water (10 mL) and treated with potassium carbonate (1.5 g), The mixture was left stirring overnight at room temperature to complete the removal of the trifluoroacetamide group. 1N HCl solution (25 mL) was added to acidify the mixture and non-basic organics were removed by extracting with dichloromethane (25 mL,×3). The dichloromethane layers were extracted with 1NHCl (50 mL). The combined aqueous layers were basified with NaOH solution and the desired amine was extracted into dichloromethane (30 mL,×3), dried over magnesium sulfate and concentrated in vacuo to provide title compound as an oil (615 mg, 93%).

D. [R-(R*,S*)]-2-[2-[[[3-[(Aminoiminomethyl)amino]propyl]amino]methyl]-1-pyrrolidinyl]-2-oxo-1-(phenylmethyl)ethyl]carbamic acid, phenylmethyl ester, trifluoroacetate (1:3) salt Part C compound (615 mg, 1.40 mmol) was dissolved in absolute ethanol (25 mL), to which amidinesulfonic acid (445 mg, 3.5 mmol) and triethylamine (560 µL, ~4 mmol) were added and the mixture left stirring 16 hours at room temperature. The mixture was filtered through a pad of celite. The pad was washed with ethanol and the filtrate was concentrated to dryness. The crude material was purified by preparative HPLC (YMC S-10 ODS 50×500 mm column, eluting with 49–58% methanol in water, containing 0.1% TFA). Fractions containing title compound were combined and lyophilized to provide a white solid (620 mg).

E. [R-(R*,S*)]-2-Amino-1-[2-[3-[(aminoiminomethyl)amino]propyl]-1-pyrrolidinyl]-3-phenyl-1-propanone, trifluoroacetate (1:3) salt The Part D TFA salt (~620 mg, ) was dissolved in methanol (30 mL)and treated with Pearlman's catalyst (150 mg). The flask was equipped with a hydrogen filled balloon via a three-way stopcock. Air inside the flask was removed under reduced pressure and replaced with hydrogen from the balloon. This process was repeated three times. The mixture was stirred under the hydrogen atmosphere for 3 hours. The catalyst was removed by filtration through Celite and the filter pad was washed with additional methanol. The filtrate was freed of solvent in vacuo to give title compound which was dissolved in water (20 mL), passed through a millipore membrane and lyophilized to provide title compound as a white solid (507 mg, 53% from Part C compound), Purity≧98%.

Analysis calcd for 2.90 TFA+0.10 H$_2$O: C, 42.10; H, 4.91; N, 12.38; F, 24.34. Found: C, 42.10 H, 4.97;, N, 12.28; F, 24.41.

EXAMPLE 14a

[S-(R*,S*)]-4-[(Aminoiminomethyl)amino]-N-[[1-(2-amino-1-oxo-3-phenylpropyl)-2-pyrrolidinyl]methyl]butanamide, trifluoroacetate (1:1) salt A. [R-(R*,S*)]-N-[[1-[2-[[(1,1-Dimethylethoxy)carbonyl]amino]-1-oxo-3-phenylpropyl]-2-pyrrolidinyl]methyl]-4-[[(phenylmethoxy)carbonyl]amino]butanamide Example 6a, Part B compound (694 mg, 2.0 mmol) and Z-4-aminobutyric acid (478 mg, 2.0 mmol) were dissolved in DMF (10 mL) at RT. HOBT (270 mg, 2.0 mmol), WSC (382 mg, 2.0 mmol) and NMM (500 µL) were added. The reaction was stirred for 16 h, diluted with ethyl acetate (50 mL) and washed with 10% KHSO$_4$ (25 mL), saturated NaHCO$_3$ (25 mL) and saturated NaCl (30 mL), dried over magnesium sulfate and concentrated in vacuo to provide title compound (1.04 g, 92%) as a viscous oil which was used without further purification.

B. [R-(R*,S*)]-4-Amino-N-[[1-[2-[[(1,1-dimethylethoxy)carbonyl]amino]-1-oxo-3-phenylpropyl]-2-pyrrolidinyl]methyl]butanamide Part A compound (1.04 g, 1.83 mmol) was dissolved in ethanol (100 mL) to which acetyl chloride (150 µL, 2 mmol) had been added and the mixture was treated with 10% palladium on carbon (400 mg). The flask was equipped with a hydrogen filled balloon via a three way stopcock. Air inside the flask was evacuated under reduced pressure and the flask was then filled with hydrogen from the balloon. This process was repeated three times. The mixture was stirred in the hydrogen atmosphere for 20 hours. The catalyst was then removed by filtration and the pad was washed with more ethanol. The solvent was removed in vacuo to give title compound as a viscous oil (932 mg,>100%). The material was characterized by NMR and MS. The NMR indicated an appreciable amount of ethanol was trapped in the product.

C. [R-(R*,S*)]-4-[(Aminoiminomethyl)amino]-N-[[1-[2-[[(1,1-dimethylethoxy)carbonyl]amino]-1-oxo-3-phenylpropyl]-2-pyrrolidinyl]methyl]butanamide Part B BOC derivative (1.83 mmol) was dissolved in ethanol (50 mL), to which amidinesulfonic acid (318 mg, 2.56 mmol) and triethylamine (690 µL, 4.94 mmol) were added. After 5 h the mixture was filtered through a pad of celite. The pad was washed with ethanol and the filtrate was concentrated to dryness to give the title BOC compound which was carried on without purification.

D. [S-(R*,S*)]-4-[(Aminoiminomethyl)amino]-N-[[1-(2-amino-1-oxo-3-phenylpropyl)-2-pyrrolidinyl]methyl]butanamide, trifluoroacetate (1:1) salt Part C BOC derivative (1.83 mmol) was dissolved in TFA (10 mL) and stirred at RT 90 min. The TFA was removed by distillation under reduced pressure and by coevaporation with toluene. The crude material was purified by preparative HPLC (YMC S-10 ODS 30×500 mm column, eluting with 38% methanol in water, containing 0.1% TFA). Fractions containing title compound were combined and lyophilized to provide a white solid (712 mg, 61% from Part A compound), Purity≧98%.

$[\alpha]_D=-55.7°$ (c=0.7, MeOH)

Analysis calcd for 2.25 TFA+0.10 H$_2$O: C, 44.60; H, 5.17; N, 13.28; F, 20.26. Found: C, 44.59; H, 5.43; N, 13.17; F, 20.40.

EXAMPLE 15a

[S-(R*,S*)]-4-[(Aminoiminomethyl)amino]-N-[[1-(2-[(methylsulfonyl)amino]-1-oxo-3-phenylpropyl)-2-pyrrolidinyl]methyl]butanamide, trifluoroacetate (1:1) salt Example 14a compound (158 mg, 0.25 mmol) was dissolved in a mixture of dichloromethane (2 mL) and dist. THF (4 mL). The solution was treated with triethyl amine (140 µL) followed by dropwise addition of methanesulfonyl chloride (24 µL, 0.3 mmol). The mixture was stirred at room temperature for 4 hours and then treated with water (~0.35 mL). The mixture was taken to dryness in vacuo. The crude material was purified by preparative HPLC to provide a white solid which was used to take NMR spectra. The material was recovered, dissolved in water (15 mL), passed through a millipore membrane and lyophilized to provide title compound as a white solid (126 mg, 85%).

Analysis calcd for 1.15 TFA+0.60 $H_2O$: C, 45.05; H, 5.82; N, 14.14; F, 11.02; S, 5.39. Found: C, 45.34 H, 5.71;, N, 13.75; F, 11.03; S, 5.50.

EXAMPLE 16a

[S-(R*,S*)]-4-[[[1-(2-Amino-1-oxo-3-phenylpropyl)-2-pyrrolidinyl]methyl]amino]benzenecarboximidamide, trifluoroacetate (1:2) salt A. (S)-2-Formyl-1-pyrrolidinecarboxylic acid, 1,1-dimethylethyl ester To a solution of oxalyl chloride (28 mL, 56.2 mmol) in 14 mL dry $CH_2Cl_2$ cooled at −78° C. (a dry ice acetone bath) was added 12 mL dry DMSO over 40 minutes. The reaction was stirred at −74° C. for additional 40 minutes and (S)-2-(hydroxymethyl)-1-pyrrolidinecarboxylic acid, 1,1-dimethylethyl ester, (5.40 g, 26.86 mmol) in 14 mL $CH_2Cl_2$ was added dropwise at −65° C. over 30 minutes. The reaction stirred additional 20 minutes at room temperature and partitioned between $Et_2O$ and $H_2O$. The $Et_2O$ layer was washed with more $H_2O$ (50 mL×4) and the $H_2O$ layers was extracted with $Et_2O$ (40 mL×3). All the $Et_2O$ layers was combined, washed with $H_2O$, brine, dried over $Na_2SO_4$ and concentrated in vacuo. The crude product was isolated by a silica-gel column using EtOAc and hexane (1:5 ratio) as an eluting solvent to give title compound (84% yield).

B. (S)-2-[[(4-Cyanophenyl)amino]methyl]-1-pyrrolidinecarboxylic acid, 1,1-dimethylethyl ester To a solution of Part A aldehyde, (2.0 g, 10.05 mmol) and 4-aminobenzonitrile, (1.3 g, 11.05 mmol) in dichloroethane (10 mL) was added acetic acid (844 μl, 14.07 mmol) dropwise at 0° C., followed by $NaB(AcO)_3H$ (2.34 g, 11.05 mmol). The ice bath was removed and the reaction stirred at room temperature for 1 hr. The reaction mixture was diluted with ethylacetate and hexane (1:1 ratio) and washed with $H_2O$ (20 mL), brine, dried over $Na_2SO_4$. The organic layer was concentrated in vacuo and isolated on a silica-gel column using $CHCl_3$/EtOAc (50:1 ratio) as an eluting solvent to give title compound (83% yield).

C. (S)-4-[(2-Pyrrolidinylmethyl)amino]benzenecarboximidamide

To a solution of Part B nitrile (1.36 g, 4.52 mmol) in dry EtOH was bubbled HCl gas at 0° C. for 10 minutes. Sealed and stirred at room temperature for 72 hrs. The reaction was concentrated in vacuo and was redissolved in dry EtOH. $NH_3$ gas was bubbled in the reaction until it is basic and the reaction was stirred at room temperature for 24 hrs and concentrated in Vacuo to give title compound (quant. yield).

D. [S-(R*,S*)]-4-[[[1-[2-[[(1,1-Dimethylethoxy)carbonyl]amino]-1-oxo-3-phenylpropyl]-2-pyrrolidinyl]methyl]amino]benzenecarboximidamide To a solution of L-Boc-phenylalanine (1.45 g, 5.50 mmol) and HOBT (743 mg, 5.50 mmol) in 26 mL DMF was added WSC (1.05 g, 5.50 mmol) and Part C compound (1.05 g, 5.50 mmol). After 5 minutes, NMM (605 μl, 5.50 mmol) was added to adjust the pH to 7.5–8.0. The reaction was stirred at room temperature for 16 hrs and partitioned between EtOAc and $H_2O$. The EtOAc layer was further washed with a sat. solution of $NaHCO_3$, a sat. solution of $KHSO_4$, brine, dried over $Na_2SO_4$ and concentrated in vacuo. The crude product was subjected to a Prep. HPLC to obtain title compound (42% yield).

E. [S-(R*,S*)]-4-[[[1-(2-Amino-1-oxo-3-phenylpropyl)-2-pyrrolidinyl]methyl]amino]benzenecarboximidamide, trifluoroacetate (1:2) salt To a solution of Part D compound (390 mg, 0.84 mmol) in 5 mL $CH_2Cl_2$ was added TFA at 0° C. Removed the ice bath and the reaction stirred at room temperature for 2 hrs.

The reaction mixture was concentrated in vacuo and subjected to a Prep. HPLC to give title compound (68% yield).

Elemental analysis $C_{21}H_{27}H_5O$.2.10 TFA.0.80 $H_2O$ Calc: C, 48.87; H, 5.00; N, 11.31; F, 19.33 Found: C, 49.13; H, 4.68; N, 10.89; F, 19.40.

EXAMPLE 17a

[S-(R*,R*)]-4-[(Aminoiminomethyl)amino]-N-[[1-[3-hydroxy-2-[[(7-methoxy-2-napthalenyl)sulfonyl]amino]-1-oxopropyl]-2-pyrrolidinyl]methyl]butanamide, trifluoroacetamide (1:1) salt A. [S-(R*,R*]-1-[2-(Azidomethyl)-1-pyrrolidinyl-2-[[(1,1-dimethylethoxy)carbonyl]amino]-3-(phenylmethoxy)-1-propanone Example 1a Part A compound (2.13 g, 9.4 mmol) was dissolved in dichloromethane (5 mL) and trifluoroacetic acid (7 mL) and stirred at RT 3 hours. The TFA and dichloromethane were removed by distillation under reduced pressure and by coevaporation with toluene to give the amine as a TFA salt. This and N-BOC-O-benzyl-L-serine (2.95 g, 10 mmol) were dissolved in DMF (50 mL). HOBT (1.35 g, 10 mmol), WSC (1.91 g, 10 mmol) and NMM (3.3 mL, 30 mmol) were added. The reaction was stirred for 8 h at room temperature, diluted with ethyl acetate (50 mL) and satd. $KHSO_4$ solution (30 mL). The layers were separated and the aqueous layer was reextracted with ethyl acetate (50 mL). The combined organic layers were washed with saturated sodium bicarbonate solution (30 mL)) and 10% lithium chloride solution (30 mL). The ethyl acetate layer was dried over magnesium sulfate and concentrated in vacuo to provide title compound (3.87 g, 100%) as an oil which was used without further purification.

B. [S-(R*,R*)]-2-Amino-1-[2-(azidomethyl)-1-pyrrolidinyl]-3-(phenylmethoxy)-1-propanone Part A BOC-azide (604 mg, 1.5 mmol) was dissolved in dichloromethane (1 mL) and TFA (2 mL) and stirred at RT 3 hours. Solvents were removed by distillation under reduced pressure and by coevaporation with toluene to give title amine as the TFA salt which was used in the next step.

C. [S-(R*,R*)]-N-[2-[2-(Azidomethyl)-1-pyrrolidinyl]-2-oxo-1-[(phenylmethoxy)methyl]ethyl]-7-methoxy-2-naphthalenesulfonamide The crude Part B TFA salt (1.5 mmol) was dissolved in dichloromethane (5 mL), cooled in an ice bath, and 7-methoxynapthene-2-sulfonyl chloride (384 mg, 1.5 mmol) was added, followed by dropwise addition of triethylamine (2 mL). The solution was stirred cold for 2 h before diluting with ethyl acetate (30 mL). This solution was washed with 1N HCl solution (10 mL), dried over magnesium sulfate and evaporated to provide crude title sulfonamide. The crude product was chromatographed on silica gel and eluted with 20 and 30% EtOAc in hexane to provide title sulfonamide as a foam (536 mg, 68% overall in two steps).

D. [S-(R*,R*)-N-[2-[2-(Aminomethyl)-1-pyrrolidinyl]-2-oxo-1-[(phenylmethoxy)methyl]ethyl]-7-methoxy-2-naphthalenesulfonamide The Part C sulfonamide (536 mg, 1 mmol) was dissolved in absolute ethanol (15 mL), and treated with 10% palladium on carbon (105 mg). The flask was equipped with a hydrogen filled balloon via a three way stopcock. Air inside the flask was evacuated under reduced pressure and the flask was then filled with hydrogen from the balloon. This process was repeated three times. The mixture was stirred eight hours in the hydrogen atmosphere. The catalyst was then removed by filtration through a pad of $MgSO_4$ and the pad was washed with ethyl acetate. The solvent was removed in vacuo to give title compound as a light yellow oil (477 mg, 94%).

E. [S-(R*,R*)]-N-[[1-[2-[[(7-Methoxy-2-naphthalenyl) sulfonyl]amino]-1-oxo-3-(phenylmethoxy)propyl]-2-pyrrolidinyl]methyl]-4-[[(phenylmethoxy) carbonyl]amino]butanamide Part D compound (477 mg, 0.96 mmol) and Z-4-aminobutyric acid (237 mg, 1.0 mmol) were dissolved in DMF (10 mL) at RT. HOBT (135 mg, 1.0 mmol), WSC (191 mg, 1.0 mmol) and NMM (330 µL) were added. The reaction was stirred for 5 h, diluted with satd $KHSO_4$ solution (15 mL) and water (15 mL). The product was extracted into ethyl acetate (2×20 mL) and washed with saturated $NaHCO_3$ (15 mL) and 10% LiCl solution (15 mL), dried over magnesium sulfate and concentrated in vacuo. The crude yellow oil was chromatographed on silica gel, eluting with 50% EtOAc in hexane followed by 1–3% MeOH in EtOAc to provide title compound as a foam (500 mg, 73%).

F. [S-(R*,R*)]-4-Amino-N-[[1-[3-hydroxy-2-[[(7-methoxy-2-naphthalenyl)sulfonyl]amino]-1-oxopropyl]-2-pyrrolidinyl]methyl]butanamide Part E compound (500 mg, 0.71 mmol) was dissolved in ethanol (60 mL) to which acetyl chloride (2.5 mL) had been added and the mixture was treated with 10% palladium on carbon (200 mg) and hydrogenated at 55 psi for 24 h. The catalyst was removed by filtration and the residual catalyst was washed with EtOH. The filtrate was concentrated in vacuo to obtain title des-benzyl, des-CBZ product. This was used without purification.

G. [S-(R*,R*)]-4-[(Aminoiminomethyl)amino]-N-[[1-[3-hydroxy-2-[[(7-methoxy-2-naphthalenyl) sulfonyl]amino]-1-oxopropyl]-2-pyrrolidinyl]methyl]butanamide, trifluoroacetamide (1:1) salt The Part F material (~0.71 mmol) was dissolved in ethanol (40 mL), to which amidinesulfonic acid (124 mg, 1.0 mmol) and triethylamine (300 µL, 2.1 mmol) were added. After 16 h the mixture was concentrated to dryness. The crude material was purified by preparative HPLC (YMC S-10 ODS 50×500 mm column, eluting with 50% methanol in water, containing 0.1% TFA). Fractions containing clean title compound were combined and lyophilized to provide a white solid (167 mg, 35%), Purity≧98%.

$[\alpha]_D$=−62.8° (c=0.5, MeOH)

Analysis: Calcd for 1.15 TFA+0.80 $H_2O$: C, 46.44; H, 5.45; N, 12.36; F, 9.64; S, 4.71. Found: C, 46.50; H, 5.34;, N, 12.23; F, 9.52; S, 4.85.

EXAMPLE 18a

[R-(R*,S*)]-N-[2-[2-[[[4-(Aminoiminomethyl)phenyl]amino]methyl]pyrrolidinyl]-2-oxo-1-(phenylmethyl)ethyl] methanesulfonamide, trifluoroacetate (1:1) salt To a solution of Example 16a compound (155 mg, 0.25 mmol) in 7 mL dry $CH_2Cl_2$ and 3 mL THF was added $Et_3N$ (139 ml, 1 mmol), followed by methanesulfonyl chloride (46 ml, 0.58 mmol). The reaction was stirred at room temperature for 2 hrs and concentrated in vacuo. The crude product was subjected to a Prep. HPLC using 40 to 90% B for 45 minutes gradient, A=90% $H_2O$/0.1% TFA; B=90% $CH_3OH$/0.1% TFA; column: YMC S-10 ODS (c=18) to give title compound (69% yield).

Elemental analysis $C_{22}H_{29}N_5O_3S$.1.25 TFA.0.60 $H_2O$ Calc: C, 49.30; H, 5.31; N, 11.73; F, 11.94 Found: C, 49.10; H, 5.18; N, 11.53; F, 12.10.

EXAMPLE 19a

[1(S),2S]-1-(Aminoiminomethyl)-N-[[1-[3-hydroxy-2-[(2-naphthalenylsulfonyl)amino]-1-oxopropyl]-2-pyrrolidinyl] methyl]-3-piperidinecarboxamide, trifluoroacetate (1:1) salt A. [S-(R*,R*)]-N-[2-[2-(Azidomethyl)-1-pyrrolidinyl]-2-oxo-1-[(phenylmethoxy)methyl]ethyl]-2-naphthalenesulfonamide Example 17a Part A BOC-azide (3.85 mg, 9.55 mmol) was dissolved in trifluoroacetic acid (TFA) (20 ml) and stirred at RT 1.5 hours. The TFA was removed by distillation under reduced pressure and by coevaporation with toluene. The residue was dissolved in dichloromethane (100 mL), cooled in an ice bath, and triethylamine (4.0 mL, 28.7 mmol) and 2-naphthalene sulfonyl chloride (2.38 g, 10.5 mmol) were added. The cooling bath was removed and the solution was stirred for 2 h. This solution was washed with $KHSO_4$ solution (25 mL×2) and $NaHCO_3$ solution (25 mL×2), dried over magnesium sulfate and evaporated to provide crude title compound. The crude product was chromatographed on silica gel to provide title sulfonamide as an oil (2.597 g, 55%).

B. [S-(R*,R*)]-N-[2-[2-(Aminomethyl)-1-pyrrolidinyl]-2-oxo-1-[(phenylmethoxy)methyl]ethyl]-2-naphthalenesulfonamide The Part A azide (2.5 g, 5 mmol) was dissolved in absolute ethanol (100 mL) and treated with 10% palladium on carbon (300 mg). The flask was equipped with a hydrogen filled balloon via a three way stopcock. Air inside the flask was evacuated under reduced pressure and the flask was then filled with hydrogen from the balloon. This process was repeated three times. The mixture was stirred overnight in the hydrogen atmosphere. The catalyst was then removed by filtration through Celite and the pad was washed with ethanol. The solvent was removed from the filtrate in vacuo to give title amine as a foam (2.236 g, 96%).

C. 1,3-Piperidinedicarboxylic acid, 1-(phenylmethyl) ester

Benzyl chloroformate (4 mL) was added dropwise to a cooled (0°–5° C.), stirred solution of piperidine-3-carboxylic acid (1.03 g, 8 mmol) in 1 N aqueous NaOH solution (25 mL). During the twenty minute addition, the pH was maintained between 8 and 9 by addition of 1N NaOH solution. After addition was complete, the mixture was stirred cold for an additional hour, maintaining the pH thoughout this period. The reaction mixture was then extracted with ether (2×40 mL). The ether extracts were discarded and the aqueous layer was acidified with 1N HCl solution. The acidified aqueous layer was then extracted with dichloromethane (2×40 mL). The combined extracts were dried over magnesium sulfate and concentrated in vacuo to give title acid as a viscous oil (1.73 g, 82%).

D. 3-[[[[(S)-1-[(S)-2-[(Naphthalenylsulfonyl)amino]-1-oxo-3-(phenylmethoxy)propyl]-2-pyrrolidinyl]methyl] amino]carbonyl]-1-piperidinecarboxylic acid, phenylmethyl ester Part B amine (820 mg, 1.75 mmol, and Part C acid (526 mg, 2.0 mmol) were dissolved in DMF (20 mL) at RT. HOBT (270 mg, 2 mmol), 4-methyl morpholine (1.5 mL) and WSC (400 mg, 2 mmol) were added. The reaction was stirred overnight at room temperature. The mixture was then diluted with ethyl acetate (50 mL), satd $KHSO_4$ solution (10 mL) and water (20 mL). The layers were separated and the aqueous layer was extracted with ethyl acetate (50 mL). The combined organic layers were washed with satd $NaHCO_3$ solution (20 mL) and 10% lithium chloride solution (2×20 mL), dried over magnesium sulfate and concentrated in vacuo The crude yellow foam was chromatographed on silica gel, eluting with 50% EtOAc in hexane followed by 75% EtOAc in hexane and finally with EtOAc to provide title sulfonamide as a foam (1.03 g, 82%).

E. N-[[(S)-1-[(S)-3-Hydroxy-2-[(naphthalenylsulfonyl)amino]-1-oxopropyl]-2-pyrrolidinyl]methyl]-3-piperidinecarbamide Part D compound (1.0 g, 1.4 mmol) was dissolved in ethanol (100 mL) to which acetyl chloride (2.0 mL) had been added and the mixture was treated with 10% palladium on carbon (300 mg) and hydrogenated at 55 psi for 44 h. The catalyst was removed by filtration and the pad was washed with EtOH. The filtrate was concentrated in vacuo to obtain crude amine hydrochloride salt.

F. [1(S), 2S]-1-(Aminoiminomethyl)-N-[[1-[3-hydroxy-2-[(2-naphthalenylsulfonyl)amino]-1-oxopropyl]-2-pyrrolidinyl]methyl]-3-piperidenecarboxamide, trifluoroacetate (1:1) salt The crude Part E amine was dissolved in dimethylformamide (3 mL). H-pyrazole-1-carboxamidine (226 mg, 1.54 mmol) and diisopropylethyl amine (540 µL, 3.1 mmol) were added. The mixture was stirred over a weekend at room temperature. Ether (15 mL) was then added. Gummy material precipitated. The ether was decanted and the precipitate was washed with more ether. The gummy material was dissolved in methanol and taken to dryness in vacuo. The remaining material was purified by preparative HPLC (YMC S-10 ODS 50×500 mm column, eluting with 50% methanol in water, containing 0.1% TFA). Fractions containing clean title compound were combined and lyophilized to provide a white solid which was used to obtain NMR spectra, recovered, dissolved in water (20 mL) and relyophilized to give title compound (399 mg, 42%), Purity≧98%.

$[\alpha]_D = -36.3°$ (c=0.6, MeOH)

Analysis: Calcd for 1.25 TFA+0.1 $H_2O$: C, 48.94; H, 5.29; N, 12.45; F, 10.56; S, 4.75. Found: C, 49.03; H, 5.30;, N, 12.27; F, 10.47; S, 4.66.

EXAMPLE 20a

[S-(R*,R*)]-1-(Aminoiminomethyl)-N-[[1-[3-hydroxy-2-[(2-naphthalenylsulfonyl)amino]-1-oxopropyl]-2-pyrrolidinyl]methyl]-4-piperidinecarboxamide, trifluoroacetate (1:1) salt A. 1,4-Piperidinedicarboxylic acid, 1-(phenylmethyl) ester Benzyl chloroformate (4 mL) was added dropwise to a cooled (0°–5° C.), stirred solution of piperidine-4-carboxylic acid (1.03 g, 8 mmol) in 1N aqueous NaOH solution (25 mL). During the twenty minute addition, the pH was maintained between 8 and 9 by addition of 1N NaOH solution. After addition was complete, the mixture was stirred cold for an additional hour, maintaining the pH thoughout this period. The reaction mixture was then extracted with ether (2×40 mL). The ether extracts were discarded and the aqueous layer was acidified with 1N HCl solution. The acidified aqueous layer was then extracted with dichloromethane (2×40 mL). The combined extracts were dried over magnesium sulfate and concentrated in vacuo to give title acid as a viscous oil (2.0 g, 95%).

B. [S-(R*,R*)]-4-[[[[1-[2-[(Naphthalenylsulfonyl)amino]-1-oxo-3-(phenylmethoxy)propyl]-2-pyrrolidinyl]methyl]amino]carbonyl]-1-piperidinecarboxylic acid, phenylmethyl ester Example 19a, Part B amine (820 mg, 1.75 mmol) and Part A acid (526 mg, 2.0 mmol) were dissolved in DMF (20 mL) at RT. HOBT (270 mg, 2 mmol), 4-methyl morpholine (1.5 mL) and WSC (400 mg, 2 mmol) were added. The reaction was stirred overnight at room temperature. The mixture was then diluted with ethyl acetate (50 mL), satd $KHSO_4$ solution (10 mL) and water (20 mL). The layers were separated and the aqueous layer was extracted with ethyl acetate (50 mL). The combined organic layers were washed with satd $NaHCO_3$ solution (20 mL) and 10% lithium chloride solution (2×20 mL), dried over magnesium sulfate and concentrated in vacuo. The crude yellow foam was chromatographed on silica gel, eluting with 50% EtOAc in hexane followed by 75% EtOAc in hexane and finally with EtOAc to provide title sulfonamide as a foam (980 mg, 78%).

C. [S-(R*,R*)]-N-[[1-[3-Hydroxy-2-[(naphthalenylsulfonyl)amino]-1-oxopropyl]-2-pyrrolidinyl]methyl]-4-piperidinecarbamide Part B compound (970 mg, 1.36 mmol) was dissolved in ethanol (100 mL) to which acetyl chloride (2.0 mL) had been added and the mixture was treated with 10% palladium on carbon (400 mg) and hydrogenated at 55 psi for 30 h. The catalyst was removed by filtration and the pad was washed with EtOH. The filtrate was concentrated in vacuo to obtain crude title compound.

D. [S-(R*,R*)]-1-(Aminoiminomethyl)-N-[[1-[3-hydroxy-2-[(2-naphthalenylsulfonyl)amino]-1-oxopropyl]-2-pyrrolidinyl]methyl]-4-piperidenecarboxamide, trifluoroacetate (1:1) salt The crude Part C amine was dissolved in dimethylformamide (3 mL). H-pyrazole-1-carboxamidine (226 mg, 1.54 mmol) and diisopropylethyl amine (540 µL, 3.1 mmol) were added. The mixture was stirred over a weekend at room temperature. Ether (15 mL) was then added. Gummy material precipitated. The ether was decanted and the precipitate was washed with more ether. The gummy material was dissolved in methanol and taken to dryness in vacuo. The remaining material was purified by preparative HPLC (YMC S-10 ODS 50×500 mm column, eluting with 50% methanol in water, containing 0.1% TFA). Fractions containing clean title compound were combined and lyophilized to provide a white solid (33269-139-26) which was used to obtain NMR spectra, recovered, dissolved in water (20 mL) and relyophilized to give title compound (264 mg, 29%), Purity≧98%.

$[\alpha]_D = -45.4°$ (c=0.6, MeOH)

Analysis: Calcd for 1.25 TFA+0.1 $H_2O$: C, 48.94; H, 5.29; N, 12.45; F, 10.56; S, 4.75. Found: C, 49.12; H, 5.42;, N, 12.45; F, 10.62; S, 4.82.

EXAMPLE 21a

N-[(S)-2-[(S)-2-[[[[1-(Aminoiminomethyl)-3-piperidinyl]acetyl]amino]methyl]-1-pyrrolidinyl]-1-(hydroxymethyl)-2-oxoethyl]-2-naphthalenesulfonamide, trifluoroacetate (1:1) salt A. [S-(R*,R*)]-N-[2-[2-(Azidomethyl)-1-pyrrolidinyl]-2-oxo-1-[(phenylmethoxy)methyl]ethyl]-2-naaphthalenesulfonamide Example 17a, Part A BOC-Azide (3.85 mg, 9.55 mmol) was dissolved in trifluoroacetic acid (TFA) (20 mL) and stirred at RT 1.5 hours. The TFA was removed by distillation under reduced pressure and by coevaporation with toluene. The residue was dissolved in dichloromethane (100 mL), cooled in an ice bath, and triethylamine (4.0 mL, 28.7 mmol) and 2-naphthalene sulfonyl chloride (2.38 g, 10.5 mmol) were added. The cooling bath was removed and the solution was stirred for 2 h. This solution was washed with $KHSO_4$ solution (25 mL×2) and $NaHCO_3$ solution (25 mL×2), dried over magnesium sulfate and evaporated to provide crude title compound. The crude product was chromatographed on silica gel and eluted with 30 and 50% EtOAc in hexane to provide title sulfonamide as an oil (2.597 g, 55%).

B. [S-(R*,R*)]-N-[2-[2-(Aminomethyl)-1-pyrrolidinyl]-2-oxo-1-[(phenylmethoxy)methyl]ethyl]-2-naphthalenesulfonamide The Part A azide (2.5 g, 5 mmol) was dissolved in absolute ethanol (100 mL) and treated with 10% palladium on carbon (300 mg). The flask was equipped with a hydrogen filled balloon via a three way stopcock. Air inside the flask was evacuated under reduced pressure and the flask was then filled with hydrogen from the balloon. This process was repeated three times. The mixture was stirred overnight in the hydrogen atmosphere. The catalyst was then removed by filtration through Celite and the pad was washed with ethanol. The solvent was removed from the filtrate in vacuo to give title amine as a foam (2.236 g, 96%).

C. 1-[(Phenylmethoxy)carbonyl]-3-piperidineacetic acid

Platinum oxide (300 mg, Alfa) was added to a solution of 3-pyridyl acetic acid (3.3 g, 24.08 mmol) in water (120 mL) and conc. HCl (2.5 mL). The solution was hydrogenated at up to 50 psi of $H_2$ pressure for 6.5 hrs. The catalyst was removed by filtration through a pad of Celite and the pad was washed with more water. The stirred aqueous solution of the 3-piperidine acetic acid was cooled (0°–5° C.) and treated with 5$\underline{N}$ aqueous NaOH solution (20 mL). Benzyl chloroformate (4 mL) was added dropwise to the cooled, stirred solution. During the ten minute addition, the pH was maintained between 10 and 12 by addition of NaOH solution. After one hour the reaction mixture was extracted with ether (2×100 mL). The ether extracts were discarded and the aqueous layer was acidified with 2$\underline{N}$ HCl solution. The acidified aqueous layer was then extracted with ethyl acetate (2×100 mL). The combined extracts were dried over magnesium sulfate and concentrated in vacuo to give title compound as an oil (7.0 g, contained EtOAc).

D. N-[(S)-2-Oxo-2-[(S)-2-[[[[1-[(phenylmethoxy)carbonyl]-3-piperidinyl]acetyl]amino]methyl]-1-pyrrolidinyl]-1-[(phenylmethoxy)methyl]ethyl]-2-naphthalenesulfonamide Part B amine (820 mg, 1.75 mmol), and Part C acid (554 mg, 2.0 mmol) were dissolved in DMF (20 mL) at RT. HOBT (270 mg, 2 mmol), 4-methyl morpholine (1.5 mL) and WSC (400 mg, 2 mmol) were added. The reaction was stirred 24 hours at room temperature. The mixture was then diluted with aqueous $KHSO_4$ solution and extracted with ethyl acetate (2×75 mL). The combined organic layers were washed with satd. $NaHCO_3$ solution (30 mL), dried over magnesium sulfate and concentrated in vacuo. The crude yellow foam was chromatographed on silica gel, eluting with 50% EtOAc in hexane, followed by 75% EtOAc in hexane, EtOAc and finally with 2% MeOH in EtOAc to provide title compound as a colorless oil (900 mg, 71%).

E. N-[(S)-1-(Hydroxymethyl)-2-oxo-2-[(S)-2-[[[[1-[(phenylmethoxy)carbonyl]-3-piperidinyl]acetyl]amino]methyl]-1-pyrrolidinyl]ethyl]-2-naphthalenesulfonamide, hydrochloride Part D compound (900 mg, 1.24 mmol) was dissolved in ethanol (100 mL) to which acetyl chloride (2.5 mL) had been added and the mixture was treated with 10% palladium on carbon (250 mg) and hydrogenated at 55 psi for 24 h. The catalyst was removed by filtration and the pad was washed with EtOH. The filtrate was concentrated in vacuo to obtain crude title compound which was used without purification.

F. N-[(S)-2-[(S)-2-[[[[1-(Aminoiminomethyl)-3-piperidinyl]acetyl]amino]methyl]-1-pyrrolidinyl]-1-(hydroxyethyl)-2-oxoethyl]-2-naphthalenesulfonamide, trifluoroacetate (1:1) salt The crude Part E amine was dissolved in dimethylformamide (3 mL). H-pyrazole-1-carboxamidine (226 mg, 1.54 mmol) and diisopropylethyl amine (536 μL, 3.1 mmol) were added. The mixture was stirred 3 days at room temperature.

Ether (15 mL) was then added. Gummy material precipitated. The ether was decanted and the precipitate was washed with more ether. The gummy material was dissolved in methanol and taken to dryness in vacuo. The remaining material was purified by preparative HPLC (YMC S-10 ODS 50×500 mm column, eluting with 49% methanol in water, containing 0.1% TFA). Fractions containing clean title compound were combined and lyophilized to provide a white solid (283 mg, 33%), Purity≧98%.

$[\alpha]_D = -39.2°$ (c=0.7, MeOH)

Analysis: Calcd for 1.2 TFA+0.4 $H_2O$: C, 49.53; H, 5.56; N, 12.20; F, 9.93; S, 4.66 Found: C, 49.54; H, 5.60; N, 12.16; F, 10.16; S, 4.79

EXAMPLE 22a

[S-(R*,R*)]-N-[2-[2-[[[[1-(Aminoiminomethyl)-4-piperidinyl]acetyl]amino]methyl]-1-pyrrolidinyl]-1-hydroxymethyl)-2-oxoethyl]-2-naphthalenesulfonamide, trifluoroacetate (1:1) salt A. 1-[(Phenylmethoxy)carbonyl]-4-piperidineacetic acid Platinum oxide (300 mg, Alfa) was added to a solution of pyridyl-4-acetic acid, hydrochloride (3.3 g, 19 mmol) in water (120 mL). The solution was hydrogenated at up to 50 psi of $H_2$ pressure for 17 hrs. The catalyst was removed by filtration through a pad of Celite and the pad was washed with more water. The stirred aqueous solution of the piperidine-4-acetic acid was cooled (0°–5° C.) and treated with 5$\underline{N}$ aqueous NaOH solution (15 mL) to pH 12. Benzyl chloroformate (4 mL) was added dropwise to the vigorously stirred cooled solution. After one hour (maintaining the pH at 10 to 12), the reaction mixture was extracted with ether (2×100 mL). The ether extracts were discarded and the aqueous layer was acidified with 2$\underline{N}$ HCl solution (50 mL). The acidified aqueous layer was then extracted with ethyl acetate (2×75 mL). The combined extracts were dried over magnesium sulfate and concentrated in vacuo to give title compound as a white solid (4.53 g, 86% yield).

B. [S-(R*,R*)]-N-[2-Oxo-2-[2-[[[[1-[(phenylmethoxy)carbonyl]-4-piperidinyl]acetyl]amino]methyl]-1-pyrrolidinyl]-1-[(phenylmethoxy)methyl]ethyl]-2-naphthalenesulfonamide Example 21a amine (820 mg, 1.75 mmol) and Part A acid (554 mg, 2.0 mmol) were dissolved in DMF (20 mL) at RT. HOBT (270 mg, 2 mmol), 4-methyl morpholine (1.5 mL) and WSC (400 mg, 2 mmol) were added. The reaction was stirred 24 hours at room temperature. The mixture was then diluted with aqueous $KHSO_4$ solution (30 mL) and extracted with ethyl acetate (2×75 mL). The combined organic layers were washed with satd. $NaHCO_3$ solution (50 mL), dried over magnesium sulfate and concentrated in vacuo. The crude yellow foam was chromatographed on silica gel, eluting with 50% EtOAc in hexane, followed by 70% EtOAc in hexane, EtOAc and finally with 2% MeOH in EtOAc to provide title compound as a colorless oil (1.0 g, 79%).

C. [S(R*,R*)]-N-[1-(Hydroxymethyl)-2-oxo-2-[2-[[[[1-[(phenylmethoxy)carbonyl]-4-piperidinyl]acetyl]amino]methyl]-1-pyrrolidinyl]ethyl]-2-naphthalenesulfonamide, hydrochloride Part B compound (1.0 g, 1.377 mmol) was dissolved in ethanol (100 mL) to which acetyl chloride (2.5 mL) had been added and the mixture was treated with 10% palladium on carbon (250 mg) and hydrogenated at 55 psi for 48 h. The catalyst was removed by filtration and the pad was washed with EtOH. The filtrate was concentrated in vacuo to obtain crude title compound which was used without purification.

D. [S-(R*,R*)]-N-[2-[2-[[[[1-(Aminoiminomethyl)-4-piperidinyl]acetyl]amino]methyl]-1-pyrrolidinyl]-1-(hydroxymethyl)-2-oxoethyl]-2-naphthalenesulfonamide, trifluoroacetate (1:1) salt The crude Part C amine was dissolved in dimethylformamide (DMF) (3 mL). H-pyrazole-1-carboxamidine (226 mg, 1.54 mmol) and diisopropylethyl amine (536 µL, 3.1 mmol) were added. The mixture was stirred 4 days at room temperature, following the course of the reaction by TLC and HPLC during this time. Ether (15 mL) was then added. Gummy material precipitated. The ether was decanted and the precipitate was washed with more ether. The gummy material was dissolved in methanol and taken to dryness in vacuo. The remaining material was purified by preparative HPLC (YMC S-10 ODS 50×500 mm column, eluting with 47% methanol in water, containing 0.1% TFA). Fractions containing clean title compound were combined and lyophilized to provide a white solid. (344 mg, 40%), Purity≧98%.

$[\alpha]_D$=–41.5° (c=0.6, MeOH)

Analysis: Calcd for 1.2 TFA+1.0 $H_2O$: C, 48.76; H, 5.65; N, 12.01; F, 9.78; S, 4.58. Found: C, 48.76; H, 5.58; N, 12.06; F, 9.63; S, 4.73

EXAMPLE 23a

[S-(R*,R*)]-N-[2-[2-[[[5-[(Aminoiminomethyl)amino]-1-oxopentyl]amino]methyl]-1-pyrrolidinyl]-1-(hydroxymethyl)-2-oxoethyl]-2-naphthalenesulfonamide, trifluoroacetate (1:1) salt Following the procedure of Examples 1a and 2a except substituting in Example 1a, Part C N-CBZ-5-aminopentanoic acid for N-CBZ-4-aminobutyric acid, the title compound was obtained. The crude material was purified by preparative HPLC (YMC S-10 ODS 50×500 mm column, eluting with 51% methanol in water, containing 0.1% TFA). Fractions containing clean title compound were combined and lyophilized to provide a white solid (199 mg, 46%), Purity≧98%.

$[\alpha]_D$=–43.5° (c=0.6, MeOH)

Analysis: Calcd for 1.0 TFA+0.70 $H_2O$: C, 48.40; H, 5.69; N, 13.02; F, 8.83; S, 4.97 Found: C, 48.42; H, 5.60; N, 12.84; F, 9.03; S, 4.79.

EXAMPLE 24a

[S-(R*,R*)]-N-[2-[2-[[[6-[(Aminoiminomethyl)amino]-1-oxohexyl]amino]methyl]-1-pyrrolidinyl]-1-(hydroxymethyl)-2-oxoethyl]-2-naphthalenesulfonamide, trifluoroacetate (1:1) salt Following the procedure of Examples 1a and 2a except substituting N-CBZ-6-aminohexanoic acid for N-CBZ-4-aminobutyric acid, the title compound was prepared. The crude material was purified by preparative HPLC to provide a white solid (160 mg), Purity≧98%. $[\alpha]_D$=–44.3° (c=0.5, MeOH)

Analysis: Calcd for 1.0 TFA+1.60 $H_2O$: C, 48.01; H, 6.00; N, 12.44; F, 8.44; S, 4.75 Found: C, 48.33; H, 5.70; N, 11.92; F, 8.18; S, 4.71.

EXAMPLE 25a

[1S[2R*(3R*)]]-N-[2-[2-[[[[1-(Aminoiminomethyl)-3-piperidinyl]carbonyl]amino]methyl]-1-pyrrolidinyl]-1-(hydroxymethyl)-2-oxoethyl]-2-naphthalenesulfonamide, trifluoroacetate (1:1) salt A. (S)-3-Piperidinecarboxylic acid, ethyl ester, D-tartrate salt Ref: Johnston, G. A. R. et al, J Neurochemistry, 1976, Vol 26, pp.1029–1032.

Ethyl nipecotate (50 g, 318 mmol) and D-tartaric acid (47.74 g, 318 mmol)were dissolved in hot abs. ethanol (250 mL). A very small amount of insoluble material was removed by filtration through a pad of Celite. The filtrate gave crystalline material on cooling. This was harvested and recrystallized eight times from absolute ethanol to give title compound as a white solid (~27 g). m.p. 155°–156° C., $[\alpha]_{365}$=–200.7° (c=2.0, 0.2% aqueous ammonium molybdate).

B. (S)-1-[(phenylmethoxy)carbonyl]-3-piperidinecarboxylic acid

The Part A tartrate salt (1.0 g) was dissolved in water (5 mL) and a solution of potassium carbonate was added to bring the pH to 9. The solution was cooled in an ice water bath and ether (5 mL) was added. Benzyl chloroformate (0.5 mL) was added dropwise to the well stirred solution. During the addition the pH was maintained between 8 and 9 by addition of potassium carbonate solution. After addition was complete, the mixture was stirred cold for an additional 1.5 hours, maintaining the pH thoughout this period. The layers were separated and the aqueous was reextracted with ether. The combined ether layers were dried over magnesium sulfate and concentrated in vacuo. The ethyl ester obtained was purified on silica gel, eluting with 25% ethyl acetate in hexane. The purified material (930 mg) was dissolved in methanol (8 mL) and treated with 1$\underline{N}$ NaOH solution (4 mL). After stirring at room temperature two hours, the methanol was removed in vacuo. The aqueous solution was acidified with 1$\underline{N}$ HCl and the acid was extracted into ethyl acetate (2×10 mL). The combined extracts were dried over magnesium sulfate and concentrated in vacuo to give title compound as a crystalline solid. (773 mg). $[\alpha]_D$=+49.9° (c=1.4, MeOH). The optical purity of this material was determined by coupling some of this material with (S)-(–)-α-methyl-benzylamine. The material obtained was submitted to the analytical HPLC group for determination of purity and was found to be 97.6%, (e.e.=95.2).

C. [1S[2R*(3R*)]]-N-[2-[2-[[[[1-(Aminoiminomethyl)-3-piperidinyl]carbonyl]amino]methyl]-1-pyrrolidinyl]-1-(hydroxymethyl)-2-oxoethyl]-2-naphthalenesulfonamide, trifluoroacetate (1:1) salt Following the procedure of Example 19a, the title compound was prepared using the Example 19a, Part B amine and the nonracemic Part B acid to give the crude product which was purified by preparative HPLC (360 mg, 46.4%), Purity≧98%.

$[\alpha]_D$=–15.1° (c=0.7, MeOH)

Analysis: Calcd for 1.20 TFA+0.4 $H_2O$: C, 48.78; H, 5.38; N, 12.46; F, 10.14; S, 4.75. Found: C, 48.71; H, 5.50;, N, 12.43; F, 10.12; S, 4.78.

EXAMPLE 26a

[1S[2R*(3S*)]]-N-[2-[2-[[[[1-(Aminoiminomethyl)-3-piperidinyl]carbonyl]amino]methyl]-1-pyrrolidinyl]-1-(hydroxymethyl)-2-oxoethyl]-2-naphthalenesulfonamide, trifluoroacetate (1:1) salt A. (R)-3-Piperidinecarboxylic acid, ethyl ester, L-tartrate salt Ref: Johnston, G. A. R. et al, J Neurochemistry, 1976, Vol. 26, pp.1029–1032.

Ethyl nipecotate (50 g, 318 mmol) and L-tartaric acid (47.74 g, 318 mmol)were dissolved in hot abs. ethanol (200 mL). Crystalline material was deposited on cooling. This was harvested and recrystallized 11 times from absolute ethanol to give title compound as a white solid (~26 g). m.p. 155°–156° C., $[\alpha]_{365}$=+202.5° (c=2.0, 0.2% aqueous ammonium molybdate).

B. (R)-1-[(Phenylmethoxy)carbonyl]-3-piperidinecarboxylic acid

The Part A tartrate salt (1.0 g) was dissolved in water (5 mL) and a solution of potassium carbonate was added to bring the pH to 9. The solution was cooled in an ice water bath and ether (5 mL) was added. Benzyl chloroformate (0.5 mL) was added dropwise to the well stirred solution. During the addition, the pH was maintained between 8 and 9 by addition of potassium carbonate solution. After addition was complete, the mixture was stirred cold for an additional 1.5 hours, maintaining the pH throughout this period. The layers were separated and the aqueous was reextracted with ether. The combined ether layers were dried over magnesium sulfate and concentrated in vacuo. The ethyl ester obtained was purified on silica gel, eluting with 25% ethyl acetate in hexane. The purified material (971 mg) was dissolved in methanol (8 mL) and treated with 1N NaOH solution (4 mL). After stirring at room temperature two hours, the methanol was removed in vacuo. The aqueous solution was acidified with 1N HCl and the acid was extracted into ethyl acetate (2×10 mL). The combined extracts were dried over magnesium sulfate and concentrated in vacuo to give title compound as a crystalline solid. (881 mg). $[\alpha]_D = -49.6°$ (c=1.4, MeOH). The optical purity of this material was determined by coupling some of this material with (S)-(−)-α-methyl-benzylamine. The material obtained was submitted to the analytical HPLC group for determination of purity and was found to be 97.3%, (e.e. =94.6).

C. [1S[2R*(3S*)]]-N-[2-[2-[[[[1-(Aminoiminomethyl)-3-piperidinyl]carbonyl]amino]methyl]-1-pyrrolidinyl]-1-(hydroxymethyl)-2-oxoethyl]-2-naphthalenesulfonamide, trifluoroacetate (1:1) salt The title compound was prepared employing the procedure of Example 19a using Example 19a, Part B amine and nonracemic Part B acid to give the crude product which was purified by preparative HPLC (133 mg, 32%), Purity ≧98%.
$[\alpha]_D = -60.9°$ (c=0.6, MeOH)

Analysis: Calcd for 1.05 TFA+1.1 H$_2$O: C, 48.57; H, 5.60; N, 12.54; F, 8.93; S, 4.78. Found: C, 48.52; H, 5.44; N, 12.31; F, 8.82; S, 4.82.

EXAMPLE 27a

[S-(R*,R*)]-N-[2-[2-[[[7-[(Aminoiminomethyl)amino]-1-oxoheptyl]amino]methyl]-1-pyrrolidinyl]-1-(hydroxymethyl)-2-oxoethyl]-2-naphthalenesulfonamide, trifluoroacetate (1:1) salt The title compound was prepared employing the procedure of Examples 1a and 2a except that N-CBZ-7-aminoheptanoic acid was employed in place of N-CBZ-4-aminobutyric acid. The crude material was purified by preparative HPLC to give (276 mg).
Purity ≧98%.
$[\alpha]_D = -42.3°$ (c=0.6, MeOH)
Analysis: Calcd for 1.05 TFA+0.60 H$_2$O: C, 49.84; H, 5.99; N, 12.41; F, 8.84; S, 4.73. Found: C, 49.77; H, 5.91; N, 12.34; F, 8.78; S, 4.93.

EXAMPLE 28a

[S-(R*,R*)]-4-(Aminomethyl)-N-[[1-[3-hydroxy-2-[(2-naphthalenylsulfonyl)amino]-1-oxopropyl]-2-pyrrolidinyl]methyl]benzamide, trifluoroacetate (1:) salt

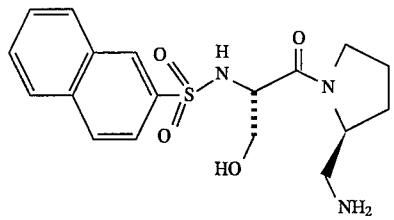

A.

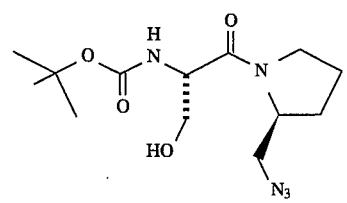

A. (1)

To a stirred solution of 1-BOC-2-(methylazide)pyrrolidine (12.54 g, 55.5 mmol) (prepared employing a procedure similar to that described in Example 1 Part A) in 10 mL of dry dichloromethane at 0° C. was added a solution of 4N HCl in dioxane (25.0 mL, 100 mmol). The solution was stirred at room temperature for 2.5 h and concentrated in vacuo to give a crude amine as an oil. To a stirred solution of this amine, N-BOC-L-serine (11.4 g, 55.5 mmol) and 1-hydroxybenzotriazole monohydrate (9.37 g, 55.5 mmol) in 240 mL of DMF was added in order N-methylmorpholine (18.3 mL, 167 mmol) and ethyl 3-(3-dimethyl amino)propyl carbodiimide hydrochloride (10.6 g, 55.5 mmol). The reaction solution was stirred at room temperature for 19 h and concentrated under pump vacuum at 45° C. The residue was dissolved in 1 L of EtOAc and washed with 5%KHSO$_4$ solution (3×0.5 L), saturated NaHCO$_3$ solution (2×0.5 L) and brine (1×0.5 L). The EtOAc layer was dried (MgSO$_4$), filtered and concentrated in vacuo to give 14.4 g (83%) of title A(1) amide.

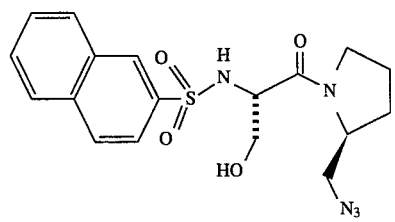

A. (2)

To a stirred solution of Part A(1) amide (14.3 g, 45.9 mmol) in 20 mL of dry dichloromethane at 0° C. was added a solution of 4N HCl in dioxane (40.0 mL, 160 mmol). The solution was stirred at room temperature for 2 h and concentrated in vacuo to give a crude amine as an oil. To a stirred solution of this amine and triethylamine (15.4 mL, 110 mmol) in 100 mL of dry dichloromethane at 0° C. was added dropwise a solution of 2-naphthalenesulfonyl chloride (10.9 g, 48.2 mmol) in 60 mL of dry dichloromethane over 40 min. The reaction was stirred at 0° C. for 1 h and at room temperature for 2 h. The solution was diluted with 1 L of dichloromethane and washed with 1N HCl solution (3×0.5 L), saturated NaHCO$_3$ solution (2×0.5 L) and brine (1×0.5 L). The dichloromethane layer was dried (MgSO$_4$), filtered and concentrated in vacuo. This was triturated in EtOAc-hexane to give 11.5 g of title A(2) azide. The triturant was concentrated in vacuo and chromatographed on silica gel to give 12.9 g of title A(2) azide.

151

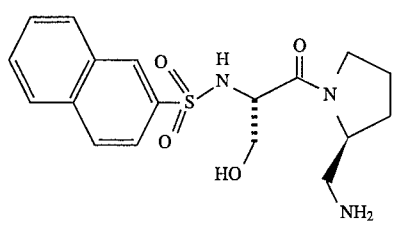

A. (3)

To a stirred solution of Part A(2) azide (11.2 g, 27.8 mmol) in 300 mL of EtOH and 600 mL of methanol was added 10%Pd/C (2.24 g). The atmosphere was replaced with hydrogen and the reaction mixture stirred at room temperature for 17 h. The catalyst was filtered off through a 4 μM polycarbonate film and rinsed with methanol (3×100 mL). The filtrate was concentrated in vacuo to give 9.9 g (94%) of crude title A amine.

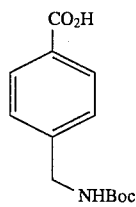

B.

To a solution of 4-(aminomethyl)benzoic acid (10.33 g, 68.3 mmol) in ethanol (137 mL) and water (68 mL) were added aqueous NaOH (10M, 7.6 mL, 76.0 mmol) and di-tert-butyl dicarbonate (16.48 g, 75.5 mmol). After 24 h, the reaction mixture was concentrated in vacuo. The residue was dissolved in EtOAc and 10% aqueous KHSO₄, the layers separated, and the aqueous layer was extracted with EtOAc. The organic layers were combined, dried over Na₂SO₄, filtered and concentrated in vacuo to give title compound (16.88 g, 98%) as a colorless solid.

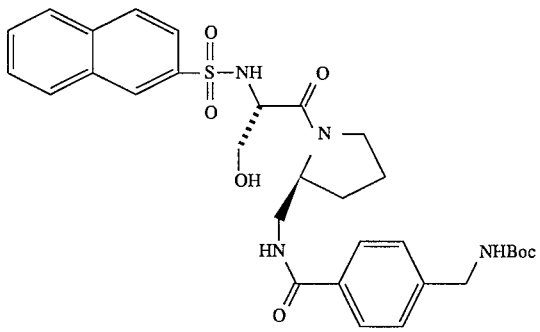

C.

To a solution of Part B acid (0.23 g, 0.93 mmol) and 1-hydroxybenzotriazole hydrate (0.13 g, 0.94 mmol) in DMF (2.8 mL) at 0° C. was added ethyl-3-(3-dimethylamino)propyl carbodiimide. HCl (0.17 g, 0.91 mmol). After 0.5 h, Part A amine (0.31 g, 0.83 mmol) in DMF (1.7 mL) was added, followed by 4methylmorpholine (0.12 mL, 1.1 mmol). The reaction mixture was stirred for 15.5 h while allowing the reaction to warm to room temperature. The reaction mixture was poured into water:brine (1:1) and extracted with EtOAc, the organic layer washed with 0.25M aqueous KHSO₄, water, saturated aqueous NaHCO₃, water and brine. The organic layer was dried over Na₂SO₄, filtered and concentrated in vacuo to give title compound (0.50 g, 98%) as a colorless foam.

152

D. S-(R*,R*)]-4-(Aminomethyl)-N-[[1-[3-hydroxy-2-[(2-naphthalenylsulfonyl)amino]-1-oxopropyl]-2-pyrrolidinyl]methyl]benzamide, trifluoroacetate (1:1) salt

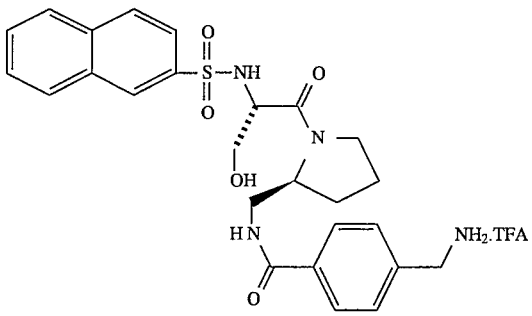

To a solution of Part C compound (0.44 g, 0.72 mmol) in CH₂Cl₂ at 0° C. was added trifluoroacetic acid (0.9 mL). After 1.5 h, the reaction mixture was concentrated in vacuo and purified by preparative HPLC. The appropriate fractions were combined, concentrated in vacuo, dissolved in H₂O and lyophilized to yield title compound (0.14 g, 32%) as a colorless solid:

$[\alpha]_D = -38.6°$ (c 1.03, MeOH)

MS (M+H)⁺=511⁺

Anal. Calc'd for $C_{26}H_{30}N_4O_5S \cdot 1.1$ TFA$\cdot 1.33$ H₂O: C, 51.32; H, 5.16; N, 8.49; S, 4.86; F, 9.50 Found: C, 51.32; H, 4.92; N, 8.42; S, 5.03; F, 9.82

EXAMPLE 29a

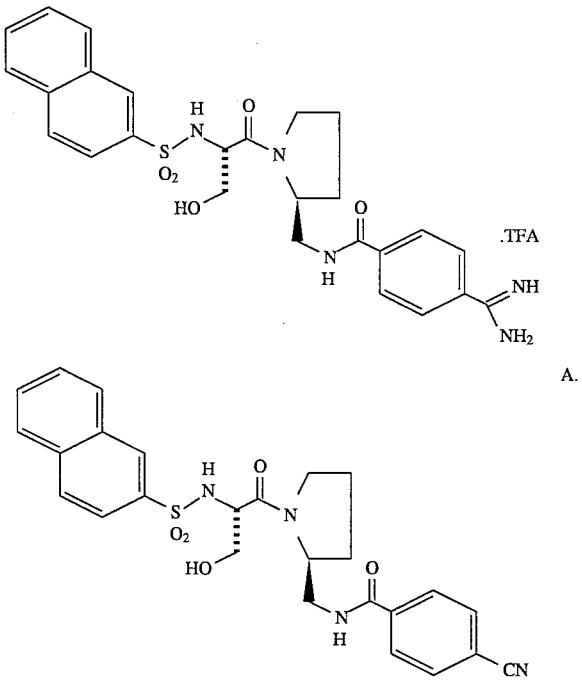

A.

Example 28a Part A amine (1.93 g, 5.15 mmol), 4-cyanobenzoic acid (757 mg, 5.15 mmol) and 1-hydroxybenzotriazole (869 mg, 6.44 mmol) were dissolved in DMF (30 mL) at RT. 4-Methylmorpholine (1.1 mL, 10 mmol) was added dropwise followed by WSC (1.03 g, 5.15 mmol). The reaction was stirred 20 hours at room temperature. The mixture was then diluted with ethyl acetate (75 mL) and KHSO₄ solution (60 mL), the layers were separated and the aqueous layer was reextracted with ethyl acetate (75 ML).

The combined organic layers was washed with saturated. NaHCO$_3$ solution (50 mL) and 10% lithium chloride solution (2×25 mL), dried over magnesium sulfate and concentrated in vacuo. The crude oil was chromatographed on silica gel, eluting with 50% EtOAc in hexane followed by 75% EtOAc in hexane, EtOAc and finally 3% MeOH in EtOAc to provide title compound as a foam (2.01 g, 78%).

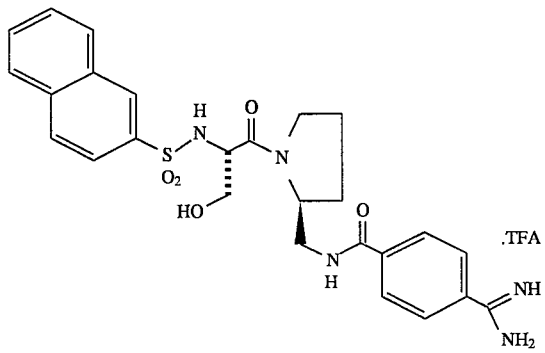

B.

Sodium pellets (~100 mg) were added to methanol (35 mL) and stirred until all the sodium had been consumed. Part A compound (759 mg, 1.5 mmol) was added and the mixture was stirred at room temperature. After three hours, additional sodium (~50 mg) was added and the mixture was stirred an additional 2 hours. After this time an equilibrium mixture of product and starting material had been obtained. Ammonium chloride (4 g) was added and the mixture was left stirring overnight at room temperature. The reaction mixture was then acidified with 1N HCl. Insoluble material was removed by filtration through Celite and the pad was washed with more methanol. The filtrate was freed of solvent in vacuo. The remaining material was purified by preparative HPLC (YMC S-15 ODS 50×500 mm column, eluting with 49% methanol in water, containing 0.1% TFA). Fractions containing clean title compound were combined and lyophilized to provide a white solid which was used to obtain NMR spectra, recovered, dissolved in water (40 mL) and relyophilized to give title compound (283 mg, 28%).

[α]$_D$=–37.6° (c=0.5, MeOH)

Analysis: Calcd for 1.08 TFA+2.1 H$_2$O: C, 49.41; H, 5.05; N, 10.23; F, 8.99; S, 4.68 Found: C, 49.02; H, 4.57; N, 10.13; F, 8.70; S, 5.12.

EXAMPLE 30a

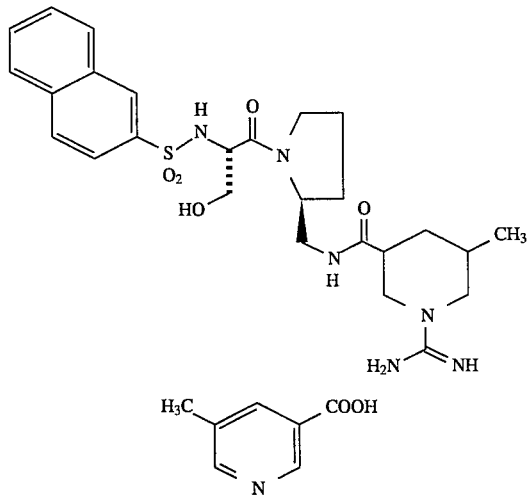

and

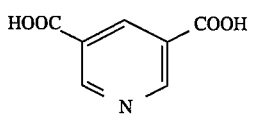

B.

Ref: J Org. Chem, 53, 3513–3521, 1988.

Potassium permangananate (29.5 g, 187 mmol) was dissolved in water (450 mL) and 3,5-lutidine (10 g, mmol) was added. After stirring for 1 hour the temperature was 40° C. and the mixture was heated in an oil bath maintained at 40°–50° C. overnight while the stirring was continued. After cooling the mixture was filtered through Celite. The colorless filtrate was concentrated to ~50 mL and then acidified with HCl. White solid precipitated and was harvested by filtration and washed with more water. Mass Spec indicated this was a mixture of the desired monoacid (A) and diacid (B) and was used in the next reaction. (5.2 g).

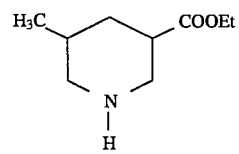

C.

and

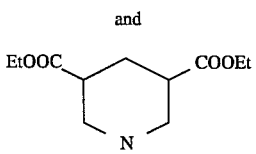

D.

The mixture of Parts A and B acids was suspended in absolute ethanol (100 mL) in a Parr bottle. Acetyl chloride (5 mL) and platinum oxide (165 mg) were added and the mixture was hydrogenated at up to 55 psi for 20 hours. The catalyst was removed by filtration and the pad was washed with ethanol. The filtrate was taken to dryness in vacuo to give title compound. Mass spec indicated this was a mixture of the ethyl ester (D) and diester (D).

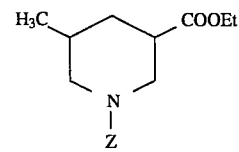

E.

The mixture of Parts C and D ethyl esters was dissolved in water (50 mL) and a solution of potassium carbonate was added to bring the pH to 8.5. The solution was cooled in an ice water bath and ether (50 mL) was added. Benzyl chloroformate (8 mL) was added dropwise to the well stirred solution. During the addition, the pH was maintained between 8 and 9 by addition of potassium carbonate solution. After addition was complete, the mixture was stirred cold for an additional hour, maintaining the pH throughout this period. The layers were separated and the aqueous was reextracted with ether. The combined ether layers were dried over magnesium sulfate and concentrated in vacuo. The material was chromatographed on silica gel, eluting with 10–20% ethyl acetate in hexane. The cis and trans isomers were separated. An NMR study of the acids indicated that the faster moving isomer (3.665 g) was the cis material.

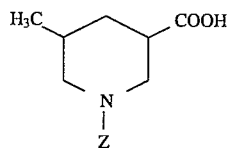

F.

A portion of the purified Part E cis compound (1.525 g, 5 mmol)) was dissolved in methanol (16 mL) and treated with 1N NaOH solution (10 mL). After stirring at room temperature two hours, the methanol was removed in vacuo. The aqueous solution was acidified with 1N HCl and the acid was extracted into ethyl acetate (3×10 mL). The combined extracts were dried over magnesium sulfate and concentrated in vacuo to give title compound as a viscous oil (1.39 g, 100%).

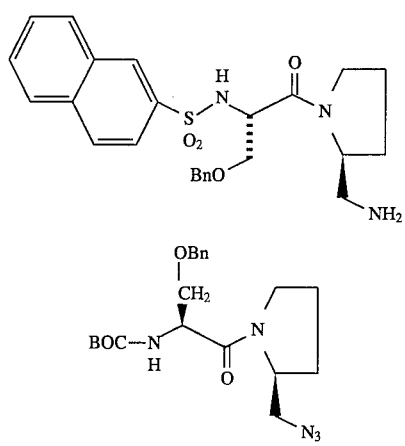

G.

G.(1)

2-Azido-N-BOC pyrrolidine (2.13 g, 9.4 mmol) was dissolved in dichloromethane (5 mL) and trifluoroacetic acid (7 mL) and stirred at RT 3 hours. The TFA and dichloromethane were removed by distillation under reduced pressure and by coevaporation with toluene to give the amine as a TFA salt. This and N-BOC-O-benzyl-L-serine (2.95 g, 10 mmol) were dissolved in DMF (50 mL). HOBT (1.35 g, 10 mmol), WSC (1.91 g, 10 mmol) and NMM (3.3 mL, 30 mmol) were added. The reaction was stirred for 8 h at room temperature, diluted with ethyl acetate (50 mL) and saturated $KHSO_4$ solution (30 mL). The layers were separated and the aqueous layer was reextracted with ethyl acetate (50 mL). The combined organic layers were washed with saturated sodium bicarbonate solution (30 mL) and 10% lithium chloride solution (30 mL). The ethyl acetate layer was dried over magnesium sulfate and concentrated in vacuo to provide title G(1) compound (3.87 g, 100%) as an oil which was used without further purification.

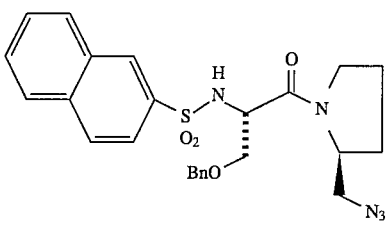

G.(2)

Part G(1) BOC-azide (3.85 mg, 9.55 mmol) was dissolved in TFA (20 mL) and stirred at RT 1.5 hours. The TFA was removed by distillation under reduced pressure and by coevaporation with toluene. The residue was dissolved in dichloromethane (100 mL), cooled in an ice bath, and triethylamine (4.0 mL, 28.7 mmol) and 2-naphthalene sulfonyl chloride (2.38 g, 10.5 mmol) were added. The cooling bath was removed and the solution was stirred for 2 h. This solution was washed with $KHSO_4$ solution (25 mL×2) and $NaHCO_3$ solution (25 mL×2), dried over magnesium sulfate and evaporated to provide crude title sulfonamide. The crude title sulfonamide product was chromatographed on silica gel and eluted with 30% and 50% EtOAc in hexane to provide A(1)sulfonamide as an oil (2.597 g, 55%).

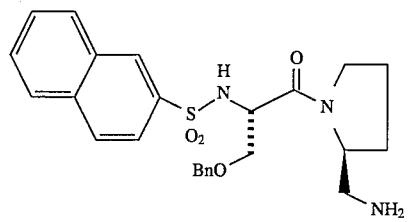

G.(3)

The Part G(2) azide (2.5 g, 5 mmol) was dissolved in absolute ethanol (100 mL) and treated with 10% palladium on carbon (300 mg). The flask was equipped with a hydrogen filled balloon via a three way stopcock. Air inside the flask was evacuated under reduced pressure and the flask was then filled with hydrogen from the balloon. This process was repeated three times. The mixture was stirred overnight in the hydrogen atmosphere. The catalyst was then removed by filtration through Celite and the pad was washed with ethanol. The solvent was removed from the filtrate in vacuo to give title amine as a foam (2.236 g, 96%).

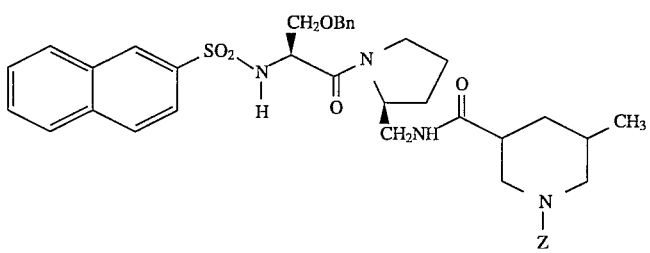

H.

Part G amine (467 mg, 1.0 mmol) and Part F acid (305 mg, 1.1 mmol) were dissolved in DMF (2 mL) at RT. HOBT (148 mg, 1.1 mmol), 4-methyl morpholine (242 μL, 2.2 mmol) and WSC (210 mg, 1.1 mmol) were added. The reaction was stirred 20 hours at room temperature. The mixture was then diluted with ethyl acetate (50 mL) and KHSO₄ solution (20 mL). The layers were separated. The organic layer was washed with saturated NaHCO₃ solution (20 mL) and 10% lithium chloride solution (2×20 mL), dried over magnesium sulfate and concentrated in vacuo. The crude oil was chromatographed on silica gel, eluting with 50% EtOAc in hexane followed by EtOAc to provide title compound (584 mg, 80%).

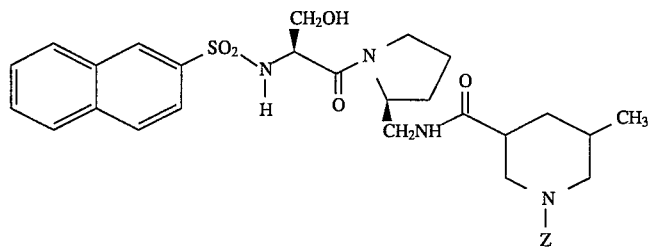

Part H compound (578 mg, 0.79 mmol) was dissolved in ethanol (100 mL) to which acetyl chloride (2.0 mL) had been added and the mixture was treated with 10% palladium on carbon (300 mg) and hydrogenated at 55 psi for 3 days. The catalyst was removed by filtration and the pad was washed with EtOH. The filtrate was concentrated in vacuo to obtain crude title compound as a foam (350 mg) which was used without purification.

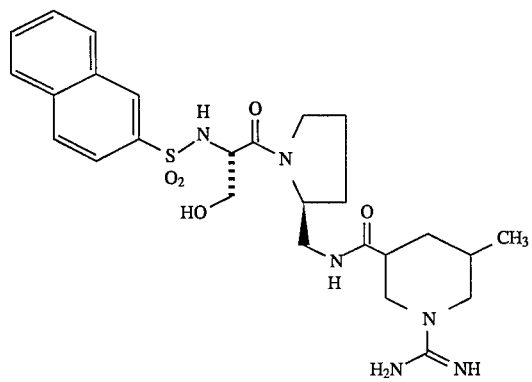

The crude Part J amine (~0.79 mmol) was dissolved in dimethylformamide (1.6 mL). H-pyrazole-1-carboxamidine (131 mg, 0.89 mmol) and diisopropylethyl amine (310 μL) were added. The mixture was stirred 24 hours at room temperature. Ether (10 mL) was then added. Gummy material precipitated. The ether was decanted and the precipitate was washed with more ether. The gummy material was dissolved in methanol and taken to dryness in vacuo. The remaining material was purified by preparative HPLC (YMC S-15 ODS 50×500 mm column, eluting with 54% methanol in water, containing 0.1% TFA). The two cis isomers were separated. The fractions that were clean by analytical HPLC were combined, concentrated to a small volume in vacuo and lyophilized. These samples were used to obtain NMR spectra, recovered, dissolved in water and relyophilized to give title compound, Isomer A (from Part H compound) and Example 48 compound, Isomer B (124 mg, 22% from Part H compound). Also obtained was a small amount of mixed fractions (54 mg, ~10%). Title compound, Isomer A: [α]$_D$=−49.0° (c=0.4, MeOH)

Analysis: Calcd for 1.15 TFA+1.3 H₂O: C, 48.61; H, 5.73; N, 12.02; F, 9.37; S, 4.59. Found: C, 48.59; H, 5.62; N, 11.92; F, 9.35; S, 4.74.

EXAMPLE 31a

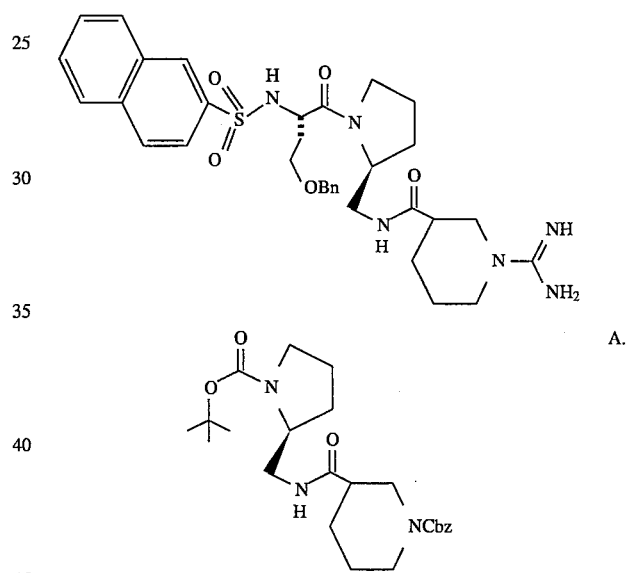

To a stirred solution of 1-BOC-2-(methylazide)pyrrolidine (3.00 g, 13.3 mmol) in 80 mL of methanol under argon was added 20%Pd(OH)₂/C (0.60 g, 20% based on the weight of the azide compound). The atmosphere was replaced with hydrogen by several vacuum-fill cycles. The reaction mixture was stirred at room temperature for 19 h. The catalyst was filtered off through a 4 μM polycarbonate film and rinsed with methanol (4×30 mL). The filtrate was concentrated in vacuo to give 2.65 g of an intermediate amine in a quantitative yield. To a stirred solution of this amine, 1-hydroxybenzotriazole monohydrate (2.62 g, 15.5 mmol) and N-carbobenzyloxy-3-piperidine carboxylic acid (4.08 g, 15.5 mmol) in 85 mL of DMF was added in order N-methylmorpholine (8.51 mL, 77.5 mmol) and ethyl 3-(3-dimethylamino)propyl carbodiimide hydrochloride (5.94 g, 31.0 mmol). The reaction solution was stirred at room temperature for 18 h and concentrated under pump vacuum at 50° C. The residue was dissolved in 500 mL of EtOAc and washed with 1N HCl solution (3×200 mL), saturated NaHCO₃ solution (2×200 ml) and brine (1×200 mL). The EtOAc layer was dried (MgSO₄), filtered and concentrated in vacuo.

Purification was effected by flash chromatography on silica gel to give 3.33 g (56%) of title carbamate.

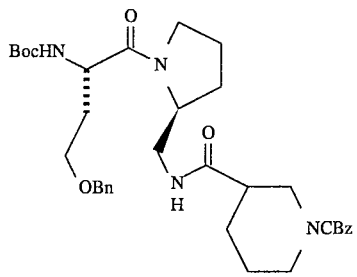
B.

To a stirred solution of Part A carbamate (3.20 g, 7.19 mmol) in 10 mL of dry dichloromethane at 0° C. was added a 4N HCl solution in dioxane (15.0 mL, 60.0 mmol). The solution was stirred at room temperature for 3 h and concentrated in vacuo. The residue was dissolved in 100 mL of dichloromethane and 100 mL of methanol. The solution was concentrated in vacuo to give an intermediate amine. To a stirred solution of this amine (1.10 g, 2.88 mmol), 1-hydroxybenzotriazole monohydrate (0.48 g, 2.88 mmol) and N-Boc-O-benzylhomoserine (0.89 g, 2.88 mmol) in 20 mL of DMF was added in order N-methylmorpholine (1.04 mL, 9.51 mmol) and ethyl 3-(3-dimethylamino)propyl carbodiimide hydrochloride (0.55 g, 2.88 mmol). The reaction solution was stirred at room temperature for 18 h and concentrated under pump vacuum at 45° C. The residue was dissolved in 300 mL of EtOAc and washed with 1N HCl solution (3×100 mL), saturated NaHCO$_3$ solution (2×100 mL) and brine (1×100 mL). The organic layer was dried (MgSO$_4$), filtered and concentrated in vacuo and chromatographed on silica gel to give 1.28 g (70%) of title amide.

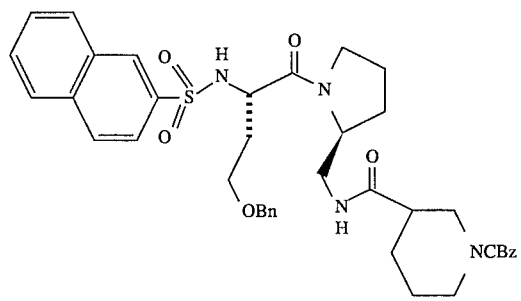
C.

To a stirred solution of Part B amide (804 mg, 1.27 mmol) in 5.0 mL of dry dichloromethane at 0° C. was added a 4N HCl solution in dioxane (10.0 mL, 40.0 mmol). The reaction solution was stirred at room temperature for 3 h and concentrated in vacuo to give a crude amine. To a stirred solution of this amine and triethyl amine (0.39 mL, 2.78 mmol) in 20 mL of dry dichloromethane under argon was added 2-naphthalenesulfonyl chloride (301 mg, 1.33 mmol). The reaction solution was stirred at room temperature for 3.5 h and diluted with 200 mL of EtOAc. The solution was washed with 1N HCl solution (3×60 mL), saturated NaHCO$_3$ solution (2×60 mL) and brine (1×60 mL). The organic layer was dried (MgSO$_4$), filtered, concentrated in vacuo and was chromatographed on silica gel to give 0.79 g (86%) of title carbamate.

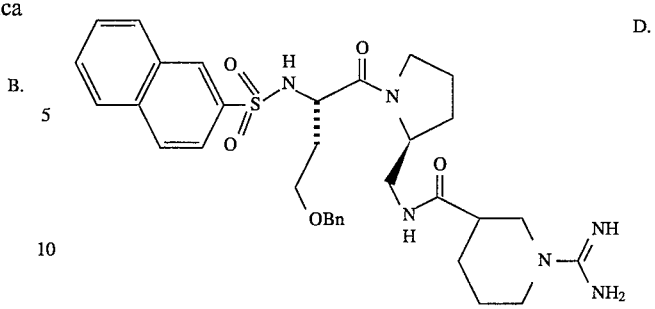
D.

To a stirred solution of Part C carbamate (0.71 g, 0.98 mmol) in 10 mL of methanol under argon was added 20%Pd(OH)$_2$/C (142 mg, 20% based on the weight of Part C compound). The atmosphere was replaced with hydrogen by several vacuum-fill cycles. The reaction mixture was stirred at room temperature for 20 h. The catalyst was filtered off through a 4 μM polycarbonate film and rinsed with methanol (5×30 mL). The filtrate was concentrated in vacuo to give 0.58 g of the intermediate amine. To a stirred solution of this amine (124 mg, 0.21 mmol) and DIEA (73.0 mL, 0.42 mmol) in 0.25 mL of DMF was added guanopyrazole hydrochloride (37.0 mg, 0.25 mmol). The reaction solution was stirred at room temperature for 24 h at which time another batch of guanopyrazole hydrochloride (6.20 mg, 0.04 mmol) was added. The solution was stirred at room temperature for 22 h. The reaction solution was then diluted with 20 mL of ether and treated with 0.15 mL of a solution of 4N HCl in dioxane. The solvent was decanted and the precipitate was purified by preparative HPLC. The fractions were concentrated in vacuo and lyophilized to give 118 mg (73%) of title guanidine.

Analysis: calc'd for 1.00 TFA+1.00 H$_2$O: C, 54.82; H, 5.91; N, 10.96; F, 7.43; S, 4.18 Found: C, 54.87; H, 5.83; N, 10.58; F, 7.82; S, 4.25.

EXAMPLE 32a

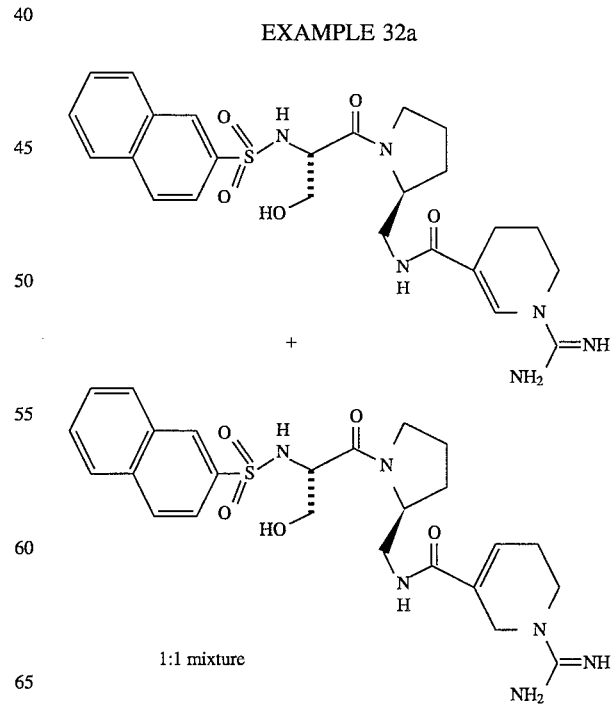

1:1 mixture

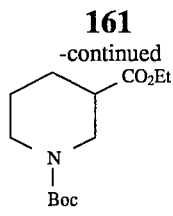

(N—Boc-nipecotate)

To a stirred solution of (±) ethyl nipecotate (5.00 g, 31.8 mmol) and triethyl amine (6.64 mL, 47.7 mmol) in 100 mL of dichloromethane at 0° C. was added portionwise a solution of di-t-butyl dicarbonate (7.64 g, 35.0 mmol) in 100 mL of dichloromethane over 5 min. The reaction solution was stirred at room temperature for 25 h and then diluted with 600 mL of EtOAc. The solution was washed with 1N HCl solution (3×200 mL), saturated NaHCO₃ solution (2×200 mL) and brine (1×200 mL). The organic layer was dried (MgSO₄), filtered and concentrated in vacuo. This was chromatographed on silica gel to give 6.44 g (79%) of title N-Boc nipecotate.

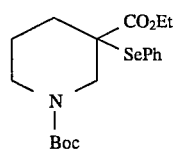

To a stirred solution of Part A nipecotate (1.00 g, 3.91 mmol) in 40 mL of dry THF under argon at −78° C. was added a 1M solution of sodium hexamethyldisilazide (4.30 mL, 4.30 mmol) over 5 min. The solution was stirred at −78° C. for 40 min at which time a solution of diphenyl diselenide (1.28 g, 4.10 mmol) in 6.0 mL of THF was added dropwise over 10 min. This reaction solution was stirred at −78° C. for 1 h and quenched dropwise with 15 mL of saturated NaHCO₃ solution. The resulting mixture was stirred vigorously without cooling for 5 min. The mixture was concentrated in vacuo. The residue was diluted with 300 mL of EtOAc and washed with 5% KHSO₄ solution (3×150 mL), saturated NaHCO₃ solution (2×150 mL) and brine (1×150 mL). The organic layer was dried (MgSO₄), filtered, concentrated in vacuo; and purified on silica gel to give 1.29 g (80%) of Part B ester.

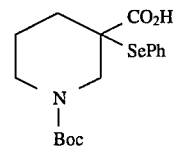

To a stirred solution of Part B ester (1.06 g, 2.57 mmol) in 65 mL of methanol and 20 mL of water was added 1N NaOH solution (7.69 mL, 7.69 mmol). The reaction solution was stirred at room temperature for 10 days. The solution was concentrated in vacuo. The remaining aqueous solution was acidified to pH 2 by the addition of 1N HCl solution. The solution was extracted with EtOAc (4×60 mL). The combined EtOAc extracts were dried (MgSO₄), filtered, concentrated in vacuo, and chromatographed on silica gel to give 350 mg (36%) of title acid and some recovered starting Part B ester.

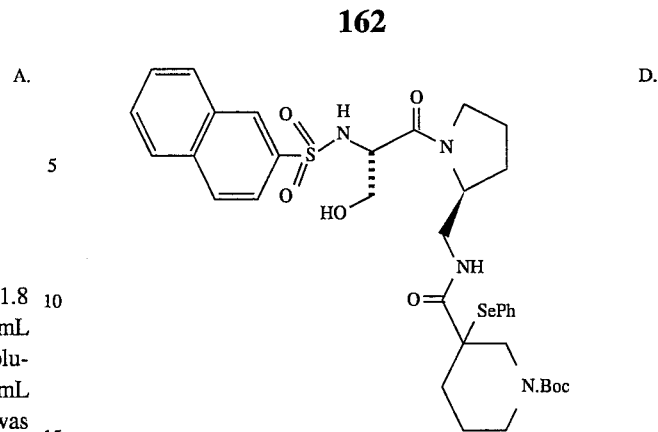

To a stirred solution of Part C acid (263 mg, 0.68 mmol), Example 30a Part G amine (283 mg, 0.68 mmol) and 1-hydroxybenzotriazole monohydrate (115 mg, 0.68 mmol) in 4.4 mL of DMF was added in order N-methylmorpholine (0.23 mL, 2.05 mmol) and ethyl 3-(3-dimethylamino)propyl carbodiimide hydrochloride (131 mg, 0.68 mmol). The reaction solution was stirred at room temperature for 16 h and concentrated under pump vacuum at 45° C. The residue was dissolved in 200 mL of EtOAc and washed with 1N HCl solution (2×60 mL), saturated NaHCO₃ solution (2×60 mL) and brine (1×60 mL). The EtOAc layer was dried (MgSO₄), filtered and concentrated in vacuo, and was chromatographed on silica gel to give 417 mg (82%) of title carbamate.

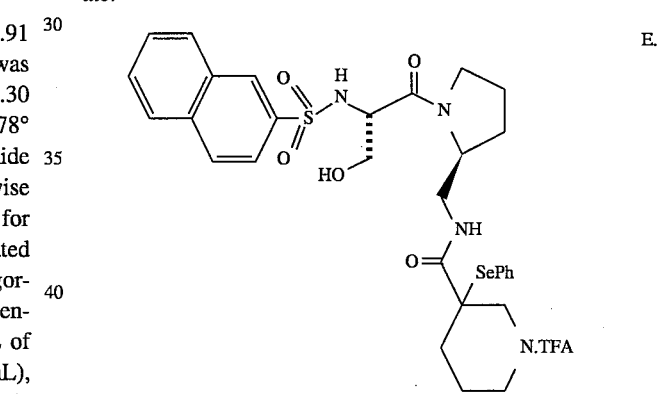

To a stirred solution of Part D carbamate (415 mg, 0.56 mmol) in 3.0 mL of dry dichloromethane was added TFA (9.00 mL, 117 mmol). The reaction solution was stirred at room temperature for 1 h and concentrated in vacuo to give title amine.TFA (384 mg, 91%).

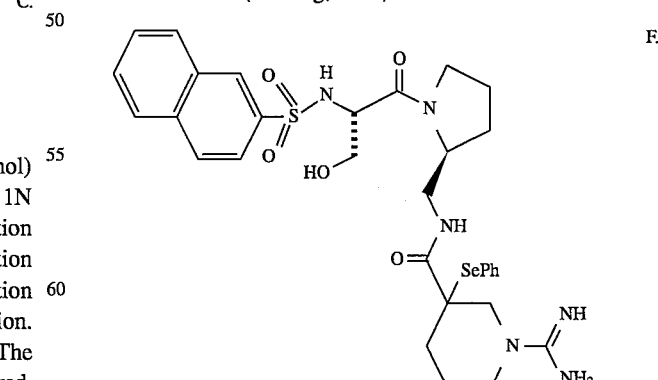

To a stirred solution of Part E amine.TFA (381 mg, 0.50 mmol) and DIEA (0.26 mL, 1.51 mmol) in 0.5 mL of DMF was added guanopyrazole hydrochloride 88.0 mg, 0.60 mmol). The reaction solution was stirred at room temperature for 24 h at which time another of batch of guanopyrazole hydrochloride (14.7 mg, 0.10 mmol) was added. The reaction solution was stirred at room temperature for 24 h and stood at room temperature for 21 h. The solution was diluted with 20 mL of ether. To this mixture was added 0.3 mL of a solution of 4N HCl in dioxane. The solution was decanted and the precipitated residue was purified by preparative HPLC. The fractions were concentrated in vacuo and lyophilized to give 236 mg (59%) of title selenide.

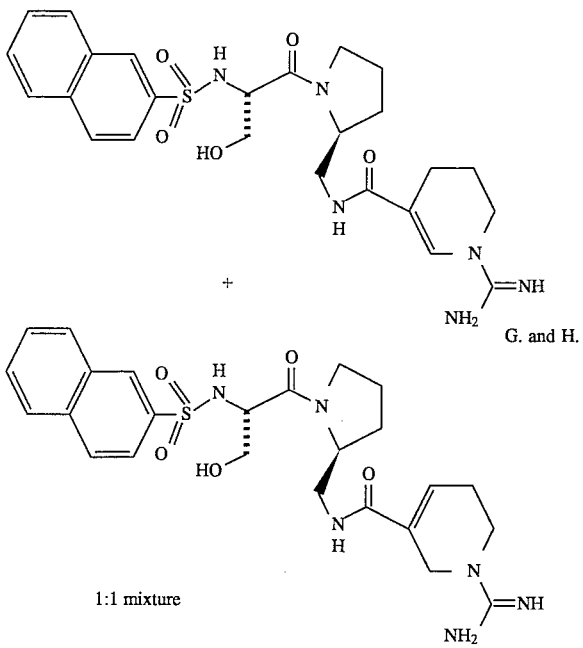

1:1 mixture

To a stirred solution of Part F selenide (190 mg, 0.24 mmol) in 9 mL of THF was added 1.6 mL of 30% $H_2O_2$ solution. The reaction solution was stirred at room temperature for 30 min, concentrated in vacuo and purified by preparative HPLC to give 95 mg (62%) of a 1:1 mixture of title G and H compounds.

MS: (M+H)+=529.

EXAMPLE 33a

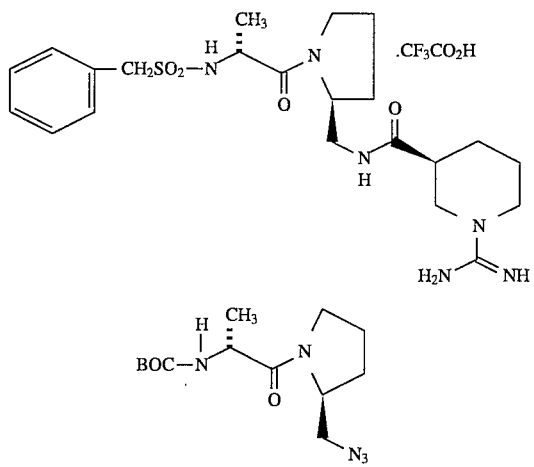

A.

A solution of 1-BOC-2-(methylazido)pyrrolidine (1.36 g, 6.0 mmol) in dichloromethane (5 mL) and trifluoroacetic acid (4 mL) was stirred at room temperature for two hours. The reaction mixture was concentrated under reduced pressure and toluene was added and removed at reduced pressure. This process was repeated two more times. The crude amine, N-BOC-D-alanine (1.14 g, 6 mmol) and 1-hydroxybenzotriazole (1.01 g, 7.5 mmol) were dissolved in DMF (30 mL) and treated with 4-methyl morpholine (1.32 mL, 12 mmol) followed by WSC (1.2 g, 6.0 mmol). The reaction mixture was stirred overnight at room temperature. The mixture was diluted with ethyl acetate (70 mL) and washed with saturated $KHSO_4$ solution (20 mL), $NaHCO_3$ solution (25 mL) and 10% lithium chloride solution (2×15 mL), dried over magnesium sulfate and concentrated in vacuo to give title compound as an oil (1.74 g, 98%) which was used without purification.

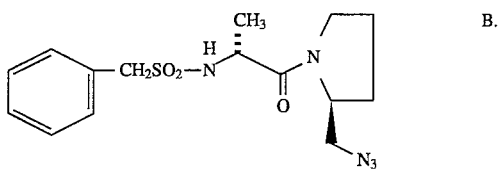

B.

A solution of Part A azide (1.74 g, 5.85 mmol) in dichloromethane (5 mL) and trifluoroacetic acid (4 mL) was stirred at room temperature for two hours. The reaction mixture was concentrated under reduced pressure and toluene was added and removed at reduced pressure. This process was repeated two more times. A solution of the crude des-BOC-amine and α-toluenesulfonyl chloride in dichloromethane (30 mL) was cooled to 0°–5° C. and triethylamine (4.2 mL, 30 mmol) was added dropwise. The mixture was stirred cold for one hour and then diluted with 1N HCl solution (50 mL). The dichloromethane layer was separated, dried over magnesium sulfate and concentrated in vacuo. The crude oil was chromatographed on silica gel, eluting with 50% and 75% ethyl acetate in hexanes to give the title benzylsulfonamide as a white foam (1.55 g, 75%).

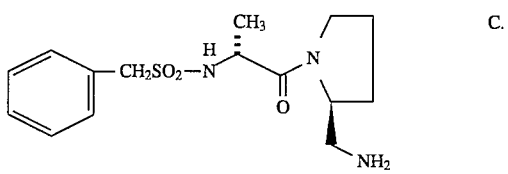

C.

The Part B azide (1.55 g, 4.42 mmol) was dissolved in absolute ethanol (60 mL) and treated with 10% palladium on carbon (310 mg). The reaction flask was equipped with a hydrogen filled balloon via a three-way stopcock. Air inside the flask was evacuated under reduced pressure and replaced with hydrogen from the balloon. This operation was repeated (3×). Hydrogenolysis was continued for twenty hours. The balloon was removed and the catalyst was removed by filtration. The pad was washed with more ethanol. The filtrate was concentrated in vacuo to obtain title amine (1.33 mg, 93%) as a foam which was used without purification.

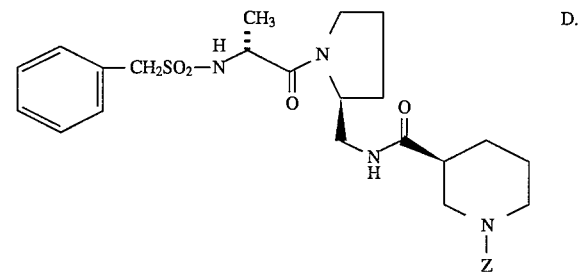

D.

Part C amine (488 mg, 1.5 mmol) and N-carbobenzyloxy-3(S)-piperidine carboxylic acid (395 mg, 1.5 mmol) were dissolved in DMF (15 mL) at RT. HOBT (270 mg, 2.0 mmol), 4-methyl morpholine (550 µL, 5 mmol) and WSC (300 mg, 1.5 mmol) were added. The reaction was stirred 20 hours at room temperature. The mixture was then diluted with ethyl acetate (50 mL) and washed with KHSO₄ solution (30 mL), saturated NaHCO₃ solution (25 mL) and 10% lithium chloride solution (3×15 mL), dried over magnesium sulfate and concentrated in vacuo to give title compound (730 mg, 85%) as a white foam.

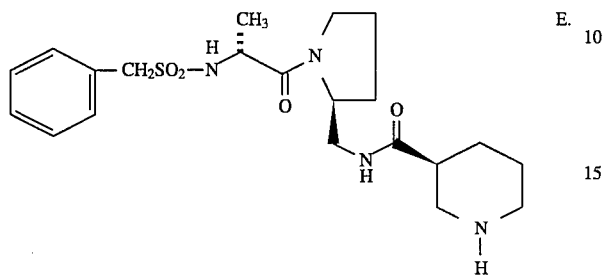

E.

Part D compound (730 mg, 1.28 mmol) was dissolved in ethanol (100 mL) and treated with Pearlman's catalyst (300 mg). The reaction flask was connected to a hydrogen filled balloon via a threeway stopcock. Air inside the flask was evacuated under reduced pressure and replaced with hydrogen from the balloon. This operation was repeated (3×). Hydrogenation was continued 18 hours. TLC indicated that a large amount of starting material remained. The catalyst was removed by filtration, the pad was washed with more ethanol and the filtrate was taken to dryness at reduced pressure. The residue was dissolved in ethanol (100 mL), acetyl chloride (1.5 mL) and 10% palladium on carbon (300 mg) were added and the mixture was hydrogenated on the Parr apparatus at 55 psi for twenty hours. The catalyst was removed by filtration. The pad was washed with more ethanol. The filtrate was concentrated in vacuo to obtain title amine which was used without purification.

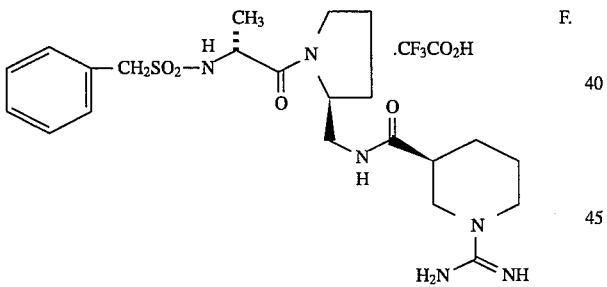

F.

The crude Part E amine was dissolved in dimethylformamide (2.5 mL). H-pyrazole-1-carboxamidine (263 mg, 1.8 mmol) and diisopropylethyl amine (700 µL) were added. The mixture was stirred 24 hours at room temperature. Ether (15 mL) was then added. Gummy material precipitated. The ether was decanted and the precipitate was washed with more ether. The gummy material was dissolved in methanol and taken to dryness in vacuo. The remaining material was purified by preparative HPLC (YMC S-15 ODS 50×500 mm column, eluting with 40% methanol in water, containing 0.1% TFA). Fractions containing clean title compound were combined and lyophilized to provide a white solid which was used to obtain NMR spectra, recovered, dissolved in water (30 mL) and relyophilized to give title compound (271 mg, 34%).

[α]_D=+39.7° (c=0.6, MeOH)

Analysis: Calcd for 1.20 TFA+0.3 H₂O: C, 47.20; H, 5.81; N, 13.54; F, 11.02; S, 5.16. Found: C, 47.26; H, 5.86; N, 13.48; F, 10.93; S, 5.24.

EXAMPLE 34a

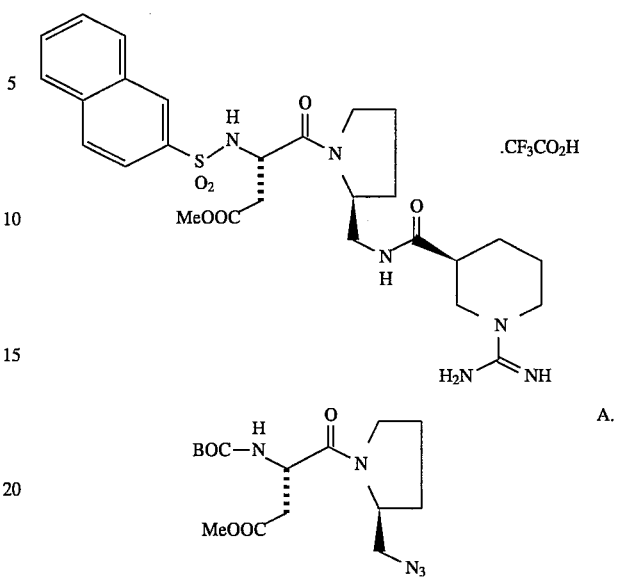

A.

A solution of 1-BOC-2-(methylazido)pyrrolidine (1.36 g, 6.0 mmol) in dichloromethane (5 mL) and trifluoroacetic acid (4 mL) was stirred at room temperature for two hours. The reaction mixture was concentrated under reduced pressure and toluene was added and removed at reduced pressure. This process was repeated two more times. The crude amine, N-BOC-L-aspartic acid, methyl ester (1.48 g, 6 mmol) and 1-hydroxybenzotriazole (1.01 g, 7.5 mmol) were dissolved in DMF (30 mL) and treated with 4-methyl morpholine (1.32 mL, 12 mmol) followed by WSC (1.2 g, 6.0 mmol). The reaction mixture was stirred overnight at room temperature. The mixture was diluted with ethyl acetate (70 mL) and washed with satd. KHSO₄ solution (20 mL), NaHCO₃ solution (25 mL) and 10% lithium chloride solution (2×15 mL), dried over magnesium sulfate and concentrated in vacuo to give title compound as a foam (1.68 g, 84%) which was used without purification.

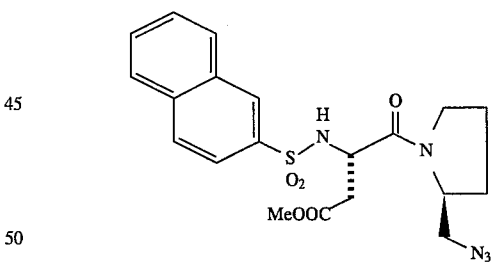

B.

A solution of Part A compound (1.68 g, 5.03 mmol) in dichloromethane (5 mL) and trifluoroacetic acid (4 mL) was stirred at room temperature for two hours. The reaction mixture was concentrated under reduced pressure and toluene was added and removed at reduced pressure. This process was repeated two more times. A solution of the crude des-BOC-amine and napthalee-2-sulfonyl chloride (1.25 g, 5.5 mmol) in dichloromethane (25 mL) was cooled to 0°–5° C. and triethylamine (2.1 mL, 15 mmol) was added dropwise. The mixture was stirred cold for two hours and then diluted with 1N HCl solution (30 mL). The dichloromethane layer was separated, dried over magnesium sulfate and concentrated in vacuo. The crude oil was chromatographed on silica gel, eluting with 50% and 75% ethyl acetate in hexanes to give the title sulfonamido adduct as a white foam (1.53 g, 68%).

C.

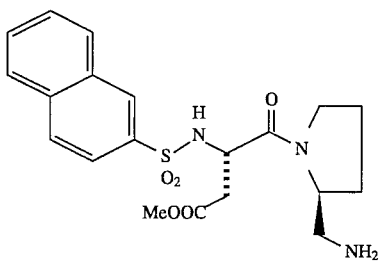

The Part B azide (1.5 g, 3.37 mmol) was dissolved in absolute ethanol (80 mL) and treated with 10% palladium on carbon (300 mg). The reaction flask was equipped with a hydrogen filled balloon via a three-way stopcock. Air inside the flask was evacuated under reduced pressure and replaced with hydrogen from the balloon. This operation was repeated (3×). Hydrogenolysis was continued for twenty hours. The balloon was removed and the catalyst was removed by filtration. The pad was washed with more ethanol. The filtrate was concentrated in vacuo to obtain title amine (Quant.) as a foam which was used without purification.

D.

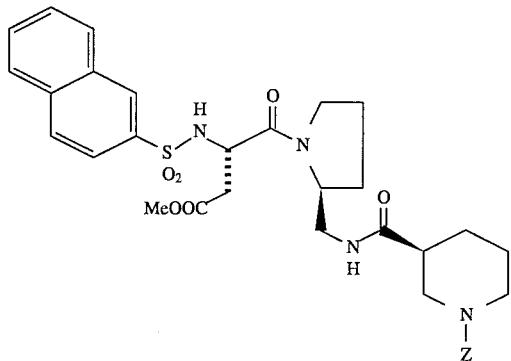

Part C amine (3.37 mmol) and N-carbobenzyloxy-3(S)-piperidine carboxylic acid (790 mg, 3.7 mmol) were dissolved in DMF (20 mL) at RT. HOBT (500 mg, 3.7 mmol), 4-methyl morpholine (1.5 mL) and WSC (708 mg, 3.7 mmol) were added. The reaction was stirred 20 hours at room temperature. The mixture was then diluted with ethyl acetate (60 mL) and washed with KHSO₄ solution (20 mL), saturated NaHCO₃ solution (15 mL) and 10% lithium chloride solution (2×15 mL), dried over magnesium sulfate and concentrated in vacuo. The material obtained was chromatographed on silica gel, eluting with ethyl acetate followed by 5% methanol in ethyl acetate to give title compound (1.56 g, 72%) as a white foam.

E.

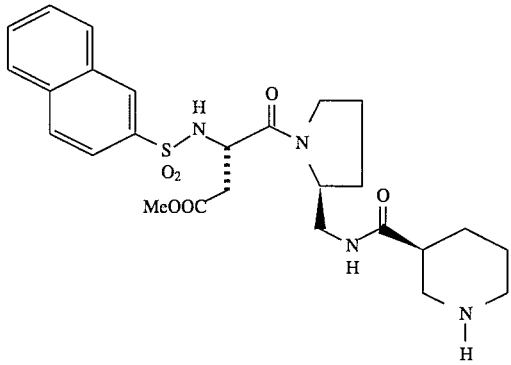

Part D compound (625 mg, 0.97 mmol) was dissolved in methanol (60 mL) and treated with Pearlman's catalyst (200 mg). The reaction flask was connected to a hydrogen filled balloon via a threeway stopcock. Air inside the flask was evacuated under reduced pressure and replaced with hydrogen from the balloon. This operation was repeated (3×). Hydrogenation was continued 18 hours. TLC indicated that the reaction was complete. The catalyst was removed by filtration, the pad was washed with more methanol and the filtrate was taken to dryness at reduced pressure to give title amine (470 mg, 96%) which was used without purification.

F.

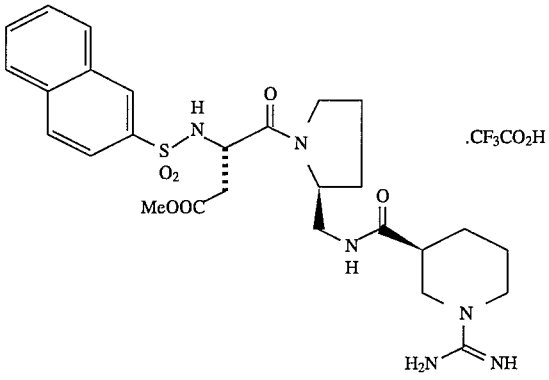

The crude Part E amine (470 mg, 0.928 mmol) was dissolved in dimethylformamide (2.0 mL). H-pyrazole-1-carboxamidine (190 mg, 1.3 mmol) and diisopropylethylamine (360 μL, 2 mmol) were added. The mixture was stirred over a weekend at room temperature. Ether (25 mL) was then added. Gummy material precipitated. The ether was decanted and the precipitate was washed with more ether. The gummy material was dissolved in methanol and taken to dryness in vacuo. The remaining material was purified by preparative HPLC (YMC S-15 ODS 50×500 mm column, eluting with 53% methanol in water, containing 0.1% TFA). Fractions containing clean title compound were combined and lyophilized to provide a white solid which was used to obtain NMR spectra, recovered, dissolved in water (30 mL) and relyophilized to give title compound (324 mg, 49%).

$[\alpha]_D = -20.3°$ (c=0.6, MeOH)

Analysis: Calcd for 1.10 TFA+0.9 H₂O: C, 49.10; H, 5.49; N, 11.77; F, 8.78; S, 4.49. Found: C, 49.11; H, 5.23; N, 11.58; F, 6.96; S, 4.42.

EXAMPLE 35a

[1S(2R*,3R*)]-N-[2-[[[[1-(Aminoiminomethyl)-3-piperidinyl]carbonyl]amino]methyl]-1-pyrrolidinyl]-1-(hydroxymethyl)-2-oxoethyl]-α-toluenesulfonamide

A.

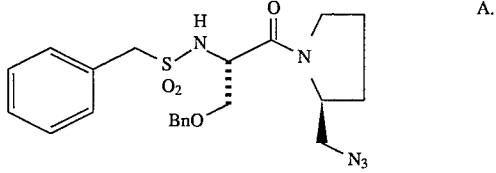

Example 30a Part G(1) BOC-azide (3.85 mg, 9.55 mmol) was dissolved in TFA (20 mL) and stirred at RT 1.5 hours. The TFA was removed by distillation under reduced pressure and by coevaporation with toluene. The residue is dissolved in dichloro-methane⁺(100 mL), cooled in an ice bath, and triethylamine (4.0 mL, 28.7 mmol) and α-toluene sulfonyl chloride (2.00 g, 10.5 mmol) are added. The cooling bath is removed and the solution is stirred for 2 h. This solution is washed with KHSO₄ solution (25 mL×2) and NaHCO₃ solution (25 mL×2), dried over magnesium sulfate and evaporated to provide crude title compound. The crude product is chromatographed on silica gel and eluted with 30% and 50% EtOAc in hexane to provide title sulfonamide (2.597 g, 55%).

B. [1S(2R*,3R*)]-N-[2-[[[[1-(Aminoiminomethyl)-3-piperidinyl]carbonyl]amino]methyl]-2-toluenesulfonamide The title compound is prepared from Part A azide following the procedure described in Example 26a.

EXAMPLE 36a

[1S(2R*,3R*)]-N-[2-[[[[1-(Aminoiminomethyl)-3-piperidinyl]carbonyl]amino]methyl]-1-pyrrolidinyl]-1-(carbomethoxymethyl)-2-oxoethyl]-α-toluenesulfonamide

A.

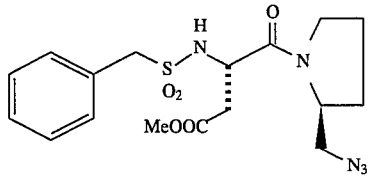

A solution of Example 34a Part A compound (1.68 g, 5.03 mmol) in dichloromethane (5 mL) and trifluoroacetic acid (4 mL) was stirred at room temperature for two hours. The reaction mixture was concentrated under reduced pressure and toluene was added and removed at reduced pressure. This process was repeated two more times. A solution of the crude des-BOC-amine and α-toluenesulfonyl chloride (1.14 g, 6 mmol) in dichloromethane (25 mL) is cooled to 0°–5° C. and triethylamine (2.1 mL, 15 mmol) is added dropwise. The mixture is stirred cold for two hours and then diluted with 1N HCl solution (30 mL). The dichloromethane layer is separated, dried over magnesium sulfate and concentrated in vacuo. The crude oil is chromatographed on silica gel, eluting with 50% and 75% ethyl acetate in hexanes to give the title sulfonamido adduct (1.53 g, 74%).

B. [1S(2R*,3R*)]-N-[2-[[[[1-(Aminoiminomethyl)-3-piperidinyl]carbonyl]amino]methyl]-1-pyrrolidinyl]-1-(carbomethoxymethyl)-2-oxoethyl]-α-toluenesulfonamide The title compound is prepared from Part A compound, following the procedure described in Example 34a.

EXAMPLE 37a

[1S(2R*,3R*)]-N-[2-[[[[1-(Aminoiminomethyl)-3-piperidinyl]carbonyl]amino]methyl]-1-pyrrolidinyl]-1-(carboxamidomethyl)-2-oxoethyl]-α-toluenesulfonamide

A.

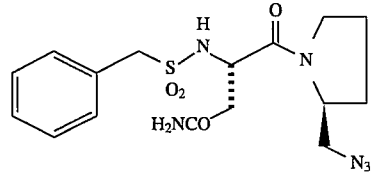

A solution of Example 36a Part A compound (816 mg, 2 mmol) in a saturated methanolic ammonia (5 mL) is stirred at room temperature in a sealed tube for 48 h. The mixture is concentrated under reduced pressure and in vacuo to form the title product.

B. [1S(2R*,3R*)]-N-[2-[[[[1-(Aminoiminomethyl)-3-piperidinyl]carbonyl]amino]methyl]-1-pyrrolidinyl]-1-(carboxamidomethyl)-2-oxoethyl]-α-toluenesulfonamide The title compound is prepared from Part A compound, following the procedure described in Example 34a.

EXAMPLES 38a to 54a

The following compounds were prepared carrying out procedures described in the specification and working examples.

38a. [S-(R*,R*)]-3-(Aminomethyl)-N-[[1-[3-hydroxy-2-[(2-napthalenylsulfonyl)amino]-1-oxopropyl]-2-pyrrolidinyl]methyl]benzamide, trifluoroacetate (1:1) salt $[\alpha]_D$=−39.4° (c 0.50, MeOH)

Anal. Calc'd for $C_{26}H_{30}N_4O_5S$. 1.26 TFA.0.97 $H_2O$: C, 50.99; H, 4.98; N, 8.34; S, 4.77; F, 10.69 Found: C, 50.99; H, 4.83; N, 8.35; S, 4.57; F, 10.72

39a. [S-(R*,R*)]-4-(Aminomethyl)-N-[[1-[3-hydroxy-2-[(2-napthalenylsulfonyl)amino]-1-oxopropyl]-2-pyrrolidinyl]methyl]benzeneacetamide, trifluoroacetate (1:1) salt $[\alpha]_D$=−43.0° (c 0.50, MeOH)

Anal. Calc'd for $C_{27}H_{32}N_4O_5S$.1.42 TFA.0.74 $H_2O$: C, 51.21; H, 5.03; N, 8.01; S, 4.58; F, 11.56 Found: C, 51.21; H, 4.95; N, 8.08; S, 4.31; F, 11.56

40a. [S-(R*,R*)]-3-(Aminomethyl)-N-[[1-[3-hydroxy-2-[(2-napthalenylsulfonyl)amino]-1-oxopropyl]-2-pyrrolidinyl]methyl]benzeneacetamide, trifluoroacetate (1:1) salt $[\alpha]_D$=−44.1° (c 1.00, MeOH)

Anal. Calc'd for $C_{27}H_{33}N_4O_5S$.1.35 TFA.1.48 $H_2O$: C, 50.58; H, 5.19; N, 7.94; S, 4.55; F, 10.91 Found: C, 50.58; H, 4.99; N, 7.84; S, 4.47; F, 11.09

41a. [3S-[3R*,3(R*,R*)]]-1-(Aminoiminomethyl)-N-[[1-[2-[(2-napthalenylsulfonyl)amino]-1-oxopropyl]-2-pyrrolidinyl]methyl]-3-piperidinecarboxamide, trifluoroacetate (2:3) salt $[\alpha]_D$=−18.3° (c 0.52, MeOH)

Anal. Calc'd for $C_{25}H_{34}N_6O_4S$.1.67 TFA.0.23 $H_2O$: C, 48.00; H, 5.13; N, 11.85; S, 4.52; F, 13.42 Found: C, 48.00; H, 5.37; N, 11.94; S, 4.45; F, 13.43

42a. [3S-[3R*,3(R*,R*)]]-1-(Aminoiminomethyl)-N-[[1-[3-hydroxy-2-[[(4-methylphenyl)sulfonyl]amino]-1-oxopropyl]-2-pyrrolidinyl]methyl]-3-piperidinecarboxamide, trifluoroacetate (1:1) salt $[\alpha]_D$=+16.0° (c 0.50, MeOH)

Anal. Calc'd for $C_{22}H_{34}N_6O_5S$.1.1 TFA.1.32 $H_2O$: C, 45.15; H, 5.91; N, 13.05; S, 4.98; F, 9.74 Found: C, 45.15; H, 5.52; N, 12.88; S, 4.95; F, 9.53

43a. [3S-[3R*,3(R*,R*)]]-1-(Aminoiminomethyl)-N-[[1-[3-hydroxy-2-[[carbobenzyloxy]amino]-1-oxopropyl]-2-pyrrolidinyl]methyl]-3-piperidinecarboxamide, trifluoroacetate (1:1) salt Anal. Calc'd for $C_{23}H_{34}N_6O_5S$.1.05 TFA.1.60 $H_2O$: C, 48.38; H, 6.19; N, 13.49; F, 9.60 Found: C, 48.39; H, 5.85; N, 13.16; F, 9.45

44a. [1S[2(R*,S*)]]-N-[2-[[[[1-(aminoiminomethyl)-4-piperidinyl]carbonyl]amino]methyl]-1-piperidinyl]-1-(hydroxymethyl)-2-oxoethyl]-2-naphthalenesulfonamide, trifluoroacetate (1:1) salt $[\alpha]_D$=+0.55° (c=0.5, MeOH), Analysis: Calcd for 0.95 TFA+1.7 $H_2O$: C, 49.02; H, 5.95; N, 12.29; F, 7.92; S, 4.69. Found: C, 49.15; H, 5.61; N, 11.95; F, 7.68; S, 4.89.

45a. [S-(R*,R*)]-3-[(aminoiminomethyl)amino]-N-[[1-[3-hydroxy-2-[[2-naphthalenesulfonyl]-amino]-1-oxopropyl]-2-pyrrolidinyl]methyl]propionamide, trifluoroacetate (1:1) salt $[\alpha]_D$=−36.8° (c=0.6, MeOH), Analysis: Calcd for 1.20 TFA+0.50 $H_2O$: C, 46.05; H, 5.10; N, 13.21; F, 10.75; S, 5.04. Found: C, 46.05; H, 4.98;, N, 13.02; F, 10.82; S, 4.97.

46a. [1S[2(R*,S*), (3R*)]]-N-[2-[[[[1-(aminoiminomethyl)-3-piperidinyl]carbonyl]amino]methyl]-1-piperidinyl]-1-(hydroxymethyl)-2-oxoethyl]-2-naphthalenesulfonamide, trifluoroacetate (1:1) salt

[α]$_D$=+24.1° (c=0.9, MeOH),

Analysis: Calcd for 1.20 TFA+0.7 H$_2$O: C, 49.14; H, 5.61; N, 12.11; F, 9.85; S, 4.62. Found: C, 49.17; H, 5.36; N, 12.04; F, 9.70; S, 4.70.

47a. [1S [2R*]]-N-[2-[[[[1-(aminoiminomethyl)-3-phenyl] carbonyl]amino]methyl]-1-pyrrolidinyl]-1-(hydroxymethyl)-2-oxoethyl]-2-naphthalenesulfonamide, trifluoroacetate (1:1) salt

[α]$_D$=−41.0° (c=0.4, MeOH),

Analysis: Calcd for 1.20 TFA+1.1 H$_2$O: C, 50.14H, 4.80; N, 10.30; F, 10.05; S, 4.71. Found: C, 50.13; H, 4.52;, N, 10.08; F, 9.78; S, 4.42.

48a. 1S[2R*]]-N-[2-[[[[1-(aminoiminomethyl) -cis-5-methyl-3-piperidinyl]carbonyl]amino]methyl]-1-pyrrolidinyl]-1-(hydroxymethyl)-2-oxoethyl]-2-naphthalenesulfonamide, trifluoroacetate (1:1) salt

[α]$_D$=−25.5° (c=0.4, MeOH)

Analysis: Calcd for 1.25 TFA+1.2 H$_2$O: C, 48.29; H, 5.64; N, 11.86; F, 10.05; S, 4.52 Found: C, 48.34; H, 5.54; N, 11.91; F, 9.99; S, 4.55.

49a. [1S[2R*]]-N-[2-[[[[1-(aminoiminomethyl)-trans-5-methyl-3-piperidinyl]carbonyl]amino]methyl]-1pyrrolidinyl]-1-(hydroxymethyl)-2-oxoethyl]-2- naphthalenesulfonamide, trifluoroacetate (1:1) salt

[α]$_D$=−28.8° (c=0.6, MeOH),

Analysis: Calcd for 1.10 TFA+1.0 H$_2$O: C, 49.22; H, 5.73; N, 12.21; F, 9.11; S, 4.66. Found: C, 48.23; H, 5.66; N, 12.08; F, 9.12; S, 4.87.

50a. [1S(2R*,3R*,4R*)]-N-[2-[[[[1-(aminoiminomethyl)-3-piperidinyl]carbonyl]amino]methyl]-1-pyrrolidinyl]-1-(1-hydroxyethyl)-2-oxoethyl]-2-naphthalenesulfonamide, trifluoroacetate (1:1) salt

[α]$_D$=−10.0° (c=0.7, MeOH),

Analysis: Calcd for 1.10 TFA+1.7 H$_2$O: C, 48.34; H, 5.83; N, 11.99; F, 8.95; S, 4.58. Found: C, 48.32; H, 5.57; N, 11.84; F, 8.83; S, 4.71.

51a. [1S(2R*,3S*,4R*)]-N-[2-[[[[1-(aminoiminomethyl)-3-piperidinyl]carbonyl]amino]methyl]-1-pyrrolidinyl]-1-(1-hydroxyethyl)-2-oxoethyl]-2-naphthalenesulfonamide, trifluoroacetate (1:1) salt

[α]$_D$=−19.5° (c=0.6, MeOH),

Analysis: Calcd for 1.10 TFA+1.0 H$_2$O: C, 49.22; H, 5.73; N, 12.21; F, 9.11; S, 4.66. Found: C, 49.12; H, 5.71; N, 12.16; F, 9.38; S, 4.99.

52a. [R-(S*,R*)]-N-[2-[2-[[[[1-(aminoiminomethyl)-4-piperidinyl]carbonyl]amino]methyl]-1-pyrrolidinyl]-1-(phenylmethyl)-2-oxoethyl]methanesulfonamide, trifluoroacetate (1:1) salt

[α]$_D$=−34.7° (c=0.6, MeOH),

Analysis: Calcd for 1.25 TFA+0.2 H$_2$O: C, 47.10; H, 5.75; N, 13.45; F, 11.40; S, 5.13. Found: C, 47.09; H, 5.84;, N, 13.15; F, 11.44; S, 5.32.

53a. [S-(R*,R*)]N[2-[[[[1-(aminoiminomethyl)-3-piperidinyl]carbonyl]amino]methyl]-1-pyrrolidinyl]-2-oxoethyl]-2-naphthalenesulfonamide, trifluoroacetate (1:1) salt

[α]$_D$=+9.1° (c=0.3, MeOH),

Analysis: Calcd for 1.20 TFA+0.8 H$_2$O: C, 48.64; H, 5.38; N, 12.89; F, 10.49; S, 4.92. Found: C, 48.95; H, 5.23; N, 12.39; F, 10.32; S, 4.93.

54a [R-(S*,R*)]-N-[2-2-[[[[1-(aminoiminomethyl)-4-piperidinyl]carbonyl]amino]methyl]-1-pyrrolidinyl]-1-(methyl)-2-oxoethyl]benzylsulfonamide, trifluoroacetate (1:1) salt

[α]$_D$=+13.5° (c=0.7, MeOH),

Analysis: Calcd for 1.30 TFA+0.2 H$_2$O: C, 46.87; H, 5.71; N, 13.33; F, 11.75; S, 5.09. Found: C, 47.23; H, 5.78; N, 12.86; F, 11.36; S, 5.29.

The following Examples represent preferred embodiments of the fourth embodiment of the present invention. Unless otherwise indicated, all temperatures are expressed in degrees Centigrade.

EXAMPLE a

N-[[1-(Aminoiminomethyl)-4-piperidinyl]methyl]-1-D-phenylalanyl-L-prolinamide

A. 4-(Aminomethyl)-N,N'-bis[(1,1-dimethylethoxy)carbonyl]-1-piperidinecarboximidamide To a stirred solution of 4-aminomethylpiperidine (0.72 g, 6.31 mmol) in 40 mL of toluene was added benzaldehyde (0.78 mL, 6.94 mmol). The reaction solution was refluxed for 18 h and water was removed by a Dean Stark trap. The reaction solution was cooled to room temperature at which time bis-Boc amidinopyrazole (1.96 g, 6.31 mmol) was added. The reaction solution was stirred at room temperature for 48 h and concentrated in vacuo. The oily residue was diluted with 15 mL of 1M (aq) KHSO$_4$ solution and stirred at room temperature for 5 h. This aqueous solution was washed with ether (2×20 mL) and basified to pH 12 by the addition of 1N NaOH solution. This basic solution was then saturated with NaCl and extracted with dichloromethane (3×60 mL). The combined dichloromethane extracts were dried (MgSO$_4$), filtered and concentrated in vacuo to give 2.10 g (93%) of title amine which was used for the next transformation without further purification.

B. (S*)-N-[[1-[[[(1,1-Dimethylethoxy)carbonyl]amino][ [(1,1-dimethylethoxy)carbonyl]imino]methyl]-4-piperidinyl]methyl]-1-[1-[[(1,1-dimethylethoxy)carbonyl]amino]-2-phenylethyl]-S-prolinamide To a stirred solution of N-Boc-D-Phe-L-Pro-OH (0.73 g, 2.02 mmol), Part A amine (0.72 g, 2.02 mmol) and 1-hydroxybenzotriazole monohydrate (0.34 g, 2.02 mmol) in 30 mL of DMF was added in order 4-methylmorpholine (0.66 mL, 6.05 mmol) and ethyl-3-(3-dimethylamino)propyl carbodiimide hydrochloride (0.39 g, 2.02 mmol). The reaction solution was stirred at room temperature for 19 h and concentrated under pump vacuum at 45° C. The residue was diluted with 100 mL of saturated NaHCO$_3$ solution and extracted with dichloromethane (4×100 mL). The combined dichloromethane extracts were dried (MgSO$_4$), filtered and concentrated in vacuo. This was chromatographed on silica gel to give 0.70 g (50%) of title bis-Boc guanidine.

C. N-[[1-(Aminoiminomethyl)-4-piperidinyl]methyl]-1-D-phenylalanyl-L-prolinamide To a stirred solution of Part B bis-Boc guanidine (0.68 g, 0.97 mmol) in 6.0 mL of dichloromethane was added trifluoroacetic acid (TFA) (6.00 mL, 77.9 mmol). The reaction solution was stirred at room temperature for 3 h and concentrated in vacuo. This was purified by prep HPLC to give 310 mg (45%) of title compound.

EXAMPLE b

N-[[1-(Aminoiminomethyl)-3-piperidinyl]methyl]-1-D-phenylalanyl-L-prolinamide

A. N-Boc-3-hydroxymethylpiperidine

To a stirred solution of 3-hydroxymethylpiperidine (15.1 g, 131 mmol) and Et$_3$N (21.9 mL, 158 mmol) in 100 mL of dichloromethane was added dropwise a solution of di-t-butyl dicarbonate (31.5 g, 144 mmol) in 100 mL of dichloromethane over 1 h. The reaction was stirred at room temperature for 18 h and then diluted with 200 mL of dichloromethane. The resulting solution was washed with 1N HCl solution (3×100 mL), saturated NaHCO$_3$ solution (2×100 mL) and brine (1×100 mL). The organic layer was dried (MgSO$_4$), filtered and concentrated in vacuo to give N-Boc-3-hydroxymethylpiperidine (27.0 g, 96%).

B. 3-(Azidomethyl)-1-piperidinecarboxylic acid, 1,1-dimethylethyl ester

To a stirred solution of Part A N-Boc-3-hydroxymethylpiperidine (27.0 g, 126 mmol) in 150 mL of dry dichloromethane under argon at 0° C. was added in order triethylamine (22.7 mL, 163 mmol) and methanesulfonyl chloride (11.7 mL, 151 mmol). The reaction was stirred at room temperature for 1.5 h and diluted with 450 mL of dichloromethane. The reaction was washed with 0° C. 1N HCl solution (2×100 mL) and brine (1×100 mL). The dichloromethane layer was dried (Na$_2$SO$_4$), filtered and concentrated in vacuo. The residue was dissolved in 200 mL of DMF and combined with sodium azide (24.5 g, 377 mmol). The mixture was stirred at room temperature for 33 h and the solid was filtered off. The filtrate was concentrated under pump vacuum at 45° C. The residue was partitioned between 400 mL of EtOAc and 10% sodium thiosulfate solution (2×100 mL) and brine (1×100 mL). The EtOAc layer was dried (MgSO$_4$), filtered and concentrated in vacuo. Purification was effected by a flash column chromatography on silica gel to give 19.5 g (65%) of title azide.

C. 3-(Aminomethyl)-1-piperidinecarboxylic acid, 1,1-dimethylethyl ester

To a stirred solution of Part B azide (19.0 g, 79.2 mmol) in 250 mL of methanol under argon was added 10%Pd/C (3.80 g, 20% based on the weight of Part B azide). The atmosphere was replaced with hydrogen by several vacuum-fill cycles. The mixture was stirred at room temperature for 15 h. The catalyst was filtered through a 4 µM polycarbonate film and rinsed with methanol (4×30 mL). The filtrate was concentrated in vacuo to give 16.3 g (96%) of title amine.

D. N-[[1-[(1,1-Dimethylethoxy)carbonyl]-3-piperidinyl]methyl]-1-[N-[(phenylmethoxy)carbonyl]-D-phenylalanyl]-L-prolinamide To a stirred solution of Part C amine (2.00 g, 9,35 mmol), N-Cbz-D-Phe-L-Pro (3.70 g, 9.35 mmol), 1-hydroxybenzotriazole monohydrate (1.58 g, 9.35 mmol) and 4-methylmorpholine (3.07 mL, 28.0 mmol) was added ethyl-3-(3-dimethylamino)propyl carbodiimide hydrochloride (1.79 g, 9.35 mmol). The reaction solution was stirred at room temperature for 17 h and concentrated under pump vacuum at 45° C. The residue was dissolved in 360 mL of EtOAc and washed with 1N HCl solution (2×120 mL), saturated NaHCO$_3$ solution (1×120 mL) and brine (1×120 mL). The EtOAc layer was dried (MgSO$_4$), filtered, concentrated in vacuo and chromatographed on silica gel to give 1.30 g (23%) of title carbamate.

E. N-[[1-(Aminoiminomethyl)-3-piperidinyl]methyl]-1-[N-[(phenylmethoxy)carbonyl]-D-phenylalanyl]-L-prolinamide To a stirred solution of Part D carbamate (2.30 g, 3.89 mmol) in 10 mL of dry dichloromethane was added 0° C. 4N HCl in dioxane (15.0 mL, 60.0 mmol). The solution was stirred at room temperature for 3 h and diluted with 300 mL of ether. The precipitate was filtered off and rinsed with ether (3×30 mL). The precipitate was dried under pump vacuum at room temperature and purified by prep HPLC to give 1.39 g (59%) of intermediate amine.TFA. To a stirred solution of the intermediate amine.TFA salt (500 mg, 0.83 mmol) and diisopropylethyl amine (0.35 mL, 1.98 mmol) in 2.0 mL of DMF was added 1H-pyrazole-1-carboxamidine (133 mg, 0.91 mmol). The reaction solution was stirred at room temperature for 6 h and diluted with 100 mL of ether. The desired oily precipitate was separated from the ether solution and purified by prep HPLC to give 250 mg (47%) of title Cbz-carbamate.

F. N-[[1-(Aminoiminomethyl)-3-piperidinyl]methyl]-1-D-phenylalanyl-L-prolinamide To a stirred solution of Part E Cbz-carbamate (240 mg, 0.37 mmol) in 10 mL of methanol under argon was added 20%Pd(OH)$_2$/C (48 mg, 20% based on the weight of Part E Cbz carbamate). The atmosphere was replaced with hydrogen by several vacuum-fill cycles. The reaction mixture was stirred at room temperature for 24 h. The catalyst was filtered off and rinsed with methanol (4×20 mL). The filtrate was concentrated in vacuo. The residue was dissolved in 50 mL of a solution of 0.1%TFA in water and lyophilized to give 220 mg (82%) of title compound.

Following the procedures of Examples a. and b., the following examples of compounds of the invention may be prepared.

TABLE

[Structure: R₃—NH—CH(R)—C(=O)—N(CH₂CH(R¹)CH(R²)—)—CH((CH₂)ₙ)—C(=O)—NH—(CH₂)ₚ—Q—A—R⁴]

| Example No. | R₃ | R | R² | R¹ | n | p | Q | A | R⁴ |
|---|---|---|---|---|---|---|---|---|---|
| c | CBZ | CH₂OH(S) | H | CH₃ | 1 | 0 | — | 1-methylpiperidin-4-yl | $H_2N-C(=NH)-$ |
| d | H | H | OH | H | 0 | 1 | CO | 2-methyl-4-methyl-3-oxomorpholin-yl | $H_2N-C(=NH)-$ |
| e | C₆H₅CO | —CH₂C₆H₅(R) | OCH₃ | CH₃ | 0 | 2 | — | 1,3-dimethyl-2-oxoazetidin-yl | $H_2N-C(=NH)-$ |
| e | CO₂CH₃ | —CH₂C₆H₅(S) | CH₃ | CH₃ | 1 | 1 | — | 1,3-dimethylpiperidin-yl | $H_2N-C(=NH)-$ |
| f | CO₂C₆H₅ | —CH₂CH₂CONH₂(S) | H | H | 1 | 0 | — | 1,4-phenylene | —CH₂NH₂ |
| g | CH₃CO | —CH₂CH₂CONH₂(R) | H | CH₃ | 1 | 1 | CO | 1,4-cyclohexylene | —CH₂NH₂ |
| h | piperidin-4-yl-C(=O)— | —CH(OH)CH₃(S—Thr) | —CHCH₂CH₂CH— | | 0 | 2 | — | 1,4-phenylene | —NH—C(=NH)—NH₂ |
| i | H | CH(OH)CH₃(S-alloThr) | CH₃ | H | 1 | 2 | CO | 1,3-dimethyl-2-oxopyrrolidin-yl | $HN=C(NH_2)-$ |

TABLE-continued

| Example No. | R₃ | R | R² | R¹ | n | p | Q | A | R⁴ |
|---|---|---|---|---|---|---|---|---|---|
| j | C₆H₅CH₂CO | 2-(indol-3-yl)ethyl (R) | SCH₃ | CH₃ | 1 | 1 | — | 3-piperidinyl (N-H) | C(=NH)NH₂ |
| k | CO₂C₆H₅ | —CH₂CH₂CO₂H(R) | H | CH₃ | 0 | 0 | CO | 3-azetidinyl | C(=NH)NH₂ |
| l | CO₂CH₂C₆H₅ | CH₂OCH₂Ph(R) | H | H | 1 | 0 | — | 2-morpholinyl | C(=NH)NH₂ |
| m | H | CH₂CH₂Ph(S) | H | H | 1 | 1 | — | 3-piperidinyl | C(=NH)NH₂ |
| n | H | (1-methylpiperidin-4-yl)methylamino | H | H | 1 | 2 | — | 3-piperidinyl | C(=NH)NH₂ |

EXAMPLE i

N-[4-[(Aminoiminomethyl)amino]butyl]-1-[N-(methylsulfonyl)-D-phenylalanyl]-L-prolinamide, trifluoroacetate (1:1) salt

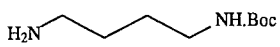
A.

To a stirred solution of 1,4-diaminobutane (50 g, 567 mmol) in 195 mL of dioxane under argon at room temperature was added dropwise a solution of di-t-butyl dicarbonate (15.7 g, 71.9 mmol) in 195 mL of dioxane over 3.5 h. Some white precipitate appeared during the addition. The mixture was stirred at room temperature for 22 h and concentrated in vacuo. The residue was diluted with 320 mL of water and the precipitate was filtered off. The aqueous filtrate was extracted with methylene chloride (3×300 mL). The combined methylene chloride extracts were washed in water (2×200 ml) and brine (1×200 mL). The organic layer was dried (MgSO₄), filtered and concentrated in vacuo to give 9.79 g (72%) of title mono-BOC.amine.

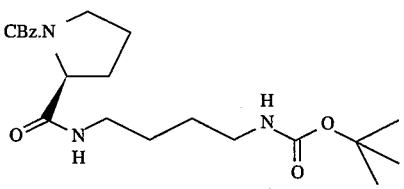
B.

To a stirred solution of N-CBz-L-proline (12.7 g, 50.9 mmol), 1-hydroxybenzotriazole monohydrate (6.49 g, 50.9 mmol) and Part A BOC.amine (9.57 g, 50.9 mmol) in 250 mL of DMF was added in order 4-methylmorpholine (11.2 mL, 102 mmol) and ethyl-3-(dimethylamino)propyl carbodiimide hydrochloride (9.76 g, 50.9 mmol). The reaction solution was stirred at room temperature for 22 h and concentrated under pump vacuum at 50° C. The residue was diluted with 600 mL of EtOAc and washed with 1N HCl solution (2×250 mL), saturated NaHCO₃ solution (2×250 mL) and brine (1×250 mL). The EtOAc layer was dried (MgSO₄), filtered and concentrated in vacuo to give 20.7 g (97%) of title CBz.amine.

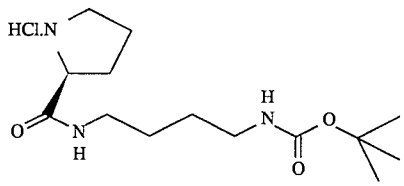

C.

To a stirred solution of Part B CBz.amine (20.2 g, 48.2 mmol) in 250 mL of methanol under argon was added 20% Pd(OH)₂/C (4.04 g, 20% based on the weight of Part B amine). The atmosphere was replaced by hydrogen with several vacuum-fill cycles. The reaction mixture was stirred at room temperature for 21 h. The catalyst was filtered off through a 4 μM polycarbonate film and rinsed with methanol (3×50 mL). The filtrate was concentrated in vacuo. The oily residue was dissolved in 200 mL of ether and treated with 1N HCl solution in ether (53.0 mL, 53.0 mmol). The solution was concentrated in vacuo. The residue was mixed with 300 mL of toluene and 30 mL of methanol and concentrated in vacuo to give title amine hydrochloride in a quantitative yield (15.5 g) as an oil.

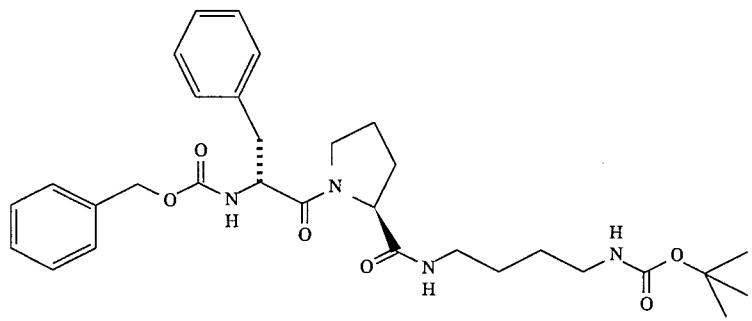

D.

A stirred solution of N-α-CBZ-D-phenylalanine (0.56 g, 1.9 mmol) in 6.5 mL of DMF at room temperature under argon was treated with 1-hydroxybenzotriazole (0.29 g, 1.9 mmol) and EDAC* (0.36 g, 1.9 mmol). After 20 minutes, Part C compound was added (0.50 g, 1.6 mmol) and stirring was carried out for 16 hours. The reaction was quenched by the addition of 75 mL of 0.25M KHSO₄ solution. The suspension was washed with EtOAc (2×40 mL), the combined EtOAc layers were washed with 0.25M KHSO₄ solution (2×40 mL), saturated aqueous KHCO₃ solution (2×40 mL), brine, dried (Na₂SO₄), and concentrated to yield 1.07 g of a white taffy, which by TLC analysis appeared to contain unreacted N-α-CBZ-D-phenylalanine. The crude product was redissolved in 60 mL of EtOAc, washed with saturated aqueous KHCO₃ solution (3×40 mL), brine, dried (Na₂SO₄), concentrated, co-evaporated several times with ether and hexane and triturated with 50 mL of hexane to yield title compound (0.78 g, 88%) as a colorless solid.

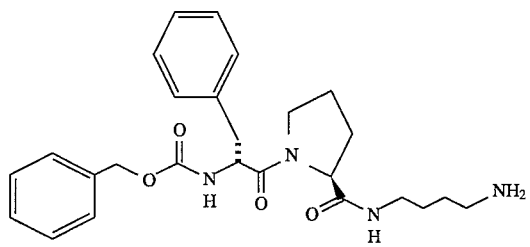

E.

Trifluoroacetic acid (3.2 mL) was added to ice-cooled Part D compound (0.78 g, 1.4 mmol). The reaction solution was stirred at room temperature for 2 hours and 45 minutes. Trifluoroacetic acid was removed under vacuum and co-evaporated several times with ether and hexane to obtain a colorless taffy.

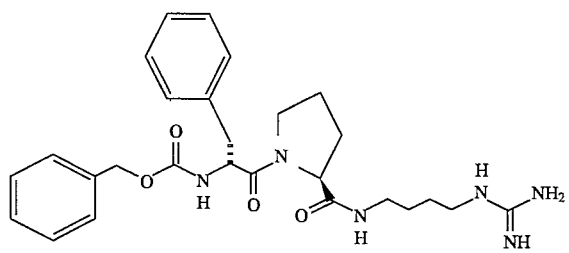

F.

A solution of Part E compound (0.80 g, 1.38 mmol) in 10.9 mL of absolute ethanol was treated with amidine sulfonic acid (0.26 g, 2.1 mmol) followed by triethylamine (0.58 mL, 4.1 mmol). After addition of the triethylamine, a yellow, homogeneous reaction solution slowly formed. After 2 hours, TLC analysis of the reaction mixture indicated it was complete. The reaction mixture was concentrated, dissolved in 25 mL of CH₃OH, and filtered. Preparative HPLC of the filtered solution provided the title compound as a colorless solid, (414.0 mg, 45%) mp 50°–140° C. with foaming.

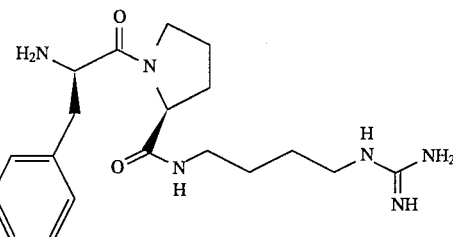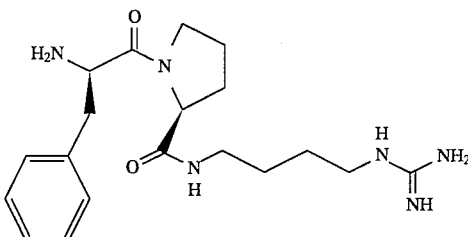

G.

A solution of 0.20 g (0.30 mmol) of Part F compound in 1.5 mL of CH₃OH with 40 mg of Pearlman's catalyst was hydrogenated at 1 atm for 3 hours. The reduction was judged complete by TLC analysis after 2.5 hours. The catalyst was removed by filtration and the filtrate was concentrated to yield an oil, which was redissolved in 10 mL of CH₃OH, acidified with 0.20 mL of trifluoroacetic acid, concentrated, dissolved in H₂O and lyophilized to yield title compound as a colorless solid (152.1 mg, 81%), mp 124°–125° C.

H. N-[4-[(Aminoiminomethyl)amino]butyl]-1-[N-(methylsulfonyl)-D-phenylalanyl]-L-prolinamide, trifluoroacetate (1:1) salt

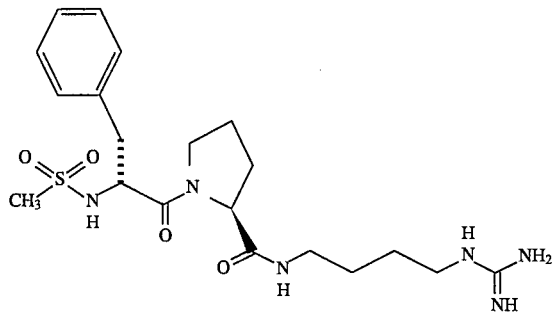

To a stirred solution of Part H compound (550 mg, 0.80 mmol) in 15 mL of dry CH₂Cl₂ and 15 mL of dry THF under argon was added Et₃N (0.44 mL, 3.20 mmol) followed by methanesulfonyl chloride (68.0 μL, 0.88 mmol). The turbid mixture was stirred at room temperature for 3 h and diluted with 0.50 mL of water. The mixture was stirred at room temperature for 10 min and concentrated in vacuo, the residue diluted with 30 mL of methanol and concentrated in vacuo. This material was purified by preparative HPLC and lyophilized to give 300 mg (75%) of title compound.

Analysis for 1.15 CF₃COOH+0.75 H₂O: C, 44.85; H, 5.85; N, 14.07; S, 5.37; F, 10.97 Found: C, 45.02; H, 5.82; N, 13.94; S, 5.34; F, 10.89

Optical rotation: $[\alpha]_D = -73.2°$ (c=1.00, MeOH)

Following the procedures of Example (i), the following examples of compounds of the invention may be prepared.

TABLE

| Example No. | Alkyl$_{1-2}$ | R | R² | R¹ | n | m | Y |
|---|---|---|---|---|---|---|---|
| 2(i) | C₂H₅ | CH₂OH(S) | H | H | 1 | 2 | NH |
| 3(i) | CH₃ | H | OH | H | 0 | 1 | NH |
| 4(i) | C₂H₅ | —CH₂C₆H₅(R) | OCH₃ | CH₃ | 0 | 2 | S |
| 5(i) | CH₃ | —CH₂C₆H₅(S) | | | | | |
| 6(i) | C₂H₅ | —CH₂CH₂CONH₂(S) | H | H | 1 | 0 | S |
| 7(i) | CH₃ | —CH₂CH₂CONH₂(R) | H | CH₃ | 1 | 1 | NH |
| 8(i) | C₂H₅ | —CH(OH)CH₃(S—Thr) | —CHCH₂CH₂CH— | | 0 | 2 | S |
| 9(i) | CH₃ | CH(OH)CH₃(S-alloThr) | CH₃ | H | 1 | 2 | NH |
| 10(i) | C₂H₅ | (indole-CH₂CH₂-, R) | SCH₃ | CH₃ | 1 | 1 | S |
| 11(i) | CH₃ | —CH₂CH₂CO₂H(R) | H | CH₃ | 0 | 3 | NH |
| 12(i) | C₂H₅ | CH₂OCH₂Ph(R) | H | H | 1 | 0 | S |
| 13(i) | CH₃ | CH₂CH₂Ph(S) | H | H | 1 | 1 | NH |

What is claimed is:
1. A compound selected from the structure I

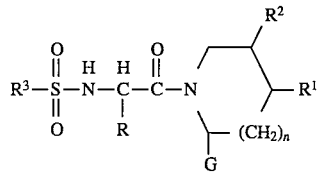

wherein n is 0, 1 or 2;

R is hydrogen, hydroxyalkyl, aminoalkyl, alkyl, cycloalkyl, aryl, arylalkyl, alkenyl, alkynyl, amidoalkyl, arylalkoxyalkyl or an amino acid side chain, either protected or unprotected;

$R^1$ and $R^2$ are independently hydrogen, lower alkyl, cycloalkyl, aryl, hydroxy, alkoxy, oxo, thioxo, thioalkyl, thioaryl, amino or alkylamino;

$R^3$ is alkyl, arylalkyl, aryl, monocyclic heteroaryl containing 5 or 6 members in an aromatic ring which includes 1 or 2 heteroatoms which are N, O or S, said monocyclic heteroaryl being optionally fused to a phenyl ring; quinolinyl, tetrahydroquinolinyl,

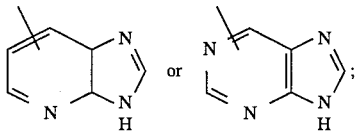

wherein G is

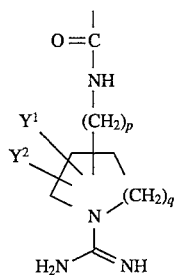

wherein p is 0, 1 or 2;
q is 0, 1, 2, 3 or 4;
$Y^1$ and $Y^2$ are independently H, lower alkyl or halo;
its stereoisomer; and
a pharmaceutically acceptable salt thereof.

2. A compound selected from the structure

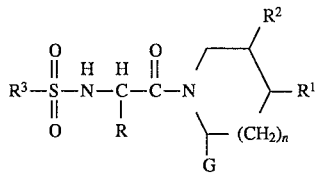

wherein n is 0, 1 or 2;

R is hydrogen, hydroxyalkyl, aminoalkyl, alkyl, cycloalkyl, aryl, arylalkyl, alkenyl, alkynyl, amidoalkyl, arylalkoxyalkyl or an amino acid side chain, either protected or unprotected;

$R^1$ and $R^2$ are independently hydrogen, lower alkyl, cycloalkyl, aryl, hydroxy, alkoxy, oxo, thioxo, thioalkyl, thioaryl, amino or alkylamino;

$R^3$ is 10-camphoryl, pentamethylchromanyl, pentafluorophenyl, pentaalkylphenyl, or trialkyl-phenyl, or carboxyphenyl, or trifluoromethylphenyl;

wherein G is

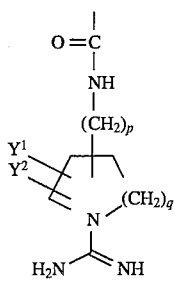

wherein p is 0, 1 or 2;
q is 0, 1, 2, 3 or 4;
its stereoisomer; and
$Y^1$ and $Y^2$ are independently H, lower alkyl or halo; and
a pharmaceutically acceptable salt thereof.

3. The compound as defined in claim 1 wherein q is 0, 1 or 2, $R^3$ is lower alkyl or aryl, R is aralkyl, arylalkoxyalkyl or hydroxyalkyl, $R^1$ and $R^2$ are each H and n is 0 or 1.

4. The compound as defined in claim 1 wherein $Y^1$ and $Y^2$ are each H, q is 2 and p is 1.

5. The compound as defined in claim 1 wherein G is

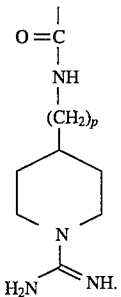

6. The compound as defined in claims 1 wherein n is 0, p is 1, q is 1 or 2, $R^3$ is $CH_3$, $CF_3CH_2$ or $C_6H_5CH_2$, and R is benzyl, phenyl or benzyloxymethyl.

7. A compound having the structure I

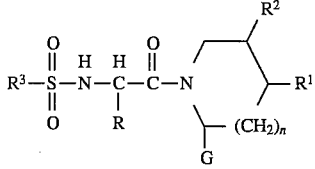

wherein G is

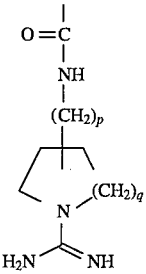

q is 1 or 2,

R$^1$ and R$^2$ are each H, R$^3$ is alkyl, arylalkyl or aryl, n is 0 or 1 and R is aralkyl or hydroxyalkyl; its stereoisomer, and a pharmaceutically acceptable salt thereof.

8. The compound as defined in claim 7 having the structure

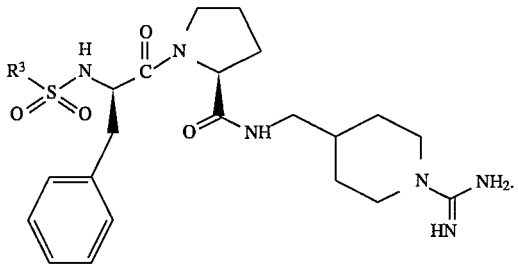

R$^3$=CH$_3$ or benzyl.

9. The compound as defined in claim 1 having the structure

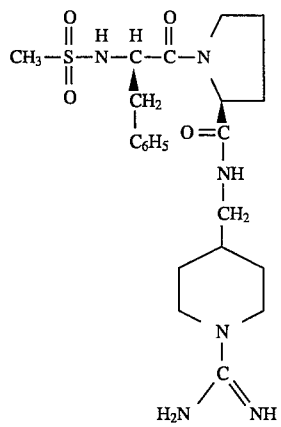

which is N-[[1-(aminoiminomethyl)-4-piperidinyl]-methyl]-1-[N-(methylsulfonyl)-D-phenylalanyl]-L-prolinamide or a pharmaceutically acceptable salt thereof.

10. The compound as defined in claim 1 which is N-[[1-(aminoiminomethyl)-3-piperidinyl]-methyl]-1-[N-(methylsulfonyl)-D-phenylalanyl]-L-prolinamide or a salt thereof;

N-[[1-(aminoiminomethyl)-4-piperidinyl]-methyl]-1-[N-(phenylmethyl)sulfonyl]-D-alanyl]-L-prolinamide, or a pharmaceutically acceptable salt thereof or its trifluoroacetate (1:1) salt;

N-[[1-(aminoiminomethyl)-4-piperidinyl]-methyl]-1-[N-[(2,2,2-trifluoroethyl)sulfonyl]-D-phenylalanyl]-L-prolinamide, or a pharmaceutically acceptable salt thereof or its trifluoroacetate (1:1) salt;

N-[[1-(aminoiminomethyl)-4-piperidinyl]-methyl]-1-[N-(phenylmethyl)sulfonyl]-L-alanyl]-L-prolinamide, or a pharmaceutically acceptable salt thereof or its trifluoroacetate (1:1) salt;

N-[[1-(aminoiminomethyl)-4-piperidinyl]-methyl]-1-[N-[(phenylmethyl)sulfonyl]glycyl]-L-prolinamide, or a pharmaceutically acceptable salt thereof or its trifluoroacetate (1:1) salt;

N-[[1-(aminoiminomethyl)-4-piperidinyl]-methyl]-1-[N-(ethylsulfonyl)-D-phenylalanyl]-L-prolinamide, or salt thereof or its trifluoroacetate (1:1) salt;

N-[[1-(aminoiminomethyl)-4-piperidinyl]-methyl]-1-[N-(propylsulfonyl)-D-phenylalanyl]-L-prolinamide, or a pharmaceutically acceptable salt thereof or its trifluoroacetate (1:1) salt;

N-[[1-(aminoiminomethyl)-4-piperidinyl]-methyl]-1-[N-[(phenylmethyl)sulfonyl]-D-phenyl-alanyl]-L-prolinamide, or a pharmaceutically acceptable salt thereof or its trifluoroacetate (1:1) salt;

N-[[1-(aminoiminomethyl)-4-piperidinyl]-methyl]-1-[N-(phenylsulfonyl)-D-phenylalanyl]-L-prolinamide, or a pharmaceutically acceptable salt thereof or its trifluoroacetate (1:1) salt; or N-[[1-(aminoiminomethyl)-4-piperidinyl]-methyl]-1-[N-[(1-methylethyl)sulfonyl]-D-phenyl-alanyl]-L-prolinamide, or a pharmaceutically acceptable salt thereof or its trifluoroacetate (2:3) salt.

11. The compound as defined in claim 2, which is N-[[1-(aminoiminomethyl)-4-piperidinyl]-methyl]-1-[N-((±)-10-camphorsulfonyl)-D-phenyl-alanyl]-L-prolinamide, or a pharmaceutically acceptable salt thereof or its trifluoroacetate (1:1) salt;

N-[[1-(aminoiminomethyl)-4-piperidinyl]-methyl]-1-[N-(pentafluorophenylsulfonyl)-D-phenyl-alanyl]-L-prolinamide, or a pharmaceutically acceptable salt thereof or its trifluoroacetate (1:1) salt;

N-[[1-(aminoiminomethyl)-4-piperidinyl]-methyl]-1-[N-(pentamethylphenylsulfonyl)-D-phenyl-alanyl]-L-prolinamide, or a pharmaceutically acceptable salt thereof or its trifluoroacetate (1:1) salt;

N-[[1-(aminoiminomethyl)-4-piperidinyl]-methyl]-1-[N-(2,4,6-isopropylphenylsulfonyl)-D-phenylalanyl]-L-prolinamide, or a pharmaceutically acceptable salt thereof or its trifluoroacetate (1:1) salt;

N-[[1-(aminoiminomethyl)-4-piperidinyl]-methyl]-1-[N-(4-carboxyphenylsulfonyl)-D-phenyl-alanyl]-L-prolinamide, or a pharmaceutically acceptable salt thereof or its trifluoroacetate (1:1) salt;

N-[[1-(aminoiminomethyl)-4-piperidinyl]-methyl]-1-[N-2,2,5,7,8-(pentamethylchroman-7-sulfonyl)-D-phenylalanyl]-L-prolinamide, or a pharmaceutically acceptable salt thereof or its trifluoroacetate (1:1) salt;

N-[[1-(aminoiminomethyl)-4-piperidinyl]-methyl]-1-[N-(3-trifluoromethylphenylsulfonyl)-D-phenylalanyl]-L-prolinamide, or a pharmaceutically acceptable salt thereof or its trifluoroacetate (1:1) salt;

N-[[1-(aminoiminomethyl)-4-piperidinyl]-methyl]-1-[N-(methylsulfonyl)-D-leucyl]-L-prolin-amide, or a pharmaceutically acceptable salt thereof or its trifluoroacetate (1:1) salt;

N-[[1-(aminoiminomethyl)-4-piperidinyl]-methyl]-1-[N-(pentamethylphenylsulfonyl)-D-phenyl-alanyl]-L-pipecolinamide, or a pharmaceutically acceptable salt thereof or its trifluoroacetate (1:1) salt; or N-[[1-(aminoiminomethyl)-4-piperidinyl]-methyl]-1-[N-(3-carboxyphenylsulfonyl)-D-phenyl-alanyl]-L-prolinamide, or a pharmaceutically acceptable salt thereof or its trifluoroacetate (1:1) salt.

12. A method of inhibiting or preventing formation of blood clots, which comprises administering to a patient in need of treatment an anti-thrombin effective amount of a compound as defined in claim 1.

13. A pharmaceutical composition comprising an anti-thrombin effective amount of a compound as defined in claim 1 and a pharmaceutically acceptable carrier therefor.

* * * * *